(12) United States Patent
Schnepf et al.

(10) Patent No.: US 7,737,263 B2
(45) Date of Patent: Jun. 15, 2010

(54) **MODIFIED *CRY*35 PROTEINS HAVING ALTERED PROTEASE STABILITY**

(75) Inventors: H. Ernest Schnepf, San Diego, CA (US); Kenneth E. Narva, Zionsville, IN (US); Steven L. Evans, Zionsville, IN (US)

(73) Assignee: Dow Agrosciences LLC, Indianapolis, IN (US)

( * ) Notice: Subject to any disclaimer, the term of this patent is extended or adjusted under 35 U.S.C. 154(b) by 281 days.

(21) Appl. No.: 11/943,814

(22) Filed: Nov. 21, 2007

(65) Prior Publication Data
US 2008/0085856 A1    Apr. 10, 2008

Related U.S. Application Data

(62) Division of application No. 10/956,448, filed on Oct. 1, 2004, now Pat. No. 7,309,785.

(60) Provisional application No. 60/508,637, filed on Oct. 3, 2003.

(51) Int. Cl.
*C07H 19/16* (2006.01)
*C07K 14/00* (2006.01)
*C12N 15/09* (2006.01)

(52) U.S. Cl. .................... 536/23.71; 530/350; 435/69.7

(58) Field of Classification Search ........................ None
See application file for complete search history.

(56) References Cited

U.S. PATENT DOCUMENTS

| 6,083,499 A | 7/2000 | Narva et al. |
| 6,127,180 A | 10/2000 | Narva et al. |
| 6,218,188 B1 | 4/2001 | Cardineau et al. |
| 6,372,480 B1 | 4/2002 | Narva et al. |
| 2003/0120054 A1* | 6/2003 | Chen et al. ................. 536/23.2 |

FOREIGN PATENT DOCUMENTS

| WO | WO 97/40162 | 10/1997 |
| WO | WO 98/23641 | 6/1998 |

(Continued)

OTHER PUBLICATIONS

Li et al., Crystal Structure of Insecticidal Delta-Endotoxin from *Bacillus thuringiensis* at 2.5 Angstrom Resolution. Nature, 1991, 353:815-821.*

(Continued)

*Primary Examiner*—Suzanne M. Noakes
(74) *Attorney, Agent, or Firm*—Jay M. Sanders; Donald R. Stuart

(57) ABSTRACT

This invention provides modified, insecticidal Cry35 proteins with enhanced properties as compared to wild-type Cry35 proteins. The modifications to these proteins were based in part on analysis of the atomic coordinates and three-dimensional (3D) structure of the ~45 kDa 149B1 protein and other proteins in the Cry35 class. The subject invention also includes polynucleotides that encode these modified proteins, and transgenic plants that produce these modified proteins. This invention further provides methods of controlling plant pests, including rootworms, with these modified proteins. The modified proteins of the subject invention include chimeric toxins involving exchanged segments, domains, and motifs as discussed herein. The subject invention also provides methods of modifying Cry35 proteins.

8 Claims, 1 Drawing Sheet
(1 of 1 Drawing Sheet(s) Filed in Color)

FOREIGN PATENT DOCUMENTS

| | | |
|---|---|---|
| WO | WO 99/31248 | 6/1999 |
| WO | WO 00/66742 | 11/2000 |
| WO | WO 01/14417 | 3/2001 |
| WO | WO 03/018810 | 3/2003 |

OTHER PUBLICATIONS

Schnepf et al. Characterization of Cry34/Cry35 Binary Insecticidal Proteins from Diverse *Bacillus thuringiensis* Strain Collections. Applied and Environmental Microbiology, Apr. 2005, 71(4):1765-1774.*

Crickmore et al. website (biols.susx.ac.uk/home/Neil_Crickmore/Bt/).

Ellis, R.T., et al., "Novel *Bacillus thuringiensis* Binary Insecticidal Crystal Proteins Active on Western . . . ," Appl. Env. Microbio. (Mar. 2002), p. 1137-1145, vol. 68, Iss. 3.

Hofte, H. et al., "Insecticidal Crystal Proteins of *Bacillus thuringiensis*," Microbiological Reviews (Jun. 1989), p. 242-255, vol. 53, No. 2.

Moellenbeck, D.J., et al., "Insecticidal Proteins from *Bacillus thuringiensis* Protect Corn from Corn Rootworms," Nature Biotechnology (Jul. 2001), pp. 668-672, vol. 19.

Voigt, C.A. et al., "Computational method to reduce the search space for directed protein evolution," Proc. Natl. Acad. Sci. U.S.A. (Mar. 27, 2001), p. 3778-83, vol. 98, No. 2.

Voigt, C.A. et al., "Computationally focusing the directed evolution of proteins," J. Cell Biochem. (2001), p. 58-63, Suppl. 37 (Abstract).

* cited by examiner

SEQUENCE LISTING

```
<160> NUMBER OF SEQ ID NOS: 30

<210> SEQ ID NO 1
<211> LENGTH: 383
<212> TYPE: PRT
<213> ORGANISM: Bacillus thuringiensis

<400> SEQUENCE: 1
```

```
Met Leu Asp Thr Asn Lys Ile Tyr Glu Ile Ser Asn Tyr Ala Asn Gly
1               5                   10                  15

Leu His Ala Ala Thr Tyr Leu Ser Leu Asp Asp Ser Gly Val Ser Leu
            20                  25                  30

Met Asn Lys Asn Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Ala Ser Ser Tyr Val Ile Gln Ser Asn Asn Gly Lys Val Leu Thr Ala
                100                 105                 110

Gly Thr Gly Gln Ser Leu Gly Leu Ile Arg Leu Thr Asp Glu Ser Pro
            115                 120                 125

Asp Asn Pro Asn Gln Gln Trp Asn Leu Thr Pro Val Gln Thr Ile Gln
130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
            195                 200                 205

Gln Tyr Trp Gln Gln Ala Val Gly Ser Asn Val Ala Leu Arg Pro His
            210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Thr Asp Glu Ile Lys
            260                 265                 270

Thr Gln Leu Asn Glu Glu Leu Lys Ile Glu Tyr Ser Arg Glu Thr Lys
            275                 280                 285

Ile Met Glu Lys Tyr Gln Glu Gln Ser Glu Ile Asp Asn Pro Thr Asp
        290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Ser Tyr Pro Asp His Gln Gln Ala
            340                 345                 350

Leu Leu Leu Leu Thr Asn His Ser Tyr Glu Glu Val Glu Glu Ile Thr
            355                 360                 365

Asn Ile Pro Lys Ile Ser Leu Lys Lys Leu Lys Lys Tyr Tyr Phe
370                 375                 380
```

<210> SEQ ID NO 2
<211> LENGTH: 380
<212> TYPE: PRT
<213> ORGANISM: Bacillus thuringiensis

<400> SEQUENCE: 2

| | | | | | | | | | | | | | | |
|---|---|---|---|---|---|---|---|---|---|---|---|---|---|---|
|Leu|Asp|Thr|Asn|Lys|Val|Tyr|Glu|Ile|Ser|Asn|His|Ala|Asn|Gly|Leu
1||||5||||10||||15||

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Phe Leu Leu Thr Asn His Ser Tyr Glu Glu Val Glu Glu Ile Thr Asn
        355                 360                 365

Ile Pro Lys Ser Thr Leu Lys Lys Leu Lys Lys Tyr
370                 375                 380

<210> SEQ ID NO 3
<211> LENGTH: 380
<212> TYPE: PRT
<213> ORGANISM: Bacillus thuringiensis

```
<400> SEQUENCE: 3

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Ile Leu Lys Lys Tyr Gln
        195                 200                 205

Tyr Trp Gln Arg Ala Val Gly Ser Asn Val Ala Leu Arg Pro His Glu
210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Ile Thr Asn
        355                 360                 365

Ile Pro Phe Ser Thr Leu Lys Lys Leu Lys Lys Tyr
370                 375                 380

<210> SEQ ID NO 4
<211> LENGTH: 380
<212> TYPE: PRT
```

<213> ORGANISM: Bacillus thuringiensis

<400> SEQUENCE: 4

| | | | | | | | | | | | | | | | |
|---|---|---|---|---|---|---|---|---|---|---|---|---|---|---|---|
| Leu | Asp | Thr | Asn | Lys | Val | Tyr | Glu | Ile | Ser | Asn | His | Ala | Asn | Gly | Leu |
| 1 | | | | 5 | | | | | 10 | | | | | 15 | |
| Tyr | Ala | Ala | Thr | Tyr | Leu | Ser | Leu | Asp | Asp | Ser | Gly | Val | Ser | Leu | Met |
| | | | 20 | | | | | 25 | | | | | 30 | | |
| Asn | Lys | Asn | Asp | Asp | Ile | Asp | Asp | Tyr | Asn | Leu | Lys | Trp | Phe | Leu | |
| | | 35 | | | | 40 | | | | | 45 | | | | |
| Phe | Pro | Ile | Asp | Asp | Gln | Tyr | Ile | Ile | Thr | Ser | Tyr | Ala | Ala | Asn | |
| | 50 | | | | | 55 | | | | | 60 | | | | |
| Asn | Cys | Lys | Val | Trp | Asn | Val | Asn | Asp | Lys | Ile | Asn | Val | Ser | Thr | |
| 65 | | | | | 70 | | | | | 75 | | | | | 80 |
| Tyr | Ser | Ser | Thr | Asn | Ser | Ile | Gln | Lys | Trp | Gln | Ile | Lys | Ala | Asn | Gly |
| | | | | 85 | | | | | 90 | | | | | 95 | |
| Ser | Ser | Tyr | Val | Ile | Gln | Ser | Asp | Asn | Gly | Lys | Val | Leu | Thr | Ala | Gly |
| | | | 100 | | | | | 105 | | | | | 110 | | |
| Thr | Gly | Gln | Ala | Leu | Gly | Leu | Ile | Arg | Leu | Thr | Asp | Glu | Ser | Ser | Asn |
| | | 115 | | | | | 120 | | | | | 125 | | | |
| Asn | Pro | Asn | Gln | Gln | Trp | Asn | Leu | Thr | Ser | Val | Gln | Thr | Ile | Gln | Leu |
| | 130 | | | | | 135 | | | | | 140 | | | | |
| Pro | Gln | Lys | Pro | Ile | Ile | Asp | Thr | Lys | Leu | Lys | Asp | Tyr | Pro | Lys | Tyr |
| 145 | | | | | 150 | | | | | 155 | | | | | 160 |
| Ser | Pro | Thr | Gly | Asn | Ile | Asp | Asn | Gly | Thr | Ser | Pro | Gln | Leu | Met | Gly |
| | | | | 165 | | | | | 170 | | | | | 175 | |
| Trp | Thr | Leu | Val | Pro | Cys | Ile | Met | Val | Asn | Asp | Pro | Asn | Ile | Asp | Lys |
| | | | 180 | | | | | 185 | | | | | 190 | | |
| Asn | Thr | Gln | Ile | Lys | Thr | Thr | Pro | Tyr | Tyr | Ile | Leu | Lys | Lys | Tyr | Gln |
| | | 195 | | | | | 200 | | | | | 205 | | | |
| Tyr | Trp | Gln | Arg | Ala | Val | Gly | Ser | Asn | Val | Ala | Leu | Arg | Pro | His | Glu |
| | 210 | | | | | 215 | | | | | 220 | | | | |
| Lys | Lys | Ser | Tyr | Thr | Tyr | Glu | Trp | Gly | Thr | Glu | Ile | Asp | Gln | Lys | Thr |
| 225 | | | | | 230 | | | | | 235 | | | | | 240 |
| Thr | Ile | Ile | Asn | Thr | Leu | Gly | Phe | Gln | Ile | Asn | Ile | Asp | Ser | Gly | Met |
| | | | | 245 | | | | | 250 | | | | | 255 | |
| Lys | Phe | Asp | Ile | Pro | Glu | Val | Gly | Gly | Gly | Thr | Asp | Glu | Ile | Lys | Thr |
| | | | 260 | | | | | 265 | | | | | 270 | | |
| Gln | Leu | Asn | Glu | Glu | Leu | Lys | Ile | Glu | Tyr | Ser | His | Glu | Thr | Lys | Ile |
| | | 275 | | | | | 280 | | | | | 285 | | | |
| Met | Glu | Lys | Tyr | Gln | Glu | Gln | Ser | Glu | Ile | Asp | Asn | Pro | Thr | Asp | Gln |
| | 290 | | | | | 295 | | | | | 300 | | | | |
| Ser | Met | Asn | Ser | Ile | Gly | Phe | Leu | Thr | Ile | Thr | Ser | Leu | Glu | Leu | Tyr |
| 305 | | | | | 310 | | | | | 315 | | | | | 320 |
| Arg | Tyr | Asn | Gly | Ser | Glu | Ile | Arg | Ile | Met | Gln | Ile | Gln | Thr | Ser | Asp |
| | | | | 325 | | | | | 330 | | | | | 335 | |
| Asn | Asp | Thr | Tyr | Asn | Val | Thr | Ser | Tyr | Pro | Asn | His | Gln | Gln | Ala | Leu |
| | | | 340 | | | | | 345 | | | | | 350 | | |
| Leu | Leu | Leu | Thr | Asn | His | Ser | Tyr | Glu | Glu | Val | Glu | Glu | Ile | Thr | Asn |
| | | 355 | | | | | 360 | | | | | 365 | | | |
| Ile | Pro | Lys | Ser | Thr | Leu | Lys | Lys | Leu | Phe | Lys | Tyr | | | | |
| | 370 | | | | | 375 | | | | | 380 | | | | |

<210> SEQ ID NO 5
<211> LENGTH: 380

<212> TYPE: PRT
<213> ORGANISM: Bacillus thuringiensis

<400> SEQUENCE: 5

```
Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ile Pro Lys Ser Thr Leu Lys Lys Leu Lys Phe Tyr
370                 375                 380
```

<210> SEQ ID NO 6

```
<211> LENGTH: 380
<212> TYPE: PRT
<213> ORGANISM: Bacillus thuringiensis

<400> SEQUENCE: 6

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ala Pro Phe Ser Thr Leu Lys Lys Leu Lys Lys Tyr
    370                 375                 380
```

```
<210> SEQ ID NO 7
<211> LENGTH: 380
<212> TYPE: PRT
<213> ORGANISM: Bacillus thuringiensis

<400> SEQUENCE: 7

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ala Pro Phe Ser Thr Leu Asn Lys Leu Lys Lys Tyr
    370                 375                 380
```

<210> SEQ ID NO 8
<211> LENGTH: 380
<212> TYPE: PRT
<213> ORGANISM: Bacillus thuringiensis

<400> SEQUENCE: 8

| Leu | Asp | Thr | Asn | Lys | Val | Tyr | Glu | Ile | Ser | Asn | His | Ala | Asn | Gly | Leu |
|---|---|---|---|---|---|---|---|---|---|---|---|---|---|---|---|
| 1 | | | | 5 | | | | | 10 | | | | | 15 | |

| Tyr | Ala | Ala | Thr | Tyr | Leu | Ser | Leu | Asp | Asp | Ser | Gly | Val | Ser | Leu | Met |
| | | | 20 | | | | | 25 | | | | | 30 | | |

| Asn | Lys | Asn | Asp | Asp | Ile | Asp | Asp | Tyr | Asn | Leu | Lys | Trp | Phe | Leu |
| | | 35 | | | | 40 | | | | | 45 | | | |

| Phe | Pro | Ile | Asp | Asp | Asp | Gln | Tyr | Ile | Ile | Thr | Ser | Tyr | Ala | Ala | Asn |
| | 50 | | | | | 55 | | | | | 60 | | | | |

| Asn | Cys | Lys | Val | Trp | Asn | Val | Asn | Asn | Asp | Lys | Ile | Asn | Val | Ser | Thr |
| 65 | | | | | 70 | | | | | 75 | | | | | 80 |

| Tyr | Ser | Ser | Thr | Asn | Ser | Ile | Gln | Lys | Trp | Gln | Ile | Lys | Ala | Asn | Gly |
| | | | | 85 | | | | | 90 | | | | | 95 | |

| Ser | Ser | Tyr | Val | Ile | Gln | Ser | Asp | Asn | Gly | Lys | Val | Leu | Thr | Ala | Gly |
| | | | 100 | | | | | 105 | | | | | 110 | | |

| Thr | Gly | Gln | Ala | Leu | Gly | Leu | Ile | Arg | Leu | Thr | Asp | Glu | Ser | Ser | Asn |
| | | | 115 | | | | | 120 | | | | | 125 | | |

| Asn | Pro | Asn | Gln | Gln | Trp | Asn | Leu | Thr | Ser | Val | Gln | Thr | Ile | Gln | Leu |
| | | 130 | | | | | 135 | | | | | 140 | | | |

| Pro | Gln | Lys | Pro | Ile | Ile | Asp | Thr | Lys | Leu | Lys | Asp | Tyr | Pro | Lys | Tyr |
| 145 | | | | | 150 | | | | | 155 | | | | | 160 |

| Ser | Pro | Thr | Gly | Asn | Ile | Asp | Asn | Gly | Thr | Ser | Pro | Gln | Leu | Met | Gly |
| | | | | 165 | | | | | 170 | | | | | 175 | |

| Trp | Thr | Leu | Val | Pro | Cys | Ile | Met | Val | Asn | Asp | Pro | Asn | Ile | Asp | Lys |
| | | | 180 | | | | | 185 | | | | | 190 | | |

| Asn | Thr | Gln | Ile | Lys | Thr | Thr | Pro | Tyr | Tyr | Ile | Leu | Lys | Lys | Tyr | Gln |
| | | | 195 | | | | | 200 | | | | | 205 | | |

| Tyr | Trp | Gln | Arg | Ala | Val | Gly | Ser | Asn | Val | Ala | Leu | Arg | Pro | His | Glu |
| 210 | | | | | 215 | | | | | 220 | | | | | |

| Lys | Lys | Ser | Tyr | Thr | Tyr | Glu | Trp | Gly | Thr | Glu | Ile | Asp | Gln | Lys | Thr |
| 225 | | | | | 230 | | | | | 235 | | | | | 240 |

| Thr | Ile | Ile | Asn | Thr | Leu | Gly | Phe | Gln | Ile | Asn | Ile | Asp | Ser | Gly | Met |
| | | | | 245 | | | | | 250 | | | | | 255 | |

| Lys | Phe | Asp | Ile | Pro | Glu | Val | Gly | Gly | Thr | Asp | Glu | Ile | Lys | Thr |
| | | | 260 | | | | | 265 | | | | | 270 | |

| Gln | Leu | Asn | Glu | Glu | Leu | Lys | Ile | Glu | Tyr | Ser | His | Glu | Thr | Lys | Ile |
| | | | 275 | | | | | 280 | | | | | 285 | | |

| Met | Glu | Lys | Tyr | Gln | Glu | Gln | Ser | Glu | Ile | Asp | Asn | Pro | Thr | Asp | Gln |
| | 290 | | | | | 295 | | | | | 300 | | | | |

| Ser | Met | Asn | Ser | Ile | Gly | Phe | Leu | Thr | Ile | Thr | Ser | Leu | Glu | Leu | Tyr |
| 305 | | | | | 310 | | | | | 315 | | | | | 320 |

| Arg | Tyr | Asn | Gly | Ser | Glu | Ile | Arg | Ile | Met | Gln | Ile | Gln | Thr | Ser | Asp |
| | | | | 325 | | | | | 330 | | | | | 335 | |

| Asn | Asp | Thr | Tyr | Asn | Val | Thr | Ser | Tyr | Pro | Asn | His | Gln | Gln | Ala | Leu |
| | | | 340 | | | | | 345 | | | | | 350 | | |

| Leu | Leu | Leu | Thr | Asn | His | Ser | Tyr | Glu | Glu | Val | Glu | Glu | Ile | Thr | Asn |
| | | | 355 | | | | | 360 | | | | | 365 | | |

| Ile | Pro | Ser | Ser | Thr | Leu | Lys | Lys | Leu | Lys | Lys | Tyr |
| | 370 | | | | | 375 | | | | | 380 |

<210> SEQ ID NO 9
<211> LENGTH: 380
<212> TYPE: PRT
<213> ORGANISM: Bacillus thuringiensis

<400> SEQUENCE: 9

```
Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ile Pro Asn Ser Thr Leu Lys Lys Leu Lys Lys Tyr
```

370                 375                 380

<210> SEQ ID NO 10
<211> LENGTH: 380
<212> TYPE: PRT
<213> ORGANISM: Bacillus thuringiensis

<400> SEQUENCE: 10

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

```
Ile Pro Lys Ser Thr Leu Ser Lys Leu Lys Lys Tyr
    370                 375                 380
```

<210> SEQ ID NO 11
<211> LENGTH: 380
<212> TYPE: PRT
<213> ORGANISM: Bacillus thuringiensis

<400> SEQUENCE: 11

```
Leu Asp Thr Asn Lys Val Tyr Glu Ile Ser Asn

Ile Pro Lys Ser Thr Leu Asn Lys Leu Lys Lys Tyr
    370                 375                 380

<210> SEQ ID NO 12
<211> LENGTH: 380
<212> TYPE: PRT
<213> ORGANISM: Bacillus thuringiensis

<400> SEQUENCE: 12

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
                20                  25                  30

Asn Lys Asn Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
                100                 105                 110

Thr Gly Gln Ala Leu Gly Leu Ile Arg Leu Thr Asp Glu Ser Ser Asn
            115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
                180                 185                 190

Asn Thr Gln Ile Lys Thr Thr Pro Tyr Tyr Ile Leu Lys Lys Tyr Gln
            195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Thr Asp Glu Ile Lys Thr
            260                 265                 270

Gln Leu Asn Glu Glu Leu Lys Ile Glu Tyr Ser His Glu Thr Lys Ile
    275                 280                 285

Met Glu Lys Tyr Gln Glu Gln Ser Glu Ile Asp Asn Pro Thr Asp Gln
290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn

```
                    355                 360                 365
Ile Pro Lys Ser Thr Leu Gln Lys Leu Lys Lys Tyr
        370                 375                 380

<210> SEQ ID NO 13
<211> LENGTH: 380
<212> TYPE: PRT
<213> ORGANISM: Bacillus thuringiensis

<400> SEQUENCE: 13

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350
```

```
Leu Leu Leu Thr Asn His Ser Tyr Glu Glu Val Glu Ile Thr Asn
        355                 360                 365

Ile Pro Lys Ser Thr Leu Lys Glu Leu Lys Lys Tyr
370                 375                 380

<210> SEQ ID NO 14
<211> LENGTH: 380
<212> TYPE: PRT
<213> ORGANISM: Bacillus thuringiensis

<400> SEQUENCE: 14

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350
```

```
Leu Leu Leu Thr Asn His Ser Tyr Glu Glu Val Glu Glu Ile Thr Asn
            355                 360                 365

Ile Pro Lys Ser Thr Leu Lys Ser Leu Lys Lys Tyr
        370                 375                 380

<210> SEQ ID NO 15
<211> LENGTH: 380
<212> TYPE: PRT
<213> ORGANISM: Bacillus thuringiensis

<400> SEQUENCE: 15

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Asp Ile Asp Asp Tyr Asn Leu Lys Trp Phe Leu
        35                  40                  45

Phe Pro Ile Asp Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
```

```
                    340                 345                 350
Leu Leu Leu Thr Asn His Ser Tyr Glu Glu Val Glu Ile Thr Asn
            355                 360                 365
Ile Pro Lys Ser Thr Leu Lys Asn Leu Lys Lys Tyr
    370                 375                 380

<210> SEQ ID NO 16
<211> LENGTH: 380
<212> TYPE: PRT
<213> ORGANISM: Bacillus thuringiensis

<400> SEQUENCE: 16

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
                20                  25                  30

Asn Lys Asn Asp Asp Asp Ile Asp Asp Tyr Asn Leu Lys Trp Phe Leu
            35                  40                  45

Phe Pro Ile Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335
```

```
Asn Asp Thr Tyr Asn Val Thr Ser Tyr Pro Asn His Gln Gln Ala Leu
                340                 345                 350
Leu Leu Leu Thr Asn His Ser Tyr Glu Glu Val Glu Glu Ile Thr Asn
            355                 360                 365
Ile Pro Lys Ser Thr Leu Lys Gln Leu Lys Lys Tyr
        370                 375                 380

<210> SEQ ID NO 17
<211> LENGTH: 380
<212> TYPE: PRT
<213> ORGANISM: Bacillus thuringiensis

<400> SEQUENCE: 17

Leu Asp Thr Asn Lys Val Tyr Glu Ile Ser Asn His Ala Asn Gly Leu
1               5                   10                  15
Tyr Ala Ala Thr Tyr Leu Ser Leu Asp Asp Ser Gly Val Ser Leu Met
                20                  25                  30
Asn Lys Asn Asp Asp Ile Asp Asp Tyr Asn Leu Lys Trp Phe Leu
            35                  40                  45
Phe Pro Ile Asp Asp Gln Tyr Ile Ile Thr Ser Tyr Ala Ala Asn
        50                  55                  60
Asn Cys Lys Val Trp Asn Val Asn Asp Lys Ile Asn Val Ser Thr
65                  70                  75                  80
Tyr Ser Ser Thr Asn Ser Ile Gln Lys Trp Gln Ile Lys Ala Asn Gly
                85                  90                  95
Ser Ser Tyr Val Ile Gln Ser Asn Gly Lys Val Leu Thr Ala Gly
                100                 105                 110
Thr Gly Gln Ala Leu Gly Leu Ile Arg Leu Thr Asp Glu Ser Ser Asn
            115                 120                 125
Asn Pro Asn Gln Gln Trp Asn Leu Thr Ser Val Gln Thr Ile Gln Leu
        130                 135                 140
Pro Gln Lys Pro Ile Ile Asp Thr Lys Leu Lys Asp Tyr Pro Lys Tyr
145                 150                 155                 160
Ser Pro Thr Gly Asn Ile Asp Asn Gly Thr Ser Pro Gln Leu Met Gly
                165                 170                 175
Trp Thr Leu Val Pro Cys Ile Met Val Asn Asp Pro Asn Ile Asp Lys
            180                 185                 190
Asn Thr Gln Ile Lys Thr Thr Pro Tyr Tyr Ile Leu Lys Lys Tyr Gln
        195                 200                 205
Tyr Trp Gln Arg Ala Val Gly Ser Asn Val Ala Leu Arg Pro His Glu
    210                 215                 220
Lys Lys Ser Tyr Thr Tyr Glu Trp Gly Thr Glu Ile Asp Gln Lys Thr
225                 230                 235                 240
Thr Ile Ile Asn Thr Leu Gly Phe Gln Ile Asn Ile Asp Ser Gly Met
                245                 250                 255
Lys Phe Asp Ile Pro Glu Val Gly Gly Thr Asp Glu Ile Lys Thr
            260                 265                 270
Gln Leu Asn Glu Glu Leu Lys Ile Glu Tyr Ser His Glu Thr Lys Ile
        275                 280                 285
Met Glu Lys Tyr Gln Glu Gln Ser Glu Ile Asp Asn Pro Thr Asp Gln
    290                 295                 300
Ser Met Asn Ser Ile Gly Phe Leu Thr Ile Thr Ser Leu Glu Leu Tyr
305                 310                 315                 320
Arg Tyr Asn Gly Ser Glu Ile Arg Ile Met Gln Ile Gln Thr Ser Asp
                325                 330                 335
```

```
Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
            355                 360                 365

Ile Pro Lys Ser Thr Leu Lys Lys Leu His Lys Tyr
370                 375                 380

<210> SEQ ID NO 18
<211> LENGTH: 380
<212> TYPE: PRT
<213> ORGANISM: Bacillus thuringiensis

<400> SEQUENCE: 18

Leu Asp Thr Asn Lys Val

```
                      325                 330                 335
Asn Asp Thr Tyr Asn Val Thr Ser Tyr Pro Asn His Gln Gln Ala Leu
            340                 345                 350
Leu Leu Leu Thr Asn His Ser Tyr Glu Glu Val Glu Glu Ile Thr Asn
            355                 360                 365
Ile Pro Lys Ser Thr Leu Lys Lys Leu Ser Lys Tyr
            370                 375                 380

<210> SEQ ID NO 19
<211> LENGTH: 380
<212> TYPE: PRT
<213> ORGANISM: Bacillus thuringiensis

<400> SEQUENCE: 19

Leu Asp Thr Asn Lys Val Tyr Glu Ile Ser Asn His Ala Asn Gly Leu
 1               5                  10                  15
Tyr Ala Ala Thr Tyr Leu Ser Leu Asp Asp Ser Gly Val Ser Leu Met
            20                  25                  30
Asn Lys Asn Asp Asp Asp Ile Asp Asp Tyr Asn Leu Lys Trp Phe Leu
            35                  40                  45
Phe Pro Ile Asp Asp Asp Gln Tyr Ile Ile Thr Ser Tyr Ala Ala Asn
 50                  55                  60
Asn Cys Lys Val Trp Asn Val Asn Asn Asp Lys Ile Asn Val Ser Thr
 65                  70                  75                  80
Tyr Ser Ser Thr Asn Ser Ile Gln Lys Trp Gln Ile Lys Ala Asn Gly
             85                  90                  95
Ser Ser Tyr Val Ile Gln Ser Asp Asn Gly Lys Val Leu Thr Ala Gly
            100                 105                 110
Thr Gly Gln Ala Leu Gly Leu Ile Arg Leu Thr Asp Glu Ser Ser Asn
            115                 120                 125
Asn Pro Asn Gln Gln Trp Asn Leu Thr Ser Val Gln Thr Ile Gln Leu
            130                 135                 140
Pro Gln Lys Pro Ile Ile Asp Thr Lys Leu Lys Asp Tyr Pro Lys Tyr
145                 150                 155                 160
Ser Pro Thr Gly Asn Ile Asp Asn Gly Thr Ser Pro Gln Leu Met Gly
                165                 170                 175
Trp Thr Leu Val Pro Cys Ile Met Val Asn Asp Pro Asn Ile Asp Lys
            180                 185                 190
Asn Thr Gln Ile Lys Thr Thr Pro Tyr Tyr Ile Leu Lys Lys Tyr Gln
            195                 200                 205
Tyr Trp Gln Arg Ala Val Gly Ser Asn Val Ala Leu Arg Pro His Glu
            210                 215                 220
Lys Lys Ser Tyr Thr Tyr Glu Trp Gly Thr Glu Ile Asp Gln Lys Thr
225                 230                 235                 240
Thr Ile Ile Asn Thr Leu Gly Phe Gln Ile Asn Ile Asp Ser Gly Met
                245                 250                 255
Lys Phe Asp Ile Pro Glu Val Gly Gly Gly Thr Asp Glu Ile Lys Thr
            260                 265                 270
Gln Leu Asn Glu Glu Leu Lys Ile Glu Tyr Ser His Glu Thr Lys Ile
            275                 280                 285
Met Glu Lys Tyr Gln Glu Gln Ser Glu Ile Asp Asn Pro Thr Asp Gln
            290                 295                 300
Ser Met Asn Ser Ile Gly Phe Leu Thr Ile Thr Ser Leu Glu Leu Tyr
305                 310                 315                 320
```

```
Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
            355                 360                 365

Ile Pro Lys Ser Thr Leu Lys Lys Leu Asn Lys Tyr
        370                 375                 380

<210> SEQ ID NO 20
<211> LENGTH: 380
<212> TYPE: PRT
<213> ORGANISM: Bacillus thuringiensis

<400> SEQUENCE: 20

Leu Asp Thr Asn Lys Val T

Arg Tyr Asn Gly Ser Glu Ile Arg Ile Met Gln Ile Gln Thr Ser Asp
            325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Ile Thr Asn
            355                 360                 365

Ile Pro Lys Ser Thr Leu Lys Lys Leu Gln Lys Tyr
            370                 375                 380

<210> SEQ ID NO 21
<211> LENGTH: 380

```
305                 310                 315                 320
Arg Tyr Asn Gly Ser Glu Ile Arg Ile Met Gln Ile Gln Thr Ser Asp
            325                 330                 335

Asn Asp Thr Tyr Asn Val Thr Ser Tyr Pro Asn His Gln Gln Ala Leu
            340                 345                 350

Leu Leu Leu Ala Pro Phe Ala Tyr Glu Glu Val Glu Glu Ile Thr Asn
            355                 360                 365

Ile Pro Lys Ser Thr Leu Lys Lys Leu Lys Lys Tyr
    370                 375                 380

<210> SEQ ID NO 22
<211> LENGTH: 380
<212> TYPE: PRT
<213> ORGANISM: Bacillus thuringiensis

<400> SEQUENCE: 22

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Asp Tyr Asn Leu Lys Trp Phe Leu
            35                  40                  45

Phe Pro Ile Asp Asp Gln Tyr Ile Ile Thr Ser Tyr Ala Ala Asn
            50                  55                  60

Asn Cys Lys Val Trp Asn Val Asn Asn Asp Lys Ile Asn Val Ser Thr
65              70                  75                  80

Tyr Ser Ser Thr Asn Ser Ile Gln Lys Trp Gln Ile Lys Ala Asn Gly
            85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
            115                 120                 125

Asn Pro Asn Gln Gln Trp Asn Leu Thr Ser Val Gln Thr Ile Gln Leu
        130                 135                 140

Pro Gln Lys Pro Ile Ile Asp Thr Lys Leu Lys Asp Tyr Pro Lys Tyr
145             150                 155                 160

Ser Pro Thr Gly Asn Ile Asp Asn Gly Thr Ser Pro Gln Leu Met Gly
            165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
            195                 200                 205

Tyr Trp Gln Arg Ala Val Gly Ser Asn Val Ala Leu Arg Pro His Glu
            210                 215                 220

Lys Lys Ser Tyr Thr Tyr Glu Trp Gly Thr Glu Ile Asp Gln Lys Thr
225             230                 235                 240

Thr Ile Ile Asn Thr Leu Gly Phe Gln Ile Asn Ile Asp Ser Gly Met
            245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Gly Thr Lys Ile
            275                 280                 285

Met Glu Lys Tyr Gln Glu Gln Ser Glu Ile Asp Asn Pro Thr Asp Gln
            290                 295                 300
```

```
Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ile Pro Lys Ser Thr Leu Lys Lys Leu Lys Glu Tyr
    370                 375                 380

<210> SEQ ID NO 23
<211> LENGTH: 380
<212> TYPE: PRT
<213> ORGANISM: Bacillus thuringiensis

<400> SEQUENCE: 23

Leu Asp Thr Asn Lys Val Tyr Glu Ile Ser Asn His Ala Asn Gly Leu
1               5                   10                  15

Tyr Ala Ala Thr Tyr

```
Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
            325                 330                 335

Asn Asp Thr Tyr Asn Val Thr Ser Tyr Pro Asn His Gln Gln Ala Leu
                340                 345                 350

Leu Leu Leu Thr Asn His Ser Tyr Glu Glu Val Glu Gly Ile Thr Asn
            355                 360                 365

Ile Pro Lys Ser Thr Leu Lys Lys Leu Lys His Tyr
    370                 375                 380

<210> SEQ ID NO 24
<211> LENGTH: 380
<212> TYPE: PRT
<213> ORGANISM: Bacillus thuringiensis

<400> SEQUENCE: 24

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
                100                 105                 110

Thr Gly Gln Ala Leu Gly Leu Ile Arg Leu Thr Asp Glu Ser Ser Asn
            115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Ile Leu Lys Lys Tyr Gln
        195                 200                 205

Tyr Trp Gln Arg Ala Val Gly Ser Asn Val Ala Leu Arg Pro His Glu
210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285

Met Glu Lys Tyr Gln Glu Gln Ser Glu Ile Asp Asn Pro Thr Asp Gln
```

```
                290                 295                 300
Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
                340                 345                 350

Leu Leu Leu Thr Asn His Ser Tyr Glu Glu Val Glu Glu Ile Thr Asn
                355                 360                 365

Ile Pro Lys Ser Thr Leu Lys Lys Leu Lys Ser Tyr
370                 375                 380

<210> SEQ ID NO 25
<211> LENGTH: 380
<212> TYPE: PRT
<213> ORGANISM: Bacillus thuringiensis

<400> SEQUENCE: 25

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
                20                  25                  30

Asn Lys Asn Asp Asp Ile Asp Asp Tyr Asn Leu Lys Trp Phe Leu
            35                  40                  45

Phe Pro Ile Asp Asp Gln Tyr Ile Ile Thr Ser Tyr Ala Ala Asn
50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
                100                 105                 110

Thr Gly Gln Ala Leu Gly Leu Ile Arg Leu Thr Asp Glu Ser Ser Asn
                115                 120                 125

Asn Pro Asn Gln Gln Trp Asn Leu Thr Ser Val Gln Thr Ile Gln Leu
130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
                180                 185                 190

Asn Thr Gln Ile Lys Thr Thr Pro Tyr Tyr Ile Leu Lys Lys Tyr Gln
                195                 200                 205

Tyr Trp Gln Arg Ala Val Gly Ser Asn Val Ala Leu Arg Pro His Glu
                210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
                260                 265                 270

Gln Leu Asn Glu Glu Leu Lys Ile Glu Tyr Ser His Glu Thr Lys Ile
                275                 280                 285
```

```
Met Glu Lys Tyr Gln Glu Gln Ser Glu Ile Asp Asn Pro Thr Asp Gln
        290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ile Pro Lys Ser Thr Leu Lys Lys Leu Lys Asn Tyr
370                 375                 380

<210> SEQ ID NO 26
<211> LENGTH: 380
<212> TYPE: PRT
<213> ORGANISM: Bacillus thuringiensis

<400> SEQUENCE: 26

Leu Asp Thr Asn Lys Val Tyr Glu Ile Ser Asn His Ala Asn Gly Leu
1               5                   10                  15

Tyr Ala Ala Thr Tyr Leu Ser Leu Asp Asp Ser Gly Val Ser Leu Met
            20                  25                  30

Asn Lys Asn Asp Asp Ile Asp Asp Tyr Asn Leu Lys Trp Phe Leu
        35                  40                  45

Phe Pro Ile Asp Asp Gln Tyr Ile Ile Thr Ser Tyr Ala Ala Asn
    50                  55                  60

Asn Cys Lys Val Trp Asn Val Asn Asn Asp Lys Ile Asn Val Ser Thr
65                  70                  75                  80

Tyr Ser Ser Thr Asn Ser Ile Gln Lys Trp Gln Ile Lys Ala Asn Gly
                85                  90                  95

Ser Ser Tyr Val Ile Gln Ser Asp Asn Gly Lys Val Leu Thr Ala Gly
            100                 105                 110

Thr Gly Gln Ala Leu Gly Leu Ile Arg Leu Thr Asp Glu Ser Ser Asn
        115                 120                 125

Asn Pro Asn Gln Gln Trp Asn Leu Thr Ser Val Gln Thr Ile Gln Leu
    130                 135                 140

Pro Gln Lys Pro Ile Ile Asp Thr Lys Leu Lys Asp Tyr Pro Lys Tyr
145                 150                 155                 160

Ser Pro Thr Gly Asn Ile Asp Asn Gly Thr Ser Pro Gln Leu Met Gly
                165                 170                 175

Trp Thr Leu Val Pro Cys Ile Met Val Asn Asp Pro Asn Ile Asp Lys
            180                 185                 190

Asn Thr Gln Ile Lys Thr Thr Pro Tyr Tyr Ile Leu Lys Lys Tyr Gln
        195                 200                 205

Tyr Trp Gln Arg Ala Val Gly Ser Asn Val Ala Leu Arg Pro His Glu
    210                 215                 220

Lys Lys Ser Tyr Thr Tyr Glu Trp Gly Thr Glu Ile Asp Gln Lys Thr
225                 230                 235                 240

Thr Ile Ile Asn Thr Leu Gly Phe Gln Ile Asn Ile Asp Ser Gly Met
                245                 250                 255

Lys Phe Asp Ile Pro Glu Val Gly Gly Gly Thr Asp Glu Ile Lys Thr
            260                 265                 270

Gln Leu Asn Glu Glu Leu Lys Ile Glu Tyr Ser His Glu Thr Lys Ile
        275                 280                 285
```

-continued

```
Met Glu Lys Tyr Gln Glu Gln Ser Glu Ile Asp Asn Pro Thr Asp Gln
    290                 295                 300

Ser Met Asn Ser Ile Gly Phe Leu Thr Ile Thr Ser Leu Glu Leu Tyr
305                 310                 315                 320

Arg Tyr Asn Gly Ser Glu Ile Arg Ile Met Gln Ile Gln Thr Ser Asp
                325                 330                 335

Asn Asp Thr Tyr Asn Val Thr Ser Tyr Pro Asn His Gln Gln Ala Leu
            340                 345                 350

Leu Leu Leu Thr Asn His Ser Tyr Glu Glu Val Glu Glu Ile Thr Asn
        355                 360                 365

Ile Pro Lys Ser Thr Leu Lys Lys Leu Lys Gln Tyr
    370                 375                 380

<210> SEQ ID NO 27
<211> LENGTH: 383
<212> TYPE: PRT
<213> ORGANISM: Bacillus thuringiensis

<400> SEQUENCE: 27

Met Leu Asp Thr Asn Lys Ile Tyr Glu Ile Ser Asn Tyr Ala Asn Gly
1               5                   10                  15

Leu His Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Arg Trp Phe
        35                  40                  45

Leu Phe Pro Ile Asp Asp Asn Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Ala Ser Ser Tyr Val Ile Gln Ser Asn Asn Gly Lys Val Leu Thr Ala
            100                 105                 110

Gly Thr Gly Gln Ser Leu Gly Leu Ile Arg Leu Thr Asp Glu Ser Pro
        115                 120                 125

Asp Asn Pro Asn Gln Gln Trp Asn Leu Thr Pro Val Gln Thr Ile Gln
    130                 135                 140

Leu Pro Pro Lys Pro Thr Ile Asp Thr Lys Leu Lys Asp Tyr Pro Lys
145                 150                 155                 160

Tyr Ser Gln Thr Gly Asn Ile Asp Lys Gly Thr Pro Pro Gln Leu Met
                165                 170                 175

Gly Trp Thr Leu Ile Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Gln Ala Val Gly Ser Asn Val Ala Leu Arg Pro His
    210                 215                 220

Glu Lys Lys Ser Tyr Ala Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Gly Thr Asp Glu Ile Lys
            260                 265                 270

Thr Gln Leu Asn Glu Glu Leu Lys Ile Glu Tyr Ser Arg Glu Thr Lys
```

```
                275                 280                 285
Ile Met Glu Lys Tyr Gln Glu Gln Ser Glu Ile Asp Asn Pro Thr Asp
    290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Ser Val Met Lys Ile Gln Thr Ser
                325                 330                 335

Asp Asn Asp Thr Tyr Asn Val Thr Ser Tyr Pro Asp His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ile Ser Leu Lys Lys Leu Lys Lys Tyr Tyr Phe
    370                 375                 380

<210> SEQ ID NO 28
<211> LENGTH: 385
<212> TYPE: PRT
<213> ORGANISM: Bacillus thuringiensis

<400> SEQUENCE: 28

Met Le

-continued

```
Thr Gln Leu Thr Glu Glu Leu Lys Val Glu Tyr Ser Thr Glu Thr Lys
            275                 280                 285

Ile Met Thr Lys Tyr Gln Glu His Ser Glu Ile Asp Asn Pro Thr Asn
        290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385

<210> SEQ ID NO 29
<211> LENGTH: 385
<212> TYPE: PRT
<213> ORGANISM: Bacillus thuringiensis

<400> SEQUENCE: 29

Met Leu Asp Thr Asn Lys Val Tyr Glu Ile Ser Asn Leu Ala Asn Gly
1               5                   10                  15

Leu Tyr Thr Ser Thr Tyr Leu Ser Leu Asp Asp Ser Gly Val Ser Leu
            20                  25                  30

Met Ser Lys Lys Asp Glu Asp Ile Asp Asp Tyr Asn Leu Lys Trp Phe
        35                  40                  45

Leu Phe Pro Ile Asp Asn Asn Gln Tyr Ile Ile Thr Ser Tyr Gly Ala
    50                  55                  60

Asn Asn Cys Lys Val Trp Asn Val Lys Asn Asp Lys Ile Asn Val Ser
65                  70                  75                  80

Thr Tyr Ser Ser Thr Asn Ser Val Gln Lys Trp Gln Ile Lys Ala Lys
                85                  90                  95

Asp Ser Ser Tyr Ile Ile Gln Ser Asp Asn Gly Lys Val Leu Thr Ala
            100                 105                 110

Gly Val Gly Glu Ser Leu Gly Ile Val Arg Leu Thr Asp Glu Phe Pro
        115                 120                 125

Glu Asn Ser Asn Gln Gln Trp Asn Leu Thr Pro Val Gln Thr Ile Gln
    130                 135                 140

Leu Pro Gln Lys Pro Lys Ile Asp Glu Lys Leu Lys Asp His Pro Glu
145                 150                 155                 160

Tyr Ser Glu Thr Gly Asn Ile Asn Pro Lys Thr Thr Pro Gln Leu Met
                165                 170                 175

Gly Trp Thr Leu Val Pro Cys Ile Met Val Asn Asp Ser Gly Ile Asp
            180                 185                 190

Lys Asn Thr Gln Ile Lys Thr Thr Pro Tyr Tyr Ile Phe Lys Lys Tyr
        195                 200                 205

Lys Tyr Trp Asn Leu Ala Lys Gly Ser Asn Val Ser Leu Leu Pro His
    210                 215                 220

Gln Lys Arg Ser Tyr Asp Tyr Glu Trp Gly Thr Glu Lys Asn Gln Lys
225                 230                 235                 240

Thr Ser Ile Ile Asn Thr Val Gly Leu Gln Ile Asn Ile Asp Ser Gly
                245                 250                 255
```

-continued

```
Met Lys Phe Glu Val Pro Glu Val Gly Gly Gly Thr Glu Asp Ile Lys
            260                 265                 270

Thr Gln Leu Thr Glu Glu Leu Lys Val Glu Tyr Ser Thr Glu Thr Lys
        275                 280                 285

Ile Met Thr Lys Tyr Gln Glu His Ser Glu Ile Asp Asn Pro Thr Asn
    290                 295                 300

Gln Pro Met Asn Ser Ile Gly Leu Leu Ile Tyr Thr Ser Leu Glu Leu
305                 310                 315                 320

Tyr Arg Tyr Asn Gly Thr Glu Ile Lys Ile Met Asp Ile Glu Thr Ser
                325                 330                 335

Asp His Asp Thr Tyr Thr Leu Thr Ser Tyr Pro Asn His Lys Glu Ala
            340                 345                 350

Leu Leu Leu Leu Thr Asn His Ser Tyr Glu Glu Val Glu Glu Ile Thr
        355                 360                 365

Lys Ile Pro Lys His Thr Leu Ile Lys Leu Lys Lys His Tyr Phe Lys
    370                 375                 380

Lys
385

<210> SEQ ID NO 30
<211> LENGTH: 387
<212> TYPE: PRT
<213> ORGANISM: Bacillus thuringiensis

<400> SEQUENCE: 30

Met Ile Glu Thr Asn Lys Ile Tyr Glu Ile Ser Asn Lys Ala Asn Gly
1               5                   10                  15

Leu Tyr Ala Thr Thr Tyr Leu Ser Phe Asp Asn Ser Gly Val Ser Leu
            20                  25                  30

Leu Asn Lys Asn Glu Ser Asp Ile Asn Asp Tyr Asn Leu Lys Trp Phe
        35                  40                  45

Leu Phe Pro Ile Asp Asn Asn Gln Tyr Ile Ile Thr Ser Tyr Gly Val
    50                  55                  60

Asn Lys Asn Lys Val Trp Thr Ala Asn Gly Asn Lys Ile Asn Val Thr
65                  70                  75                  80

Thr Tyr Ser Ala Glu Asn Ser Ala Gln Gln Trp Gln Ile Arg Asn Ser
                85                  90                  95

Ser Ser Gly Tyr Ile Ile Glu Asn Asn Asn Gly Lys Ile Leu Thr Ala
            100                 105                 110

Gly Thr Gly Gln Ser Leu Gly Leu Leu Tyr Leu Thr Asp Glu Ile Pro
        115                 120                 125

Glu Asp Ser Asn Gln Gln Trp Asn Leu Thr Ser Ile Gln Thr Ile Ser
    130                 135                 140

Leu Pro Ser Gln Pro Ile Ile Asp Thr Thr Leu Val Asp Tyr Pro Lys
145                 150                 155                 160

Tyr Ser Thr Thr Gly Ser Ile Asn Tyr Asn Gly Thr Ala Leu Gln Leu
                165                 170                 175

Met Gly Trp Thr Leu Ile Pro Cys Ile Met Val Tyr Asp Lys Thr Ile
            180                 185                 190

Ala Ser Thr His Thr Gln Ile Thr Thr Thr Pro Tyr Tyr Ile Leu Lys
        195                 200                 205

Lys Tyr Gln Arg Trp Val Leu Ala Thr Gly Ser Gly Leu Ser Val Pro
    210                 215                 220

Ala His Val Lys Ser Thr Phe Glu Tyr Glu Trp Gly Thr Asp Thr Asp
```

-continued

```
225                 230                 235                 240

Gln Lys Thr Ser Val Ile Asn Thr Leu Gly Phe Gln Ile Asn Thr Asp
                245                 250                 255

Thr Lys Leu Lys Ala Thr Val Pro Glu Val Gly Gly Gly Thr Thr Asp
            260                 265                 270

Ile Arg Thr Gln Ile Thr Glu Glu Leu Lys Val Glu Tyr Ser Ser Glu
        275                 280                 285

Asn Lys Glu Met Arg Lys Tyr Lys Gln Ser Phe Asp Val Asp Asn Leu
    290                 295                 300

Asn Tyr Asp Glu Ala Leu Asn Ala Val Gly Phe Ile Val Glu Thr Ser
305                 310                 315                 320

Phe Glu Leu Tyr Arg Met Asn Gly Asn Val Leu Ile Thr Ser Ile Lys
                325                 330                 335

Thr Thr Asn Lys Asp Thr Tyr Asn Thr Val Thr Tyr Pro Asn His Lys
            340                 345                 350

Glu Val Leu Leu Leu Leu Thr Asn His Ser Tyr Glu Glu Val Thr Ala
        355                 360                 365

Leu Thr Gly Ile Ser Lys Glu Arg Leu Gln Asn Leu Lys Asn Asn Trp
    370                 375                 380

Lys Lys Arg
385
```

MODIFIED *CRY*35 PROTEINS HAVING ALTERED PROTEASE STABILITY

CROSS-REFERENCE TO A RELATED APPLICATIONS

This application is a division of U.S. Ser. No. 10/956,448, now U.S. Pat. No. 7,309,785 filed Oct. 1, 2004, which claims the benefit of U.S. Provisional Application Ser. No. 60/508,637, filed Oct. 3, 2003, which is hereby incorporated by reference herein in its entirety, including any figures, tables, nucleic acid sequences, amino acid sequences or drawings.

The Sequence Listing for this application is being provided electronically, is labeled "DAS-107XD1-seq-list.txt", was created on Nov. 20, 2007, and is 98 KB. The entire content of the document is incorporated herein by reference in its entirety.

BACKGROUND OF THE INVENTION

Coleopterans are a significant group of agricultural pests that cause extensive damage to crops each year. Examples of coleopteran pests include corn rootworm and alfalfa weevils. Additional notable examples include Colorado potato beetle, boll weevil, and Japanese beetle.

Insecticidal crystal proteins from some strains of *Bacillus thuringiensis* (B.t.) are well-known in the art. See, e.g., Höfte et al., *Microbial Reviews, Vol.* 53, No. 2, pp. 242-255 (1989). These proteins are typically produced by the bacteria as approximately 130 kDa protoxins that are then cleaved by proteases in the insect midgut, after ingestion by the insect, to yield a roughly 60 kDa core toxin. These proteins are known as crystal proteins because distinct crystalline inclusions can be observed with spores in some strains of B.t, These crystalline inclusions are often composed of several distinct proteins.

A new insecticidal protein system was discovered in *Bacillus thuringiensis* as disclosed in WO 97/40162. This system comprises two proteins—one of approximately 15 kDa and the other of about 45 kDa. See also U.S. Pat. Nos. 6,083,499 and 6,127,180. These proteins have now been assigned to their own classes, and accordingly received the Cry designations of Cry34 and Cry35, respectively. (See Crickmore et al. website (biols.susx.ac.uk/home/Neil_Crickmore/Bt/). Many other related proteins of this type of system have now been disclosed. See e.g. U.S. Pat. No. 6,372,480; WO 01/14417; and WO 00/66742. Plant-optimized genes that encode such proteins, wherein the genes are engineered to use codons for optimized expression in plants, have also been disclosed. See e.g. U.S. Pat. No. 6,218,188.

Details of the three-dimensional structure of these proteins have not, heretofore, been disclosed. With information regarding the three-dimensional structures of these proteins, it would be possible to rationally design modifications to the natural, bacterial proteins to improve various desirable characteristics of these proteins. Such information can also aid efforts to engineer B.t. proteins in general by, for example, focusing or restricting improvement or directed evolution programs.

However, obtaining purified crystals of B.t. insect toxins has been a difficult process (although some examples do exist; see e.g. WO 98/23641 and WO 99/31248). While some examples do exist, it has been difficult to obtain sufficiently purified crystals of adequate quality. For example, there has been a tendency of these proteins to form aggregates that are not suitable for refinement of the structure to high resolution. In addition, B.t. tends to be an inferior protein producer for the level and quality of protein required for x-ray crystallography and biochemical purposes. This is due to factors such as its lower production levels, protease contamination, and the like, and to the fact that there is usually a mixture of proteins in the crystalline inclusions produced by native strains.

BRIEF SUMMARY OF THE INVENTION

This invention provides modified, insecticidal Cry35 proteins with enhanced properties as compared to wild-type Cry35 proteins. The modifications to these proteins as discussed below were made possible in part due to the surprising creation of highly purified crystals of the ~45 kDa 149B1 protein and subsequent analysis based in part on an analysis of the three-dimensional (3D) structure of this protein and other proteins in the Cry35 class. The subject invention also includes polynucleotides that encode these modified proteins, and transgenic plants that produce these modified proteins. This invention further provides methods of controlling plant pests, including rootworms, with these modified proteins.

The modified proteins of the subject invention include chimeric toxins involving exchanged segments, domains, and motifs as discussed herein.

The subject invention also provides methods of modifying Cry35 proteins. However, the modifications described herein can be applied to other (structurally similar) proteins and peptides as well.

BRIEF DESCRIPTION OF THE FIGURES

The instant patent or application file contains at least one drawing executed in color. Copies of this patent or patent application publication with color drawing(s) will be provided by the Office upon request and payment of the necessary fee.

BRIEF DESCRIPTION OF THE SEQUENCE

Figure 1:
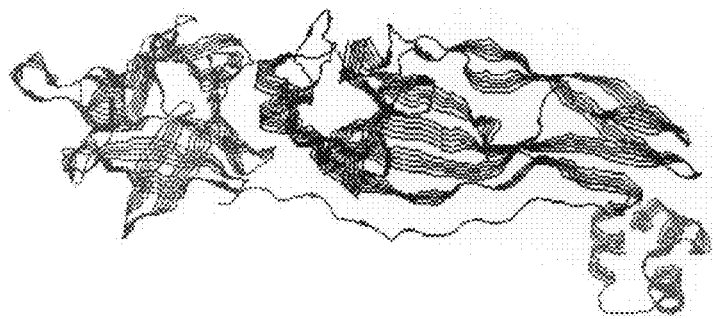
FIG. 1 shows a diagram depicting the three-dimensional structure of typical Cry35 proteins, with the three main domains being indicated (from left to right) by blue ("Domain 1"), black ("Domain 2"), and red ("Domain 3").

SEQ ID NO:1 is the amino acid sequence of the wild-type 149B1~45 kDa (Cry35Ab1) protein.

SEQ ID NO:2 is a Cry35-M protein with an L354F modification.

SEQ ID NO:3 is a Cry35-M protein with a K372F modification.

SEQ ID NO:4 is a Cry35-M protein with a K379F modification.

SEQ ID NO:5 is a Cry35-M protein with a K380F modification.

SEQ ID NO:6 is a Cry35-M protein with a modified ~370-372 loop having an insect-preferred protease cleavage site.

SEQ ID NO:7 is the Cry35-M protein of SEQ ID NO:6 further comprising a modified 376 residue that removes a plant-preferred protease cleavage site.

SEQ ID NO:8 is a Cry35-M protein with a K372S modification.

SEQ ID NO:9 is a Cry35-M protein with a K372N modification.

SEQ ID NO:10 is a Cry35-M protein with a K376S modification.

SEQ ID NO:11 is a Cry35-M protein with a K376N modification.

SEQ ID NO:12 is a Cry35-M protein with a K376Q modification.

SEQ ID NO:13 is a Cry35-M protein with a K377E modification.

SEQ ID NO:14 is a Cry35-M protein with a K377S modification.

SEQ ID NO:15 is a Cry35-M protein with a K377N modification.

SEQ ID NO:16 is a Cry35-M protein with a K377Q modification.

SEQ ID NO:17 is a Cry35-M protein with a K379H modification.

SEQ ID NO:18 is a Cry35-M protein with a K379S modification.

SEQ ID NO:19 is a Cry35-M protein with a K379N modification.

SEQ ID NO:20 is a Cry35-M protein with a K379Q modification.

SEQ ID NO:21 is a Cry35-M protein with a modified ~357-360 loop having an insect-preferred protease cleavage site.

SEQ ID NO:22 is a Cry35-M protein with a K380E modification.

SEQ ID NO:23 is a Cry35-M protein with a K380H modification.

SEQ ID NO:24 is a Cry35-M protein with a K380S modification.

SEQ ID NO:25 is a Cry35-M protein with a K380N modification.

SEQ ID NO:26 is a Cry35-M protein with a K380Q modification.

SEQ ID NO:27 is the amino acid sequence of the wild-type 167H2~45 kDa protein.

SEQ ID NO:28 is the amino acid sequence of the wild-type 80JJ1 ~45 kDa protein.

SEQ ID NO:29 is the amino acid sequence of the wild-type 69Q ~45 kDa protein.

SEQ ID NO:30 is the amino acid sequence of the wild-type 201 L3~45 kDa protein.

BRIEF DESCRIPTION OF THE APPENDICES

Appendix A provides the atomic coordinates for the 149B1 Cry35 protein (SEQ ID NO:1).

Appendix 1 is a spreadsheet that includes accessibility information regarding the amino acid residues of Cry35Ab1.

Appendix 2 is a sequence alignment of various Cry35 proteins (SEQ ID NOS: 1 and 27-30).

Appendix 3 is a sequence alignment of various Cry35 proteins (SEQ ID NOS: 1 and 27-30) showing similarities and differences in the chemical properties of each residue.

Appendix 4 is a spreadsheet highlighting preferred residues for substitution (SEQ ID NOS:1 and 30).

DETAILED DESCRIPTION

This invention provides modified, insecticidal Cry35 proteins with enhanced properties as compared to wild-type Cry35 proteins. The modifications to these proteins as discussed below were based in part on analysis of the three-dimensional (3D) structure of the ~45 kDa 149B1 protein and other proteins in the Cry35 class, together with other analytic approaches. The subject invention also includes polynucleotides that encode these modified proteins, and transgenic plants that produce these modified proteins, and seeds and other plant material (such as pollen and germplasm) produced by such plants. This invention further provides methods of controlling plant pests, including rootworms, by using these modified proteins.

As referred to herein, Cry35-M proteins are any proteins modified or produced synthetically (that differ from wild-type Cry35 proteins) according to the methods disclosed and/or suggested herein.

Synthetic proteins of the subject invention include Cry35-M proteins with increased stability in plants and/or increased activity against insects.

Some synthetic proteins of the subject invention have one or more amino acid substitutions that improve binding, protease resistance (in plants, for example) and/or susceptibility (in insect guts, for example), hydrophobicity/hydrophilicity, charge distribution, and like characteristics of the synthetic proteins as compared to wild-type Cry35 proteins.

Some synthetic proteins of the subject invention are the result of modifying one or more amino acid residues of a given wild-type Cry35 protein (a Cry35A protein, for example) to make the resulting synthetic sequence more or less like that of a different wild-type Cry35 protein (a Cry35B protein, for example). This approach was based in part on substituting residues based on sequence diversity in homologous protein toxins together with analyzing the corresponding crystal structure.

The modified proteins of the subject invention include chimeric toxins involving exchanged domains and motifs as discussed herein.

Further proteins of the subject invention are obtainable by focused sequence shuffling or site saturation mutagenesis, wherein said shuffling is directed, as described herein, to certain regions or segments of Cry35 proteins.

Still further, proteins of the subject invention include those that were obtained in part by using computational molecular evolution based in part on structural data. That is, while sequence alignments/comparisons of various Cry35 proteins can provide some clues as to differences between given proteins in this class, sequence alignments alone are not able to convey similar structural motifs that might be shared by various proteins, including Cry35-class proteins. The conservation of sequence in the alignments tends to highlight the less variant hydrophobic core of the proteins which is not as amendable to mutagenesis, and is not as relevant to protein improvement as the generally more variable surface residues.

Atomic coordinates for the 149B1 Cry35 protein are provided in Appendix A.

Basic Structure and Mechanism of Action of Cry35 Proteins

As illustrated by FIG. 1, the 149B1 Cry35 protein appears to comprise three main domains. As further discussed herein, all known Cry35 wild-type proteins appear to have the same basic structure, although there are some important differences in their amino acid residues at certain positions. The "first domain," shown in blue at the left side of the molecule in this illustration, appears to be a binding domain, which corresponds to approximately amino acid residues 1-147. The overall characteristics of this domain are consistent with a trefoil domain, a common protein fold for binding a number of different ligands. The N terminus is visible towards the bottom of this domain as illustrated. This domain is connected via a long polypeptide tether, also visible towards the bottom of the molecule as illustrated, to the beta barrel-like domain; this is the central domain and is shown in black. This central domain (domain 2) corresponds to approximately amino acid residues 148-348. The third domain is shown in red and corresponds approximately to amino acid residues 349-381 (the C terminus). This domain (residues 355 to the C terminus) is cleaved off by proteases in the insect gut; this domain is also referred to as an activation domain as discussed in more detail below.

The location of these domains is approximate and somewhat arbitrary in part. For example, the long strand or tether extending from residues ~140-160, which connects domains 1 and 2, could be considered to be part of either domain. It could be considered part of the β-barrel structure of domain 2, or it could be considered part of domain 1 that transitions and connects domain 1 to domain 2. It could also be an unstructured tether connecting the two domains. It should also be noted that the use of "~" before a range of numbers (e.g., ~1-9) signifies that this is an approximate range of residues (unless otherwise specified). Thus, ~1-9 means the same as ~1-9 unless otherwise indicated. Some examples of overlapping segment definitions can be found herein.

The Cry35 proteins have some structural features that are similar to other known proteins. For example, other proteins have the same general motif where an activation domain like that of the subject Domain 3 is proteolytically removed to allow assembly of multimers. Thus, without being limited by any single theory of mechanism of action, it appears that individual Cry35 monomers could assemble into multimers following removal of the activation Domain 3 of each Cry35 protein. The removal of the activation domain, Domain 3, would allow the Cry35 proteins to associate with each other and form multimers. The removal of Domain 3 could thus facilitate overall binding and assembly on/in the cellular target, as is observed with other proteins having this basic structure. This is also interesting because the Cry35 protein is known to act with the Cry34 (~15 kDa) protein. (The 3D structure of the Cry34 protein is discussed in more detail in U.S. Application Ser. No. 60/508,567 entitled, "Modified Cry34 Proteins.") The Cry34 protein binding to the multimeric form of assembled Cry35 proteins via a cross-subunit binding site would explain the inability of Cry34/35 to form associations in vitro in initial observations. (Thus, it appears unlikely that a membrane-bound Cry35 monomer associates with the membrane and then with the 15 kDa as a binding partner.) It would be consistent with other protein models if the Cry35 multimer associates with the cellular membrane, embedding using a beta-hairpin-based membrane interaction domain. Upon multimerization, this would form a beta barrel of the Cry35 subunits—usually seven. (The beta hairpin is from residues ~238-262, centered at 254 and 255, and is structurally similar to other proposed hairpins for other known proteins.) The multimer in that case facilitates entry of the 15 kDa protein, which may have a cellular target via binding, or may form pores on its own (i.e. beta barrel via a loop of residues ~28-~55).

It should be understood that while the specific residue numbers referred to herein relate primarily to the exemplified 149B1 protein, the subject disclosure shows that all Cry35 proteins have similar structures to those exemplified herein. Thus, as one skilled in the art would know, with the benefit of this disclosure, corresponding residues and segments are now identifiable in the other Cry35 proteins. Thus, the specific examples for the 149B1 protein can be applied to the other proteins in the Cry35 family. The exact numbering of the residues might not strictly correspond to the 149B13 protein, but the corresponding residues are readily identifiable in light of the subject disclosure. Appendix 2 is one illustration of this. The sequences of various Cry35 proteins and genes are described in various patent references and elsewhere. For example, the following protein sequences can be used according to the subject invention:

| Cry designation | Source isolate | GENBANK Acc. No. |
|---|---|---|
| 35Aa1 | PS80JJ1 | AAG50342 |
| 35Aa2 | EG5899 | AAK64561 |
| 35Ab1 | PS149B1 | AAG41672 |
| 35Ab2 | EG9444 | AAK64563 |
| 35Ac1 | PS167H2 | AAG50117 |
| 35Ba1 | EG4851 | AAK64566 |

35Aa1, 35Ab1, and 35Ac1 are also disclosed in WO 01/14417 as follows.

| Source isolate | SEQ ID NO: IN WO 01/14417 |
|---|---|
| PS80JJ1 | 11 |
| PS167H2 | 38 |
| PS149B1 | 43 |

There are many additional Cry35 sequences disclosed in WO 01/14417 that can be used according to the subject invention. For example:

| Source isolate | SEQ ID NO: IN WO 01/14417 |
|---|---|
| PS131W2 | 54 |
| PS158T3 | 58 |
| PS185FF | 64 |
| PS185GG | 68 |
| PS187F3 | 78 |
| PS187L14 | 86 |
| PS187Y2 | 90 |
| PS69Q | 116 |
| KR589 | 126 |
| PS201L3 | 136 |
| PS187G1 | 140 |
| PS201HH2 | 144 |
| KR1369 | 148 |

Several other source isolates are also disclosed in WO 01/14417. The PS designation of the source isolate can be dropped for ease of reference when referring to a protein obtainable from that isolate. Various polynucleotides that encode these proteins are also known in the art and are disclosed in various references cited herein.

For residues that are identified herein as being ideal for substitution, conservative changes can be made as defined below in Example 5. However, in some cases, nonconservative changes would be preferred. The efficacy of such changes can be initially analyzed using computer modeling such as Voigt, C. A., Mayo, S. L., Arnold, F. H., and Wang, Z. G., "Computationally focusing the directed evolution of proteins," *J Cell Biochem*. (2001), Suppl. 37:58-63; and Voigt, C. A., Mayo, S. L., Arnold, F. H., and Wang, Z. G., "Computational method to reduce the search space for directed protein evolution," *Proc. Natl. Acad. Sci. U.S.A.* (Mar. 27, 2001), 98(7):3778-83. Techniques for producing and confirming the activity of proteins modified accordingly are well-known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Modified Cry35 Proteins Having Increased Stability in Plants and Increased Activity in Insects; Introduction of Insect-Preferred, Plant-Disfavored Cleavage Site and Residue Substitutions in Domain 3

Some preferred embodiments of the subject invention include Cry35-M proteins having modifications that confer greater stability to the proteins in plants, as compared to wild-type Cry35 proteins and, preferably, that also facilitate better processing of the proteins in insects after the insects ingest the proteins. There are plant (protease) processing sites near the C-terminus of Cry35. Modifications can be made here that hinder processing in plants while facilitating processing in insects such as corn rootworms. WO 03/018810 (by Syngenta) discusses some possibilities for adding wCRW cathepsin G favored sites (AAPF, AAPM, AVPF, PFLF) to B.t. Cry3A proteins. Similar insect-preferred/plant-disfavored protease cleavage sites, and other insect-preferred/plant-disfavored protease cleavage sites, can be added to this region of the subject Cry35 proteins. In some cases the insect-preferred site maybe introduced in a manner that eliminates a plant-preferred site, but in other cases, the insect-preferred site is introduced without destroying a plant-preferred site, or a plant-preferred protease site is removed without creating an insect-preferred site.

The fully processed Cry35 polypeptide has leucine 354 as its C-terminus, and additional protease-sensitive sites may be present at one or more of several lysine residues: K372 (adjacent to a loop), K376/K377, and K379/K380 (dibasic sites). Thus, position 354 can be modified to phenylalanine (SEQ ID NO:2) to favor processing by the wCRW cathepsin G protease (Tanaka et al. Biochemistry 24:2040, 1985). Single residue changes to phenylalanine may also be made at residue 372 (SEQ ID NO:3), 379 (SEQ ID NO:4) or 380 (SEQ ID NO:5). More extensive changes to the K372 area may be made by modifying the adjacent loop to have "APF" at residues 370-372 to create a cathepsin G favored site (SEQ ID NO:6). This latter modified protein may be additionally modified to remove an additional lysine at 376 by replacement with asparagine (SEQ ID NO:7).

An additional example is introducing one of the cathepsin G sites in another loop of domain 3. The loop from residues 357 to 360 may be replaced by the sequence "APFA". See SEQ ID NO:21. The 345-352 area is also a possible site for accommodating a cathepsin G site.

Eliminating Lysines and modifying cleavage sites at non-basic residues in the 3$^{rd}$ domain is another approach to reducing processing in plants without necessarily improving processing in insects. The lysine residues noted above may additionally be modified as follows: K372 changed to serine (SEQ ID NO:8), or more preferably asparagines (SEQ ID NO:9); K376 changed to serine (SEQ ID NO:10), or more preferably asparagines (SEQ ID NO:11) or glutamine (SEQ ID NO:12); K377 changed to glutamate (SEQ ID NO:13), serine (SEQ ID NO:14), or more preferably asparagines (SEQ ID NO:15) or glutamine (SEQ ID NO:16); K379 changed to histidine (SEQ ID NO:17), serine (SEQ ID NO:18), or more preferably asparagine (SEQ ID NO:19) or glutamine (SEQ ID NO:20); and K380 changed to glutamate (SEQ ID NO:22), histidine (SEQ ID NO:23), serine (SEQ ID NO:24), or more preferably asparagines (SEQ ID NO:25) or glutamine (SEQ ID NO:26).

Residue 355 is at the beginning of the activation peptide portion of Domain 3, which appears to be protealytically cleaved off to allow Cry35 monomers to associate with each other to form an "active" multimeric complex. To the extent that Cry35 proteins have the capacity to form pores in plants, such Cry35-M proteins that prevent activation in plants are highly preferred. That is, these Cry35-M proteins are more stable in plants, and thus can accumulate to high concentrations without adversely affecting plants due to pore formation (and thereby increasing the amount of pesticidally active protein present in the insect-resistant plant). However, they are still properly processed in the insect that ingests the protein.

EXAMPLE 2

Construction of Chimeric Cry35-M Proteins and Chimeric Proteins Comprising Cry35 and Cry35-M Domains According to the subject invention, Domains 1, 2, and/or 3 can be swapped between Cry35 homologoues. That is, for example, some embodiments of the subject invention include chimeric Cry35-M proteins comprising a Domain 1 from one Cry35 homologue and a heterologous domain from another Cry35 homologue. Also, some embodiments of the subject invention include chimeric Cry35-M proteins comprising a Domain 3 from one Cry35 homologue and a heterologous domain from another Cry35 homologue.

More specifically, Domain 1 exchanges (preferably of residues ~1-143, but could be as far as ~152) can be made between homologues, according to the subject invention. In addition, domain exchanges of residues ~348 through the C-terminus can be made between homologues, according to the subject invention.

Chimerics exchanging segments from the R222-H224 loop through the P302-S306 loop can also be constructed according to the subject invention. The structural integrity of such Cry35-M proteins would be maintained due to the relatively fewer connections of this segment to the rest of Domain 2.

In order to illustrate the usefulness of the 3D crystal structure of the subject Cry35 proteins in guiding rationale design and improvements to wild-type Cry35 proteins, one should consider chimeric Cry35 proteins that were constructed without having the benefit of the 3D crystal structures to assist the analysis and design.

Two Cry35 chimeric proteins were constructed, consisting of fragments of Cry35Aa1 and Cry35Ab1. Cry35Aa1 (PS80JJ1) was selected based on sequence diversity and known bioactivity. Cry35 chimera 1 consists of residues 1-201 from Cry35Ab1 and residues 202-354 from Cry35Aa1. Cry35 chimera 2 consists of the same fragments, except residues 1-201 are from Cry35Aa1 and residues 202-354 are from Cry35Ab1. Both Cry35 chimerae are truncated after residue 354, with a stop codon introduced at the native C-terminal processing site.

Figure 2:
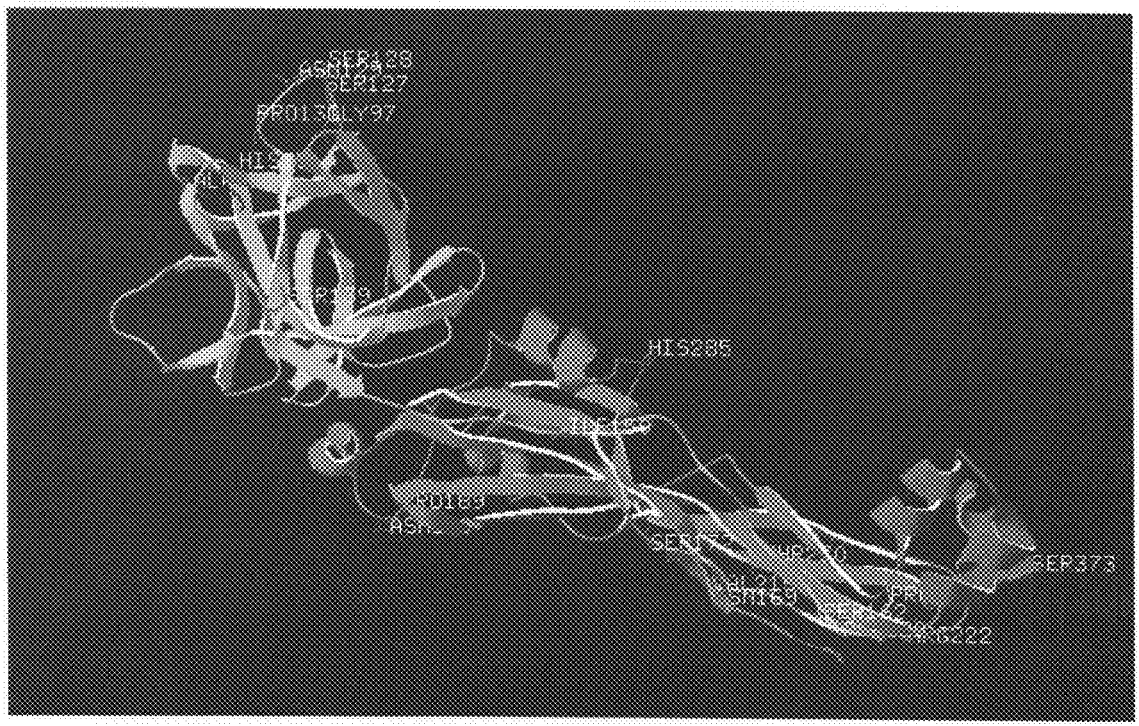
FIG. 2 shows a ribbon diagram showing the general shape, direction, and location of the various segments of the Cry35 proteins. Domain 1 (on the left) is shown in yellow, Domain 2 (in the middle) is shown in blue, and Domain 3 (on the right) is shown in green.

As shown in FIG. 2 and in Appendix 2, the conserved block of residues (202-210; colored purple in FIG. 2) were used to design reciprocal chimeric proteins before the 3D structure of these proteins was solved. As can now be seen with the benefit of the disclosed 3D crystal structure, these residues reside in a conserved beta strand and as such are not a good choice for generating hybrid proteins. Perturbations to the hairpin strands are likely to destabilize the protein.

Instead, one preferred approach to creating chimeric Cry35-M proteins is based on exchange of structural domains and motifs as described herein. For example, three domains are colored and illustrated in FIG. 2: Domain 1 (residues ~1-162; yellow), Domain 2 (residues ~165-346; blue) and Domain 3 (residues ~347-381; green).

Chimeric proteins with improved binding, activity, or other properties can be generated by creating hybrids that swap domains as identified herein. Molecular modeling, as disclosed herein, can be used to choose the best junction sequence to make these domain swaps. Another approach, according to the subject invention, is that a series of crossover points localized at the domain junctions can be made and designed to have increased resistance to degradation by plant proteases.

Yet another example of chimeric proteins of the subject invention are chimeric proteins comprising the binding Domain 1 attached to another, heterologous, non-Cry35 protein. One option is a non-Cry35 Bacillus thuringiensis insecticidal protein toxin (such as Cry1, Cry2, Cry3, Cry9, etc.). Other toxins and Bacillus toxins can also be used in this manner. For example, Bacillus sphaericus insecticidal protein toxins are good candidates (for domain swapping) because of their sequence and structural similarity. See also U.S. Pat. Nos. 5,290,914 and 6,051,556.

EXAMPLE 3

Preferred Site-Specific Modifications (Residue Substitutions) Based on Sequence Diversity in Homologous Protein Toxins Together with Analysis of Crystallographic Data and Similarities to Evolutionarily Related Proteins According to the subject invention, certain residues, areas, and/or segments of wild-type Cry35 proteins are preferred for site-specific changes.

One approach for such changes is to direct modifications to surface residues that are not in conserved areas. Cry35-M proteins resulting from such modifications maintain the structural integrity of the wild-type protein from which they are derived, but the Cry35-M proteins can be constructed to have improved properties (as compared to a wild-type). Thus, while avoiding the conserved areas, residues for substitution (to modify action and other properties) should be residues that are near concentrations of conserved residues. This is illustrated more concretely with reference to Appendix 1. These residues are identified in bold with asterisks in the accessibility column in the table of Appendix 1. More specifically, a Cry35-M protein of the subject invention includes a Cry35 protein comprising one or more amino acid substitutions at one or more of the following surface-exposed, non-conserved residue positions: 2, 13, 25, 27, 34, 36, 41, 46, 73, 76, 81, 85, 95, 98, 114, 116, 118, 125, 126, 128, 129, 144, 147, 148, 150, 153, 154, 156, 166, 168, 169, 172, 173, 189, 190, 192, 212, 213, 215, 218, 222, 228, 236, 238, 261, 285, 287, 294, 296, 298, 304, 306, 327, 329, 350, 351, 366, 367, 369, 373, 377, 380, and 381. The method of Voigt et aL could also be used to identify outward facing residues and appropriate replacements. See, e.g., Voigt, C. A., Mayo, S. L., Arnold, F. H., and Wang, Z. G., "Computationally focusing the directed evolution of proteins," *J Cell Biochem*. (2001). Suppl. 37:58-63; and Voigt, C. A., Mayo, S. L., Arnold, F. H., and Wang, Z. G., "Computational method to reduce the search space for directed protein evolution," *Proc. Natl. Acad. Sci. U.S.A.* (Mar. 27, 2001), 98(7):3778-83.

EXAMPLE 4

Substructural Approach

Another approach for identifying good residues for modification is by identifying suitable residues in ideal structural features of Cry35 proteins, as presently disclosed. For example, Cry35-M proteins obtained by modifying one or more wild-type residues 81-85 and/or 245-248 (the latter of which is at a domain boundary and also just C-terminal to a beta-hairpin) are particularly preferred. Residues 239-262, centered on 254/255, are part of a beta hairpin.

Residues in and near the unstructured area 261-271 are suitable for modification according to the subject invention. In contrast, residues 184-187 are conserved; thus, modification here may not be appropriate.

According to the subject invention, modeling can also be used to generate a more appropriate amphipathic structure that would be stable.

Thus, according to the above guidance, one can align and compare the sequences of all known Cry35 homologues. One alignment of some Cry35 alleles is shown in Appendix 2. A further level of analysis is to compare the chemical properties of the residues in such an alignment. One such alignment is provided in Appendix 3. This type of further, combined analysis is discussed in more detail below in other Examples.

EXAMPLE 5

Analyzing Multiple Sequence Alignments

Another method of the subject invention is to, for example, introduce any one or more or all possible changes observed (from such alignments) in one Cry35 protein as compared to other Cry35 proteins, if these changes are in regions of the protein that would tolerate change, based on an analysis of the 3D structure of the proteins as disclosed herein. One aspect of the subject invention includes making the Cry35Ab1 protein more like one or more of the other Cry35 proteins at one or more of the herein-identified loci. Conversely, the subject invention includes making, for example, the 201L3 protein (Cry35B) more like another Cry35 protein, such as the 149B1 Cry35 protein, if these changes are in regions of the protein that would tolerate change, based on an analysis of the 3D structure of the proteins as disclosed herein. The 201L3 binary toxins are the most divergent, by sequence, and are also less active than the 149B1 binary toxins; however, the 201L3 14 kDa protein, for example, is more susceptible to processing by some proteases than is the 149B1 protein.

Unlike Cry3, for example, there are multiple alleles of Cry35. Thus, one has more guidance in the subject context in assessing which changes can be tolerated, based on aligning these alleles and analyzing evolutionarily changed residues in light of the 3D structure.

As can be seen from Appendix 4, and as discussed in more detail below, one striking observation is that most, if not all, of the residue substitutions where Cry35Ab1 is the outlier (flagged yellow in the spreadsheet of Appendix 4 and identified on the structure of FIG. 2) are on surface-facing loops and strands. Of particular note are the substitutions to residues on surface loops in Domain 1. These residues are particularly interesting targets for mutagenesis because they appear to be involved in receptor binding analogous to domain 2 loops in the Cry1 class of B.t. toxins.

In addition to naturally occurring substitutions, the subject invention includes the use of molecular computer modeling of other residue substitutions at the nonconserved positions. For example, one can engineer changes to introduce amino acid residues with other chemically different side groups, such as opposite polarity, opposite charge, or bulky versus small, to probe the toxin for improvements.

As described below in other Examples, multiple sequence alignments for the Cry35 protein sequences were aligned using ClustalW default parameters at the ClustalW WWW Service at the European Bioinformatics Institute website (ebi.ac.uk/clustalw). Various sequence analysis software is available for displaying various alignments, including the free GENEDOC package available at (psc.edu/biomed/genedoc/).

Cry35 multiple sequence alignments were analyzed using two GENEDOC functions:

1) Conservation mode produces a display that emphasizes the degree of conservation in each column in the alignment. Positions with 60, 80 or 100% identity are shaded in different grayscale tones. Residue similarity scoring was enabled, such that residue similarity groups (Blossum 62) are given arbitrary numbers on the consensus line. The results of this analysis are attached as Appendix 2.

2) Chemical properties highlights sequence residues that share a defined set of properties. In this analysis default shading was used to highlight the following groups by color:

| negatively charged | positively charged | Amide | alcohol | aliphatic | aromatic | small | sulfur | other |
|---|---|---|---|---|---|---|---|---|
| D, E | H, K, R | N, Q | S, T | L, I, V | F, Y, W | A, G | M, C | P |

The results of this analysis are attached as Appendix 3.

Residue substitutions were identified by scanning the length of the sequence alignment; the substitutions are cataloged in Appendix 4. This table lists all observed residue substitutions among the five Cry35 homologues. Residue changes where Cry35Ab1 (149B1) is the outlier are highlighted yellow; these residues are also highlighted in Appendix 4. Residue substitutions found only in the 201L3 protein, the most distantly related member of the class, are also indicated in the spreadsheet.

With all of that said, one can align the sequences of various Cry35 proteins and look for "outlying" amino acids (residues that are different, i.e. of a different chemical class, as compared to others at a corresponding position).

Again, the 149B1 and 201L3 Cry35 proteins are good reference points, in part because the 149B1 Cry34l Cry35 combination is one of the most active binary toxin combinations (wild-type) known to date. On the other hand, the 201L3 Cry34/Cry35 combination is one of the least active binary toxin combinations (wild-type) known to date.

The benefit of having the atomic coordinates for, and the 3D structure of, the 149B1 protein is important for further understanding the significance of these outlying residues. For example, based on simple sequence alignments without the benefit of the atomic coordinates, chimerics were constructed, as discussed above in Example 2, where a conserved region was selected as the transition segment. However, it is now clear that this transition region was involved with folding and binding of the protein strands, as discussed above. Thus, these chimerics (designed without the 3D model) were, in hindsight, poor designs (which would not have been active). This illustrates that sequence alignments, alone, can be misleading when one is trying to construct modified proteins.

Using the atomic coordinates and guidance provided herein, one can conduct molecular modeling with other residue substitutions at the nonconserved positions to probe the toxin for improvements. One can engineer changes to introduce amino acid residues with other chemically different side groups, such as opposite polarity, opposite charge, or bulky versus small.

EXAMPLE 6

Residue Substitutions in Domain 1

Based in part on the combined analysis, as discussed above, preferred residues to modify, and general structural features of the Cry35 proteins, are as follows. As evolutionary changes are apparent at the amino acid positions discussed below, and these changes all happen to be on exposed areas of the protein (as opposed to integral regions that are apparently involved in folding and the like) these changes would not be expected to adversely affect the activity and overall structural integrity of the resulting Cry35-M protein. That is, the changes discussed below can be used to improve the function of the modified proteins, but they would not detrimentally affect the structure of the protein.

Domain 1, beginning with residue 1, is consistent with being a knot-like binding domain.

Residue 13 (Histidine in 149B1) is on an exposed loop in this domain, as can be seen on FIG. 2. As compared to the other proteins at this residue, this represents a nonconservative change; hydrophobic groups predominate in other homologues (although 201L3 and 149B1 are similar at this residue). Thus, a preferred Cry35-M protein of the subject invention comprises a Cry35 protein comprising at least one amino acid substitution, said substitution being made at this residue.

The other residues through and including residue 96 are relatively conserved in the Cry35 family.

Residue 97 of 149B1 represents a nonconserved change/a different amino acid sidechain (Asp to Glu). This residue occurs at a gap right at the end of a loop. See FIG. 2. Again, this occurs at an exposed/outer-facing region of the binding domain 1. Thus, a preferred Cry35-M protein of the subject invention comprises a Cry35 protein comprising an amino acid substitution at this position/residue.

Another point of divergence occurs at residue 117. This evolutionary change (Arg to Leu) occurs at or near the end of a loop (on the loop, just before the turn of this loop; not at the apex of a loop, as seen with residue 97). Thus, a preferred Cry35-M protein of the subject invention comprises a Cry35 protein comprising an amino acid substitution at this position/residue.

The segment running from residue 127 to 131 is interesting. This is a very exposed loop, on the top of the molecule as illustrated in FIG. 2. Residue 127 in 149B1 is a serine residue. In other homologues, there is a nonconservative change to a nonpolar aromatic. Another nonconservative change occurs at residue 128. Residue 129 is changed to a polar-charged residue. The residues at position 130 are similar to each other. Another nonconservative change occurs at residue 131. Thus, preferred Cry35-M proteins of the subject invention comprises a Cry35 protein comprising one or more amino acid substitutions at any residue in the loop from approximately residue 127 to approximately 131 (i.e., a modification at residue 127, 128, 129, 130, and/or 131). Further preferred embodiments of such Cry35-M proteins comprise a substitution at residue position 127, 128, 129, and/or 139.

A strand extends down from this loop, followed by the long tether that marks the transition from domain 1 to domain 2. Another nonconservative change occurs at residue 139, just before the tether. This residue is on an exposed side of this chain extending down from the 127-131 loop and, again, preceding the tether. Thus, a preferred Cry35-M protein of the subject invention comprises a Cry35 protein comprising an amino acid substitution at residue position 139.

Nonconservative changes are observed at residue 150 (from an aliphatic residue in 149B1 to a polar uncharged residue in 167H2, another highly active [first tier] binary toxin combination; and to a polar-charged residue in 80JJ1 and 69Q, which in their native binary forms could be considered to have "second tier" activity [the native 201L3 binary combination has "third tier" activity]). Thus, a preferred Cry35-M protein of the subject invention comprises a Cry35 protein comprising an amino acid substitution at residue position 150. As the above illustrates that some changes can be made to the "tether" region of Cry35 molecules, Cry35 proteins of the subject invention include a modified Cry35 protein, wherein at least one modification occurs in the tether region from approximately residue 140 to approximately 159.

To test whether the tether needs to be intact, a protease cleavage site, for example, could be inserted in this region. It is possible that the non-covalent associations between Domains 1 and 2 are adequate after the protein is folded. Also, the run from 162 through 168 has a higher B-factor, meaning they are more mobile.

It should be noted, however, that this tether region appears to be involved with Cry35 proteins associating with each other to form multimers. Furthermore, this tether could interact with the anti-parallel β sheets of Domain 2 (illustrated in blue in FIG. 2). Thus, radical changes in this region, aside from residue 150, might not be very tolerated, though changes here could be designed to improve the ability of the monomers to associate with each other.

EXAMPLE 7

Residue Substitutions in Domains 2 and 3

As mentioned above, Domain 2 begins at about residue 160. At residue 160, prolines are conserved in the various homologues. Prolines are known in the art to introduce turns in protein structures. A nonconservative change (in 149B1 compared to others) occurs at residue 163. This is in a loop observable at the end of the protein. Thus, a preferred Cry35-M protein of the subject invention comprises a Cry35 protein comprising an amino acid substitution at residue position 163. As the above illustrates that some changes can be made to the loop region immediately following the "tether" region of Cry35 molecules, the subject invention includes Cry35-M proteins comprising a modified Cry35 protein, wherein at least one modification occurs in the loop region, following the tether segment, from approximately residue 160 to approximately 168. While this is loosely called a "loop" here, this is an unstructured segment that generally traces a reverse turn and includes residues 163 and 164 that do not show up in the crystals (probably because their position varies too much from molecule to molecule in the crystal).

After the "loop" discussed immediately above, the first strand of the Domain 2 (blue) region travels back into, but on the surface of molecule. Residue 169 is suited for modification/substitution. A nonconservative change is apparent here, comparing 149B1 (N) with 80JJ1 (P), 69Q (P), and 201L3 (Tyr); the other homologue, 167H2, has a K substitution here. The latter is deemed to be a conservative change here, based on similar hydropathy scores. Similarly, residue 172 is suited for modification/substitution. A nonconservative change is apparent here, comparing 149B1 with 167H2. Residues 169 and 172 exist at exposed surfaces of this strand. Thus, a preferred Cry35-M protein of the subject invention comprises a Cry35 protein comprising an amino acid substitution at residue positions 169 and/or 172. As the above illustrates that some changes can be made to the beginning of the first stand in domain 2, the subject invention includes Cry35-M proteins comprising a modified Cry35 protein, wherein at least one modification occurs in the first strand of domain 2 before residue 173. (As discussed above, the segment used to construct chimerics before an examination of the 3D structure resulted in inactive proteins; thus, the latter half of this first segment, which is internal, is not preferred for modification).

Immediately after the segment(s) discussed in the preceding paragraph, a coil is evident followed by another loop that includes residues 189 and 190. These residues are suited for modification, as they occur on an exposed loop, and modifications are tolerated in homologues. The observable changes at these residues are discussed in Appendix 4. Thus, a preferred Cry35-M protein of the subject invention comprises a Cry35 protein comprising an amino acid substitution at residue positions 189 and/or 190. As the above illustrates that some changes can be made to the loop following the coil that follows the first strand of Domain 2, the subject invention thus includes Cry35-M proteins comprising a modified Cry35 protein, wherein at least one modification occurs in the loop following the coil that follows the first strand of Domain 2.

The segment from approximately 202-210 extends internally after the loop discussed above and extends to the backside of the molecule as illustrated in FIG. 2. After this strand again becomes exposed on the surface of the protein, residue 215 is ideal for modification. This residue occurs on the exposed surface of a β strand (on the backside of the molecule as illustrated in FIG. 2). This residue is a valine in 149B1, but a polar-uncharged and a polar-charged evolutionary changes are tolerated at this position in homologues. Thus, a preferred Cry35-M protein of the subject invention comprises a Cry35 protein comprising an amino acid substitution at residue position 215, more preferably a polar-uncharged or a polar-charged change (as defined herein). As the above illustrates that some changes can be made to the exposed segment following the loop that follows the coil that follows the first strand of domain 2, the subject invention thus includes Cry35-M proteins comprising a modified Cry35 protein, wherein at least one modification occurs in the exposed segment following the loop that follows the coil that follows the first strand of Domain 2.

The above strand leads into an exposed loop. The end of this strand, just prior to the end loop, is ideal for modification. Residues 220 and 222, in particular, are ideal for modification. Changes at these two positions are tolerated in homologues of 149B1. As can be seen on FIG. 2, the relatively conserved loop occurs at the end of the strand, just after residues 220 and 222. The end of this strand is exposed, as it leads to the exposed loop at an end portion of Domain 2 (near Domain 3). Thus, a preferred Cry35-M protein of the subject invention comprises a Cry35 protein comprising an amino acid substitution at residue position 220 and/or 222. As the above illustrates that some changes can be made to the end of the segment (ending with approximately residue 222) prior to the loop, the subject invention thus includes Cry35-M proteins comprising a modified Cry35 protein, wherein at least one modification occurs at an exposed region of the segment ending with approximately residue 222, just prior to the end loop that follows this segment.

After the loop mentioned in the preceding paragraph, another strand extends after that turn and heads back toward the center of this molecule. There is another exposed surface of this β strand. More specifically, a nonconservative change is tolerated at position 230. Thus, a preferred Cry35-M protein of the subject invention comprises a Cry35 protein comprising an amino acid substitution at residue position 230. As the above illustrates that some changes can be made to the exposed surface of the strand that includes residue 230, the subject invention thus includes Cry35-M proteins comprising a modified Cry35 protein, wherein at least one modification occurs at an exposed surface of the strand that includes residue 230.

Residue 285 occurs in an exposed coil and is another residue that is ideal for modification. The histidine residue in 149B1 is changed to a polar-uncharged residue in two other homologues. Thus, a preferred Cry35-M protein of the subject invention comprises a Cry35 protein comprising an amino acid substitution at residue position 285. The above illustrates that some changes can be made to the coil that includes residue 285, so long as the modification(s) do not affect the coil-shape (3D structure) of this region. Thus, the subject invention includes Cry35-M proteins comprising a modified Cry35 protein, wherein at least one modification occurs in the coil that includes residue 285, so long as such modifications are at an exposed surface of the strand that includes residue 230. This coil, residue 285 in particular, wraps around a small loop in the back (in FIG. 2) of the molecule, and is on an exposed area at the start of another β strand.

Two strands follow this coil, in an anti-parallel configuration. These strands are conserved and appear to be important for the structural integrity of the protein, including any conformational changes that the protein might make. Changes in this region are not preferred.

Modifications in the ~345-372 area are discussed above in Example 1.

Residue 373 is another ideal target for accelerated evolution. A nonconservative (from serine in 149B1 to a non-polar isoleucine) is tolerated in a homologue of 149B1. This is part of a coil of Domain 3. This Domain 3 is cleaved off, and thus does not appear to be a functional part of the protein. However, some modifications in this region might be desirable for some applications. Thus, the subject invention includes Cry35-M proteins comprising a modified Cry35 protein, wherein at least one modification occurs in the coil that includes residue 373. The subject invention also includes a preferred Cry35-M protein comprising a Cry35 protein comprising an amino acid substitution at residue position 373.

EXAMPLE 8

Focused Sequence Shuffling or Site Saturation Mutagenesis

The subject disclosure of the 3D structure of Cry 35 proteins will now make site- or region-directed "gene shuffling" much easier and more efficient. U.S. Pat. No. 5,605,793, for example, describes methods for generating additional molecular diversity by using DNA reassembly after random fragmentation. For example, examination of the Cry35 multiple sequence alignment reveals that approximately two thirds of the residues are evolutionarily conserved (i.e., identical or similar). Those conserved residues in critical regions of the molecule as discussed above should be avoided in molecular evolution approaches using shuffling or site saturation mutagenesis. This type of "shuffling" and molecular evolution can now be focused on segments, and nonconserved residues for example, in ideal regions as discussed above.

APPENDIX A

| | | | |
|---|---|---|---|
| REMARK 3 | REFINEMENT. | | |
| REMARK 3 | PROGRAM: REFMAC 5.0 | | |
| REMARK 3 | AUTHORS: MURSHUDOV, VAGIN, DODSON | | |
| REMARK 3 | | | |
| REMARK 3 | REFINEMENT TARGET: MAXIMUM LIKELIHOOD | | |
| REMARK 3 | | | |
| REMARK 3 | DATA USED IN REFINEMENT. | | |
| REMARK 3 | RESOLUTION RANGE HIGH (ANGSTROMS): | | 1.80 |
| REMARK 3 | RESOLUTION RANGE LOW (ANGSTROMS): | | 15.00 |
| REMARK 3 | DATA CUTOFF | (SIGMA(F)): | NONE |
| REMARK 3 | COMPLETENESS FOR RANGE | (%): | 99.11 |
| REMARK 3 | NUMBER OF REFLECTIONS: | | 31479 |
| REMARK 3 | | | |
| REMARK 3 | FIT TO DATA USED IN REFINEMENT. | | |
| REMARK 3 | CROSS-VALIDATION METHOD: | | THROUGHOUT |
| REMARK 3 | FREE R VALUE TEST SET SELECTION: | | RANDOM |
| REMARK 3 | R VALUE (WORKING + TEST SET): | | 0.18685 |
| REMARK 3 | R VALUE (WORKING SET): | | 0.18147 |
| REMARK 3 | FREE R VALUE: | | 0.23403 |
| REMARK 3 | FREE R VALUE TEST SET SIZE (%): | | 10.0 |
| REMARK 3 | FREE R VALUE TEST SET COUNT: | | 3504 |
| REMARK 3 | | | |
| REMARK 3 | FIT IN THE HIGHEST RESOLUTION BIN. | | |
| REMARK 3 | TOTAL NUMBER OF BINS USED: | | 20 |
| REMARK 3 | BIN RESOLUTION RANGE HIGH: | | 1.800 |

APPENDIX A-continued

```
REMARK  3    BIN RESOLUTION RANGE LOW:                          1.846
REMARK  3    REFLECTION IN BIN      (WORKING SET):    2146
REMARK  3    BIN R VALUE            (WORKING SET):       0.326
REMARK  3    BIN FREE R VALUE SET COUNT:                234
REMARK  3    BIN FREE R VALUE:                            0.431
REMARK  3
REMARK  3    NUMBER OF NON-HYDROGEN ATOMS USED IN REFINEMENT.
REMARK  3      ALL ATOMS: 3348
REMARK  3
REMARK  3    B VALUES.
REMARK  3      FROM WILSON PLOT          (A**2): NULL
REMARK  3      MEAN B VALUE      (OVERALL, A**2):  25.839
REMARK  3      OVERALL ANISOTROPIC B VALUE.
REMARK  3        B11 (A**2):   −0.95
REMARK  3        B22 (A**2):    1.42
REMARK  3        B33 (A**2):   −0.48
REMARK  3        B12 (A**2):    0.00
REMARK  3        B13 (A**2):    0.00
REMARK  3        B23 (A**2):    0.00
REMARK  3
REMARK  3    ESTIMATED OVERALL COORDINATE ERROR.
REMARK  3      ESU BASED ON R VALUE                     (A):   0.535
REMARK  3      ESU BASED ON FREE R VALUE                (A):   0.143
REMARK  3      ESU BASED ON MAXIMUM LIKELIHOOD          (A):   0.096
REMARK  3      ESU FOR B VALUES BASED ON MAXIMUM LIKELIHOOD (A**2):   7.422
REMARK  3
REMARK  3   CORRELATION COEFFICIENTS.
REMARK  3      CORRELATION COEFFICIENT FO-FC       : 0.956
REMARK  3      CORRELATION COEFFICIENT FO-FC FREE: 0.937
REMARK  3
REMARK  3    RMS DEVIATIONS FROM IDEAL VALUES        COUNT     RMS    WEIGHT
REMARK  3      BOND LENGTHS REFINED ATOMS      (A):  3113 ;   0.014 ;   0.021
REMARK  3      BOND ANGLES REFINED ATOMS  (DEGREES):  4235 ;   1.526 ;   1.939
REMARK  3      TORSION ANGLES, PERIOD 1   (DEGREES):   376 ;   4.851 ;   3.000
REMARK  3      TORSION ANGLES, PERIOD 3   (DEGREES):   579 ;  15.324 ;  15.000
REMARK  3      CHIRAL-CENTER RESTRAINTS      (A**3):   480 ;   0.113 ;   0.200
REMARK  3      GENERAL PLANES REFINED ATOMS    (A):  2346 ;   0.006 ;   0.020
REMARK  3      NON-BONDED CONTACTS REFINED ATOMS (A): 1305 ;   0.225 ;   0.300
REMARK  3      H-BOND (X . . . Y) REFINED ATOMS  (A):   395 ;   0.166 ;   0.500
REMARK  3      SYMMETRY VDW REFINED ATOMS       (A):    55 ;   0.206 ;    .300
REMARK  3      SYMMETRY H-BOND REFINED ATOMS    (A):    26 ;   0.383 ;   0.500
REMARK  3
REMARK  3    ISOTROPIC THERMAL FACTOR RESTRAINTS.    COUNT     RMS    WEIGHT
REMARK  3      MAIN-CHAIN BOND REFINED ATOMS  (A**2): 1889 ;   1.531 ;   1.500
REMARK  3      MAIN-CHAIN ANGLE REFINED ATOMS (A**2): 3094 ;   2.462 ;   2.000
REMARK  3      SIDE-CHAIN BOND REFINED ATOMS  (A**2): 1224 ;   3.873 ;   3.000
REMARK  3      SIDE-CHAIN ANGLE REFINED ATOMS (A**2): 1141 ;   5.811 ;   4.500
REMARK  3
REMARK  3    NCS RESTRAINTS STATISTICS
REMARK  3      NUMBER OF NCS GROUPS: NULL
REMARK  3
REMARK  3
REMARK  3    TLS DETAILS
REMARK  3      NUMBER OF TLS GROUPS: NULL
REMARK  3
REMARK  3
REMARK  3    BULK SOLVENT MODELLING.
REMARK  3      METHOD USED: BABINET MODEL WITH MASK
REMARK  3      PARAMETERS FOR MASK CALCULATION
REMARK  3      VDW PROBE RADIUS:    1.40
REMARK  3      ION PROBE RADIUS:    0.80
REMARK  3      SHRINKAGE RADIUS:    0.80
REMARK  3
REMARK  3    OTHER REFINEMENT REMARKS: NULL
REMARK  3
LINK           SER A 162                        GLY A 165              gap
CISPEP  1 TYR A  346      PRO A  347                    0.00
CRYST1   48.664   65.128  117.431  90.00  90.00  90.00 P 21 21 21
SCALE1    0.020549  0.000000  0.000000        0.00000
SCALE2    0.000000  0.015354  0.000000        0.00000
SCALE3    0.000000  0.000000  0.008516        0.00000
ATOM      1   N   LEU    2      11.829  20.249  45.366  1.00  28.13    7
ATOM      2   CA  LEU    2      12.119  19.810  46.758  1.00  26.51    6
ATOM      3   CB  LEU    2      11.192  18.647  47.084  1.00  27.31    6
ATOM      4   CG  LEU    2       9.746  18.949  47.384  1.00  31.50    6
ATOM      5   CD1 LEU    2       8.989  17.756  46.919  1.00  31.98    6
ATOM      6   CD2 LEU    2       9.557  19.176  48.858  1.00  36.39    6
ATOM      7   C   LEU    2      13.553  19.292  46.887  1.00  24.51    6
ATOM      8   O   LEU    2      14.144  18.893  45.891  1.00  25.01    8
```

APPENDIX A-continued

| | | | | | | | | | |
|---|---|---|---|---|---|---|---|---|---|
| ATOM | 9 | N | ASP | 3 | 14.106 | 19.264 | 48.096 | 1.00 | 21.57 | 7 |
| ATOM | 10 | CA | ASP | 3 | 15.395 | 18.605 | 48.286 | 1.00 | 19.72 | 6 |
| ATOM | 11 | CB | ASP | 3 | 15.932 | 18.790 | 49.708 | 1.00 | 20.29 | 6 |
| ATOM | 12 | CG | ASP | 3 | 16.218 | 20.236 | 50.052 | 1.00 | 23.74 | 6 |
| ATOM | 13 | OD1 | ASP | 3 | 16.659 | 20.997 | 49.167 | 1.00 | 25.72 | 8 |
| ATOM | 14 | OD2 | ASP | 3 | 16.017 | 20.694 | 51.192 | 1.00 | 26.08 | 8 |
| ATOM | 15 | C | ASP | 3 | 15.221 | 17.114 | 48.064 | 1.00 | 18.60 | 6 |
| ATOM | 16 | O | ASP | 3 | 14.246 | 16.518 | 48.549 | 1.00 | 18.18 | 8 |
| ATOM | 17 | N | THR | 4 | 16.168 | 16.485 | 47.377 | 1.00 | 15.87 | 7 |
| ATOM | 18 | CA | THR | 4 | 16.075 | 15.059 | 47.143 | 1.00 | 15.28 | 6 |
| ATOM | 19 | CB | THR | 4 | 15.994 | 14.757 | 45.635 | 1.00 | 16.03 | 6 |
| ATOM | 20 | OG1 | THR | 4 | 17.028 | 15.477 | 44.937 | 1.00 | 15.30 | 8 |
| ATOM | 21 | CG2 | THR | 4 | 14.671 | 15.326 | 45.061 | 1.00 | 14.28 | 6 |
| ATOM | 22 | C | THR | 4 | 17.205 | 14.263 | 47.807 | 1.00 | 14.66 | 6 |
| ATOM | 23 | O | THR | 4 | 17.570 | 13.171 | 47.330 | 1.00 | 15.56 | 8 |
| ATOM | 24 | N | ASN | 5 | 17.773 | 14.804 | 48.872 | 1.00 | 14.43 | 7 |
| ATOM | 25 | CA | ASN | 5 | 18.747 | 14.058 | 49.651 | 1.00 | 14.85 | 6 |
| ATOM | 26 | CB | ASN | 5 | 20.103 | 14.777 | 49.659 | 1.00 | 15.93 | 6 |
| ATOM | 27 | CG | ASN | 5 | 20.039 | 16.122 | 50.351 | 1.00 | 18.26 | 6 |
| ATOM | 28 | OD1 | ASN | 5 | 18.997 | 16.800 | 50.365 | 1.00 | 17.55 | 8 |
| ATOM | 29 | ND2 | ASN | 5 | 21.163 | 16.523 | 50.926 | 1.00 | 18.82 | 7 |
| ATOM | 30 | C | ASN | 5 | 18.230 | 13.875 | 51.060 | 1.00 | 15.21 | 6 |
| ATOM | 31 | O | ASN | 5 | 18.978 | 13.842 | 52.019 | 1.00 | 14.17 | 8 |
| ATOM | 32 | N | LYS | 6 | 16.920 | 13.723 | 51.172 | 1.00 | 14.62 | 7 |
| ATOM | 33 | CA | LYS | 6 | 16.287 | 13.555 | 52.478 | 1.00 | 14.36 | 6 |
| ATOM | 34 | CB | LYS | 6 | 15.427 | 14.797 | 52.782 | 1.00 | 13.92 | 6 |
| ATOM | 35 | CG | LYS | 6 | 16.268 | 16.023 | 53.104 | 1.00 | 13.88 | 6 |
| ATOM | 36 | CD | LYS | 6 | 15.371 | 17.262 | 53.298 | 1.00 | 19.07 | 6 |
| ATOM | 37 | CE | LYS | 6 | 16.192 | 18.410 | 53.874 | 1.00 | 19.16 | 6 |
| ATOM | 38 | NZ | LYS | 6 | 15.519 | 19.693 | 53.602 | 1.00 | 22.03 | 7 |
| ATOM | 39 | C | LYS | 6 | 15.393 | 12.341 | 52.566 | 1.00 | 14.50 | 6 |
| ATOM | 40 | O | LYS | 6 | 14.812 | 11.889 | 51.557 | 1.00 | 13.25 | 8 |
| ATOM | 41 | N | VAL | 7 | 15.218 | 11.864 | 53.792 | 1.00 | 13.53 | 7 |
| ATOM | 42 | CA | VAL | 7 | 14.229 | 10.844 | 54.069 | 1.00 | 14.20 | 6 |
| ATOM | 43 | CB | VAL | 7 | 14.736 | 9.839 | 55.173 | 1.00 | 14.69 | 6 |
| ATOM | 44 | CG1 | VAL | 7 | 13.662 | 8.813 | 55.476 | 1.00 | 13.89 | 6 |
| ATOM | 45 | CG2 | VAL | 7 | 16.037 | 9.143 | 54.707 | 1.00 | 16.62 | 6 |
| ATOM | 46 | C | VAL | 7 | 13.024 | 11.621 | 54.628 | 1.00 | 15.07 | 6 |
| ATOM | 47 | O | VAL | 7 | 13.166 | 12.401 | 55.571 | 1.00 | 14.31 | 8 |
| ATOM | 48 | N | TYR | 8 | 11.854 | 11.419 | 54.041 | 1.00 | 12.81 | 7 |
| ATOM | 49 | CA | TYR | 8 | 10.677 | 12.174 | 54.406 | 1.00 | 14.30 | 6 |
| ATOM | 50 | CB | TYR | 8 | 10.068 | 12.764 | 53.129 | 1.00 | 14.12 | 6 |
| ATOM | 51 | CG | TYR | 8 | 10.821 | 13.904 | 52.513 | 1.00 | 15.45 | 6 |
| ATOM | 52 | CD1 | TYR | 8 | 11.594 | 13.714 | 51.365 | 1.00 | 15.06 | 6 |
| ATOM | 53 | CE1 | TYR | 8 | 12.263 | 14.792 | 50.784 | 1.00 | 15.27 | 6 |
| ATOM | 54 | CZ | TYR | 8 | 12.155 | 16.053 | 51.335 | 1.00 | 14.82 | 6 |
| ATOM | 55 | OH | TYR | 8 | 12.800 | 17.095 | 50.735 | 1.00 | 13.42 | 8 |
| ATOM | 56 | CE2 | TYR | 8 | 11.425 | 16.257 | 52.469 | 1.00 | 16.58 | 6 |
| ATOM | 57 | CD2 | TYR | 8 | 10.739 | 15.184 | 53.049 | 1.00 | 14.83 | 6 |
| ATOM | 58 | C | TYR | 8 | 9.601 | 11.302 | 54.995 | 1.00 | 14.22 | 6 |
| ATOM | 59 | O | TYR | 8 | 9.487 | 10.153 | 54.636 | 1.00 | 15.60 | 8 |
| ATOM | 60 | N | GLU | 9 | 8.780 | 11.871 | 55.860 | 1.00 | 14.53 | 7 |
| ATOM | 61 | CA | GLU | 9 | 7.533 | 11.220 | 56.268 | 1.00 | 14.85 | 6 |
| ATOM | 62 | CB | GLU | 9 | 7.353 | 11.291 | 57.802 | 1.00 | 15.19 | 6 |
| ATOM | 63 | CG | GLU | 9 | 8.300 | 10.323 | 58.490 | 1.00 | 16.72 | 6 |
| ATOM | 64 | CD | GLU | 9 | 8.199 | 10.355 | 59.994 | 1.00 | 22.49 | 6 |
| ATOM | 65 | OE1 | GLU | 9 | 7.580 | 11.292 | 60.556 | 1.00 | 25.51 | 8 |
| ATOM | 66 | OE2 | GLU | 9 | 8.752 | 9.436 | 60.607 | 1.00 | 25.51 | 8 |
| ATOM | 67 | C | GLU | 9 | 6.465 | 12.036 | 55.575 | 1.00 | 15.08 | 6 |
| ATOM | 68 | O | GLU | 9 | 6.611 | 13.250 | 55.433 | 1.00 | 15.82 | 8 |
| ATOM | 69 | N | ILE | 10 | 5.408 | 11.404 | 55.121 | 1.00 | 13.45 | 7 |
| ATOM | 70 | CA | ILE | 10 | 4.346 | 12.121 | 54.372 | 1.00 | 12.86 | 6 |
| ATOM | 71 | CB | ILE | 10 | 4.209 | 11.548 | 52.944 | 1.00 | 12.95 | 6 |
| ATOM | 72 | CG1 | ILE | 10 | 5.499 | 11.758 | 52.161 | 1.00 | 13.84 | 6 |
| ATOM | 73 | CD1 | ILE | 10 | 5.471 | 11.018 | 50.792 | 1.00 | 15.14 | 6 |
| ATOM | 74 | CG2 | ILE | 10 | 3.069 | 12.187 | 52.182 | 1.00 | 13.07 | 6 |
| ATOM | 75 | C | ILE | 10 | 3.029 | 11.980 | 55.129 | 1.00 | 13.43 | 6 |
| ATOM | 76 | O | ILE | 10 | 2.574 | 10.879 | 55.390 | 1.00 | 12.91 | 8 |
| ATOM | 77 | N | SER | 11 | 2.449 | 13.101 | 55.536 | 1.00 | 13.78 | 7 |
| ATOM | 78 | CA | SER | 11 | 1.230 | 13.057 | 56.345 | 1.00 | 13.73 | 6 |
| ATOM | 79 | CB | SER | 11 | 1.507 | 13.512 | 57.798 | 1.00 | 14.83 | 6 |
| ATOM | 80 | OG | SER | 11 | 2.041 | 14.815 | 57.846 | 1.00 | 14.66 | 8 |
| ATOM | 81 | C | SER | 11 | 0.116 | 13.901 | 55.746 | 1.00 | 13.77 | 6 |
| ATOM | 82 | O | SER | 11 | 0.371 | 14.879 | 55.044 | 1.00 | 14.46 | 8 |
| ATOM | 83 | N | ASN | 12 | −1.123 | 13.540 | 56.061 | 1.00 | 12.65 | 7 |
| ATOM | 84 | CA | ASN | 12 | −2.244 | 14.230 | 55.481 | 1.00 | 13.16 | 6 |
| ATOM | 85 | CB | ASN | 12 | −3.432 | 13.297 | 55.406 | 1.00 | 13.52 | 6 |
| ATOM | 86 | CG | ASN | 12 | −4.597 | 13.913 | 54.648 | 1.00 | 13.51 | 6 |
| ATOM | 87 | OD1 | ASN | 12 | −5.567 | 14.354 | 55.245 | 1.00 | 13.32 | 8 |

APPENDIX A-continued

| ATOM | 88 | ND2 | ASN | 12 | −4.490 | 13.953 | 53.323 | 1.00 | 13.72 | 7 |
| --- | --- | --- | --- | --- | --- | --- | --- | --- | --- | --- |
| ATOM | 89 | C | ASN | 12 | −2.660 | 15.498 | 56.252 | 1.00 | 14.18 | 6 |
| ATOM | 90 | O | ASN | 12 | −2.731 | 15.513 | 57.495 | 1.00 | 12.74 | 8 |
| ATOM | 91 | N | HIS | 13 | −2.924 | 16.560 | 55.507 | 1.00 | 12.99 | 7 |
| ATOM | 92 | CA | HIS | 13 | −3.332 | 17.824 | 56.135 | 1.00 | 14.32 | 6 |
| ATOM | 93 | CB | HIS | 13 | −3.484 | 18.901 | 55.056 | 1.00 | 13.88 | 6 |
| ATOM | 94 | CG | HIS | 13 | −4.056 | 20.206 | 55.543 | 1.00 | 16.42 | 6 |
| ATOM | 95 | ND1 | HIS | 13 | −3.315 | 21.133 | 56.242 | 1.00 | 17.36 | 7 |
| ATOM | 96 | CE1 | HIS | 13 | −4.043 | 22.211 | 56.466 | 1.00 | 21.05 | 6 |
| ATOM | 97 | NE2 | HIS | 13 | −5.235 | 22.015 | 55.939 | 1.00 | 21.14 | 7 |
| ATOM | 98 | CD2 | HIS | 13 | −5.257 | 20.781 | 55.236 | 1.00 | 19.39 | 6 |
| ATOM | 99 | C | HIS | 13 | −4.632 | 17.692 | 56.920 | 1.00 | 14.28 | 6 |
| ATOM | 100 | O | HIS | 13 | −4.721 | 18.193 | 58.034 | 1.00 | 14.59 | 8 |
| ATOM | 101 | N | ALA | 14 | −5.625 | 17.013 | 56.347 | 1.00 | 13.70 | 7 |
| ATOM | 102 | CA | ALA | 14 | −6.941 | 16.905 | 56.998 | 1.00 | 13.58 | 6 |
| ATOM | 103 | CB | ALA | 14 | −8.023 | 16.380 | 56.034 | 1.00 | 13.57 | 6 |
| ATOM | 104 | C | ALA | 14 | −6.950 | 16.007 | 58.227 | 1.00 | 13.75 | 6 |
| ATOM | 105 | O | ALA | 14 | −7.514 | 16.380 | 59.239 | 1.00 | 14.64 | 8 |
| ATOM | 106 | N | ASN | 15 | −6.340 | 14.833 | 58.129 | 1.00 | 12.96 | 7 |
| ATOM | 107 | CA | ASN | 15 | −6.523 | 13.822 | 59.176 | 1.00 | 13.50 | 6 |
| ATOM | 108 | CB | ASN | 15 | −7.170 | 12.581 | 58.561 | 1.00 | 14.04 | 6 |
| ATOM | 109 | CG | ASN | 15 | −6.247 | 11.817 | 57.615 | 1.00 | 13.50 | 6 |
| ATOM | 110 | OD1 | ASN | 15 | −5.013 | 11.793 | 57.758 | 1.00 | 13.99 | 8 |
| ATOM | 111 | ND2 | ASN | 15 | −6.857 | 11.119 | 56.678 | 1.00 | 14.24 | 7 |
| ATOM | 112 | C | ASN | 15 | −5.294 | 13.469 | 60.011 | 1.00 | 14.37 | 6 |
| ATOM | 113 | O | ASN | 15 | −5.388 | 12.696 | 60.966 | 1.00 | 13.33 | 8 |
| ATOM | 114 | N | GLY | 16 | −4.145 | 14.007 | 59.612 | 1.00 | 13.60 | 7 |
| ATOM | 115 | CA | GLY | 16 | −2.904 | 13.891 | 60.385 | 1.00 | 13.79 | 6 |
| ATOM | 116 | C | GLY | 16 | −2.249 | 12.511 | 60.382 | 1.00 | 14.07 | 6 |
| ATOM | 117 | O | GLY | 16 | −1.280 | 12.268 | 61.128 | 1.00 | 14.65 | 8 |
| ATOM | 118 | N | LEU | 17 | −2.753 | 11.622 | 59.533 | 1.00 | 13.58 | 7 |
| ATOM | 119 | CA | LEU | 17 | −2.226 | 10.256 | 59.389 | 1.00 | 12.86 | 6 |
| ATOM | 120 | CB | LEU | 17 | −3.351 | 9.333 | 58.940 | 1.00 | 14.21 | 6 |
| ATOM | 121 | CG | LEU | 17 | −4.564 | 9.250 | 59.886 | 1.00 | 12.90 | 6 |
| ATOM | 122 | CD1 | LEU | 17 | −5.546 | 8.246 | 59.274 | 1.00 | 14.87 | 6 |
| ATOM | 123 | CD2 | LEU | 17 | −4.117 | 8.826 | 61.305 | 1.00 | 16.94 | 6 |
| ATOM | 124 | C | LEU | 17 | −1.057 | 10.211 | 58.438 | 1.00 | 13.58 | 6 |
| ATOM | 125 | O | LEU | 17 | −0.933 | 11.107 | 57.604 | 1.00 | 12.13 | 8 |
| ATOM | 126 | N | TYR | 18 | −0.167 | 9.219 | 58.599 | 1.00 | 13.52 | 7 |
| ATOM | 127 | CA | TYR | 18 | 1.039 | 9.116 | 57.769 | 1.00 | 13.56 | 6 |
| ATOM | 128 | CB | TYR | 18 | 2.253 | 8.881 | 58.661 | 1.00 | 14.05 | 6 |
| ATOM | 129 | CG | TYR | 18 | 2.600 | 10.123 | 59.473 | 1.00 | 14.00 | 6 |
| ATOM | 130 | CD1 | TYR | 18 | 1.852 | 10.503 | 60.590 | 1.00 | 14.18 | 6 |
| ATOM | 131 | CE1 | TYR | 18 | 2.191 | 11.675 | 61.346 | 1.00 | 13.58 | 6 |
| ATOM | 132 | CZ | TYR | 18 | 3.271 | 12.429 | 60.970 | 1.00 | 14.79 | 6 |
| ATOM | 133 | OH | TYR | 18 | 3.610 | 13.562 | 61.681 | 1.00 | 17.06 | 8 |
| ATOM | 134 | CE2 | TYR | 18 | 4.035 | 12.060 | 59.870 | 1.00 | 15.56 | 6 |
| ATOM | 135 | CD2 | TYR | 18 | 3.686 | 10.901 | 59.130 | 1.00 | 14.40 | 6 |
| ATOM | 136 | C | TYR | 18 | 0.985 | 7.985 | 56.743 | 1.00 | 13.68 | 6 |
| ATOM | 137 | O | TYR | 18 | 0.563 | 6.863 | 57.054 | 1.00 | 12.84 | 8 |
| ATOM | 138 | N | ALA | 19 | 1.477 | 8.276 | 55.541 | 1.00 | 11.84 | 7 |
| ATOM | 139 | CA | ALA | 19 | 1.527 | 7.272 | 54.496 | 1.00 | 12.68 | 6 |
| ATOM | 140 | CB | ALA | 19 | 2.043 | 7.906 | 53.194 | 1.00 | 12.37 | 6 |
| ATOM | 141 | C | ALA | 19 | 2.475 | 6.169 | 54.970 | 1.00 | 14.43 | 6 |
| ATOM | 142 | O | ALA | 19 | 3.592 | 6.461 | 55.470 | 1.00 | 14.16 | 8 |
| ATOM | 143 | N | ALA | 20 | 2.070 | 4.913 | 54.781 | 1.00 | 14.51 | 7 |
| ATOM | 144 | CA | ALA | 20 | 2.810 | 3.787 | 55.371 | 1.00 | 14.74 | 6 |
| ATOM | 145 | CB | ALA | 20 | 2.240 | 3.516 | 56.759 | 1.00 | 15.80 | 6 |
| ATOM | 146 | C | ALA | 20 | 2.701 | 2.502 | 54.563 | 1.00 | 14.76 | 6 |
| ATOM | 147 | O | ALA | 20 | 1.698 | 2.270 | 53.917 | 1.00 | 14.52 | 8 |
| ATOM | 148 | N | THR | 21 | 3.729 | 1.652 | 54.611 | 1.00 | 15.55 | 7 |
| ATOM | 149 | CA | THR | 21 | 3.604 | 0.300 | 54.064 | 1.00 | 15.29 | 6 |
| ATOM | 150 | CB | THR | 21 | 4.639 | 0.007 | 52.959 | 1.00 | 16.12 | 6 |
| ATOM | 151 | OG1 | THR | 21 | 5.911 | 0.494 | 53.354 | 1.00 | 14.94 | 8 |
| ATOM | 152 | CG2 | THR | 21 | 4.340 | 0.748 | 51.702 | 1.00 | 15.88 | 6 |
| ATOM | 153 | C | THR | 21 | 3.871 | −0.681 | 55.194 | 1.00 | 16.74 | 6 |
| ATOM | 154 | O | THR | 21 | 4.531 | −0.314 | 56.187 | 1.00 | 16.14 | 8 |
| ATOM | 155 | N | TYR | 22 | 3.420 | −1.932 | 55.025 | 1.00 | 16.92 | 7 |
| ATOM | 156 | CA | TYR | 22 | 3.680 | −2.978 | 56.023 | 1.00 | 19.27 | 6 |
| ATOM | 157 | CB | TYR | 22 | 2.772 | −4.210 | 55.804 | 1.00 | 20.93 | 6 |
| ATOM | 158 | CG | TYR | 22 | 1.323 | −4.112 | 56.242 | 1.00 | 28.28 | 6 |
| ATOM | 159 | CD1 | TYR | 22 | 0.632 | −5.249 | 56.709 | 1.00 | 34.08 | 6 |
| ATOM | 160 | CE1 | TYR | 22 | −0.696 | −5.176 | 57.095 | 1.00 | 37.40 | 6 |
| ATOM | 161 | CZ | TYR | 22 | −1.354 | −3.975 | 57.027 | 1.00 | 38.60 | 6 |
| ATOM | 162 | OH | TYR | 22 | −2.670 | −3.891 | 57.418 | 1.00 | 45.29 | 8 |
| ATOM | 163 | CE2 | TYR | 22 | −0.715 | −2.855 | 56.569 | 1.00 | 38.01 | 6 |
| ATOM | 164 | CD2 | TYR | 22 | 0.625 | −2.929 | 56.164 | 1.00 | 33.05 | 6 |
| ATOM | 165 | C | TYR | 22 | 5.128 | −3.410 | 55.777 | 1.00 | 18.59 | 6 |
| ATOM | 166 | O | TYR | 22 | 5.495 | −3.634 | 54.640 | 1.00 | 18.30 | 8 |

APPENDIX A-continued

| | | | | | | | | | |
|---|---|---|---|---|---|---|---|---|---|
| ATOM | 167 | N   | LEU | 23 | 5.946  | −3.524 | 56.813 | 1.00 | 18.63 | 7 |
| ATOM | 168 | CA  | LEU | 23 | 7.357  | −3.854 | 56.612 | 1.00 | 20.31 | 6 |
| ATOM | 169 | CB  | LEU | 23 | 8.130  | −3.737 | 57.940 | 1.00 | 20.42 | 6 |
| ATOM | 170 | CG  | LEU | 23 | 8.536  | −2.374 | 58.429 | 1.00 | 20.93 | 6 |
| ATOM | 171 | CD1 | LEU | 23 | 9.180  | −2.497 | 59.792 | 1.00 | 20.83 | 6 |
| ATOM | 172 | CD2 | LEU | 23 | 9.491  | −1.686 | 57.425 | 1.00 | 19.72 | 6 |
| ATOM | 173 | C   | LEU | 23 | 7.625  | −5.258 | 56.116 | 1.00 | 21.85 | 6 |
| ATOM | 174 | O   | LEU | 23 | 8.631  | −5.505 | 55.449 | 1.00 | 23.24 | 8 |
| ATOM | 175 | N   | SER | 24 | 6.747  | −6.175 | 56.475 | 1.00 | 21.33 | 7 |
| ATOM | 176 | CA  | SER | 24 | 6.994  | −7.575 | 56.230 | 1.00 | 24.30 | 6 |
| ATOM | 177 | CB  | SER | 24 | 6.611  | −8.375 | 57.465 | 1.00 | 25.01 | 6 |
| ATOM | 178 | OG  | SER | 24 | 7.596  | −8.157 | 58.462 | 1.00 | 26.64 | 8 |
| ATOM | 179 | C   | SER | 24 | 6.333  | −8.112 | 54.965 | 1.00 | 24.55 | 6 |
| ATOM | 180 | O   | SER | 24 | 6.422  | −9.319 | 54.694 | 1.00 | 24.01 | 8 |
| ATOM | 181 | N   | LEU | 25 | 5.696  | −7.217 | 54.194 | 1.00 | 23.93 | 7 |
| ATOM | 182 | CA  | LEU | 25 | 5.131  | −7.607 | 52.901 | 1.00 | 23.90 | 6 |
| ATOM | 183 | CB  | LEU | 25 | 3.612  | −7.423 | 52.856 | 1.00 | 23.99 | 6 |
| ATOM | 184 | CG  | LEU | 25 | 2.776  | −8.457 | 53.602 | 1.00 | 25.68 | 6 |
| ATOM | 185 | CD1 | LEU | 25 | 1.301  | −8.029 | 53.715 | 1.00 | 26.34 | 6 |
| ATOM | 186 | CD2 | LEU | 25 | 2.876  | −9.793 | 52.878 | 1.00 | 29.65 | 6 |
| ATOM | 187 | C   | LEU | 25 | 5.809  | −6.763 | 51.823 | 1.00 | 23.80 | 6 |
| ATOM | 188 | O   | LEU | 25 | 5.549  | −5.569 | 51.704 | 1.00 | 22.87 | 8 |
| ATOM | 189 | N   | ASP | 26 | 6.669  | −7.379 | 51.017 | 1.00 | 23.78 | 7 |
| ATOM | 190 | CA  | ASP | 26 | 7.407  | −6.582 | 50.045 | 1.00 | 24.63 | 6 |
| ATOM | 191 | CB  | ASP | 26 | 8.427  | −7.426 | 49.300 | 1.00 | 26.49 | 6 |
| ATOM | 192 | CG  | ASP | 26 | 9.779  | −7.500 | 50.023 | 1.00 | 31.57 | 6 |
| ATOM | 193 | OD1 | ASP | 26 | 9.911  | −7.080 | 51.198 | 1.00 | 34.96 | 8 |
| ATOM | 194 | OD2 | ASP | 26 | 10.781 | −7.966 | 49.465 | 1.00 | 38.62 | 8 |
| ATOM | 195 | C   | ASP | 26 | 6.511  | −5.814 | 49.042 | 1.00 | 23.58 | 6 |
| ATOM | 196 | O   | ASP | 26 | 6.869  | −4.720 | 48.643 | 1.00 | 23.37 | 8 |
| ATOM | 197 | N   | ASP | 27 | 5.365  | −6.367 | 48.642 | 1.00 | 21.28 | 7 |
| ATOM | 198 | CA  | ASP | 27 | 4.507  | −5.670 | 47.656 | 1.00 | 21.38 | 6 |
| ATOM | 199 | CB  | ASP | 27 | 3.892  | −6.678 | 46.708 | 1.00 | 22.57 | 6 |
| ATOM | 200 | CG  | ASP | 27 | 4.937  | −7.486 | 45.998 | 1.00 | 28.36 | 6 |
| ATOM | 201 | OD1 | ASP | 27 | 5.764  | −6.855 | 45.312 | 1.00 | 33.23 | 8 |
| ATOM | 202 | OD2 | ASP | 27 | 5.024  | −8.738 | 46.096 | 1.00 | 35.26 | 8 |
| ATOM | 203 | C   | ASP | 27 | 3.368  | −4.892 | 48.287 | 1.00 | 19.83 | 6 |
| ATOM | 204 | O   | ASP | 27 | 2.299  | −4.667 | 47.668 | 1.00 | 18.68 | 8 |
| ATOM | 205 | N   | SER | 28 | 3.590  | −4.517 | 49.530 | 1.00 | 17.39 | 7 |
| ATOM | 206 | CA  | SER | 28 | 2.601  | −3.809 | 50.320 | 1.00 | 16.94 | 6 |
| ATOM | 207 | CB  | SER | 28 | 3.307  | −3.190 | 51.532 | 1.00 | 15.66 | 6 |
| ATOM | 208 | OG  | SER | 28 | 2.358  | −2.638 | 52.426 | 1.00 | 17.08 | 8 |
| ATOM | 209 | C   | SER | 28 | 1.898  | −2.668 | 49.625 | 1.00 | 16.05 | 6 |
| ATOM | 210 | O   | SER | 28 | 2.538  | −1.845 | 48.939 | 1.00 | 15.73 | 8 |
| ATOM | 211 | N   | GLY | 29 | 0.590  | −2.560 | 49.887 | 1.00 | 15.13 | 7 |
| ATOM | 212 | CA  | GLY | 29 | −0.153 | −1.365 | 49.521 | 1.00 | 14.99 | 6 |
| ATOM | 213 | C   | GLY | 29 | 0.281  | −0.247 | 50.457 | 1.00 | 14.08 | 6 |
| ATOM | 214 | O   | GLY | 29 | 0.860  | −0.494 | 51.520 | 1.00 | 14.47 | 8 |
| ATOM | 215 | N   | VAL | 30 | 0.000  | 0.993  | 50.074 | 1.00 | 13.01 | 7 |
| ATOM | 216 | CA  | VAL | 30 | 0.258  | 2.153  | 50.909 | 1.00 | 13.65 | 6 |
| ATOM | 217 | CB  | VAL | 30 | 0.758  | 3.338  | 50.074 | 1.00 | 13.47 | 6 |
| ATOM | 218 | CG1 | VAL | 30 | 0.997  | 4.566  | 50.984 | 1.00 | 15.05 | 6 |
| ATOM | 219 | CG2 | VAL | 30 | 2.035  | 2.958  | 49.358 | 1.00 | 15.13 | 6 |
| ATOM | 220 | C   | VAL | 30 | −1.056 | 2.551  | 51.588 | 1.00 | 14.00 | 6 |
| ATOM | 221 | O   | VAL | 30 | −2.085 | 2.671  | 50.931 | 1.00 | 13.69 | 8 |
| ATOM | 222 | N   | SER | 31 | −1.018 | 2.729  | 52.901 | 1.00 | 13.35 | 7 |
| ATOM | 223 | CA  | SER | 31 | −2.196 | 3.143  | 53.675 | 1.00 | 14.16 | 6 |
| ATOM | 224 | CB  | SER | 31 | −2.634 | 2.025  | 54.628 | 1.00 | 14.62 | 6 |
| ATOM | 225 | OG  | SER | 31 | −1.510 | 1.688  | 55.489 | 1.00 | 16.14 | 8 |
| ATOM | 226 | C   | SER | 31 | −1.856 | 4.360  | 54.519 | 1.00 | 13.09 | 6 |
| ATOM | 227 | O   | SER | 31 | −0.766 | 4.887  | 54.433 | 1.00 | 11.66 | 8 |
| ATOM | 228 | N   | LEU | 32 | −2.789 | 4.783  | 55.355 | 1.00 | 13.24 | 7 |
| ATOM | 229 | CA  | LEU | 32 | −2.548 | 5.893  | 56.264 | 1.00 | 13.83 | 6 |
| ATOM | 230 | CB  | LEU | 32 | −3.559 | 7.036  | 56.035 | 1.00 | 15.20 | 6 |
| ATOM | 231 | CG  | LEU | 32 | −3.416 | 7.767  | 54.687 | 1.00 | 15.61 | 6 |
| ATOM | 232 | CD1 | LEU | 32 | −4.497 | 8.868  | 54.471 | 1.00 | 15.38 | 6 |
| ATOM | 233 | CD2 | LEU | 32 | −1.996 | 8.364  | 54.581 | 1.00 | 15.81 | 6 |
| ATOM | 234 | C   | LEU | 32 | −2.651 | 5.389  | 57.685 | 1.00 | 14.96 | 6 |
| ATOM | 235 | O   | LEU | 32 | −3.689 | 4.841  | 58.080 | 1.00 | 15.15 | 8 |
| ATOM | 236 | N   | MET | 33 | −1.616 | 5.658  | 58.486 | 1.00 | 14.20 | 7 |
| ATOM | 237 | CA  | MET | 33 | −1.557 | 5.138  | 59.859 | 1.00 | 15.68 | 6 |
| ATOM | 238 | CB  | MET | 33 | −0.359 | 4.180  | 60.018 | 1.00 | 16.03 | 6 |
| ATOM | 239 | CG  | MET | 33 | −0.523 | 2.858  | 59.255 | 1.00 | 18.44 | 6 |
| ATOM | 240 | SD  | MET | 33 | −1.868 | 1.869  | 59.992 | 1.00 | 22.86 | 16 |
| ATOM | 241 | CE  | MET | 33 | −1.154 | 1.623  | 61.616 | 1.00 | 25.07 | 6 |
| ATOM | 242 | C   | MET | 33 | −1.339 | 6.270  | 60.825 | 1.00 | 16.36 | 6 |
| ATOM | 243 | O   | MET | 33 | −0.677 | 7.259  | 60.475 | 1.00 | 14.34 | 8 |
| ATOM | 244 | N   | ASN | 34 | −1.831 | 6.091  | 62.061 | 1.00 | 17.81 | 7 |
| ATOM | 245 | CA  | ASN | 34 | −1.565 | 7.040  | 63.140 | 1.00 | 19.44 | 6 |

APPENDIX A-continued

| | | | | | | | | | |
|---|---|---|---|---|---|---|---|---|---|
| ATOM | 246 | CB | ASN | 34 | −2.618 | 6.939 | 64.240 | 1.00 | 20.23 | 6 |
| ATOM | 247 | CG | ASN | 34 | −2.461 | 8.027 | 65.279 | 1.00 | 21.46 | 6 |
| ATOM | 248 | OD1 | ASN | 34 | −1.396 | 8.205 | 65.840 | 1.00 | 22.25 | 8 |
| ATOM | 249 | ND2 | ASN | 34 | −3.525 | 8.780 | 65.516 | 1.00 | 24.08 | 7 |
| ATOM | 250 | C | ASN | 34 | −0.179 | 6.731 | 63.714 | 1.00 | 20.94 | 6 |
| ATOM | 251 | O | ASN | 34 | 0.135 | 5.567 | 63.967 | 1.00 | 20.31 | 8 |
| ATOM | 252 | N | LYS | 35 | 0.652 | 7.750 | 63.900 | 1.00 | 22.13 | 7 |
| ATOM | 253 | CA | LYS | 35 | 2.036 | 7.483 | 64.289 | 1.00 | 26.44 | 6 |
| ATOM | 254 | CB | LYS | 35 | 2.966 | 8.697 | 64.108 | 1.00 | 26.05 | 6 |
| ATOM | 255 | CG | LYS | 35 | 2.663 | 9.878 | 65.013 | 1.00 | 28.47 | 6 |
| ATOM | 256 | CD | LYS | 35 | 3.361 | 11.142 | 64.436 | 1.00 | 29.59 | 6 |
| ATOM | 257 | CE | LYS | 35 | 3.070 | 12.403 | 65.234 | 1.00 | 33.63 | 6 |
| ATOM | 258 | NZ | LYS | 35 | 3.922 | 13.564 | 64.761 | 1.00 | 30.54 | 7 |
| ATOM | 259 | C | LYS | 35 | 2.136 | 6.902 | 65.669 | 1.00 | 27.95 | 6 |
| ATOM | 260 | O | LYS | 35 | 3.199 | 6.406 | 66.043 | 1.00 | 29.08 | 8 |
| ATOM | 261 | N | ASN | 36 | 1.028 | 6.891 | 66.401 | 1.00 | 29.47 | 7 |
| ATOM | 262 | CA | ASN | 36 | 1.036 | 6.297 | 67.743 | 1.00 | 32.08 | 6 |
| ATOM | 263 | CB | ASN | 36 | 0.622 | 7.338 | 68.788 | 1.00 | 33.83 | 6 |
| ATOM | 264 | CG | ASN | 36 | 1.639 | 8.467 | 68.910 | 1.00 | 37.42 | 6 |
| ATOM | 265 | OD1 | ASN | 36 | 2.808 | 8.231 | 69.211 | 1.00 | 43.27 | 8 |
| ATOM | 266 | ND2 | ASN | 36 | 1.207 | 9.696 | 68.650 | 1.00 | 40.29 | 7 |
| ATOM | 267 | C | ASN | 36 | 0.187 | 5.025 | 67.824 | 1.00 | 31.91 | 6 |
| ATOM | 268 | O | ASN | 36 | −0.253 | 4.582 | 68.889 | 1.00 | 32.56 | 8 |
| ATOM | 269 | N | ASP | 37 | −0.054 | 4.422 | 66.669 | 1.00 | 30.80 | 7 |
| ATOM | 270 | CA | ASP | 37 | −0.754 | 3.155 | 66.639 | 1.00 | 30.24 | 6 |
| ATOM | 271 | CB | ASP | 37 | −0.910 | 2.712 | 65.173 | 1.00 | 30.14 | 6 |
| ATOM | 272 | CG | ASP | 37 | −1.798 | 1.496 | 65.031 | 1.00 | 32.52 | 6 |
| ATOM | 273 | OD1 | ASP | 37 | −1.278 | 0.351 | 65.049 | 1.00 | 31.93 | 8 |
| ATOM | 274 | OD2 | ASP | 37 | −3.032 | 1.600 | 64.896 | 1.00 | 33.63 | 8 |
| ATOM | 275 | C | ASP | 37 | 0.069 | 2.104 | 67.406 | 1.00 | 29.39 | 6 |
| ATOM | 276 | O | ASP | 37 | 1.306 | 2.134 | 67.356 | 1.00 | 27.38 | 8 |
| ATOM | 277 | N | ASP | 38 | −0.607 | 1.164 | 68.080 | 1.00 | 29.46 | 7 |
| ATOM | 278 | CA | ASP | 38 | 0.085 | 0.100 | 68.824 | 1.00 | 30.42 | 6 |
| ATOM | 279 | CB | ASP | 38 | −0.899 | −0.812 | 69.608 | 1.00 | 31.60 | 6 |
| ATOM | 280 | CG | ASP | 38 | −1.693 | −1.760 | 68.692 | 1.00 | 35.93 | 6 |
| ATOM | 281 | OD1 | ASP | 38 | −2.066 | −1.343 | 67.582 | 1.00 | 41.03 | 8 |
| ATOM | 282 | OD2 | ASP | 38 | −1.991 | −2.941 | 68.996 | 1.00 | 42.77 | 8 |
| ATOM | 283 | C | ASP | 38 | 0.999 | −0.759 | 67.953 | 1.00 | 29.58 | 6 |
| ATOM | 284 | O | ASP | 38 | 1.953 | −1.363 | 68.452 | 1.00 | 30.06 | 8 |
| ATOM | 285 | N | ASP | 39 | 0.705 | −0.839 | 66.665 | 1.00 | 28.23 | 7 |
| ATOM | 286 | CA | ASP | 39 | 1.526 | −1.638 | 65.780 | 1.00 | 27.08 | 6 |
| ATOM | 287 | CB | ASP | 39 | 0.680 | −2.613 | 64.939 | 1.00 | 29.01 | 6 |
| ATOM | 288 | CG | ASP | 39 | −0.078 | −3.647 | 65.770 | 1.00 | 32.51 | 6 |
| ATOM | 289 | OD1 | ASP | 39 | 0.433 | −4.161 | 66.809 | 1.00 | 37.61 | 8 |
| ATOM | 290 | OD2 | ASP | 39 | −1.210 | −4.030 | 65.419 | 1.00 | 36.42 | 8 |
| ATOM | 291 | C | ASP | 39 | 2.323 | −0.769 | 64.799 | 1.00 | 25.36 | 6 |
| ATOM | 292 | O | ASP | 39 | 2.710 | −1.263 | 63.738 | 1.00 | 23.48 | 8 |
| ATOM | 293 | N | ILE | 40 | 2.573 | 0.496 | 65.121 | 1.00 | 23.58 | 7 |
| ATOM | 294 | CA | ILE | 40 | 3.304 | 1.359 | 64.158 | 1.00 | 23.63 | 6 |
| ATOM | 295 | CB | ILE | 40 | 3.404 | 2.830 | 64.629 | 1.00 | 23.67 | 6 |
| ATOM | 296 | CG1 | ILE | 40 | 3.734 | 3.744 | 63.453 | 1.00 | 20.64 | 6 |
| ATOM | 297 | CD1 | ILE | 40 | 2.618 | 3.891 | 62.432 | 1.00 | 19.80 | 6 |
| ATOM | 298 | CG2 | ILE | 40 | 4.446 | 2.977 | 65.757 | 1.00 | 23.70 | 6 |
| ATOM | 299 | C | ILE | 40 | 4.678 | 0.816 | 63.810 | 1.00 | 22.77 | 6 |
| ATOM | 300 | O | ILE | 40 | 5.188 | 1.054 | 62.705 | 1.00 | 21.59 | 8 |
| ATOM | 301 | N | ASP | 41 | 5.286 | 0.090 | 64.746 | 1.00 | 22.23 | 7 |
| ATOM | 302 | CA | ASP | 41 | 6.611 | −0.464 | 64.486 | 1.00 | 23.13 | 6 |
| ATOM | 303 | CBA | ASP | 41 | 7.242 | −0.953 | 65.791 | 0.50 | 23.22 | 6 |
| ATOM | 304 | CBB | ASP | 41 | 7.273 | −0.959 | 65.802 | 0.50 | 23.25 | 6 |
| ATOM | 305 | CGA | ASP | 41 | 7.646 | 0.192 | 66.703 | 0.50 | 25.13 | 6 |
| ATOM | 306 | CGB | ASP | 41 | 6.496 | −2.093 | 66.507 | 0.50 | 25.73 | 6 |
| ATOM | 307 | OD1 | ASP | 41 | 7.842 | −0.062 | 67.913 | 0.50 | 30.32 | 8 |
| ATOM | 308 | OD1 | ASP | 41 | 5.265 | −2.180 | 66.397 | 0.50 | 27.42 | 8 |
| ATOM | 309 | OD2 | ASP | 41 | 7.790 | 1.373 | 66.309 | 0.50 | 26.11 | 8 |
| ATOM | 310 | OD2 | ASP | 41 | 7.042 | −2.943 | 67.250 | 0.50 | 28.02 | 8 |
| ATOM | 311 | C | ASP | 41 | 6.631 | −1.560 | 63.408 | 1.00 | 22.40 | 6 |
| ATOM | 312 | O | ASP | 41 | 7.689 | −1.956 | 62.963 | 1.00 | 24.40 | 8 |
| ATOM | 313 | N | ASP | 42 | 5.475 | −2.034 | 62.974 | 1.00 | 21.32 | 7 |
| ATOM | 314 | CA | ASP | 42 | 5.400 | −3.019 | 61.872 | 1.00 | 21.65 | 6 |
| ATOM | 315 | CB | ASP | 42 | 4.231 | −3.968 | 62.099 | 1.00 | 23.18 | 6 |
| ATOM | 316 | CG | ASP | 42 | 4.387 | −4.797 | 63.365 | 1.00 | 25.96 | 6 |
| ATOM | 317 | OD1 | ASP | 42 | 5.496 | −5.268 | 63.664 | 1.00 | 28.78 | 8 |
| ATOM | 318 | OD2 | ASP | 42 | 3.434 | −5.046 | 64.107 | 1.00 | 29.57 | 8 |
| ATOM | 319 | C | ASP | 42 | 5.214 | −2.350 | 60.505 | 1.00 | 20.81 | 6 |
| ATOM | 320 | O | ASP | 42 | 5.021 | −3.020 | 59.471 | 1.00 | 20.92 | 8 |
| ATOM | 321 | N | TYR | 43 | 5.258 | −1.029 | 60.493 | 1.00 | 17.85 | 7 |
| ATOM | 322 | CA | TYR | 43 | 5.110 | −0.308 | 59.226 | 1.00 | 17.29 | 6 |
| ATOM | 323 | CB | TYR | 43 | 3.936 | 0.653 | 59.302 | 1.00 | 17.31 | 6 |
| ATOM | 324 | CG | TYR | 43 | 2.604 | −0.041 | 59.382 | 1.00 | 17.79 | 6 |

APPENDIX A-continued

| | | | | | | | | | |
|---|---|---|---|---|---|---|---|---|---|
| ATOM | 325 | CD1 | TYR | 43 | 2.164 | −0.591 | 60.581 | 1.00 | 20.66 | 6 |
| ATOM | 326 | CE1 | TYR | 43 | 0.937 | −1.248 | 60.668 | 1.00 | 22.99 | 6 |
| ATOM | 327 | CZ | TYR | 43 | 0.136 | −1.376 | 59.543 | 1.00 | 23.29 | 6 |
| ATOM | 328 | OH | TYR | 43 | −1.077 | −2.034 | 59.653 | 1.00 | 23.88 | 8 |
| ATOM | 329 | CE2 | TYR | 43 | 0.553 | −0.867 | 58.322 | 1.00 | 21.50 | 6 |
| ATOM | 330 | CD2 | TYR | 43 | 1.808 | −0.197 | 58.243 | 1.00 | 19.72 | 6 |
| ATOM | 331 | C | TYR | 43 | 6.331 | 0.539 | 58.933 | 1.00 | 17.02 | 6 |
| ATOM | 332 | O | TYR | 43 | 7.062 | 0.920 | 59.845 | 1.00 | 16.55 | 8 |
| ATOM | 333 | N | ASN | 44 | 6.502 | 0.879 | 57.663 | 1.00 | 14.43 | 7 |
| ATOM | 334 | CA | ASN | 44 | 7.484 | 1.861 | 57.263 | 1.00 | 14.76 | 6 |
| ATOM | 335 | CB | ASN | 44 | 8.194 | 1.437 | 55.976 | 1.00 | 14.36 | 6 |
| ATOM | 336 | CG | ASN | 44 | 9.071 | 2.545 | 55.432 | 1.00 | 13.75 | 6 |
| ATOM | 337 | OD1 | ASN | 44 | 9.905 | 3.058 | 56.151 | 1.00 | 14.57 | 8 |
| ATOM | 338 | ND2 | ASN | 44 | 8.822 | 2.984 | 54.176 | 1.00 | 10.00 | 7 |
| ATOM | 339 | C | ASN | 44 | 6.786 | 3.181 | 56.951 | 1.00 | 14.38 | 6 |
| ATOM | 340 | O | ASN | 44 | 5.833 | 3.178 | 56.176 | 1.00 | 13.46 | 8 |
| ATOM | 341 | N | LEU | 45 | 7.266 | 4.286 | 57.523 | 1.00 | 14.04 | 7 |
| ATOM | 342 | CA | LEU | 45 | 6.745 | 5.621 | 57.195 | 1.00 | 13.84 | 6 |
| ATOM | 343 | CB | LEU | 45 | 6.368 | 6.384 | 58.481 | 1.00 | 13.53 | 6 |
| ATOM | 344 | CG | LEU | 45 | 5.520 | 5.675 | 59.532 | 1.00 | 18.03 | 6 |
| ATOM | 345 | CD1 | LEU | 45 | 5.147 | 6.593 | 60.705 | 1.00 | 19.76 | 6 |
| ATOM | 346 | CD2 | LEU | 45 | 4.296 | 5.132 | 58.879 | 1.00 | 18.23 | 6 |
| ATOM | 347 | C | LEU | 45 | 7.765 | 6.491 | 56.464 | 1.00 | 13.38 | 6 |
| ATOM | 348 | O | LEU | 45 | 7.512 | 7.684 | 56.266 | 1.00 | 11.95 | 8 |
| ATOM | 349 | N | LYS | 46 | 8.890 | 5.904 | 56.041 | 1.00 | 12.55 | 7 |
| ATOM | 350 | CA | LYS | 46 | 10.020 | 6.689 | 55.530 | 1.00 | 13.23 | 6 |
| ATOM | 351 | CB | LYS | 46 | 11.344 | 6.205 | 56.128 | 1.00 | 13.93 | 6 |
| ATOM | 352 | CG | LYS | 46 | 11.493 | 6.523 | 57.628 | 1.00 | 15.23 | 6 |
| ATOM | 353 | CD | LYS | 46 | 12.846 | 6.071 | 58.164 | 1.00 | 18.61 | 6 |
| ATOM | 354 | CE | LYS | 46 | 12.914 | 6.233 | 59.685 | 1.00 | 21.99 | 6 |
| ATOM | 355 | NZ | LYS | 46 | 14.301 | 6.013 | 60.211 | 1.00 | 23.17 | 7 |
| ATOM | 356 | C | LYS | 46 | 10.096 | 6.573 | 54.035 | 1.00 | 13.11 | 6 |
| ATOM | 357 | O | LYS | 46 | 10.141 | 5.464 | 53.526 | 1.00 | 12.38 | 8 |
| ATOM | 358 | N | TRP | 47 | 10.167 | 7.730 | 53.374 | 1.00 | 11.82 | 7 |
| ATOM | 359 | CA | TRP | 47 | 10.140 | 7.801 | 51.923 | 1.00 | 13.58 | 6 |
| ATOM | 360 | CB | TRP | 47 | 8.803 | 8.415 | 51.436 | 1.00 | 13.68 | 6 |
| ATOM | 361 | CG | TRP | 47 | 7.684 | 7.713 | 52.023 | 1.00 | 15.01 | 6 |
| ATOM | 362 | CD1 | TRP | 47 | 6.846 | 8.166 | 53.011 | 1.00 | 16.16 | 6 |
| ATOM | 363 | NE1 | TRP | 47 | 5.940 | 7.184 | 53.329 | 1.00 | 14.23 | 7 |
| ATOM | 364 | CE2 | TRP | 47 | 6.208 | 6.068 | 52.578 | 1.00 | 18.32 | 6 |
| ATOM | 365 | CD2 | TRP | 47 | 7.281 | 6.383 | 51.724 | 1.00 | 14.41 | 6 |
| ATOM | 366 | CE3 | TRP | 47 | 7.752 | 5.391 | 50.834 | 1.00 | 15.79 | 6 |
| ATOM | 367 | CZ3 | TRP | 47 | 7.115 | 4.134 | 50.812 | 1.00 | 16.77 | 6 |
| ATOM | 368 | CH2 | TRP | 47 | 6.031 | 3.871 | 51.667 | 1.00 | 19.40 | 6 |
| ATOM | 369 | CZ2 | TRP | 47 | 5.577 | 4.801 | 52.567 | 1.00 | 18.91 | 6 |
| ATOM | 370 | C | TRP | 47 | 11.327 | 8.626 | 51.404 | 1.00 | 13.61 | 6 |
| ATOM | 371 | O | TRP | 47 | 11.725 | 9.620 | 52.036 | 1.00 | 13.73 | 8 |
| ATOM | 372 | N | PHE | 48 | 11.909 | 8.185 | 50.288 | 1.00 | 12.61 | 7 |
| ATOM | 373 | CA | PHE | 48 | 13.031 | 8.916 | 49.675 | 1.00 | 13.26 | 6 |
| ATOM | 374 | CB | PHE | 48 | 14.280 | 8.020 | 49.594 | 1.00 | 14.29 | 6 |
| ATOM | 375 | CG | PHE | 48 | 15.556 | 8.778 | 49.448 | 1.00 | 13.80 | 6 |
| ATOM | 376 | CD1 | PHE | 48 | 16.348 | 9.026 | 50.563 | 1.00 | 13.84 | 6 |
| ATOM | 377 | CE1 | PHE | 48 | 17.535 | 9.728 | 50.446 | 1.00 | 14.91 | 6 |
| ATOM | 378 | CZ | PHE | 48 | 17.954 | 10.189 | 49.205 | 1.00 | 15.69 | 6 |
| ATOM | 379 | CE2 | PHE | 48 | 17.181 | 9.948 | 48.077 | 1.00 | 13.22 | 6 |
| ATOM | 380 | CD2 | PHE | 48 | 15.985 | 9.230 | 48.198 | 1.00 | 13.16 | 6 |
| ATOM | 381 | C | PHE | 48 | 12.623 | 9.361 | 48.295 | 1.00 | 13.47 | 6 |
| ATOM | 382 | O | PHE | 48 | 12.122 | 8.547 | 47.486 | 1.00 | 13.20 | 8 |
| ATOM | 383 | N | LEU | 49 | 12.772 | 10.653 | 48.028 | 1.00 | 11.97 | 7 |
| ATOM | 384 | CA | LEU | 49 | 12.397 | 11.187 | 46.736 | 1.00 | 13.59 | 6 |
| ATOM | 385 | CB | LEU | 49 | 11.952 | 12.636 | 46.883 | 1.00 | 13.41 | 6 |
| ATOM | 386 | CG | LEU | 49 | 10.756 | 12.928 | 47.766 | 1.00 | 17.31 | 6 |
| ATOM | 387 | CD1 | LEU | 49 | 10.385 | 14.414 | 47.617 | 1.00 | 18.94 | 6 |
| ATOM | 388 | CD2 | LEU | 49 | 9.604 | 12.027 | 47.358 | 1.00 | 18.89 | 6 |
| ATOM | 389 | C | LEU | 49 | 13.600 | 11.192 | 45.816 | 1.00 | 13.48 | 6 |
| ATOM | 390 | O | LEU | 49 | 14.656 | 11.664 | 46.202 | 1.00 | 13.49 | 8 |
| ATOM | 391 | N | PHE | 50 | 13.459 | 10.619 | 44.629 | 1.00 | 12.65 | 7 |
| ATOM | 392 | CA | PHE | 50 | 14.510 | 10.780 | 43.589 | 1.00 | 14.67 | 6 |
| ATOM | 393 | CB | PHE | 50 | 14.934 | 9.438 | 43.040 | 1.00 | 14.12 | 6 |
| ATOM | 394 | CG | PHE | 50 | 15.758 | 8.612 | 44.021 | 1.00 | 14.77 | 6 |
| ATOM | 395 | CD1 | PHE | 50 | 15.247 | 7.469 | 44.583 | 1.00 | 16.32 | 6 |
| ATOM | 396 | CE1 | PHE | 50 | 16.006 | 6.684 | 45.432 | 1.00 | 15.77 | 6 |
| ATOM | 397 | CZ | PHE | 50 | 17.276 | 7.063 | 45.766 | 1.00 | 14.79 | 6 |
| ATOM | 398 | CE2 | PHE | 50 | 17.797 | 8.224 | 45.247 | 1.00 | 15.73 | 6 |
| ATOM | 399 | CD2 | PHE | 50 | 17.038 | 8.994 | 44.362 | 1.00 | 14.90 | 6 |
| ATOM | 400 | C | PHE | 50 | 13.966 | 11.636 | 42.449 | 1.00 | 14.32 | 6 |
| ATOM | 401 | O | PHE | 50 | 12.815 | 11.460 | 42.026 | 1.00 | 15.12 | 8 |
| ATOM | 402 | N | PRO | 51 | 14.771 | 12.564 | 41.947 | 1.00 | 13.95 | 7 |
| ATOM | 403 | CA | PRO | 51 | 14.323 | 13.438 | 40.873 | 1.00 | 15.25 | 6 |

APPENDIX A-continued

| | | | | | | | | | |
|---|---|---|---|---|---|---|---|---|---|
| ATOM | 404 | CB | PRO | 51 | 15.235 | 14.666 | 41.033 | 1.00 | 15.88 | 6 |
| ATOM | 405 | CG | PRO | 51 | 16.587 | 14.040 | 41.473 | 1.00 | 13.65 | 6 |
| ATOM | 406 | CD | PRO | 51 | 16.187 | 12.813 | 42.314 | 1.00 | 14.66 | 6 |
| ATOM | 407 | C | PRO | 51 | 14.554 | 12.764 | 39.513 | 1.00 | 16.16 | 6 |
| ATOM | 408 | O | PRO | 51 | 15.550 | 12.055 | 39.327 | 1.00 | 15.19 | 8 |
| ATOM | 409 | N | ILE | 52 | 13.619 | 13.000 | 38.590 | 1.00 | 16.21 | 7 |
| ATOM | 410 | CA | ILE | 52 | 13.750 | 12.539 | 37.217 | 1.00 | 16.54 | 6 |
| ATOM | 411 | CB | ILE | 52 | 12.836 | 11.317 | 36.946 | 1.00 | 18.07 | 6 |
| ATOM | 412 | CG1 | ILE | 52 | 11.358 | 11.640 | 37.218 | 1.00 | 17.81 | 6 |
| ATOM | 413 | CD1 | ILE | 52 | 10.410 | 10.475 | 36.800 | 1.00 | 19.78 | 6 |
| ATOM | 414 | CG2 | ILE | 52 | 13.303 | 10.101 | 37.778 | 1.00 | 16.45 | 6 |
| ATOM | 415 | C | ILE | 52 | 13.456 | 13.693 | 36.284 | 1.00 | 17.84 | 6 |
| ATOM | 416 | O | ILE | 52 | 13.198 | 14.836 | 36.721 | 1.00 | 16.51 | 8 |
| ATOM | 417 | N | ASP | 53 | 13.524 | 13.435 | 34.990 | 1.00 | 18.11 | 7 |
| ATOM | 418 | CA | ASP | 53 | 13.351 | 14.516 | 34.045 | 1.00 | 19.49 | 6 |
| ATOM | 419 | CB | ASP | 53 | 13.523 | 14.025 | 32.591 | 1.00 | 19.08 | 6 |
| ATOM | 420 | CG | ASP | 53 | 14.957 | 13.590 | 32.246 | 1.00 | 20.79 | 6 |
| ATOM | 421 | OD1 | ASP | 53 | 15.946 | 13.972 | 32.939 | 1.00 | 18.78 | 8 |
| ATOM | 422 | OD2 | ASP | 53 | 15.175 | 12.846 | 31.243 | 1.00 | 20.45 | 8 |
| ATOM | 423 | C | ASP | 53 | 11.983 | 15.210 | 34.177 | 1.00 | 20.58 | 6 |
| ATOM | 424 | O | ASP | 53 | 11.022 | 14.662 | 34.701 | 1.00 | 19.50 | 8 |
| ATOM | 425 | N | ASP | 54 | 11.934 | 16.446 | 33.702 | 1.00 | 20.38 | 7 |
| ATOM | 426 | CA | ASP | 54 | 10.700 | 17.220 | 33.621 | 1.00 | 22.77 | 6 |
| ATOM | 427 | CB | ASP | 54 | 9.750 | 16.601 | 32.570 | 1.00 | 23.32 | 6 |
| ATOM | 428 | CG | ASP | 54 | 10.416 | 16.422 | 31.196 | 1.00 | 28.71 | 6 |
| ATOM | 429 | OD1 | ASP | 54 | 10.948 | 17.404 | 30.646 | 1.00 | 32.98 | 8 |
| ATOM | 430 | OD2 | ASP | 54 | 10.449 | 15.323 | 30.574 | 1.00 | 35.58 | 8 |
| ATOM | 431 | C | ASP | 54 | 9.999 | 17.464 | 34.967 | 1.00 | 21.98 | 6 |
| ATOM | 432 | O | ASP | 54 | 8.764 | 17.354 | 35.075 | 1.00 | 21.04 | 8 |
| ATOM | 433 | N | ASP | 55 | 10.807 | 17.792 | 35.972 | 1.00 | 22.13 | 7 |
| ATOM | 434 | CA | ASP | 55 | 10.318 | 18.194 | 37.277 | 1.00 | 22.38 | 6 |
| ATOM | 435 | CBA | ASP | 55 | 9.656 | 19.573 | 37.203 | 0.50 | 23.17 | 6 |
| ATOM | 436 | CBB | ASP | 55 | 9.621 | 19.556 | 37.161 | 0.50 | 22.97 | 6 |
| ATOM | 437 | CGA | ASP | 55 | 10.557 | 20.629 | 36.563 | 0.50 | 24.45 | 6 |
| ATOM | 438 | CGB | ASP | 55 | 9.414 | 20.236 | 38.507 | 0.50 | 23.53 | 6 |
| ATOM | 439 | OD1 | ASP | 55 | 11.747 | 20.745 | 36.938 | 0.50 | 26.14 | 8 |
| ATOM | 440 | OD1 | ASP | 55 | 10.101 | 19.877 | 39.477 | 0.50 | 25.15 | 8 |
| ATOM | 441 | OD2 | ASP | 55 | 10.158 | 21.392 | 35.670 | 0.50 | 27.80 | 8 |
| ATOM | 442 | OD2 | ASP | 55 | 8.562 | 21.134 | 38.690 | 0.50 | 26.27 | 8 |
| ATOM | 443 | C | ASP | 55 | 9.373 | 17.157 | 37.887 | 1.00 | 21.59 | 6 |
| ATOM | 444 | O | ASP | 55 | 8.313 | 17.487 | 38.433 | 1.00 | 22.56 | 8 |
| ATOM | 445 | N | GLN | 56 | 9.747 | 15.892 | 37.777 | 1.00 | 19.50 | 7 |
| ATOM | 446 | CA | GLN | 56 | 8.971 | 14.806 | 38.393 | 1.00 | 18.67 | 6 |
| ATOM | 447 | CB | GLN | 56 | 8.429 | 13.857 | 37.349 | 1.00 | 18.13 | 6 |
| ATOM | 448 | CG | GLN | 56 | 7.296 | 14.481 | 36.509 | 1.00 | 21.04 | 6 |
| ATOM | 449 | CD | GLN | 56 | 6.835 | 13.534 | 35.411 | 1.00 | 22.29 | 6 |
| ATOM | 450 | OE1 | GLN | 56 | 7.575 | 13.247 | 34.487 | 1.00 | 31.14 | 8 |
| ATOM | 451 | NE2 | GLN | 56 | 5.635 | 13.052 | 35.516 | 1.00 | 26.52 | 7 |
| ATOM | 452 | C | GLN | 56 | 9.821 | 14.043 | 39.391 | 1.00 | 17.67 | 6 |
| ATOM | 453 | O | GLN | 56 | 11.027 | 14.283 | 39.475 | 1.00 | 17.08 | 8 |
| ATOM | 454 | N | TYR | 57 | 9.188 | 13.134 | 40.136 | 1.00 | 15.93 | 7 |
| ATOM | 455 | CA | TYR | 57 | 9.870 | 12.392 | 41.165 | 1.00 | 16.53 | 6 |
| ATOM | 456 | CB | TYR | 57 | 9.487 | 12.930 | 42.553 | 1.00 | 16.14 | 6 |
| ATOM | 457 | CG | TYR | 57 | 9.804 | 14.372 | 42.749 | 1.00 | 18.89 | 6 |
| ATOM | 458 | CD1 | TYR | 57 | 8.875 | 15.349 | 42.439 | 1.00 | 20.44 | 6 |
| ATOM | 459 | CE1 | TYR | 57 | 9.143 | 16.673 | 42.612 | 1.00 | 21.36 | 6 |
| ATOM | 460 | CZ | TYR | 57 | 10.368 | 17.057 | 43.084 | 1.00 | 25.69 | 6 |
| ATOM | 461 | OH | TYR | 57 | 10.629 | 18.403 | 43.243 | 1.00 | 25.22 | 8 |
| ATOM | 462 | CE2 | TYR | 57 | 11.331 | 16.103 | 43.383 | 1.00 | 23.89 | 6 |
| ATOM | 463 | CD2 | TYR | 57 | 11.049 | 14.765 | 43.202 | 1.00 | 18.35 | 6 |
| ATOM | 464 | C | TYR | 57 | 9.452 | 10.938 | 41.191 | 1.00 | 16.34 | 6 |
| ATOM | 465 | O | TYR | 57 | 8.334 | 10.605 | 40.754 | 1.00 | 14.85 | 8 |
| ATOM | 466 | N | ILE | 58 | 10.335 | 10.105 | 41.763 | 1.00 | 13.41 | 7 |
| ATOM | 467 | CA | ILE | 58 | 10.013 | 8.715 | 42.083 | 1.00 | 13.64 | 6 |
| ATOM | 468 | CB | ILE | 58 | 11.118 | 7.754 | 41.593 | 1.00 | 14.10 | 6 |
| ATOM | 469 | CG1 | ILE | 58 | 11.254 | 7.819 | 40.066 | 1.00 | 16.70 | 6 |
| ATOM | 470 | CD1 | ILE | 58 | 9.939 | 7.427 | 39.326 | 1.00 | 17.76 | 6 |
| ATOM | 471 | CG2 | ILE | 58 | 10.792 | 6.338 | 42.048 | 1.00 | 15.03 | 6 |
| ATOM | 472 | C | ILE | 58 | 9.977 | 8.686 | 43.607 | 1.00 | 13.60 | 6 |
| ATOM | 473 | O | ILE | 58 | 10.887 | 9.212 | 44.264 | 1.00 | 13.88 | 8 |
| ATOM | 474 | N | ILE | 59 | 8.938 | 8.111 | 44.188 | 1.00 | 11.87 | 7 |
| ATOM | 475 | CA | ILE | 59 | 8.839 | 8.054 | 45.658 | 1.00 | 12.35 | 6 |
| ATOM | 476 | CB | ILE | 59 | 7.414 | 8.428 | 46.090 | 1.00 | 12.85 | 6 |
| ATOM | 477 | CG1 | ILE | 59 | 7.028 | 9.812 | 45.517 | 1.00 | 14.38 | 6 |
| ATOM | 478 | CD1 | ILE | 59 | 5.558 | 10.283 | 45.873 | 1.00 | 15.53 | 6 |
| ATOM | 479 | CG2 | ILE | 59 | 7.298 | 8.331 | 47.641 | 1.00 | 11.54 | 6 |
| ATOM | 480 | C | ILE | 59 | 9.185 | 6.617 | 46.108 | 1.00 | 13.15 | 6 |
| ATOM | 481 | O | ILE | 59 | 8.453 | 5.630 | 45.783 | 1.00 | 12.85 | 8 |
| ATOM | 482 | N | THR | 60 | 10.276 | 6.503 | 46.867 | 1.00 | 12.78 | 7 |

APPENDIX A-continued

| ATOM | 483 | CA | THR | 60 | 10.867 | 5.200 | 47.162 | 1.00 | 12.71 | 6 |
| --- | --- | --- | --- | --- | --- | --- | --- | --- | --- | --- |
| ATOM | 484 | CB | THR | 60 | 12.363 | 5.260 | 46.853 | 1.00 | 13.03 | 6 |
| ATOM | 485 | OG1 | THR | 60 | 12.540 | 5.693 | 45.487 | 1.00 | 13.37 | 8 |
| ATOM | 486 | CG2 | THR | 60 | 13.027 | 3.861 | 46.971 | 1.00 | 13.41 | 6 |
| ATOM | 487 | C | THR | 60 | 10.733 | 4.819 | 48.601 | 1.00 | 13.32 | 6 |
| ATOM | 488 | O | THR | 60 | 10.991 | 5.642 | 49.479 | 1.00 | 12.80 | 8 |
| ATOM | 489 | N | SER | 61 | 10.324 | 3.584 | 48.848 | 1.00 | 12.50 | 7 |
| ATOM | 490 | CA | SER | 61 | 10.233 | 3.109 | 50.232 | 1.00 | 12.79 | 6 |
| ATOM | 491 | CB | SER | 61 | 9.583 | 1.732 | 50.263 | 1.00 | 13.35 | 6 |
| ATOM | 492 | OG | SER | 61 | 9.274 | 1.389 | 51.596 | 1.00 | 12.55 | 8 |
| ATOM | 493 | C | SER | 61 | 11.676 | 3.053 | 50.776 | 1.00 | 13.87 | 6 |
| ATOM | 494 | O | SER | 61 | 12.549 | 2.325 | 50.256 | 1.00 | 13.63 | 8 |
| ATOM | 495 | N | TYR | 62 | 11.928 | 3.789 | 51.846 | 1.00 | 12.30 | 7 |
| ATOM | 496 | CA | TYR | 62 | 13.315 | 3.939 | 52.282 | 1.00 | 13.00 | 6 |
| ATOM | 497 | CB | TYR | 62 | 13.502 | 5.257 | 53.047 | 1.00 | 12.71 | 6 |
| ATOM | 498 | CG | TYR | 62 | 14.936 | 5.514 | 53.477 | 1.00 | 12.87 | 6 |
| ATOM | 499 | CD1 | TYR | 62 | 15.894 | 5.894 | 52.553 | 1.00 | 13.36 | 6 |
| ATOM | 500 | CE1 | TYR | 62 | 17.212 | 6.135 | 52.946 | 1.00 | 13.08 | 6 |
| ATOM | 501 | CZ | TYR | 62 | 17.562 | 5.955 | 54.279 | 1.00 | 14.52 | 6 |
| ATOM | 502 | OH | TYR | 62 | 18.851 | 6.228 | 54.685 | 1.00 | 16.37 | 8 |
| ATOM | 503 | CE2 | TYR | 62 | 16.612 | 5.585 | 55.199 | 1.00 | 13.60 | 6 |
| ATOM | 504 | CD2 | TYR | 62 | 15.325 | 5.350 | 54.800 | 1.00 | 14.50 | 6 |
| ATOM | 505 | C | TYR | 62 | 13.803 | 2.762 | 53.093 | 1.00 | 13.91 | 6 |
| ATOM | 506 | O | TYR | 62 | 13.466 | 2.634 | 54.254 | 1.00 | 13.78 | 8 |
| ATOM | 507 | N | ALA | 63 | 14.572 | 1.877 | 52.454 | 1.00 | 14.08 | 7 |
| ATOM | 508 | CA | ALA | 63 | 15.143 | 0.705 | 53.116 | 1.00 | 14.63 | 6 |
| ATOM | 509 | CB | ALA | 63 | 16.119 | 1.114 | 54.195 | 1.00 | 16.12 | 6 |
| ATOM | 510 | C | ALA | 63 | 14.046 | −0.163 | 53.724 | 1.00 | 16.27 | 6 |
| ATOM | 511 | O | ALA | 63 | 14.217 | −0.766 | 54.808 | 1.00 | 14.96 | 8 |
| ATOM | 512 | N | ALA | 64 | 12.904 | −0.183 | 53.043 | 1.00 | 14.50 | 7 |
| ATOM | 513 | CA | ALA | 64 | 11.838 | −1.104 | 53.388 | 1.00 | 14.37 | 6 |
| ATOM | 514 | CB | ALA | 64 | 10.785 | −0.423 | 54.195 | 1.00 | 13.44 | 6 |
| ATOM | 515 | C | ALA | 64 | 11.242 | −1.621 | 52.081 | 1.00 | 14.11 | 6 |
| ATOM | 516 | O | ALA | 64 | 11.387 | −0.968 | 51.046 | 1.00 | 12.65 | 8 |
| ATOM | 517 | N | ASN | 65 | 10.562 | −2.758 | 52.136 | 1.00 | 14.06 | 7 |
| ATOM | 518 | CA | ASN | 65 | 9.957 | −3.362 | 50.930 | 1.00 | 15.03 | 6 |
| ATOM | 519 | CB | ASN | 65 | 8.706 | −2.560 | 50.496 | 1.00 | 14.85 | 6 |
| ATOM | 520 | CG | ASN | 65 | 7.833 | −2.155 | 51.674 | 1.00 | 16.13 | 6 |
| ATOM | 521 | OD1 | ASN | 65 | 7.814 | −0.986 | 52.078 | 1.00 | 14.10 | 8 |
| ATOM | 522 | ND2 | ASN | 65 | 7.085 | −3.119 | 52.212 | 1.00 | 13.15 | 7 |
| ATOM | 523 | C | ASN | 65 | 10.928 | −3.449 | 49.767 | 1.00 | 15.26 | 6 |
| ATOM | 524 | O | ASN | 65 | 10.540 | −3.262 | 48.627 | 1.00 | 13.34 | 8 |
| ATOM | 525 | N | ASN | 66 | 12.188 | −3.764 | 50.060 | 1.00 | 15.61 | 7 |
| ATOM | 526 | CA | ASN | 66 | 13.208 | −3.886 | 49.012 | 1.00 | 16.72 | 6 |
| ATOM | 527 | CB | ASN | 66 | 12.946 | −5.148 | 48.135 | 1.00 | 17.93 | 6 |
| ATOM | 528 | CG | ASN | 66 | 14.202 | −5.679 | 47.477 | 1.00 | 20.99 | 6 |
| ATOM | 529 | OD1 | ASN | 66 | 15.294 | −5.648 | 48.058 | 1.00 | 21.87 | 8 |
| ATOM | 530 | ND2 | ASN | 66 | 14.063 | −6.145 | 46.242 | 1.00 | 22.06 | 7 |
| ATOM | 531 | C | ASN | 66 | 13.366 | −2.622 | 48.164 | 1.00 | 15.97 | 6 |
| ATOM | 532 | O | ASN | 66 | 13.761 | −2.684 | 46.973 | 1.00 | 15.33 | 8 |
| ATOM | 533 | N | CYS | 67 | 13.087 | −1.467 | 48.777 | 1.00 | 13.92 | 7 |
| ATOM | 534 | CA | CYS | 67 | 13.219 | −0.191 | 48.098 | 1.00 | 14.68 | 6 |
| ATOM | 535 | CB | CYS | 67 | 14.689 | 0.131 | 47.773 | 1.00 | 14.77 | 6 |
| ATOM | 536 | SG | CYS | 67 | 15.643 | 0.405 | 49.280 | 1.00 | 15.62 | 16 |
| ATOM | 537 | C | CYS | 67 | 12.363 | −0.156 | 46.835 | 1.00 | 13.98 | 6 |
| ATOM | 538 | O | CYS | 67 | 12.772 | 0.392 | 45.836 | 1.00 | 14.97 | 8 |
| ATOM | 539 | N | LYS | 68 | 11.209 | −0.808 | 46.872 | 1.00 | 13.74 | 7 |
| ATOM | 540 | CA | LYS | 68 | 10.226 | −0.638 | 45.806 | 1.00 | 14.61 | 6 |
| ATOM | 541 | CB | LYS | 68 | 9.132 | −1.675 | 45.927 | 1.00 | 14.79 | 6 |
| ATOM | 542 | CG | LYS | 68 | 9.589 | −3.115 | 45.537 | 1.00 | 15.42 | 6 |
| ATOM | 543 | CD | LYS | 68 | 8.462 | −4.071 | 45.808 | 1.00 | 17.68 | 6 |
| ATOM | 544 | CE | LYS | 68 | 8.936 | −5.537 | 45.788 | 1.00 | 24.80 | 6 |
| ATOM | 545 | NZ | LYS | 68 | 9.286 | −6.025 | 44.444 | 1.00 | 24.28 | 7 |
| ATOM | 546 | C | LYS | 68 | 9.653 | 0.804 | 45.908 | 1.00 | 14.59 | 6 |
| ATOM | 547 | O | LYS | 68 | 9.863 | 1.516 | 46.903 | 1.00 | 14.46 | 8 |
| ATOM | 548 | N | VAL | 69 | 8.944 | 1.242 | 44.874 | 1.00 | 14.31 | 7 |
| ATOM | 549 | CA | VAL | 69 | 8.505 | 2.612 | 44.779 | 1.00 | 13.97 | 6 |
| ATOM | 550 | CB | VAL | 69 | 9.162 | 3.300 | 43.541 | 1.00 | 14.60 | 6 |
| ATOM | 551 | CG1 | VAL | 69 | 10.715 | 3.130 | 43.588 | 1.00 | 14.70 | 6 |
| ATOM | 552 | CG2 | VAL | 69 | 8.642 | 2.694 | 42.252 | 1.00 | 15.82 | 6 |
| ATOM | 553 | C | VAL | 69 | 6.999 | 2.736 | 44.627 | 1.00 | 13.43 | 6 |
| ATOM | 554 | O | VAL | 69 | 6.313 | 1.798 | 44.201 | 1.00 | 12.09 | 8 |
| ATOM | 555 | N | TRP | 70 | 6.471 | 3.912 | 44.938 | 1.00 | 12.75 | 7 |
| ATOM | 556 | CA | TRP | 70 | 5.026 | 4.081 | 44.819 | 1.00 | 14.37 | 6 |
| ATOM | 557 | CB | TRP | 70 | 4.573 | 5.479 | 45.251 | 1.00 | 14.05 | 6 |
| ATOM | 558 | CG | TRP | 70 | 4.564 | 5.744 | 46.734 | 1.00 | 17.46 | 6 |
| ATOM | 559 | CD1 | TRP | 70 | 5.232 | 5.067 | 47.735 | 1.00 | 14.84 | 6 |
| ATOM | 560 | NE1 | TRP | 70 | 4.982 | 5.672 | 48.955 | 1.00 | 13.61 | 7 |
| ATOM | 561 | CE2 | TRP | 70 | 4.138 | 6.730 | 48.747 | 1.00 | 17.08 | 6 |

APPENDIX A-continued

| | | | | | | | | | | |
|---|---|---|---|---|---|---|---|---|---|---|
| ATOM | 562 | CD2 | TRP | 70 | 3.869 | 6.800 | 47.364 | 1.00 | 15.12 | 6 |
| ATOM | 563 | CE3 | TRP | 70 | 3.028 | 7.806 | 46.894 | 1.00 | 16.01 | 6 |
| ATOM | 564 | CZ3 | TRP | 70 | 2.493 | 8.700 | 47.808 | 1.00 | 19.85 | 6 |
| ATOM | 565 | CH2 | TRP | 70 | 2.780 | 8.596 | 49.164 | 1.00 | 21.27 | 6 |
| ATOM | 566 | CZ2 | TRP | 70 | 3.588 | 7.623 | 49.658 | 1.00 | 17.53 | 6 |
| ATOM | 567 | C | TRP | 70 | 4.585 | 3.788 | 43.388 | 1.00 | 14.12 | 6 |
| ATOM | 568 | O | TRP | 70 | 5.188 | 4.264 | 42.401 | 1.00 | 13.65 | 8 |
| ATOM | 569 | N | ASN | 71 | 3.488 | 3.058 | 43.281 | 1.00 | 13.62 | 7 |
| ATOM | 570 | CA | ASN | 71 | 3.052 | 2.540 | 42.027 | 1.00 | 15.34 | 6 |
| ATOM | 571 | CB | ASN | 71 | 3.586 | 1.106 | 41.929 | 1.00 | 15.49 | 6 |
| ATOM | 572 | CG | ASN | 71 | 3.150 | 0.379 | 40.670 | 1.00 | 19.06 | 6 |
| ATOM | 573 | OD1 | ASN | 71 | 3.828 | 0.464 | 39.628 | 1.00 | 21.46 | 8 |
| ATOM | 574 | ND2 | ASN | 71 | 2.070 | −0.421 | 40.771 | 1.00 | 17.86 | 7 |
| ATOM | 575 | C | ASN | 71 | 1.543 | 2.550 | 42.015 | 1.00 | 16.04 | 6 |
| ATOM | 576 | O | ASN | 71 | 0.922 | 2.102 | 42.954 | 1.00 | 16.08 | 8 |
| ATOM | 577 | N | VAL | 72 | 0.957 | 3.123 | 40.970 | 1.00 | 17.21 | 7 |
| ATOM | 578 | CA | VAL | 72 | −0.482 | 3.265 | 40.927 | 1.00 | 18.34 | 6 |
| ATOM | 579 | CB | VAL | 72 | −0.872 | 4.618 | 40.313 | 1.00 | 19.93 | 6 |
| ATOM | 580 | CG1 | VAL | 72 | −2.405 | 4.776 | 40.212 | 1.00 | 19.09 | 6 |
| ATOM | 581 | CG2 | VAL | 72 | −0.242 | 5.751 | 41.124 | 1.00 | 19.94 | 6 |
| ATOM | 582 | C | VAL | 72 | −1.130 | 2.168 | 40.107 | 1.00 | 20.34 | 6 |
| ATOM | 583 | O | VAL | 72 | −0.757 | 1.932 | 38.948 | 1.00 | 20.03 | 8 |
| ATOM | 584 | N | ASN | 73 | −2.103 | 1.503 | 40.706 | 1.00 | 20.07 | 7 |
| ATOM | 585 | CA | ASN | 73 | −2.888 | 0.502 | 39.977 | 1.00 | 22.40 | 6 |
| ATOM | 586 | CB | ASN | 73 | −2.539 | −0.887 | 40.440 | 1.00 | 23.86 | 6 |
| ATOM | 587 | CG | ASN | 73 | −1.186 | −1.339 | 40.001 | 1.00 | 29.82 | 6 |
| ATOM | 588 | OD1 | ASN | 73 | −0.383 | −1.841 | 40.822 | 1.00 | 36.94 | 8 |
| ATOM | 589 | ND2 | ASN | 73 | −0.918 | −1.238 | 39.694 | 1.00 | 37.79 | 7 |
| ATOM | 590 | C | ASN | 73 | −4.345 | 0.730 | 40.313 | 1.00 | 21.88 | 6 |
| ATOM | 591 | O | ASN | 73 | −4.713 | 0.682 | 41.477 | 1.00 | 20.35 | 8 |
| ATOM | 592 | N | ASN | 74 | −5.168 | 1.008 | 39.314 | 1.00 | 21.83 | 7 |
| ATOM | 593 | CA | ASN | 74 | −6.595 | 1.196 | 39.589 | 1.00 | 22.16 | 6 |
| ATOM | 594 | CB | ASN | 74 | −7.237 | −0.181 | 39.786 | 1.00 | 23.66 | 6 |
| ATOM | 595 | CG | ASN | 74 | −7.103 | −1.069 | 38.533 | 1.00 | 26.53 | 6 |
| ATOM | 596 | OD1 | ASN | 74 | −7.402 | −0.623 | 37.428 | 1.00 | 31.19 | 8 |
| ATOM | 597 | ND2 | ASN | 74 | −6.652 | −2.314 | 38.707 | 1.00 | 30.14 | 7 |
| ATOM | 598 | C | ASN | 74 | −6.893 | 2.120 | 40.774 | 1.00 | 21.39 | 6 |
| ATOM | 599 | O | ASN | 74 | −7.645 | 1.782 | 41.683 | 1.00 | 20.33 | 8 |
| ATOM | 600 | N | ASN | 75 | −6.244 | 3.279 | 40.764 | 1.00 | 20.34 | 7 |
| ATOM | 601 | CA | ASN | 75 | −6.456 | 4.336 | 41.760 | 1.00 | 21.34 | 6 |
| ATOM | 602 | CB | ASN | 75 | −7.929 | 4.774 | 41.844 | 1.00 | 21.68 | 6 |
| ATOM | 603 | CG | ASN | 75 | −8.481 | 5.175 | 40.500 | 1.00 | 26.75 | 6 |
| ATOM | 604 | OD1 | ASN | 75 | −7.816 | 5.895 | 39.743 | 1.00 | 26.42 | 8 |
| ATOM | 605 | ND2 | ASN | 75 | −9.695 | 4.709 | 40.180 | 1.00 | 29.40 | 7 |
| ATOM | 606 | C | ASN | 75 | −5.961 | 4.034 | 43.137 | 1.00 | 20.26 | 6 |
| ATOM | 607 | O | ASN | 75 | −6.193 | 4.820 | 44.045 | 1.00 | 19.07 | 8 |
| ATOM | 608 | N | LYS | 76 | −5.307 | 2.889 | 43.306 | 1.00 | 18.67 | 7 |
| ATOM | 609 | CA | LYS | 76 | −4.755 | 2.554 | 44.613 | 1.00 | 19.49 | 6 |
| ATOM | 610 | CB | LYS | 76 | −5.182 | 1.140 | 45.008 | 1.00 | 20.57 | 6 |
| ATOM | 611 | CG | LYS | 76 | −6.695 | 1.002 | 45.158 | 1.00 | 22.60 | 6 |
| ATOM | 612 | CD | LYS | 76 | −7.184 | −0.435 | 45.117 | 1.00 | 29.49 | 6 |
| ATOM | 613 | CE | LYS | 76 | −7.405 | −0.987 | 43.715 | 1.00 | 28.72 | 6 |
| ATOM | 614 | NZ | LYS | 76 | −8.641 | −0.479 | 43.061 | 1.00 | 26.99 | 7 |
| ATOM | 615 | C | LYS | 76 | −3.250 | 2.646 | 44.488 | 1.00 | 17.93 | 6 |
| ATOM | 616 | O | LYS | 76 | −2.733 | 2.610 | 43.368 | 1.00 | 17.57 | 8 |
| ATOM | 617 | N | ILE | 77 | −2.538 | 2.762 | 45.612 | 1.00 | 15.33 | 7 |
| ATOM | 618 | CA | ILE | 77 | −1.099 | 2.860 | 45.558 | 1.00 | 16.29 | 6 |
| ATOM | 619 | CB | ILE | 77 | −0.562 | 4.138 | 46.281 | 1.00 | 15.95 | 6 |
| ATOM | 620 | CG1 | ILE | 77 | −1.227 | 5.422 | 45.769 | 1.00 | 20.41 | 6 |
| ATOM | 621 | CD1 | ILE | 77 | −1.202 | 5.545 | 44.276 | 1.00 | 27.67 | 6 |
| ATOM | 622 | CG2 | ILE | 77 | 0.937 | 4.177 | 46.108 | 1.00 | 16.94 | 6 |
| ATOM | 623 | C | ILE | 77 | −0.519 | 1.683 | 46.310 | 1.00 | 15.85 | 6 |
| ATOM | 624 | O | ILE | 77 | −0.964 | 1.372 | 47.426 | 1.00 | 14.74 | 8 |
| ATOM | 625 | N | ASN | 78 | 0.464 | 1.036 | 45.709 | 1.00 | 15.46 | 7 |
| ATOM | 626 | CA | ASN | 78 | 1.243 | 0.053 | 46.406 | 1.00 | 16.38 | 6 |
| ATOM | 627 | CB | ASN | 78 | 0.820 | −1.396 | 46.010 | 1.00 | 17.12 | 6 |
| ATOM | 628 | CG | ASN | 78 | 1.251 | −1.754 | 44.620 | 1.00 | 19.86 | 6 |
| ATOM | 629 | OD1 | ASN | 78 | 1.747 | −0.911 | 43.882 | 1.00 | 21.17 | 8 |
| ATOM | 630 | ND2 | ASN | 78 | 1.091 | −3.027 | 44.249 | 1.00 | 26.45 | 7 |
| ATOM | 631 | C | ASN | 78 | 2.702 | 0.333 | 46.082 | 1.00 | 17.04 | 6 |
| ATOM | 632 | O | ASN | 78 | 3.004 | 1.351 | 45.445 | 1.00 | 17.72 | 8 |
| ATOM | 633 | N | VAL | 79 | 3.625 | −0.480 | 46.601 | 1.00 | 16.43 | 7 |
| ATOM | 634 | CA | VAL | 79 | 5.008 | −0.310 | 46.182 | 1.00 | 15.65 | 6 |
| ATOM | 635 | CB | VAL | 79 | 6.023 | −0.182 | 47.354 | 1.00 | 16.22 | 6 |
| ATOM | 636 | CG1 | VAL | 79 | 5.919 | 1.181 | 48.021 | 1.00 | 15.51 | 6 |
| ATOM | 637 | CG2 | VAL | 79 | 5.872 | −1.375 | 48.411 | 1.00 | 14.11 | 6 |
| ATOM | 638 | C | VAL | 79 | 5.370 | −1.457 | 45.259 | 1.00 | 16.01 | 6 |
| ATOM | 639 | O | VAL | 79 | 5.022 | −2.629 | 45.544 | 1.00 | 16.35 | 8 |
| ATOM | 640 | N | SER | 80 | 6.028 | −1.122 | 44.139 | 1.00 | 15.10 | 7 |

APPENDIX A-continued

| ATOM | 641 | CA | SER | 80 | 6.433 | −2.147 | 43.182 | 1.00 | 15.46 | 6 |
|------|-----|-----|-----|----|-------|--------|--------|------|-------|---|
| ATOM | 642 | CBA | SER | 80 | 5.452 | −2.252 | 42.001 | 0.33 | 16.23 | 6 |
| ATOM | 643 | CBB | SER | 80 | 5.525 | −2.145 | 41.938 | 0.34 | 15.91 | 6 |
| ATOM | 644 | CBC | SER | 80 | 5.465 | −2.187 | 41.991 | 0.33 | 15.86 | 6 |
| ATOM | 645 | OGA | SER | 80 | 5.626 | −1.196 | 41.076 | 0.33 | 17.88 | 8 |
| ATOM | 646 | OGB | SER | 80 | 4.156 | −2.311 | 42.247 | 0.34 | 14.87 | 8 |
| ATOM | 647 | OGC | SER | 80 | 5.655 | −3.359 | 41.217 | 0.33 | 14.39 | 8 |
| ATOM | 648 | C | SER | 80 | 7.853 | −1.880 | 42.708 | 1.00 | 15.99 | 6 |
| ATOM | 649 | O | SER | 80 | 8.383 | −0.776 | 42.858 | 1.00 | 15.38 | 8 |
| ATOM | 650 | N | THR | 81 | 8.465 | −2.886 | 42.114 | 1.00 | 15.62 | 7 |
| ATOM | 651 | CA | THR | 81 | 9.801 | −2.697 | 41.571 | 1.00 | 16.85 | 6 |
| ATOM | 652 | CB | THR | 81 | 10.223 | −3.984 | 40.852 | 1.00 | 17.85 | 6 |
| ATOM | 653 | OG1 | THR | 81 | 10.215 | −5.063 | 41.792 | 1.00 | 19.59 | 8 |
| ATOM | 654 | CG2 | THR | 81 | 11.672 | −3.892 | 40.364 | 1.00 | 18.97 | 6 |
| ATOM | 655 | C | THR | 81 | 9.862 | −1.510 | 40.586 | 1.00 | 17.50 | 6 |
| ATOM | 656 | O | THR | 81 | 9.077 | −1.430 | 39.634 | 1.00 | 15.97 | 8 |
| ATOM | 657 | N | TYR | 82 | 10.842 | −0.629 | 40.775 | 1.00 | 16.63 | 7 |
| ATOM | 658 | CA | TYR | 82 | 10.977 | 0.509 | 39.916 | 1.00 | 17.98 | 6 |
| ATOM | 659 | CB | TYR | 82 | 12.199 | 1.361 | 40.305 | 1.00 | 17.99 | 6 |
| ATOM | 660 | CG | TYR | 82 | 12.470 | 2.455 | 39.308 | 1.00 | 18.88 | 6 |
| ATOM | 661 | CD1 | TYR | 82 | 11.513 | 3.455 | 39.059 | 1.00 | 19.83 | 6 |
| ATOM | 662 | CE1 | TYR | 82 | 11.741 | 4.474 | 38.141 | 1.00 | 18.68 | 6 |
| ATOM | 663 | CZ | TYR | 82 | 12.936 | 4.487 | 37.449 | 1.00 | 20.30 | 6 |
| ATOM | 664 | OH | TYR | 82 | 13.185 | 5.494 | 36.555 | 1.00 | 20.14 | 8 |
| ATOM | 665 | CE2 | TYR | 82 | 13.902 | 3.507 | 37.676 | 1.00 | 19.60 | 6 |
| ATOM | 666 | CD2 | TYR | 82 | 13.664 | 2.494 | 38.595 | 1.00 | 18.97 | 6 |
| ATOM | 667 | C | TYR | 82 | 11.145 | 0.063 | 38.494 | 1.00 | 19.24 | 6 |
| ATOM | 668 | O | TYR | 82 | 11.879 | −0.888 | 38.210 | 1.00 | 19.44 | 8 |
| ATOM | 669 | N | SER | 83 | 10.431 | 0.723 | 37.600 | 1.00 | 20.62 | 7 |
| ATOM | 670 | CA | SER | 83 | 10.630 | 0.495 | 36.174 | 1.00 | 22.65 | 6 |
| ATOM | 671 | CB | SER | 83 | 9.455 | −0.267 | 35.586 | 1.00 | 23.47 | 6 |
| ATOM | 672 | OG | SER | 83 | 9.512 | −0.139 | 34.165 | 1.00 | 24.27 | 8 |
| ATOM | 673 | C | SER | 83 | 10.739 | 1.852 | 35.475 | 1.00 | 24.50 | 6 |
| ATOM | 674 | O | SER | 83 | 9.788 | 2.654 | 35.576 | 1.00 | 23.82 | 8 |
| ATOM | 675 | N | SER | 84 | 11.853 | 2.104 | 34.755 | 1.00 | 24.56 | 7 |
| ATOM | 676 | CA | SER | 84 | 12.031 | 3.414 | 34.139 | 1.00 | 26.32 | 6 |
| ATOM | 677 | CB | SER | 84 | 13.509 | 3.737 | 33.824 | 1.00 | 26.59 | 6 |
| ATOM | 678 | OG | SER | 84 | 14.013 | 2.908 | 32.784 | 1.00 | 27.25 | 8 |
| ATOM | 679 | C | SER | 84 | 11.139 | 3.596 | 32.913 | 1.00 | 27.18 | 6 |
| ATOM | 680 | O | SER | 84 | 11.112 | 4.658 | 32.322 | 1.00 | 27.38 | 8 |
| ATOM | 681 | N | THR | 85 | 10.377 | 2.568 | 32.565 | 1.00 | 28.29 | 7 |
| ATOM | 682 | CA | THR | 85 | 9.470 | 2.690 | 31.450 | 1.00 | 29.65 | 6 |
| ATOM | 683 | CB | THR | 85 | 9.765 | 1.609 | 30.384 | 1.00 | 30.76 | 6 |
| ATOM | 684 | OG1 | THR | 85 | 9.895 | 0.319 | 31.004 | 1.00 | 33.59 | 8 |
| ATOM | 685 | CG2 | THR | 85 | 11.149 | 1.848 | 29.777 | 1.00 | 32.40 | 6 |
| ATOM | 686 | C | THR | 85 | 8.023 | 2.651 | 31.895 | 1.00 | 29.92 | 6 |
| ATOM | 687 | O | THR | 85 | 7.125 | 2.604 | 31.053 | 1.00 | 30.57 | 8 |
| ATOM | 688 | N | ASN | 86 | 7.792 | 2.685 | 33.208 | 1.00 | 28.43 | 7 |
| ATOM | 689 | CA | ASN | 86 | 6.438 | 2.644 | 33.744 | 1.00 | 29.34 | 6 |
| ATOM | 690 | CB | ASN | 86 | 6.339 | 1.642 | 34.893 | 1.00 | 29.37 | 6 |
| ATOM | 691 | CG | ASN | 86 | 4.922 | 1.218 | 35.146 | 1.00 | 31.66 | 6 |
| ATOM | 692 | OD1 | ASN | 86 | 3.996 | 1.832 | 34.622 | 1.00 | 31.05 | 8 |
| ATOM | 693 | ND2 | ASN | 86 | 4.737 | 0.135 | 35.904 | 1.00 | 34.08 | 7 |
| ATOM | 694 | C | ASN | 86 | 5.958 | 4.005 | 34.249 | 1.00 | 28.70 | 6 |
| ATOM | 695 | O | ASN | 86 | 6.335 | 4.436 | 35.351 | 1.00 | 27.44 | 8 |
| ATOM | 696 | N | SER | 87 | 5.095 | 4.648 | 33.459 | 1.00 | 28.32 | 7 |
| ATOM | 697 | CA | SER | 87 | 4.641 | 6.015 | 33.749 | 1.00 | 28.30 | 6 |
| ATOM | 698 | CB | SER | 87 | 3.794 | 6.570 | 32.597 | 1.00 | 28.66 | 6 |
| ATOM | 699 | OG | SER | 87 | 2.430 | 6.178 | 32.697 | 1.00 | 30.82 | 8 |
| ATOM | 700 | C | SER | 87 | 3.884 | 6.139 | 35.071 | 1.00 | 27.25 | 6 |
| ATOM | 701 | O | SER | 87 | 3.898 | 7.199 | 35.709 | 1.00 | 26.82 | 8 |
| ATOM | 702 | N | ILE | 88 | 3.264 | 5.042 | 35.492 | 1.00 | 25.49 | 7 |
| ATOM | 703 | CA | ILE | 88 | 2.465 | 5.056 | 36.715 | 1.00 | 22.57 | 6 |
| ATOM | 704 | CB | ILE | 88 | 1.636 | 3.787 | 36.815 | 1.00 | 24.88 | 6 |
| ATOM | 705 | CG1 | ILE | 88 | 2.593 | 2.581 | 36.954 | 1.00 | 23.95 | 6 |
| ATOM | 706 | CD1 | ILE | 88 | 1.938 | 1.278 | 37.543 | 1.00 | 24.38 | 6 |
| ATOM | 707 | CG2 | ILE | 88 | 0.677 | 3.668 | 35.639 | 1.00 | 25.00 | 6 |
| ATOM | 708 | C | ILE | 88 | 3.285 | 5.112 | 37.963 | 1.00 | 20.72 | 6 |
| ATOM | 709 | O | ILE | 88 | 2.730 | 4.940 | 39.045 | 1.00 | 19.56 | 8 |
| ATOM | 710 | N | GLN | 89 | 4.604 | 5.242 | 37.850 | 1.00 | 17.84 | 7 |
| ATOM | 711 | CA | GLN | 89 | 5.398 | 5.416 | 39.055 | 1.00 | 17.84 | 6 |
| ATOM | 712 | CB | GLN | 89 | 6.546 | 4.424 | 39.074 | 1.00 | 17.42 | 6 |
| ATOM | 713 | CG | GLN | 89 | 6.054 | 2.973 | 39.160 | 1.00 | 18.05 | 6 |
| ATOM | 714 | CD | GLN | 89 | 7.175 | 1.979 | 39.016 | 1.00 | 17.81 | 6 |
| ATOM | 715 | OE1 | GLN | 89 | 8.278 | 2.342 | 38.632 | 1.00 | 16.72 | 8 |
| ATOM | 716 | NE2 | GLN | 89 | 6.898 | 0.729 | 39.306 | 1.00 | 17.28 | 7 |
| ATOM | 717 | C | GLN | 89 | 5.930 | 6.845 | 39.154 | 1.00 | 17.01 | 6 |
| ATOM | 718 | O | GLN | 89 | 6.690 | 7.155 | 40.054 | 1.00 | 16.41 | 8 |
| ATOM | 719 | N | LYS | 90 | 5.555 | 7.706 | 38.208 | 1.00 | 16.50 | 7 |

APPENDIX A-continued

| | | | | | | | | | |
|---|---|---|---|---|---|---|---|---|---|
| ATOM | 720 | CA | LYS | 90 | 6.064 | 9.103 | 38.223 | 1.00 | 17.26 | 6 |
| ATOM | 721 | CB | LYS | 90 | 6.327 | 9.603 | 36.791 | 1.00 | 17.17 | 6 |
| ATOM | 722 | CG | LYS | 90 | 7.335 | 8.741 | 35.999 | 1.00 | 18.77 | 6 |
| ATOM | 723 | CD | LYS | 90 | 7.727 | 9.450 | 34.684 | 1.00 | 23.15 | 6 |
| ATOM | 724 | CE | LYS | 90 | 6.599 | 9.353 | 33.695 | 1.00 | 24.99 | 6 |
| ATOM | 725 | NZ | LYS | 90 | 6.889 | 9.986 | 32.313 | 1.00 | 29.11 | 7 |
| ATOM | 726 | C | LYS | 90 | 5.125 | 10.085 | 38.935 | 1.00 | 16.82 | 6 |
| ATOM | 727 | O | LYS | 90 | 3.902 | 10.038 | 38.757 | 1.00 | 17.33 | 8 |
| ATOM | 728 | N | TRP | 91 | 5.680 | 10.988 | 39.727 | 1.00 | 16.18 | 7 |
| ATOM | 729 | CA | TRP | 91 | 4.864 | 11.920 | 40.503 | 1.00 | 16.64 | 6 |
| ATOM | 730 | CB | TRP | 91 | 4.981 | 11.580 | 42.015 | 1.00 | 16.38 | 6 |
| ATOM | 731 | CG | TRP | 91 | 4.572 | 10.160 | 42.278 | 1.00 | 16.66 | 6 |
| ATOM | 732 | CD1 | TRP | 91 | 5.353 | 9.055 | 42.206 | 1.00 | 16.46 | 6 |
| ATOM | 733 | NE1 | TRP | 91 | 4.606 | 7.934 | 42.467 | 1.00 | 16.23 | 7 |
| ATOM | 734 | CE2 | TRP | 91 | 3.311 | 8.136 | 42.719 | 1.00 | 17.14 | 6 |
| ATOM | 735 | CD2 | TRP | 91 | 3.259 | 9.713 | 42.593 | 1.00 | 16.43 | 6 |
| ATOM | 736 | CE3 | TRP | 91 | 2.036 | 10.365 | 42.796 | 1.00 | 15.88 | 6 |
| ATOM | 737 | CZ3 | TRP | 91 | 0.922 | 9.606 | 43.125 | 1.00 | 16.49 | 6 |
| ATOM | 738 | CH2 | TRP | 91 | 1.001 | 8.218 | 43.225 | 1.00 | 17.44 | 6 |
| ATOM | 739 | CZ2 | TRP | 91 | 2.189 | 7.548 | 43.048 | 1.00 | 17.50 | 6 |
| ATOM | 740 | C | TRP | 91 | 5.300 | 13.359 | 40.307 | 1.00 | 17.61 | 6 |
| ATOM | 741 | O | TRP | 91 | 6.466 | 13.626 | 39.980 | 1.00 | 16.28 | 8 |
| ATOM | 742 | N | GLN | 92 | 4.348 | 14.277 | 40.517 | 1.00 | 17.76 | 7 |
| ATOM | 743 | CA | GLN | 92 | 4.616 | 15.701 | 40.606 | 1.00 | 19.22 | 6 |
| ATOM | 744 | CB | GLN | 92 | 3.752 | 16.510 | 39.624 | 1.00 | 20.23 | 6 |
| ATOM | 745 | CG | GLN | 92 | 4.211 | 16.397 | 38.198 | 1.00 | 25.10 | 6 |
| ATOM | 746 | CD | GLN | 92 | 3.303 | 17.149 | 37.253 | 1.00 | 31.44 | 6 |
| ATOM | 747 | OE1 | GLN | 92 | 2.772 | 16.563 | 36.316 | 1.00 | 38.31 | 8 |
| ATOM | 748 | NE2 | GLN | 92 | 3.100 | 18.455 | 37.507 | 1.00 | 34.15 | 7 |
| ATOM | 749 | C | GLN | 92 | 4.253 | 16.084 | 42.015 | 1.00 | 19.26 | 6 |
| ATOM | 750 | O | GLN | 92 | 3.282 | 15.551 | 42.548 | 1.00 | 18.42 | 8 |
| ATOM | 751 | N | ILE | 93 | 5.041 | 16.955 | 42.649 | 1.00 | 19.04 | 7 |
| ATOM | 752 | CA | ILE | 93 | 4.706 | 17.424 | 44.002 | 1.00 | 20.20 | 6 |
| ATOM | 753 | CB | ILE | 93 | 5.791 | 16.973 | 44.980 | 1.00 | 21.08 | 6 |
| ATOM | 754 | CG1 | ILE | 93 | 5.857 | 15.451 | 44.967 | 1.00 | 19.50 | 6 |
| ATOM | 755 | CD1 | ILE | 93 | 6.924 | 14.916 | 45.924 | 1.00 | 23.85 | 6 |
| ATOM | 756 | CG2 | ILE | 93 | 5.491 | 17.427 | 46.380 | 1.00 | 19.96 | 6 |
| ATOM | 757 | C | ILE | 93 | 4.606 | 18.926 | 43.902 | 1.00 | 21.64 | 6 |
| ATOM | 758 | O | ILE | 93 | 5.582 | 19.600 | 43.613 | 1.00 | 22.65 | 8 |
| ATOM | 759 | N | LYS | 94 | 3.400 | 19.445 | 44.095 | 1.00 | 20.93 | 7 |
| ATOM | 760 | CA | LYS | 94 | 3.081 | 20.819 | 43.770 | 1.00 | 22.55 | 6 |
| ATOM | 761 | CB | LYS | 94 | 1.808 | 20.822 | 42.901 | 1.00 | 22.15 | 6 |
| ATOM | 762 | CG | LYS | 94 | 1.822 | 19.836 | 41.714 | 1.00 | 25.93 | 6 |
| ATOM | 763 | CD | LYS | 94 | 0.627 | 20.063 | 40.719 | 1.00 | 25.54 | 6 |
| ATOM | 764 | CE | LYS | 94 | −0.745 | 19.729 | 41.374 | 1.00 | 26.45 | 6 |
| ATOM | 765 | NZ | LYS | 94 | −1.950 | 20.147 | 40.522 | 1.00 | 29.07 | 7 |
| ATOM | 766 | C | LYS | 94 | 2.787 | 21.598 | 45.035 | 1.00 | 22.39 | 6 |
| ATOM | 767 | O | LYS | 94 | 1.878 | 21.247 | 45.758 | 1.00 | 20.46 | 8 |
| ATOM | 768 | N | ALA | 95 | 3.563 | 22.648 | 45.297 | 1.00 | 24.15 | 7 |
| ATOM | 769 | CA | ALA | 95 | 3.299 | 23.511 | 46.445 | 1.00 | 25.47 | 6 |
| ATOM | 770 | CB | ALA | 95 | 4.334 | 24.622 | 46.517 | 1.00 | 27.33 | 6 |
| ATOM | 771 | C | ALA | 95 | 1.895 | 24.118 | 46.356 | 1.00 | 27.13 | 6 |
| ATOM | 772 | O | ALA | 95 | 1.484 | 24.614 | 45.285 | 1.00 | 25.71 | 8 |
| ATOM | 773 | N | ASN | 96 | 1.163 | 24.086 | 47.469 | 1.00 | 27.12 | 7 |
| ATOM | 774 | CA | ASN | 96 | −0.191 | 24.653 | 47.511 | 1.00 | 29.30 | 6 |
| ATOM | 775 | CB | ASN | 96 | −1.256 | 23.580 | 47.239 | 1.00 | 30.09 | 6 |
| ATOM | 776 | CG | ASN | 96 | −2.626 | 24.167 | 46.931 | 1.00 | 31.39 | 6 |
| ATOM | 777 | OD1 | ASN | 96 | −2.740 | 25.222 | 46.284 | 1.00 | 33.09 | 8 |
| ATOM | 778 | ND2 | ASN | 96 | −3.673 | 23.475 | 47.362 | 1.00 | 29.56 | 7 |
| ATOM | 779 | C | ASN | 96 | −0.372 | 25.247 | 48.884 | 1.00 | 30.19 | 6 |
| ATOM | 780 | O | ASN | 96 | −0.799 | 24.571 | 49.817 | 1.00 | 30.06 | 8 |
| ATOM | 781 | N | GLY | 97 | −0.009 | 26.513 | 49.003 | 1.00 | 30.69 | 7 |
| ATOM | 782 | CA | GLY | 97 | −0.012 | 27.174 | 50.282 | 1.00 | 32.03 | 6 |
| ATOM | 783 | C | GLY | 97 | 1.026 | 26.508 | 51.165 | 1.00 | 31.58 | 6 |
| ATOM | 784 | O | GLY | 97 | 2.181 | 26.328 | 50.785 | 1.00 | 31.99 | 8 |
| ATOM | 785 | N | SER | 98 | 0.601 | 26.097 | 52.347 | 1.00 | 31.77 | 7 |
| ATOM | 786 | CA | SER | 98 | 1.534 | 25.533 | 53.306 | 1.00 | 31.15 | 6 |
| ATOM | 787 | CB | SER | 98 | 1.077 | 25.908 | 54.724 | 1.00 | 32.58 | 6 |
| ATOM | 788 | OG | SER | 98 | −0.340 | 25.754 | 54.838 | 1.00 | 34.42 | 8 |
| ATOM | 789 | C | SER | 98 | 1.697 | 24.014 | 53.178 | 1.00 | 29.68 | 6 |
| ATOM | 790 | O | SER | 98 | 2.427 | 23.386 | 53.945 | 1.00 | 29.64 | 8 |
| ATOM | 791 | N | SER | 99 | 1.034 | 23.410 | 52.205 | 1.00 | 28.04 | 7 |
| ATOM | 792 | CA | SER | 99 | 1.142 | 21.962 | 52.056 | 1.00 | 24.66 | 6 |
| ATOM | 793 | CB | SER | 99 | −0.175 | 21.322 | 52.438 | 1.00 | 24.97 | 6 |
| ATOM | 794 | OG | SER | 99 | −0.424 | 21.486 | 53.838 | 1.00 | 24.15 | 8 |
| ATOM | 795 | C | SER | 99 | 1.510 | 21.632 | 50.613 | 1.00 | 23.66 | 6 |
| ATOM | 796 | O | SER | 99 | 2.045 | 22.470 | 49.899 | 1.00 | 24.62 | 8 |
| ATOM | 797 | N | TYR | 100 | 1.221 | 20.422 | 50.188 | 1.00 | 20.31 | 7 |
| ATOM | 798 | CA | TYR | 100 | 1.504 | 20.008 | 48.822 | 1.00 | 19.69 | 6 |

APPENDIX A-continued

| ATOM | 799 | CB | TYR | 100 | 2.773 | 19.151 | 48.775 | 1.00 | 19.66 | 6 |
|------|-----|-----|-----|-----|-------|--------|--------|------|-------|---|
| ATOM | 800 | CG | TYR | 100 | 4.062 | 19.849 | 49.122 | 1.00 | 20.61 | 6 |
| ATOM | 801 | CD1 | TYR | 100 | 4.604 | 19.761 | 50.400 | 1.00 | 22.69 | 6 |
| ATOM | 802 | CE1 | TYR | 100 | 5.800 | 20.371 | 50.719 | 1.00 | 25.87 | 6 |
| ATOM | 803 | CZ | TYR | 100 | 6.481 | 21.085 | 49.760 | 1.00 | 27.67 | 6 |
| ATOM | 804 | OH | TYR | 100 | 7.682 | 21.715 | 50.069 | 1.00 | 29.36 | 8 |
| ATOM | 805 | CE2 | TYR | 100 | 5.968 | 21.181 | 48.487 | 1.00 | 26.47 | 6 |
| ATOM | 806 | CD2 | TYR | 100 | 4.758 | 20.569 | 48.170 | 1.00 | 21.13 | 6 |
| ATOM | 807 | C | TYR | 100 | 0.423 | 19.126 | 48.256 | 1.00 | 18.39 | 6 |
| ATOM | 808 | O | TYR | 100 | −0.204 | 18.368 | 48.973 | 1.00 | 16.92 | 8 |
| ATOM | 809 | N | VAL | 101 | 0.239 | 19.213 | 46.946 | 1.00 | 17.37 | 7 |
| ATOM | 810 | CA | VAL | 101 | −0.635 | 18.296 | 46.228 | 1.00 | 17.71 | 6 |
| ATOM | 811 | CB | VAL | 101 | −1.460 | 19.038 | 45.146 | 1.00 | 18.05 | 6 |
| ATOM | 812 | CG1 | VAL | 101 | −2.202 | 18.037 | 44.203 | 1.00 | 17.24 | 6 |
| ATOM | 813 | CG2 | VAL | 101 | −2.441 | 20.011 | 45.824 | 1.00 | 20.95 | 6 |
| ATOM | 814 | C | VAL | 101 | 0.298 | 17.304 | 45.560 | 1.00 | 17.65 | 6 |
| ATOM | 815 | O | VAL | 101 | 1.336 | 17.715 | 44.970 | 1.00 | 17.58 | 8 |
| ATOM | 816 | N | ILE | 102 | −0.013 | 16.011 | 45.682 | 1.00 | 15.00 | 7 |
| ATOM | 817 | CA | ILE | 102 | 0.839 | 14.979 | 45.102 | 1.00 | 14.82 | 6 |
| ATOM | 818 | CB | ILE | 102 | 1.255 | 13.911 | 46.160 | 1.00 | 14.94 | 6 |
| ATOM | 819 | CG1 | ILE | 102 | 2.110 | 14.580 | 47.240 | 1.00 | 14.78 | 6 |
| ATOM | 820 | CD1 | ILE | 102 | 2.335 | 13.747 | 48.543 | 1.00 | 13.89 | 6 |
| ATOM | 821 | CG2 | ILE | 102 | 2.056 | 12.807 | 45.486 | 1.00 | 15.12 | 6 |
| ATOM | 822 | C | ILE | 102 | 0.066 | 14.396 | 43.949 | 1.00 | 15.07 | 6 |
| ATOM | 823 | O | ILE | 102 | −0.993 | 13.809 | 44.121 | 1.00 | 14.13 | 8 |
| ATOM | 824 | N | GLN | 103 | 0.594 | 14.592 | 42.752 | 1.00 | 14.02 | 7 |
| ATOM | 825 | CA | GLN | 103 | −0.156 | 14.223 | 41.560 | 1.00 | 14.70 | 6 |
| ATOM | 826 | CB | GLN | 103 | −0.294 | 15.457 | 40.693 | 1.00 | 15.00 | 6 |
| ATOM | 827 | CG | GLN | 103 | −1.036 | 15.229 | 39.348 | 1.00 | 18.49 | 6 |
| ATOM | 828 | CD | GLN | 103 | −1.252 | 16.531 | 38.612 | 1.00 | 25.50 | 6 |
| ATOM | 829 | OE1 | GLN | 103 | −1.865 | 17.456 | 39.141 | 1.00 | 28.50 | 8 |
| ATOM | 830 | NE2 | GLN | 103 | −0.735 | 16.612 | 37.387 | 1.00 | 29.23 | 7 |
| ATOM | 831 | C | GLN | 103 | 0.537 | 13.109 | 40.762 | 1.00 | 15.95 | 6 |
| ATOM | 832 | O | GLN | 103 | 1.742 | 13.171 | 40.468 | 1.00 | 15.09 | 8 |
| ATOM | 833 | N | SER | 104 | −0.239 | 12.094 | 40.417 | 1.00 | 15.20 | 7 |
| ATOM | 834 | CA | SER | 104 | 0.266 | 11.010 | 39.576 | 1.00 | 16.31 | 6 |
| ATOM | 835 | CB | SER | 104 | −0.724 | 9.829 | 39.605 | 1.00 | 16.47 | 6 |
| ATOM | 836 | OG | SER | 104 | −0.409 | 8.874 | 38.585 | 1.00 | 17.07 | 8 |
| ATOM | 837 | C | SER | 104 | 0.459 | 11.482 | 38.118 | 1.00 | 17.83 | 6 |
| ATOM | 838 | O | SER | 104 | −0.157 | 12.460 | 37.659 | 1.00 | 16.35 | 8 |
| ATOM | 839 | N | ASP | 105 | 1.328 | 10.786 | 37.404 | 1.00 | 18.28 | 7 |
| ATOM | 840 | CA | ASP | 105 | 1.471 | 10.985 | 35.970 | 1.00 | 20.15 | 6 |
| ATOM | 841 | CB | ASP | 105 | 2.365 | 9.902 | 35.355 | 1.00 | 22.41 | 6 |
| ATOM | 842 | CG | ASP | 105 | 2.708 | 10.219 | 33.929 | 1.00 | 26.43 | 6 |
| ATOM | 843 | OD1 | ASP | 105 | 2.170 | 9.573 | 32.988 | 1.00 | 31.22 | 8 |
| ATOM | 844 | OD2 | ASP | 105 | 3.467 | 11.174 | 33.671 | 1.00 | 32.10 | 8 |
| ATOM | 845 | C | ASP | 105 | 0.132 | 10.901 | 35.242 | 1.00 | 20.42 | 6 |
| ATOM | 846 | O | ASP | 105 | −0.041 | 11.531 | 34.198 | 1.00 | 19.81 | 8 |
| ATOM | 847 | N | ASN | 106 | −0.813 | 10.141 | 35.779 | 1.00 | 20.26 | 7 |
| ATOM | 848 | CA | ASN | 106 | −2.117 | 10.021 | 35.154 | 1.00 | 20.66 | 6 |
| ATOM | 849 | CB | ASN | 106 | −2.795 | 8.699 | 35.532 | 1.00 | 21.24 | 6 |
| ATOM | 850 | CG | ASN | 106 | −3.342 | 8.690 | 36.925 | 1.00 | 21.93 | 6 |
| ATOM | 851 | OD1 | ASN | 106 | −3.287 | 9.692 | 37.649 | 1.00 | 20.78 | 8 |
| ATOM | 852 | ND2 | ASN | 106 | −3.880 | 7.546 | 37.327 | 1.00 | 22.41 | 7 |
| ATOM | 853 | C | ASN | 106 | −3.041 | 11.228 | 35.399 | 1.00 | 20.46 | 6 |
| ATOM | 854 | O | ASN | 106 | −4.186 | 11.241 | 34.953 | 1.00 | 20.19 | 8 |
| ATOM | 855 | N | GLY | 107 | −2.533 | 12.221 | 36.122 | 1.00 | 19.03 | 7 |
| ATOM | 856 | CA | GLY | 107 | −3.263 | 13.439 | 36.368 | 1.00 | 18.28 | 6 |
| ATOM | 857 | C | GLY | 107 | −4.113 | 13.486 | 37.637 | 1.00 | 18.58 | 6 |
| ATOM | 858 | O | GLY | 107 | −4.574 | 14.579 | 38.046 | 1.00 | 18.49 | 8 |
| ATOM | 859 | N | LYS | 108 | −4.366 | 12.332 | 38.242 | 1.00 | 16.26 | 7 |
| ATOM | 860 | CA | LYS | 108 | −5.134 | 12.295 | 39.498 | 1.00 | 16.83 | 6 |
| ATOM | 861 | CB | LYS | 108 | −5.774 | 10.922 | 39.709 | 1.00 | 16.16 | 6 |
| ATOM | 862 | CG | LYS | 108 | −6.723 | 10.573 | 38.536 | 1.00 | 19.36 | 6 |
| ATOM | 863 | CD | LYS | 108 | −7.554 | 9.309 | 38.762 | 1.00 | 19.43 | 6 |
| ATOM | 864 | CE | LYS | 108 | −7.930 | 8.642 | 37.437 | 1.00 | 20.82 | 6 |
| ATOM | 865 | NZ | LYS | 108 | −8.884 | 7.509 | 37.625 | 1.00 | 21.21 | 7 |
| ATOM | 866 | C | LYS | 108 | −4.224 | 12.636 | 40.670 | 1.00 | 16.22 | 6 |
| ATOM | 867 | O | LYS | 108 | −3.002 | 12.597 | 40.526 | 1.00 | 15.05 | 8 |
| ATOM | 868 | N | VAL | 109 | −4.813 | 12.920 | 41.832 | 1.00 | 14.38 | 7 |
| ATOM | 869 | CA | VAL | 109 | −4.011 | 13.370 | 42.958 | 1.00 | 14.07 | 6 |
| ATOM | 870 | CB | VAL | 109 | −4.246 | 14.885 | 43.278 | 1.00 | 13.76 | 6 |
| ATOM | 871 | CG1 | VAL | 109 | −5.715 | 15.139 | 43.789 | 1.00 | 14.54 | 6 |
| ATOM | 872 | CG2 | VAL | 109 | −3.943 | 15.810 | 42.059 | 1.00 | 15.23 | 6 |
| ATOM | 873 | C | VAL | 109 | −4.286 | 12.514 | 44.173 | 1.00 | 14.38 | 6 |
| ATOM | 874 | O | VAL | 109 | −5.377 | 11.959 | 44.327 | 1.00 | 13.50 | 8 |
| ATOM | 875 | N | LEU | 110 | −3.282 | 12.422 | 45.041 | 1.00 | 14.11 | 7 |
| ATOM | 876 | CA | LEU | 110 | −3.365 | 11.632 | 46.269 | 1.00 | 14.69 | 6 |
| ATOM | 877 | CB | LEU | 110 | −2.038 | 11.763 | 47.008 | 1.00 | 15.76 | 6 |

APPENDIX A-continued

| ATOM | 878 | CG | LEU | 110 | −1.596 | 10.625 | 47.887 | 1.00 | 19.14 | 6 |
| --- | --- | --- | --- | --- | --- | --- | --- | --- | --- | --- |
| ATOM | 879 | CD1 | LEU | 110 | −1.373 | 9.410 | 46.951 | 1.00 | 23.85 | 6 |
| ATOM | 880 | CD2 | LEU | 110 | −0.309 | 10.998 | 48.699 | 1.00 | 19.85 | 6 |
| ATOM | 881 | C | LEU | 110 | −4.464 | 12.207 | 47.163 | 1.00 | 14.25 | 6 |
| ATOM | 882 | O | LEU | 110 | −4.461 | 13.410 | 47.481 | 1.00 | 14.02 | 8 |
| ATOM | 883 | N | THR | 111 | −5.381 | 11.343 | 47.588 | 1.00 | 13.98 | 7 |
| ATOM | 884 | CA | THR | 111 | −6.539 | 11.744 | 48.378 | 1.00 | 14.40 | 6 |
| ATOM | 885 | CB | THR | 111 | −7.729 | 11.712 | 47.443 | 1.00 | 14.80 | 6 |
| ATOM | 886 | OG1 | THR | 111 | −7.451 | 12.565 | 46.311 | 1.00 | 15.67 | 8 |
| ATOM | 887 | CG2 | THR | 111 | −8.942 | 12.323 | 48.077 | 1.00 | 15.24 | 6 |
| ATOM | 888 | C | THR | 111 | −6.811 | 10.794 | 49.565 | 1.00 | 14.88 | 6 |
| ATOM | 889 | O | THR | 111 | −6.929 | 9.571 | 49.386 | 1.00 | 16.50 | 8 |
| ATOM | 890 | N | ALA | 112 | −6.922 | 11.332 | 50.776 | 1.00 | 14.19 | 7 |
| ATOM | 891 | CA | ALA | 112 | −7.270 | 10.511 | 51.925 | 1.00 | 14.56 | 6 |
| ATOM | 892 | CB | ALA | 112 | −6.835 | 11.192 | 53.240 | 1.00 | 14.32 | 6 |
| ATOM | 893 | C | ALA | 112 | −8.759 | 10.253 | 51.960 | 1.00 | 15.71 | 6 |
| ATOM | 894 | O | ALA | 112 | −9.564 | 11.179 | 51.794 | 1.00 | 15.63 | 8 |
| ATOM | 895 | N | GLY | 113 | −9.122 | 8.990 | 52.174 | 1.00 | 15.48 | 7 |
| ATOM | 896 | CA | GLY | 113 | −10.533 | 8.598 | 52.367 | 1.00 | 15.77 | 6 |
| ATOM | 897 | C | GLY | 113 | −11.028 | 9.151 | 53.685 | 1.00 | 16.43 | 6 |
| ATOM | 898 | O | GLY | 113 | −10.229 | 9.451 | 54.572 | 1.00 | 14.70 | 8 |
| ATOM | 899 | N | THR | 114 | −12.348 | 9.280 | 53.805 | 1.00 | 17.22 | 7 |
| ATOM | 900 | CA | THR | 114 | −12.997 | 9.747 | 55.017 | 1.00 | 19.03 | 6 |
| ATOM | 901 | CB | THR | 114 | −13.693 | 11.094 | 54.742 | 1.00 | 20.20 | 6 |
| ATOM | 902 | OG1 | THR | 114 | −14.752 | 10.930 | 53.771 | 1.00 | 21.42 | 8 |
| ATOM | 903 | CG2 | THR | 114 | −12.732 | 12.055 | 54.090 | 1.00 | 19.19 | 6 |
| ATOM | 904 | C | THR | 114 | −14.057 | 8.756 | 55.504 | 1.00 | 19.78 | 6 |
| ATOM | 905 | O | THR | 114 | −14.516 | 7.873 | 54.761 | 1.00 | 18.71 | 8 |
| ATOM | 906 | N | GLY | 115 | −14.467 | 8.913 | 56.754 | 1.00 | 19.57 | 7 |
| ATOM | 907 | CA | GLY | 115 | −15.531 | 8.075 | 57.297 | 1.00 | 21.68 | 6 |
| ATOM | 908 | C | GLY | 115 | −15.138 | 6.620 | 57.347 | 1.00 | 22.69 | 6 |
| ATOM | 909 | O | GLY | 115 | −14.132 | 6.244 | 57.995 | 1.00 | 21.80 | 8 |
| ATOM | 910 | N | GLN | 116 | −15.932 | 5.795 | 56.662 | 1.00 | 22.33 | 7 |
| ATOM | 911 | CA | GLN | 116 | −15.680 | 4.363 | 56.648 | 1.00 | 22.61 | 6 |
| ATOM | 912 | CB | GLN | 116 | −16.814 | 3.584 | 56.003 | 1.00 | 22.93 | 6 |
| ATOM | 913 | CG | GLN | 116 | −18.107 | 3.514 | 56.815 | 1.00 | 29.03 | 6 |
| ATOM | 914 | CD | GLN | 116 | −17.943 | 2.810 | 58.161 | 1.00 | 35.31 | 6 |
| ATOM | 915 | OE1 | GLN | 116 | −17.757 | 1.586 | 58.214 | 1.00 | 38.73 | 8 |
| ATOM | 916 | NE2 | GLN | 116 | −17.995 | 3.581 | 59.245 | 1.00 | 39.27 | 7 |
| ATOM | 917 | C | GLN | 116 | −14.397 | 4.104 | 55.892 | 1.00 | 22.05 | 6 |
| ATOM | 918 | O | GLN | 116 | −13.815 | 3.029 | 56.006 | 1.00 | 21.95 | 8 |
| ATOM | 919 | N | ALA | 117 | −13.954 | 5.073 | 55.101 | 1.00 | 20.68 | 7 |
| ATOM | 920 | CA | ALA | 117 | −12.682 | 4.907 | 54.394 | 1.00 | 19.28 | 6 |
| ATOM | 921 | CB | ALA | 117 | −12.831 | 5.334 | 52.947 | 1.00 | 20.19 | 6 |
| ATOM | 922 | C | ALA | 117 | −11.513 | 5.673 | 55.060 | 1.00 | 19.51 | 6 |
| ATOM | 923 | O | ALA | 117 | −10.457 | 5.909 | 54.432 | 1.00 | 18.70 | 8 |
| ATOM | 924 | N | LEU | 118 | −11.687 | 6.090 | 56.312 | 1.00 | 19.17 | 7 |
| ATOM | 925 | CA | LEU | 118 | −10.574 | 6.753 | 57.014 | 1.00 | 17.85 | 6 |
| ATOM | 926 | CB | LEU | 118 | −11.014 | 7.316 | 58.361 | 1.00 | 18.88 | 6 |
| ATOM | 927 | CG | LEU | 118 | −9.881 | 7.937 | 59.181 | 1.00 | 19.05 | 6 |
| ATOM | 928 | CD1 | LEU | 118 | −9.296 | 9.195 | 58.536 | 1.00 | 15.47 | 6 |
| ATOM | 929 | CD2 | LEU | 118 | −10.474 | 8.318 | 60.530 | 1.00 | 21.37 | 6 |
| ATOM | 930 | C | LEU | 118 | −9.439 | 5.710 | 57.216 | 1.00 | 18.24 | 6 |
| ATOM | 931 | O | LEU | 118 | −9.670 | 4.575 | 57.667 | 1.00 | 16.81 | 8 |
| ATOM | 932 | N | GLY | 119 | −8.238 | 6.086 | 56.811 | 1.00 | 16.18 | 7 |
| ATOM | 933 | CA | GLY | 119 | −7.130 | 5.147 | 56.789 | 1.00 | 16.82 | 6 |
| ATOM | 934 | C | GLY | 119 | −6.761 | 4.770 | 55.363 | 1.00 | 16.60 | 6 |
| ATOM | 935 | O | GLY | 119 | −5.663 | 4.282 | 55.136 | 1.00 | 17.28 | 8 |
| ATOM | 936 | N | LEU | 120 | −7.674 | 4.960 | 54.411 | 1.00 | 16.46 | 7 |
| ATOM | 937 | CA | LEU | 120 | −7.388 | 4.610 | 53.020 | 1.00 | 16.83 | 6 |
| ATOM | 938 | CB | LEU | 120 | −8.678 | 4.185 | 52.284 | 1.00 | 18.09 | 6 |
| ATOM | 939 | CG | LEU | 120 | −9.426 | 2.961 | 52.817 | 1.00 | 20.35 | 6 |
| ATOM | 940 | CD1 | LEU | 120 | −10.439 | 2.522 | 51.761 | 1.00 | 21.73 | 6 |
| ATOM | 941 | CD2 | LEU | 120 | −8.486 | 1.841 | 53.160 | 1.00 | 23.00 | 6 |
| ATOM | 942 | C | LEU | 120 | −6.761 | 5.778 | 52.255 | 1.00 | 16.58 | 6 |
| ATOM | 943 | O | LEU | 120 | −6.981 | 6.924 | 52.599 | 1.00 | 13.65 | 8 |
| ATOM | 944 | N | ILE | 121 | −5.923 | 5.474 | 51.253 | 1.00 | 16.33 | 7 |
| ATOM | 945 | CA | ILE | 121 | −5.407 | 6.544 | 50.388 | 1.00 | 17.42 | 6 |
| ATOM | 946 | CB | ILE | 121 | −3.943 | 6.910 | 50.727 | 1.00 | 18.57 | 6 |
| ATOM | 947 | CG1 | ILE | 121 | −3.399 | 8.060 | 49.844 | 1.00 | 20.10 | 6 |
| ATOM | 948 | CD1 | ILE | 121 | −1.983 | 8.475 | 50.375 | 1.00 | 21.16 | 6 |
| ATOM | 949 | CG2 | ILE | 121 | −3.023 | 5.734 | 50.523 | 1.00 | 19.62 | 6 |
| ATOM | 950 | C | ILE | 121 | −5.635 | 6.089 | 48.936 | 1.00 | 18.00 | 6 |
| ATOM | 951 | O | ILE | 121 | −5.444 | 4.934 | 48.599 | 1.00 | 15.34 | 8 |
| ATOM | 952 | N | ARG | 122 | −6.139 | 6.998 | 48.115 | 1.00 | 17.49 | 7 |
| ATOM | 953 | CA | ARG | 122 | −6.490 | 6.685 | 46.728 | 1.00 | 18.05 | 6 |
| ATOM | 954 | CB | ARG | 122 | −8.015 | 6.565 | 46.665 | 1.00 | 18.59 | 6 |
| ATOM | 955 | CG | ARG | 122 | −8.626 | 5.333 | 47.404 | 1.00 | 18.55 | 6 |
| ATOM | 956 | CD | ARG | 122 | −8.187 | 3.994 | 46.769 | 1.00 | 19.64 | 6 |

APPENDIX A-continued

| ATOM | 957 | NE | ARG | 122 | −8.783 | 2.791 | 47.373 | 1.00 | 20.92 | 7 |
| --- | --- | --- | --- | --- | --- | --- | --- | --- | --- | --- |
| ATOM | 958 | CZ | ARG | 122 | −8.235 | 2.066 | 48.327 | 1.00 | 20.82 | 6 |
| ATOM | 959 | NH1 | ARG | 122 | −7.062 | 2.420 | 48.839 | 1.00 | 18.28 | 7 |
| ATOM | 960 | NH2 | ARG | 122 | −8.839 | 0.951 | 48.741 | 1.00 | 17.95 | 7 |
| ATOM | 961 | C | ARG | 122 | −6.102 | 7.847 | 45.826 | 1.00 | 18.07 | 6 |
| ATOM | 962 | O | ARG | 122 | −5.764 | 8.907 | 46.311 | 1.00 | 19.23 | 8 |
| ATOM | 963 | N | LEU | 123 | −6.135 | 7.641 | 44.504 | 1.00 | 17.67 | 7 |
| ATOM | 964 | CA | LEU | 123 | −5.926 | 8.719 | 43.572 | 1.00 | 16.97 | 6 |
| ATOM | 965 | CB | LEU | 123 | −5.140 | 8.249 | 42.349 | 1.00 | 17.56 | 6 |
| ATOM | 966 | CG | LEU | 123 | −3.644 | 8.028 | 42.636 | 1.00 | 19.28 | 6 |
| ATOM | 967 | CD1 | LEU | 123 | −3.041 | 7.497 | 41.372 | 1.00 | 27.05 | 6 |
| ATOM | 968 | CD2 | LEU | 123 | −3.013 | 9.374 | 42.974 | 1.00 | 21.91 | 6 |
| ATOM | 969 | C | LEU | 123 | −7.317 | 9.084 | 43.112 | 1.00 | 17.22 | 6 |
| ATOM | 970 | O | LEU | 123 | −8.134 | 8.184 | 42.833 | 1.00 | 16.91 | 8 |
| ATOM | 971 | N | THR | 124 | −7.615 | 10.381 | 43.087 | 1.00 | 15.96 | 7 |
| ATOM | 972 | CA | THR | 124 | −8.850 | 10.825 | 42.454 | 1.00 | 16.61 | 6 |
| ATOM | 973 | CB | THR | 124 | −10.046 | 10.725 | 43.380 | 1.00 | 17.21 | 6 |
| ATOM | 974 | OG1 | THR | 124 | −11.238 | 10.855 | 42.586 | 1.00 | 21.30 | 8 |
| ATOM | 975 | CG2 | THR | 124 | −10.065 | 11.903 | 44.327 | 1.00 | 17.66 | 6 |
| ATOM | 976 | C | THR | 124 | −8.687 | 12.217 | 41.850 | 1.00 | 15.46 | 6 |
| ATOM | 977 | O | THR | 124 | −7.607 | 12.812 | 41.903 | 1.00 | 15.27 | 8 |
| ATOM | 978 | N | ASP | 125 | −9.732 | 12.711 | 41.205 | 1.00 | 14.55 | 7 |
| ATOM | 979 | CA | ASP | 125 | −9.612 | 13.979 | 40.513 | 1.00 | 15.97 | 6 |
| ATOM | 980 | CB | ASP | 125 | −10.836 | 14.161 | 39.654 | 1.00 | 15.07 | 6 |
| ATOM | 981 | CG | ASP | 125 | −11.188 | 12.883 | 38.943 | 1.00 | 17.28 | 6 |
| ATOM | 982 | OD1 | ASP | 125 | −10.501 | 12.544 | 37.951 | 1.00 | 16.07 | 8 |
| ATOM | 983 | OD2 | ASP | 125 | −12.105 | 12.128 | 39.329 | 1.00 | 17.10 | 8 |
| ATOM | 984 | C | ASP | 125 | −9.435 | 15.132 | 41.489 | 1.00 | 16.09 | 6 |
| ATOM | 985 | O | ASP | 125 | −10.055 | 15.151 | 42.551 | 1.00 | 15.49 | 8 |
| ATOM | 986 | N | GLU | 126 | −8.585 | 16.093 | 41.130 | 1.00 | 16.78 | 7 |
| ATOM | 987 | CA | GLU | 126 | −8.336 | 17.218 | 42.017 | 1.00 | 17.17 | 6 |
| ATOM | 988 | CB | GLU | 126 | −7.128 | 18.024 | 41.539 | 1.00 | 18.64 | 6 |
| ATOM | 989 | CG | GLU | 126 | −6.765 | 19.097 | 42.564 | 1.00 | 19.41 | 6 |
| ATOM | 990 | CD | GLU | 126 | −5.467 | 19.828 | 42.285 | 1.00 | 23.39 | 6 |
| ATOM | 991 | OE1 | GLU | 126 | −4.750 | 19.498 | 41.317 | 1.00 | 23.16 | 8 |
| ATOM | 992 | OE2 | GLU | 126 | −5.166 | 20.756 | 43.058 | 1.00 | 22.67 | 8 |
| ATOM | 993 | C | GLU | 126 | −9.565 | 18.128 | 42.135 | 1.00 | 17.89 | 6 |
| ATOM | 994 | O | GLU | 126 | −10.236 | 18.461 | 41.118 | 1.00 | 15.93 | 8 |
| ATOM | 995 | N | SER | 127 | −9.904 | 18.501 | 43.362 | 1.00 | 17.93 | 7 |
| ATOM | 996 | CA | SER | 127 | −11.029 | 19.392 | 43.546 | 1.00 | 21.43 | 6 |
| ATOM | 997 | CB | SER | 127 | −12.096 | 18.811 | 44.471 | 1.00 | 22.40 | 6 |
| ATOM | 998 | OG | SER | 127 | −11.554 | 18.592 | 45.739 | 1.00 | 25.11 | 8 |
| ATOM | 999 | C | SER | 127 | −10.534 | 20.777 | 44.014 | 1.00 | 23.51 | 6 |
| ATOM | 1000 | O | SER | 127 | −9.373 | 20.935 | 44.370 | 1.00 | 22.63 | 8 |
| ATOM | 1001 | N | SER | 128 | −11.431 | 21.757 | 44.000 | 1.00 | 24.74 | 7 |
| ATOM | 1002 | CA | SER | 128 | −11.060 | 23.143 | 44.257 | 1.00 | 29.00 | 6 |
| ATOM | 1003 | CB | SER | 128 | −12.289 | 24.034 | 44.199 | 1.00 | 28.64 | 6 |
| ATOM | 1004 | OG | SER | 128 | −12.777 | 23.953 | 42.877 | 1.00 | 33.06 | 8 |
| ATOM | 1005 | C | SER | 128 | −10.321 | 23.325 | 45.548 | 1.00 | 30.84 | 6 |
| ATOM | 1006 | O | SER | 128 | −9.190 | 23.822 | 45.538 | 1.00 | 32.42 | 8 |
| ATOM | 1007 | N | ASN | 129 | −10.964 | 22.986 | 46.655 | 1.00 | 31.39 | 7 |
| ATOM | 1008 | CA | ASN | 129 | −10.197 | 22.897 | 47.893 | 1.00 | 33.53 | 6 |
| ATOM | 1009 | CB | ASN | 129 | −9.815 | 24.193 | 48.564 | 1.00 | 35.00 | 6 |
| ATOM | 1010 | CG | ASN | 129 | −8.567 | 24.010 | 49.416 | 1.00 | 39.57 | 6 |
| ATOM | 1011 | OD1 | ASN | 129 | −8.625 | 23.444 | 50.527 | 1.00 | 44.01 | 8 |
| ATOM | 1012 | ND2 | ASN | 129 | −7.408 | 24.405 | 48.864 | 1.00 | 44.00 | 7 |
| ATOM | 1013 | C | ASN | 129 | −10.612 | 21.854 | 48.896 | 1.00 | 31.53 | 6 |
| ATOM | 1014 | O | ASN | 129 | −11.482 | 22.041 | 49.773 | 1.00 | 33.45 | 8 |
| ATOM | 1015 | N | ASN | 130 | −9.911 | 20.750 | 48.757 | 1.00 | 28.33 | 7 |
| ATOM | 1016 | CA | ASN | 130 | −10.173 | 19.565 | 49.503 | 1.00 | 24.72 | 6 |
| ATOM | 1017 | CB | ASN | 130 | −10.279 | 18.416 | 48.524 | 1.00 | 25.42 | 6 |
| ATOM | 1018 | CG | ASN | 130 | −10.697 | 17.151 | 49.166 | 1.00 | 25.45 | 6 |
| ATOM | 1019 | OD1 | ASN | 130 | −10.640 | 17.009 | 50.390 | 1.00 | 25.89 | 8 |
| ATOM | 1020 | ND2 | ASN | 130 | −11.132 | 16.198 | 48.346 | 1.00 | 26.18 | 7 |
| ATOM | 1021 | C | ASN | 130 | −8.961 | 19.386 | 50.389 | 1.00 | 22.06 | 6 |
| ATOM | 1022 | O | ASN | 130 | −7.890 | 19.082 | 49.915 | 1.00 | 20.66 | 8 |
| ATOM | 1023 | N | PRO | 131 | −9.139 | 19.621 | 51.679 | 1.00 | 19.20 | 7 |
| ATOM | 1024 | CA | PRO | 131 | −8.039 | 19.462 | 52.634 | 1.00 | 17.88 | 6 |
| ATOM | 1025 | CB | PRO | 131 | −8.694 | 19.832 | 53.975 | 1.00 | 18.73 | 6 |
| ATOM | 1026 | CG | PRO | 131 | −10.143 | 19.580 | 53.736 | 1.00 | 20.29 | 6 |
| ATOM | 1027 | CD | PRO | 131 | −10.388 | 20.073 | 52.322 | 1.00 | 19.43 | 6 |
| ATOM | 1028 | C | PRO | 131 | −7.530 | 18.022 | 52.625 | 1.00 | 16.21 | 6 |
| ATOM | 1029 | O | PRO | 131 | −6.378 | 17.805 | 53.023 | 1.00 | 15.81 | 8 |
| ATOM | 1030 | N | ASN | 132 | −8.367 | 17.061 | 52.200 | 1.00 | 15.06 | 7 |
| ATOM | 1031 | CA | ASN | 132 | −7.950 | 15.663 | 52.105 | 1.00 | 16.21 | 6 |
| ATOM | 1032 | CB | ASN | 132 | −9.172 | 14.748 | 52.061 | 1.00 | 17.08 | 6 |
| ATOM | 1033 | CG | ASN | 132 | −9.849 | 14.637 | 53.448 | 1.00 | 18.52 | 6 |
| ATOM | 1034 | OD1 | ASN | 132 | −9.340 | 13.947 | 54.336 | 1.00 | 18.60 | 8 |
| ATOM | 1035 | ND2 | ASN | 132 | −10.949 | 15.351 | 53.641 | 1.00 | 16.40 | 7 |

APPENDIX A-continued

| ATOM | 1036 | C | ASN | 132 | −6.991 | 15.369 | 50.930 | 1.00 | 15.55 | 6 |
| ATOM | 1037 | O | ASN | 132 | −6.415 | 14.280 | 50.835 | 1.00 | 16.88 | 8 |
| ATOM | 1038 | N | GLN | 133 | −6.771 | 16.364 | 50.095 | 1.00 | 14.72 | 7 |
| ATOM | 1039 | CA | GLN | 133 | −5.843 | 16.254 | 48.991 | 1.00 | 13.66 | 6 |
| ATOM | 1040 | CB | GLN | 133 | −6.550 | 16.721 | 47.702 | 1.00 | 14.97 | 6 |
| ATOM | 1041 | CG | GLN | 133 | −7.655 | 15.708 | 47.290 | 1.00 | 14.64 | 6 |
| ATOM | 1042 | CD | GLN | 133 | −8.340 | 16.088 | 45.997 | 1.00 | 15.54 | 6 |
| ATOM | 1043 | OE1 | GLN | 133 | −8.324 | 17.248 | 45.620 | 1.00 | 16.61 | 8 |
| ATOM | 1044 | NE2 | GLN | 133 | −8.890 | 15.099 | 45.286 | 1.00 | 14.98 | 7 |
| ATOM | 1045 | C | GLN | 133 | −4.578 | 17.083 | 49.273 | 1.00 | 14.44 | 6 |
| ATOM | 1046 | O | GLN | 133 | −3.753 | 17.286 | 48.395 | 1.00 | 13.28 | 8 |
| ATOM | 1047 | N | GLN | 134 | −4.396 | 17.512 | 50.525 | 1.00 | 14.60 | 7 |
| ATOM | 1048 | CA | GLN | 134 | −3.203 | 18.281 | 50.864 | 1.00 | 14.93 | 6 |
| ATOM | 1049 | CB | GLN | 134 | −3.541 | 19.602 | 51.550 | 1.00 | 15.85 | 6 |
| ATOM | 1050 | CG | GLN | 134 | −4.711 | 20.409 | 50.946 | 1.00 | 21.39 | 6 |
| ATOM | 1051 | CD | GLN | 134 | −4.487 | 20.732 | 49.497 | 1.00 | 25.50 | 6 |
| ATOM | 1052 | OE1 | GLN | 134 | −3.428 | 21.245 | 49.142 | 1.00 | 23.84 | 8 |
| ATOM | 1053 | NE2 | GLN | 134 | −5.493 | 20.456 | 48.647 | 1.00 | 27.34 | 7 |
| ATOM | 1054 | C | GLN | 134 | −2.294 | 17.444 | 51.796 | 1.00 | 14.06 | 6 |
| ATOM | 1055 | O | GLN | 134 | −2.778 | 16.786 | 52.716 | 1.00 | 12.60 | 8 |
| ATOM | 1056 | N | TRP | 135 | −0.985 | 17.545 | 51.586 | 1.00 | 12.91 | 7 |
| ATOM | 1057 | CA | TRP | 135 | −0.006 | 16.679 | 52.238 | 1.00 | 13.22 | 6 |
| ATOM | 1058 | CB | TRP | 135 | 0.475 | 15.603 | 51.231 | 1.00 | 12.70 | 6 |
| ATOM | 1059 | CG | TRP | 135 | −0.671 | 14.783 | 50.707 | 1.00 | 12.72 | 6 |
| ATOM | 1060 | CD1 | TRP | 135 | −1.474 | 15.081 | 49.673 | 1.00 | 15.31 | 6 |
| ATOM | 1061 | NE1 | TRP | 135 | −2.483 | 14.153 | 49.553 | 1.00 | 11.45 | 7 |
| ATOM | 1062 | CE2 | TRP | 135 | −2.356 | 13.236 | 50.561 | 1.00 | 13.24 | 6 |
| ATOM | 1063 | CD2 | TRP | 135 | −1.227 | 13.620 | 51.326 | 1.00 | 12.91 | 6 |
| ATOM | 1064 | CE3 | TRP | 135 | −0.838 | 12.817 | 52.404 | 1.00 | 11.29 | 6 |
| ATOM | 1065 | CZ3 | TRP | 135 | −1.588 | 11.673 | 52.699 | 1.00 | 11.13 | 6 |
| ATOM | 1066 | CH2 | TRP | 135 | −2.729 | 11.327 | 51.922 | 1.00 | 12.77 | 6 |
| ATOM | 1067 | CZ2 | TRP | 135 | −3.121 | 12.104 | 50.855 | 1.00 | 13.88 | 6 |
| ATOM | 1068 | C | TRP | 135 | 1.199 | 17.467 | 52.720 | 1.00 | 14.26 | 6 |
| ATOM | 1069 | O | TRP | 135 | 1.624 | 18.432 | 52.080 | 1.00 | 13.97 | 8 |
| ATOM | 1070 | N | ASN | 136 | 1.763 | 17.009 | 53.839 | 1.00 | 14.79 | 7 |
| ATOM | 1071 | CA | ASN | 136 | 2.929 | 17.619 | 54.420 | 1.00 | 15.15 | 6 |
| ATOM | 1072 | CB | ASN | 136 | 2.646 | 17.917 | 55.882 | 1.00 | 15.39 | 6 |
| ATOM | 1073 | CG | ASN | 136 | 1.550 | 18.969 | 56.040 | 1.00 | 18.49 | 6 |
| ATOM | 1074 | OD1 | ASN | 136 | 1.569 | 20.016 | 55.366 | 1.00 | 19.46 | 8 |
| ATOM | 1075 | ND2 | ASN | 136 | 0.580 | 18.683 | 56.885 | 1.00 | 19.54 | 7 |
| ATOM | 1076 | C | ASN | 136 | 4.092 | 16.675 | 54.334 | 1.00 | 16.45 | 6 |
| ATOM | 1077 | O | ASN | 136 | 3.913 | 15.487 | 54.524 | 1.00 | 12.77 | 8 |
| ATOM | 1078 | N | LEU | 137 | 5.283 | 17.235 | 54.073 | 1.00 | 17.22 | 7 |
| ATOM | 1079 | CA | LEU | 137 | 6.511 | 16.449 | 54.020 | 1.00 | 19.22 | 6 |
| ATOM | 1080 | CB | LEU | 137 | 7.222 | 16.608 | 52.668 | 1.00 | 20.68 | 6 |
| ATOM | 1081 | CG | LEU | 137 | 6.793 | 15.552 | 51.618 | 1.00 | 22.00 | 6 |
| ATOM | 1082 | CD1 | LEU | 137 | 5.381 | 15.736 | 51.151 | 1.00 | 25.06 | 6 |
| ATOM | 1083 | CD2 | LEU | 137 | 7.751 | 15.581 | 50.409 | 1.00 | 26.96 | 6 |
| ATOM | 1084 | C | LEU | 137 | 7.396 | 16.852 | 55.171 | 1.00 | 19.98 | 6 |
| ATOM | 1085 | O | LEU | 137 | 7.733 | 18.060 | 55.330 | 1.00 | 23.01 | 8 |
| ATOM | 1086 | N | THR | 138 | 7.762 | 15.877 | 55.993 | 1.00 | 17.30 | 7 |
| ATOM | 1087 | CA | THR | 138 | 8.590 | 16.146 | 57.148 | 1.00 | 18.88 | 6 |
| ATOM | 1088 | CB | THR | 138 | 7.897 | 15.537 | 58.380 | 1.00 | 19.48 | 6 |
| ATOM | 1089 | OG1 | THR | 138 | 6.592 | 16.126 | 58.534 | 1.00 | 20.61 | 8 |
| ATOM | 1090 | CG2 | THR | 138 | 8.662 | 15.876 | 59.675 | 1.00 | 23.60 | 6 |
| ATOM | 1091 | C | THR | 138 | 9.937 | 15.466 | 56.956 | 1.00 | 17.88 | 6 |
| ATOM | 1092 | O | THR | 138 | 9.979 | 14.264 | 56.774 | 1.00 | 17.56 | 8 |
| ATOM | 1093 | N | SER | 139 | 11.022 | 16.224 | 56.981 | 1.00 | 17.65 | 7 |
| ATOM | 1094 | CA | SER | 139 | 12.370 | 15.638 | 56.853 | 1.00 | 17.75 | 6 |
| ATOM | 1095 | CB | SER | 139 | 13.369 | 16.706 | 56.437 | 1.00 | 19.18 | 6 |
| ATOM | 1096 | OG | SER | 139 | 14.658 | 16.085 | 56.290 | 1.00 | 21.78 | 8 |
| ATOM | 1097 | C | SER | 139 | 12.861 | 14.995 | 58.146 | 1.00 | 17.41 | 6 |
| ATOM | 1098 | O | SER | 139 | 12.918 | 15.663 | 59.182 | 1.00 | 17.76 | 8 |
| ATOM | 1099 | N | VAL | 140 | 13.210 | 13.712 | 58.108 | 1.00 | 15.65 | 7 |
| ATOM | 1100 | CA | VAL | 140 | 13.690 | 13.051 | 59.321 | 1.00 | 16.04 | 6 |
| ATOM | 1101 | CB | VAL | 140 | 12.854 | 11.749 | 59.685 | 1.00 | 17.32 | 6 |
| ATOM | 1102 | CG1 | VAL | 140 | 11.438 | 12.126 | 60.008 | 1.00 | 18.92 | 6 |
| ATOM | 1103 | CG2 | VAL | 140 | 12.889 | 10.739 | 58.536 | 1.00 | 15.67 | 6 |
| ATOM | 1104 | C | VAL | 140 | 15.144 | 12.712 | 59.216 | 1.00 | 15.79 | 6 |
| ATOM | 1105 | O | VAL | 140 | 15.743 | 12.332 | 60.224 | 1.00 | 15.33 | 8 |
| ATOM | 1106 | N | GLN | 141 | 15.715 | 12.833 | 58.009 | 1.00 | 14.19 | 7 |
| ATOM | 1107 | CA | GLN | 141 | 17.152 | 12.616 | 57.821 | 1.00 | 14.84 | 6 |
| ATOM | 1108 | CB | GLN | 141 | 17.498 | 11.120 | 57.753 | 1.00 | 14.51 | 6 |
| ATOM | 1109 | CG | GLN | 141 | 19.019 | 10.858 | 57.738 | 1.00 | 16.36 | 6 |
| ATOM | 1110 | CD | GLN | 141 | 19.352 | 9.375 | 57.831 | 1.00 | 21.09 | 6 |
| ATOM | 1111 | OE1 | GLN | 141 | 18.469 | 8.550 | 58.046 | 1.00 | 23.27 | 8 |
| ATOM | 1112 | NE2 | GLN | 141 | 20.607 | 9.044 | 57.671 | 1.00 | 20.02 | 7 |
| ATOM | 1113 | C | GLN | 141 | 17.612 | 13.308 | 56.551 | 1.00 | 14.51 | 6 |
| ATOM | 1114 | O | GLN | 141 | 16.901 | 13.312 | 55.557 | 1.00 | 11.83 | 8 |

APPENDIX A-continued

| ATOM | 1115 | N | THR | 142 | 18.792 | 13.909 | 56.596 | 1.00 | 14.48 | 7 |
|---|---|---|---|---|---|---|---|---|---|---|
| ATOM | 1116 | CA | THR | 142 | 19.394 | 14.476 | 55.402 | 1.00 | 15.16 | 6 |
| ATOM | 1117 | CB | THR | 142 | 19.614 | 16.000 | 55.567 | 1.00 | 15.21 | 6 |
| ATOM | 1118 | OG1 | THR | 142 | 18.351 | 16.653 | 55.721 | 1.00 | 12.80 | 8 |
| ATOM | 1119 | CG2 | THR | 142 | 20.182 | 16.605 | 54.256 | 1.00 | 14.55 | 6 |
| ATOM | 1120 | C | THR | 142 | 20.751 | 13.771 | 55.194 | 1.00 | 16.28 | 6 |
| ATOM | 1121 | O | THR | 142 | 21.551 | 13.641 | 56.146 | 1.00 | 16.55 | 8 |
| ATOM | 1122 | N | ILE | 143 | 20.996 | 13.331 | 53.968 | 1.00 | 15.88 | 7 |
| ATOM | 1123 | CA | ILE | 143 | 22.236 | 12.682 | 53.594 | 1.00 | 17.68 | 6 |
| ATOM | 1124 | CB | ILE | 143 | 21.947 | 11.449 | 52.702 | 1.00 | 18.78 | 6 |
| ATOM | 1125 | CG1 | ILE | 143 | 20.880 | 10.561 | 53.310 | 1.00 | 21.23 | 6 |
| ATOM | 1126 | CD1 | ILE | 143 | 21.269 | 10.052 | 54.581 | 1.00 | 24.36 | 6 |
| ATOM | 1127 | CG2 | ILE | 143 | 23.269 | 10.655 | 52.413 | 1.00 | 19.65 | 6 |
| ATOM | 1128 | C | ILE | 143 | 23.042 | 13.660 | 52.781 | 1.00 | 18.40 | 6 |
| ATOM | 1129 | O | ILE | 143 | 22.567 | 14.176 | 51.769 | 1.00 | 18.57 | 8 |
| ATOM | 1130 | N | GLN | 144 | 24.277 | 13.903 | 53.190 | 1.00 | 19.27 | 7 |
| ATOM | 1131 | CA | GLN | 144 | 25.157 | 14.803 | 52.443 | 1.00 | 19.97 | 6 |
| ATOM | 1132 | CB | GLN | 144 | 26.350 | 15.241 | 53.320 | 1.00 | 21.19 | 6 |
| ATOM | 1133 | CG | GLN | 144 | 25.988 | 15.993 | 54.647 | 1.00 | 23.14 | 6 |
| ATOM | 1134 | CD | GLN | 144 | 25.273 | 17.338 | 54.425 | 1.00 | 26.96 | 6 |
| ATOM | 1135 | OE1 | GLN | 144 | 25.462 | 17.986 | 53.391 | 1.00 | 26.94 | 8 |
| ATOM | 1136 | NE2 | GLN | 144 | 24.466 | 17.765 | 55.408 | 1.00 | 23.43 | 7 |
| ATOM | 1137 | C | GLN | 144 | 25.631 | 14.073 | 51.180 | 1.00 | 21.13 | 6 |
| ATOM | 1138 | O | GLN | 144 | 26.032 | 12.897 | 51.221 | 1.00 | 21.82 | 8 |
| ATOM | 1139 | N | LEU | 145 | 25.568 | 14.762 | 50.051 | 1.00 | 20.56 | 7 |
| ATOM | 1140 | CA | LEU | 145 | 25.891 | 14.126 | 48.772 | 1.00 | 20.65 | 6 |
| ATOM | 1141 | CB | LEU | 145 | 24.903 | 14.581 | 47.716 | 1.00 | 20.76 | 6 |
| ATOM | 1142 | CG | LEU | 145 | 23.458 | 14.145 | 47.985 | 1.00 | 23.99 | 6 |
| ATOM | 1143 | CD1 | LEU | 145 | 22.685 | 14.202 | 46.695 | 1.00 | 25.50 | 6 |
| ATOM | 1144 | CD2 | LEU | 145 | 23.405 | 12.726 | 48.550 | 1.00 | 25.45 | 6 |
| ATOM | 1145 | C | LEU | 145 | 27.311 | 14.408 | 48.320 | 1.00 | 20.13 | 6 |
| ATOM | 1146 | O | LEU | 145 | 27.903 | 15.373 | 48.746 | 1.00 | 18.05 | 8 |
| ATOM | 1147 | N | PRO | 146 | 27.858 | 13.545 | 47.472 | 1.00 | 21.52 | 7 |
| ATOM | 1148 | CA | PRO | 146 | 29.200 | 13.762 | 46.918 | 1.00 | 21.20 | 6 |
| ATOM | 1149 | CB | PRO | 146 | 29.378 | 12.595 | 45.926 | 1.00 | 21.36 | 6 |
| ATOM | 1150 | CG | PRO | 146 | 28.356 | 11.583 | 46.279 | 1.00 | 23.02 | 6 |
| ATOM | 1151 | CD | PRO | 146 | 27.217 | 12.313 | 46.967 | 1.00 | 21.73 | 6 |
| ATOM | 1152 | C | PRO | 146 | 29.191 | 15.097 | 46.182 | 1.00 | 21.53 | 6 |
| ATOM | 1153 | O | PRO | 146 | 28.217 | 15.411 | 45.523 | 1.00 | 19.60 | 8 |
| ATOM | 1154 | N | GLN | 147 | 30.274 | 15.844 | 46.319 | 1.00 | 22.38 | 7 |
| ATOM | 1155 | CA | GLN | 147 | 30.504 | 17.165 | 45.765 | 1.00 | 23.96 | 6 |
| ATOM | 1156 | CB | GLN | 147 | 31.589 | 17.811 | 46.650 | 1.00 | 26.09 | 6 |
| ATOM | 1157 | CG | GLN | 147 | 32.086 | 19.184 | 46.227 | 1.00 | 30.54 | 6 |
| ATOM | 1158 | CD | GLN | 147 | 33.426 | 19.591 | 46.901 | 1.00 | 39.44 | 6 |
| ATOM | 1159 | OE1 | GLN | 147 | 33.818 | 19.047 | 47.953 | 1.00 | 42.38 | 8 |
| ATOM | 1160 | NE2 | GLN | 147 | 34.110 | 20.561 | 46.298 | 1.00 | 40.66 | 7 |
| ATOM | 1161 | C | GLN | 147 | 31.044 | 17.006 | 44.333 | 1.00 | 22.70 | 6 |
| ATOM | 1162 | O | GLN | 147 | 31.915 | 16.190 | 44.113 | 1.00 | 21.98 | 8 |
| ATOM | 1163 | N | LYS | 148 | 30.470 | 17.717 | 43.363 | 1.00 | 20.91 | 7 |
| ATOM | 1164 | CA | LYS | 148 | 30.945 | 17.643 | 41.991 | 1.00 | 20.12 | 6 |
| ATOM | 1165 | CB | LYS | 148 | 29.934 | 18.357 | 41.088 | 1.00 | 21.36 | 6 |
| ATOM | 1166 | CG | LYS | 148 | 30.253 | 18.356 | 39.602 | 1.00 | 23.72 | 6 |
| ATOM | 1167 | CD | LYS | 148 | 29.055 | 18.971 | 38.869 | 1.00 | 30.65 | 6 |
| ATOM | 1168 | CE | LYS | 148 | 29.114 | 18.774 | 37.378 | 1.00 | 34.43 | 6 |
| ATOM | 1169 | NZ | LYS | 148 | 27.720 | 18.603 | 36.803 | 1.00 | 38.38 | 7 |
| ATOM | 1170 | C | LYS | 148 | 32.341 | 18.279 | 41.864 | 1.00 | 18.67 | 6 |
| ATOM | 1171 | O | LYS | 148 | 32.570 | 19.402 | 42.298 | 1.00 | 18.36 | 8 |
| ATOM | 1172 | N | PRO | 149 | 33.277 | 17.551 | 41.288 | 1.00 | 17.89 | 7 |
| ATOM | 1173 | CA | PRO | 149 | 34.647 | 18.039 | 41.104 | 1.00 | 17.39 | 6 |
| ATOM | 1174 | CB | PRO | 149 | 35.428 | 16.731 | 40.887 | 1.00 | 17.58 | 6 |
| ATOM | 1175 | CG | PRO | 149 | 34.468 | 15.916 | 40.090 | 1.00 | 17.89 | 6 |
| ATOM | 1176 | CD | PRO | 149 | 33.075 | 16.227 | 40.677 | 1.00 | 16.99 | 6 |
| ATOM | 1177 | C | PRO | 149 | 34.758 | 18.993 | 39.894 | 1.00 | 17.40 | 6 |
| ATOM | 1178 | O | PRO | 149 | 33.761 | 19.348 | 39.246 | 1.00 | 16.58 | 8 |
| ATOM | 1179 | N | ILE | 150 | 35.964 | 19.453 | 39.614 | 1.00 | 16.50 | 7 |
| ATOM | 1180 | CA | ILE | 150 | 36.190 | 20.323 | 38.466 | 1.00 | 16.44 | 6 |
| ATOM | 1181 | CB | ILE | 150 | 37.593 | 20.905 | 38.582 | 1.00 | 17.41 | 6 |
| ATOM | 1182 | CG1 | ILE | 150 | 37.634 | 21.818 | 39.815 | 1.00 | 19.76 | 6 |
| ATOM | 1183 | CD1 | ILE | 150 | 39.051 | 21.983 | 40.389 | 1.00 | 23.31 | 6 |
| ATOM | 1184 | CG2 | ILE | 150 | 37.980 | 21.631 | 37.278 | 1.00 | 17.96 | 6 |
| ATOM | 1185 | C | ILE | 150 | 36.073 | 19.534 | 37.173 | 1.00 | 16.95 | 6 |
| ATOM | 1186 | O | ILE | 150 | 36.698 | 18.479 | 37.012 | 1.00 | 15.77 | 8 |
| ATOM | 1187 | N | ILE | 151 | 35.287 | 20.047 | 36.236 | 1.00 | 15.91 | 7 |
| ATOM | 1188 | CA | ILE | 151 | 35.045 | 19.331 | 34.993 | 1.00 | 16.89 | 6 |
| ATOM | 1189 | CB | ILE | 151 | 33.543 | 19.428 | 34.686 | 1.00 | 17.08 | 6 |
| ATOM | 1190 | CG1 | ILE | 151 | 32.776 | 18.973 | 35.925 | 1.00 | 18.71 | 6 |
| ATOM | 1191 | CD1 | ILE | 151 | 33.020 | 17.521 | 36.201 | 1.00 | 19.68 | 6 |
| ATOM | 1192 | CG2 | ILE | 151 | 33.150 | 18.538 | 33.473 | 1.00 | 19.18 | 6 |
| ATOM | 1193 | C | ILE | 151 | 35.791 | 20.005 | 33.879 | 1.00 | 18.47 | 6 |

APPENDIX A-continued

| ATOM | 1194 | O   | ILE | 151 | 35.706 | 21.243 | 33.771 | 1.00 | 18.48 | 8 |
| ATOM | 1195 | N   | ASP | 152 | 36.471 | 19.232 | 33.021 | 1.00 | 18.30 | 7 |
| ATOM | 1196 | CA  | ASP | 152 | 37.160 | 19.868 | 31.879 | 1.00 | 20.87 | 6 |
| ATOM | 1197 | CB  | ASP | 152 | 38.268 | 18.967 | 31.308 | 1.00 | 20.72 | 6 |
| ATOM | 1198 | CG  | ASP | 152 | 39.531 | 18.968 | 32.144 | 1.00 | 21.08 | 6 |
| ATOM | 1199 | OD1 | ASP | 152 | 39.567 | 19.608 | 33.230 | 1.00 | 21.55 | 8 |
| ATOM | 1200 | OD2 | ASP | 152 | 40.552 | 18.361 | 31.770 | 1.00 | 21.06 | 8 |
| ATOM | 1201 | C   | ASP | 152 | 36.168 | 20.171 | 30.749 | 1.00 | 21.66 | 6 |
| ATOM | 1202 | O   | ASP | 152 | 35.134 | 19.521 | 30.657 | 1.00 | 22.58 | 8 |
| ATOM | 1203 | N   | THR | 153 | 36.491 | 21.115 | 29.866 | 1.00 | 22.92 | 7 |
| ATOM | 1204 | CA  | THR | 153 | 35.613 | 21.413 | 28.726 | 1.00 | 25.56 | 6 |
| ATOM | 1205 | CB  | THR | 153 | 35.051 | 22.831 | 28.802 | 1.00 | 27.01 | 6 |
| ATOM | 1206 | OG1 | THR | 153 | 36.142 | 23.763 | 28.766 | 1.00 | 29.16 | 8 |
| ATOM | 1207 | CG2 | THR | 153 | 34.400 | 23.080 | 30.151 | 1.00 | 27.69 | 6 |
| ATOM | 1208 | C   | THR | 153 | 36.317 | 21.282 | 27.387 | 1.00 | 26.14 | 6 |
| ATOM | 1209 | O   | THR | 153 | 35.657 | 21.278 | 26.345 | 1.00 | 27.53 | 8 |
| ATOM | 1210 | N   | LYS | 154 | 37.643 | 21.208 | 27.411 | 1.00 | 25.28 | 7 |
| ATOM | 1211 | CA  | LYS | 154 | 38.424 | 21.089 | 26.174 | 1.00 | 25.72 | 6 |
| ATOM | 1212 | CB  | LYS | 154 | 39.205 | 22.366 | 25.933 | 1.00 | 26.61 | 6 |
| ATOM | 1213 | CG  | LYS | 154 | 39.896 | 22.423 | 24.592 | 1.00 | 30.17 | 6 |
| ATOM | 1214 | CD  | LYS | 154 | 40.705 | 23.712 | 24.426 | 1.00 | 38.04 | 6 |
| ATOM | 1215 | CE  | LYS | 154 | 42.170 | 23.510 | 24.849 | 1.00 | 42.25 | 6 |
| ATOM | 1216 | NZ  | LYS | 154 | 43.134 | 24.580 | 24.409 | 1.00 | 43.27 | 7 |
| ATOM | 1217 | C   | LYS | 154 | 39.383 | 19.902 | 26.177 | 1.00 | 25.11 | 6 |
| ATOM | 1218 | O   | LYS | 154 | 40.280 | 19.821 | 26.989 | 1.00 | 24.26 | 8 |
| ATOM | 1219 | N   | LEU | 155 | 39.204 | 18.997 | 25.231 | 1.00 | 24.77 | 7 |
| ATOM | 1220 | CA  | LEU | 155 | 40.053 | 17.826 | 25.159 | 1.00 | 24.50 | 6 |
| ATOM | 1221 | CB  | LEU | 155 | 39.415 | 16.806 | 24.209 | 1.00 | 24.06 | 6 |
| ATOM | 1222 | CG  | LEU | 155 | 40.094 | 15.467 | 24.055 | 1.00 | 22.89 | 6 |
| ATOM | 1223 | CD1 | LEU | 155 | 39.817 | 14.638 | 25.318 | 1.00 | 23.34 | 6 |
| ATOM | 1224 | CD2 | LEU | 155 | 39.503 | 14.772 | 22.836 | 1.00 | 27.18 | 6 |
| ATOM | 1225 | C   | LEU | 155 | 41.431 | 18.234 | 24.651 | 1.00 | 24.69 | 6 |
| ATOM | 1226 | O   | LEU | 155 | 41.545 | 18.952 | 23.664 | 1.00 | 26.57 | 8 |
| ATOM | 1227 | N   | LYS | 156 | 42.474 | 17.793 | 25.314 | 1.00 | 24.32 | 7 |
| ATOM | 1228 | CA  | LYS | 156 | 43.840 | 18.090 | 24.848 | 1.00 | 25.47 | 6 |
| ATOM | 1229 | CB  | LYS | 156 | 44.861 | 17.465 | 25.780 | 1.00 | 25.51 | 6 |
| ATOM | 1230 | CG  | LYS | 156 | 44.912 | 18.129 | 27.182 | 1.00 | 28.37 | 6 |
| ATOM | 1231 | CD  | LYS | 156 | 45.328 | 17.059 | 28.212 | 1.00 | 33.90 | 6 |
| ATOM | 1232 | CE  | LYS | 156 | 46.011 | 17.641 | 29.457 | 1.00 | 37.02 | 6 |
| ATOM | 1233 | NZ  | LYS | 156 | 45.278 | 18.807 | 30.016 | 1.00 | 37.14 | 7 |
| ATOM | 1234 | C   | LYS | 156 | 44.056 | 17.572 | 23.439 | 1.00 | 25.89 | 6 |
| ATOM | 1235 | O   | LYS | 156 | 43.329 | 16.702 | 22.990 | 1.00 | 26.06 | 8 |
| ATOM | 1236 | N   | ASP | 157 | 45.033 | 18.141 | 22.735 | 1.00 | 26.19 | 7 |
| ATOM | 1237 | CA  | ASP | 157 | 45.360 | 17.691 | 21.377 | 1.00 | 27.14 | 6 |
| ATOM | 1238 | CB  | ASP | 157 | 46.440 | 18.582 | 20.804 | 1.00 | 28.08 | 6 |
| ATOM | 1239 | CG  | ASP | 157 | 45.957 | 19.983 | 20.476 | 1.00 | 30.20 | 6 |
| ATOM | 1240 | OD1 | ASP | 157 | 44.740 | 20.301 | 20.580 | 1.00 | 33.55 | 8 |
| ATOM | 1241 | OD2 | ASP | 157 | 46.778 | 20.827 | 20.056 | 1.00 | 34.97 | 8 |
| ATOM | 1242 | C   | ASP | 157 | 45.906 | 16.258 | 21.366 | 1.00 | 26.68 | 6 |
| ATOM | 1243 | O   | ASP | 157 | 46.489 | 15.822 | 22.348 | 1.00 | 26.14 | 8 |
| ATOM | 1244 | N   | TYR | 158 | 45.740 | 15.532 | 20.260 | 1.00 | 26.68 | 7 |
| ATOM | 1245 | CA  | TYR | 158 | 46.345 | 14.199 | 20.157 | 1.00 | 27.35 | 6 |
| ATOM | 1246 | CB  | TYR | 158 | 45.781 | 13.384 | 18.995 | 1.00 | 26.84 | 6 |
| ATOM | 1247 | CG  | TYR | 158 | 45.881 | 14.042 | 17.645 | 1.00 | 28.58 | 6 |
| ATOM | 1248 | CD1 | TYR | 158 | 47.021 | 13.893 | 16.859 | 1.00 | 27.47 | 6 |
| ATOM | 1249 | CE1 | TYR | 158 | 47.113 | 14.492 | 15.623 | 1.00 | 27.60 | 6 |
| ATOM | 1250 | CZ  | TYR | 158 | 46.055 | 15.241 | 15.145 | 1.00 | 29.20 | 6 |
| ATOM | 1251 | OH  | TYR | 158 | 46.130 | 15.841 | 13.919 | 1.00 | 29.65 | 8 |
| ATOM | 1252 | CE2 | TYR | 158 | 44.918 | 15.400 | 15.898 | 1.00 | 29.94 | 6 |
| ATOM | 1253 | CD2 | TYR | 158 | 44.832 | 14.802 | 17.142 | 1.00 | 28.22 | 6 |
| ATOM | 1254 | C   | TYR | 158 | 47.853 | 14.381 | 20.052 | 1.00 | 27.02 | 6 |
| ATOM | 1255 | O   | TYR | 158 | 48.312 | 15.445 | 19.635 | 1.00 | 27.19 | 8 |
| ATOM | 1256 | N   | PRO | 159 | 48.624 | 13.358 | 20.428 | 1.00 | 26.43 | 7 |
| ATOM | 1257 | CA  | PRO | 159 | 50.084 | 13.475 | 20.475 | 1.00 | 26.68 | 6 |
| ATOM | 1258 | CB  | PRO | 159 | 50.528 | 12.118 | 21.026 | 1.00 | 27.11 | 6 |
| ATOM | 1259 | CG  | PRO | 159 | 49.267 | 11.605 | 21.765 | 1.00 | 26.14 | 6 |
| ATOM | 1260 | CD  | PRO | 159 | 48.162 | 12.021 | 20.829 | 1.00 | 26.49 | 6 |
| ATOM | 1261 | C   | PRO | 159 | 50.679 | 13.681 | 19.104 | 1.00 | 27.92 | 6 |
| ATOM | 1262 | O   | PRO | 159 | 50.086 | 13.280 | 18.102 | 1.00 | 26.74 | 8 |
| ATOM | 1263 | N   | LYS | 160 | 51.845 | 14.309 | 19.070 | 1.00 | 28.98 | 7 |
| ATOM | 1264 | CA  | LYS | 160 | 52.554 | 14.500 | 17.798 | 1.00 | 30.89 | 6 |
| ATOM | 1265 | CB  | LYS | 160 | 52.636 | 15.987 | 17.441 | 1.00 | 31.22 | 6 |
| ATOM | 1266 | CG  | LYS | 160 | 51.317 | 16.709 | 17.470 | 1.00 | 31.99 | 6 |
| ATOM | 1267 | CD  | LYS | 160 | 50.460 | 16.346 | 16.267 | 1.00 | 34.32 | 6 |
| ATOM | 1268 | CE  | LYS | 160 | 49.181 | 17.176 | 16.254 | 1.00 | 34.66 | 6 |
| ATOM | 1269 | NZ  | LYS | 160 | 48.519 | 17.228 | 17.607 | 1.00 | 36.15 | 7 |
| ATOM | 1270 | C   | LYS | 160 | 53.945 | 13.951 | 17.957 | 1.00 | 31.54 | 6 |
| ATOM | 1271 | O   | LYS | 160 | 54.450 | 13.875 | 19.077 | 1.00 | 32.03 | 8 |
| ATOM | 1272 | N   | TYR | 161 | 54.573 | 13.566 | 16.847 | 1.00 | 32.01 | 7 |

APPENDIX A-continued

| | | | | | | | | |
|---|---|---|---|---|---|---|---|---|
| ATOM | 1273 | CA | TYR | 161 | 55.924 | 13.030 | 16.910 | 1.00 33.89 6 |
| ATOM | 1274 | CB | TYR | 161 | 56.364 | 12.501 | 15.554 | 1.00 32.39 6 |
| ATOM | 1275 | CG | TYR | 161 | 55.884 | 11.118 | 15.211 | 1.00 30.55 6 |
| ATOM | 1276 | CD1 | TYR | 161 | 54.776 | 10.933 | 14.390 | 1.00 27.46 6 |
| ATOM | 1277 | CE1 | TYR | 161 | 54.353 | 9.651 | 14.040 | 1.00 29.64 6 |
| ATOM | 1278 | CZ | TYR | 161 | 55.035 | 8.534 | 14.516 | 1.00 29.20 6 |
| ATOM | 1279 | OH | TYR | 161 | 54.604 | 7.258 | 14.170 | 1.00 30.22 8 |
| ATOM | 1280 | CE2 | TYR | 161 | 56.160 | 8.705 | 15.317 | 1.00 27.79 6 |
| ATOM | 1281 | CD2 | TYR | 161 | 56.572 | 9.988 | 15.658 | 1.00 28.36 6 |
| ATOM | 1282 | C | TYR | 161 | 56.914 | 14.097 | 17.375 | 1.00 35.36 6 |
| ATOM | 1283 | O | TYR | 161 | 56.746 | 15.285 | 17.101 | 1.00 36.02 8 |
| ATOM | 1284 | N | SER | 162 | 57.929 | 13.652 | 18.102 | 1.00 37.39 7 |
| ATOM | 1285 | CA | SER | 162 | 58.987 | 14.536 | 18.593 | 1.00 39.24 6 |
| ATOM | 1286 | CB | SER | 162 | 59.585 | 13.980 | 19.874 | 1.00 39.46 6 |
| ATOM | 1287 | OG | SER | 162 | 60.604 | 13.038 | 19.545 | 1.00 40.71 8 |
| ATOM | 1288 | C | SER | 162 | 60.087 | 14.527 | 17.551 | 1.00 39.64 6 |
| ATOM | 1289 | O | SER | 162 | 60.567 | 13.447 | 17.201 | 1.00 40.73 8 |
| ATOM | 1290 | N | GLY | 165 | 62.264 | 10.745 | 16.267 | 1.00 38.26 7 |
| ATOM | 1291 | CA | GLY | 165 | 60.829 | 10.615 | 15.990 | 1.00 37.30 6 |
| ATOM | 1292 | C | GLY | 165 | 60.034 | 9.682 | 16.894 | 1.00 37.05 6 |
| ATOM | 1293 | O | GLY | 165 | 59.579 | 8.616 | 16.481 | 1.00 37.40 8 |
| ATOM | 1294 | N | ASN | 166 | 59.837 | 10.089 | 18.141 | 1.00 36.15 7 |
| ATOM | 1295 | CA | ASN | 166 | 59.081 | 9.275 | 19.086 | 1.00 35.22 6 |
| ATOM | 1296 | CB | ASN | 166 | 59.842 | 9.094 | 20.396 | 1.00 35.97 6 |
| ATOM | 1297 | CG | ASN | 166 | 61.140 | 8.328 | 20.216 | 1.00 38.88 6 |
| ATOM | 1298 | OD1 | ASN | 166 | 61.174 | 7.102 | 20.336 | 1.00 41.61 8 |
| ATOM | 1299 | ND2 | ASN | 166 | 62.219 | 9.052 | 19.941 | 1.00 41.62 7 |
| ATOM | 1300 | C | ASN | 166 | 57.758 | 9.933 | 19.378 | 1.00 33.17 6 |
| ATOM | 1301 | O | ASN | 166 | 57.598 | 11.135 | 19.196 | 1.00 32.94 8 |
| ATOM | 1302 | N | ILE | 167 | 56.809 | 9.151 | 19.862 | 1.00 32.01 7 |
| ATOM | 1303 | CA | ILE | 167 | 55.492 | 9.705 | 20.156 | 1.00 30.48 6 |
| ATOM | 1304 | CB | ILE | 167 | 54.635 | 9.659 | 18.888 | 1.00 30.83 6 |
| ATOM | 1305 | CG1 | ILE | 167 | 53.299 | 10.398 | 19.063 | 1.00 29.08 6 |
| ATOM | 1306 | CD1 | ILE | 167 | 52.600 | 10.603 | 17.723 | 1.00 27.22 6 |
| ATOM | 1307 | CG2 | ILE | 167 | 54.393 | 8.227 | 18.476 | 1.00 31.20 6 |
| ATOM | 1308 | C | ILE | 167 | 54.818 | 8.939 | 21.281 | 1.00 30.46 6 |
| ATOM | 1309 | O | ILE | 167 | 55.043 | 7.718 | 21.452 | 1.00 29.72 8 |
| ATOM | 1310 | N | ASP | 168 | 53.998 | 9.657 | 22.048 | 1.00 28.32 7 |
| ATOM | 1311 | CA | ASP | 168 | 53.266 | 9.067 | 23.135 | 1.00 28.43 6 |
| ATOM | 1312 | CB | ASP | 168 | 52.611 | 10.160 | 23.981 | 1.00 28.24 6 |
| ATOM | 1313 | CG | ASP | 168 | 53.596 | 10.924 | 24.840 | 1.00 30.13 6 |
| ATOM | 1314 | OD1 | ASP | 168 | 54.764 | 10.494 | 24.984 | 1.00 30.00 8 |
| ATOM | 1315 | OD2 | ASP | 168 | 53.266 | 11.976 | 25.430 | 1.00 33.90 8 |
| ATOM | 1316 | C | ASP | 168 | 52.163 | 8.152 | 22.603 | 1.00 27.81 6 |
| ATOM | 1317 | O | ASP | 168 | 51.678 | 8.334 | 21.501 | 1.00 27.36 8 |
| ATOM | 1318 | N | ASN | 169 | 51.713 | 7.218 | 23.432 | 1.00 27.85 7 |
| ATOM | 1319 | CA | ASN | 169 | 50.655 | 6.303 | 23.028 | 1.00 27.24 6 |
| ATOM | 1320 | CB | ASN | 169 | 50.776 | 4.955 | 23.755 | 1.00 28.25 6 |
| ATOM | 1321 | CG | ASN | 169 | 52.044 | 4.207 | 23.377 | 1.00 32.42 6 |
| ATOM | 1322 | OD1 | ASN | 169 | 52.646 | 4.474 | 22.319 | 1.00 35.24 8 |
| ATOM | 1323 | ND2 | ASN | 169 | 52.476 | 3.283 | 24.245 | 1.00 34.41 7 |
| ATOM | 1324 | C | ASN | 169 | 49.276 | 6.867 | 23.244 | 1.00 25.25 6 |
| ATOM | 1325 | O | ASN | 169 | 48.297 | 6.266 | 22.833 | 1.00 24.29 8 |
| ATOM | 1326 | N | GLY | 170 | 49.196 | 7.984 | 23.946 | 1.00 23.58 7 |
| ATOM | 1327 | CA | GLY | 170 | 47.908 | 8.597 | 24.206 | 1.00 22.58 6 |
| ATOM | 1328 | C | GLY | 170 | 48.018 | 9.794 | 25.105 | 1.00 21.55 6 |
| ATOM | 1329 | O | GLY | 170 | 49.127 | 10.269 | 25.370 | 1.00 21.45 8 |
| ATOM | 1330 | N | THR | 171 | 46.882 | 10.307 | 25.554 | 1.00 21.08 7 |
| ATOM | 1331 | CA | THR | 171 | 46.878 | 11.394 | 26.526 | 1.00 19.82 6 |
| ATOM | 1332 | CB | THR | 171 | 46.200 | 12.661 | 25.999 | 1.00 19.91 6 |
| ATOM | 1333 | OG1 | THR | 171 | 44.839 | 12.380 | 25.598 | 1.00 19.72 8 |
| ATOM | 1334 | CG2 | THR | 171 | 46.956 | 13.225 | 24.746 | 1.00 18.60 6 |
| ATOM | 1335 | C | THR | 171 | 46.166 | 10.982 | 27.810 | 1.00 19.99 6 |
| ATOM | 1336 | O | THR | 171 | 45.524 | 9.957 | 27.852 | 1.00 19.59 8 |
| ATOM | 1337 | N | SER | 172 | 46.237 | 11.822 | 28.837 | 1.00 18.17 7 |
| ATOM | 1338 | CA | SER | 172 | 45.659 | 11.418 | 30.127 | 1.00 19.93 6 |
| ATOM | 1339 | CB | SER | 172 | 46.349 | 12.171 | 31.251 | 1.00 20.25 6 |
| ATOM | 1340 | OG | SER | 172 | 47.724 | 11.791 | 31.228 | 1.00 23.89 8 |
| ATOM | 1341 | C | SER | 172 | 44.163 | 11.615 | 30.195 | 1.00 18.99 6 |
| ATOM | 1342 | O | SER | 172 | 43.661 | 12.565 | 29.648 | 1.00 18.89 8 |
| ATOM | 1343 | N | PRO | 173 | 43.451 | 10.725 | 30.874 | 1.00 18.43 7 |
| ATOM | 1344 | CA | PRO | 173 | 41.994 | 10.856 | 30.989 | 1.00 18.31 6 |
| ATOM | 1345 | CB | PRO | 173 | 41.629 | 9.738 | 31.963 | 1.00 19.50 6 |
| ATOM | 1346 | CG | PRO | 173 | 42.732 | 8.749 | 31.755 | 1.00 20.96 6 |
| ATOM | 1347 | CD | PRO | 173 | 43.962 | 9.543 | 31.585 | 1.00 19.10 6 |
| ATOM | 1348 | C | PRO | 173 | 41.588 | 12.229 | 31.554 | 1.00 18.06 6 |
| ATOM | 1349 | O | PRO | 173 | 42.118 | 12.670 | 32.563 | 1.00 17.49 8 |
| ATOM | 1350 | N | GLN | 174 | 40.672 | 12.907 | 30.876 | 1.00 16.24 7 |
| ATOM | 1351 | CA | GLN | 174 | 40.121 | 14.181 | 31.373 | 1.00 16.01 6 |

APPENDIX A-continued

| | | | | | | | | | |
|---|---|---|---|---|---|---|---|---|---|
| ATOM | 1352 | CB | GLN | 174 | 40.209 | 15.248 | 30.291 | 1.00 | 15.12 | 6 |
| ATOM | 1353 | CG | GLN | 174 | 41.617 | 15.618 | 29.920 | 1.00 | 15.95 | 6 |
| ATOM | 1354 | CD | GLN | 174 | 41.664 | 16.572 | 28.728 | 1.00 | 18.04 | 6 |
| ATOM | 1355 | OE1 | GLN | 174 | 42.097 | 16.191 | 27.642 | 1.00 | 18.71 | 8 |
| ATOM | 1356 | NE2 | GLN | 174 | 41.225 | 17.808 | 28.934 | 1.00 | 17.24 | 7 |
| ATOM | 1357 | C | GLN | 174 | 38.651 | 13.980 | 31.709 | 1.00 | 15.37 | 6 |
| ATOM | 1358 | O | GLN | 174 | 37.917 | 13.383 | 30.928 | 1.00 | 13.84 | 8 |
| ATOM | 1359 | N | LEU | 175 | 38.229 | 14.432 | 32.888 | 1.00 | 16.06 | 7 |
| ATOM | 1360 | CA | LEU | 175 | 36.830 | 14.270 | 33.282 | 1.00 | 16.37 | 6 |
| ATOM | 1361 | CB | LEU | 175 | 36.693 | 14.515 | 34.775 | 1.00 | 17.09 | 6 |
| ATOM | 1362 | CG | LEU | 175 | 35.262 | 14.372 | 35.313 | 1.00 | 16.58 | 6 |
| ATOM | 1363 | CD1 | LEU | 175 | 34.760 | 12.935 | 35.194 | 1.00 | 17.05 | 6 |
| ATOM | 1364 | CD2 | LEU | 175 | 35.250 | 14.864 | 36.760 | 1.00 | 15.02 | 6 |
| ATOM | 1365 | C | LEU | 175 | 36.004 | 15.302 | 32.552 | 1.00 | 16.74 | 6 |
| ATOM | 1366 | O | LEU | 175 | 36.123 | 16.481 | 32.845 | 1.00 | 16.94 | 8 |
| ATOM | 1367 | N | MET | 176 | 35.116 | 14.843 | 31.661 | 1.00 | 15.96 | 7 |
| ATOM | 1368 | CA | MET | 176 | 34.338 | 15.718 | 30.810 | 1.00 | 16.88 | 6 |
| ATOM | 1369 | CB | MET | 176 | 34.369 | 15.225 | 29.353 | 1.00 | 16.72 | 6 |
| ATOM | 1370 | CG | MET | 176 | 35.768 | 15.040 | 28.804 | 1.00 | 20.68 | 6 |
| ATOM | 1371 | SD | MET | 176 | 36.655 | 16.627 | 28.675 | 1.00 | 26.26 | 16 |
| ATOM | 1372 | CE | MET | 176 | 35.808 | 17.252 | 27.161 | 1.00 | 27.73 | 6 |
| ATOM | 1373 | C | MET | 176 | 32.906 | 15.819 | 31.261 | 1.00 | 16.08 | 6 |
| ATOM | 1374 | O | MET | 176 | 32.176 | 16.670 | 30.758 | 1.00 | 16.59 | 8 |
| ATOM | 1375 | N | GLY | 177 | 32.483 | 14.935 | 32.172 | 1.00 | 15.79 | 7 |
| ATOM | 1376 | CA | GLY | 177 | 31.095 | 14.954 | 32.661 | 1.00 | 15.74 | 6 |
| ATOM | 1377 | C | GLY | 177 | 30.972 | 14.129 | 33.935 | 1.00 | 15.87 | 6 |
| ATOM | 1378 | O | GLY | 177 | 31.714 | 13.162 | 34.107 | 1.00 | 14.69 | 8 |
| ATOM | 1379 | N | TRP | 178 | 30.035 | 14.499 | 34.812 | 1.00 | 15.40 | 7 |
| ATOM | 1380 | CA | TRP | 178 | 29.883 | 13.852 | 36.106 | 1.00 | 15.50 | 6 |
| ATOM | 1381 | CB | TRP | 178 | 30.852 | 14.533 | 37.081 | 1.00 | 17.06 | 6 |
| ATOM | 1382 | CG | TRP | 178 | 31.005 | 14.071 | 38.487 | 1.00 | 16.40 | 6 |
| ATOM | 1383 | CD1 | TRP | 178 | 32.071 | 13.400 | 39.007 | 1.00 | 17.19 | 6 |
| ATOM | 1384 | NE1 | TRP | 178 | 31.913 | 13.223 | 40.365 | 1.00 | 18.25 | 7 |
| ATOM | 1385 | CE2 | TRP | 178 | 30.739 | 13.806 | 40.761 | 1.00 | 17.40 | 6 |
| ATOM | 1386 | CD2 | TRP | 178 | 30.146 | 14.382 | 39.608 | 1.00 | 16.95 | 6 |
| ATOM | 1387 | CE3 | TRP | 178 | 28.919 | 15.045 | 39.741 | 1.00 | 17.55 | 6 |
| ATOM | 1388 | CZ3 | TRP | 178 | 28.346 | 15.153 | 41.006 | 1.00 | 19.07 | 6 |
| ATOM | 1389 | CH2 | TRP | 178 | 28.962 | 14.580 | 42.130 | 1.00 | 17.46 | 6 |
| ATOM | 1390 | CZ2 | TRP | 178 | 30.174 | 13.909 | 42.030 | 1.00 | 18.75 | 6 |
| ATOM | 1391 | C | TRP | 178 | 28.441 | 14.094 | 36.518 | 1.00 | 16.32 | 6 |
| ATOM | 1392 | O | TRP | 178 | 27.921 | 15.207 | 36.369 | 1.00 | 15.38 | 8 |
| ATOM | 1393 | N | THR | 179 | 27.772 | 13.068 | 37.008 | 1.00 | 15.20 | 7 |
| ATOM | 1394 | CA | THR | 179 | 26.366 | 13.262 | 37.369 | 1.00 | 15.95 | 6 |
| ATOM | 1395 | CB | THR | 179 | 25.490 | 13.246 | 36.106 | 1.00 | 16.50 | 6 |
| ATOM | 1396 | OG1 | THR | 179 | 24.149 | 13.678 | 36.402 | 1.00 | 19.50 | 8 |
| ATOM | 1397 | CG2 | THR | 179 | 25.352 | 11.828 | 35.541 | 1.00 | 18.66 | 6 |
| ATOM | 1398 | C | THR | 179 | 25.962 | 12.207 | 38.388 | 1.00 | 15.60 | 6 |
| ATOM | 1399 | O | THR | 179 | 26.597 | 11.182 | 38.487 | 1.00 | 13.95 | 8 |
| ATOM | 1400 | N | LEU | 180 | 24.939 | 12.507 | 39.178 | 1.00 | 15.33 | 7 |
| ATOM | 1401 | CA | LEU | 180 | 24.515 | 11.605 | 40.252 | 1.00 | 15.13 | 6 |
| ATOM | 1402 | CB | LEU | 180 | 24.113 | 12.417 | 41.466 | 1.00 | 15.64 | 6 |
| ATOM | 1403 | CG | LEU | 180 | 25.287 | 13.127 | 42.136 | 1.00 | 14.40 | 6 |
| ATOM | 1404 | CD1 | LEU | 180 | 24.822 | 13.887 | 43.374 | 1.00 | 17.73 | 6 |
| ATOM | 1405 | CD2 | LEU | 180 | 26.324 | 12.113 | 42.515 | 1.00 | 18.47 | 6 |
| ATOM | 1406 | C | LEU | 180 | 23.313 | 10.783 | 39.799 | 1.00 | 16.38 | 6 |
| ATOM | 1407 | O | LEU | 180 | 22.322 | 11.337 | 39.272 | 1.00 | 16.70 | 8 |
| ATOM | 1408 | N | VAL | 181 | 23.391 | 9.474 | 40.000 | 1.00 | 14.96 | 7 |
| ATOM | 1409 | CA | VAL | 181 | 22.315 | 8.601 | 39.543 | 1.00 | 14.25 | 6 |
| ATOM | 1410 | CB | VAL | 181 | 22.860 | 7.521 | 38.560 | 1.00 | 15.81 | 6 |
| ATOM | 1411 | CG1 | VAL | 181 | 21.749 | 6.518 | 38.111 | 1.00 | 15.66 | 6 |
| ATOM | 1412 | CG2 | VAL | 181 | 23.507 | 8.217 | 37.367 | 1.00 | 14.09 | 6 |
| ATOM | 1413 | C | VAL | 181 | 21.626 | 7.926 | 40.707 | 1.00 | 14.59 | 6 |
| ATOM | 1414 | O | VAL | 181 | 22.259 | 7.264 | 41.502 | 1.00 | 13.29 | 8 |
| ATOM | 1415 | N | PRO | 182 | 20.320 | 8.099 | 40.803 | 1.00 | 14.22 | 7 |
| ATOM | 1416 | CA | PRO | 182 | 19.538 | 7.427 | 41.842 | 1.00 | 14.45 | 6 |
| ATOM | 1417 | CB | PRO | 182 | 18.117 | 7.633 | 41.355 | 1.00 | 14.83 | 6 |
| ATOM | 1418 | CG | PRO | 182 | 18.155 | 9.030 | 40.713 | 1.00 | 14.85 | 6 |
| ATOM | 1419 | CD | PRO | 182 | 19.506 | 8.963 | 39.946 | 1.00 | 15.08 | 6 |
| ATOM | 1420 | C | PRO | 182 | 19.842 | 5.913 | 41.903 | 1.00 | 14.17 | 6 |
| ATOM | 1421 | O | PRO | 182 | 19.838 | 5.225 | 40.871 | 1.00 | 12.59 | 8 |
| ATOM | 1422 | N | CYS | 183 | 20.044 | 5.389 | 43.104 | 1.00 | 13.26 | 7 |
| ATOM | 1423 | CA | CYS | 183 | 20.403 | 3.988 | 43.253 | 1.00 | 14.77 | 6 |
| ATOM | 1424 | CB | CYS | 183 | 20.762 | 3.636 | 44.721 | 1.00 | 13.67 | 6 |
| ATOM | 1425 | SG | CYS | 183 | 19.397 | 3.897 | 45.878 | 1.00 | 15.75 | 16 |
| ATOM | 1426 | C | CYS | 183 | 19.324 | 3.060 | 42.705 | 1.00 | 15.38 | 6 |
| ATOM | 1427 | O | CYS | 183 | 19.652 | 1.986 | 42.248 | 1.00 | 15.57 | 8 |
| ATOM | 1428 | N | ILE | 184 | 18.062 | 3.494 | 42.726 | 1.00 | 14.66 | 7 |
| ATOM | 1429 | CA | ILE | 184 | 16.989 | 2.680 | 42.188 | 1.00 | 15.88 | 6 |
| ATOM | 1430 | CB | ILE | 184 | 15.585 | 3.306 | 42.467 | 1.00 | 15.53 | 6 |

APPENDIX A-continued

| ATOM | 1431 | CG1 | ILE | 184 | 15.530 | 4.746 | 41.944 | 1.00 | 15.99 | 6 |
|------|------|-----|-----|-----|--------|-------|--------|------|-------|---|
| ATOM | 1432 | CD1 | ILE | 184 | 14.087 | 5.326 | 41.877 | 1.00 | 16.70 | 6 |
| ATOM | 1433 | CG2 | ILE | 184 | 15.287 | 3.273 | 43.988 | 1.00 | 16.06 | 6 |
| ATOM | 1434 | C | ILE | 184 | 17.167 | 2.387 | 40.708 | 1.00 | 15.73 | 6 |
| ATOM | 1435 | O | ILE | 184 | 16.611 | 1.410 | 40.210 | 1.00 | 16.10 | 8 |
| ATOM | 1436 | N | MET | 185 | 17.924 | 3.233 | 40.013 | 1.00 | 16.27 | 7 |
| ATOM | 1437 | CA | MET | 185 | 18.157 | 3.067 | 38.578 | 1.00 | 16.20 | 6 |
| ATOM | 1438 | CB | MET | 185 | 18.278 | 4.439 | 37.913 | 1.00 | 16.13 | 6 |
| ATOM | 1439 | CG | MET | 185 | 17.020 | 5.260 | 38.023 | 1.00 | 16.35 | 6 |
| ATOM | 1440 | SD | MET | 185 | 17.284 | 6.944 | 37.497 | 1.00 | 18.18 | 16 |
| ATOM | 1441 | CE | MET | 185 | 15.793 | 7.707 | 38.150 | 1.00 | 22.35 | 6 |
| ATOM | 1442 | C | MET | 185 | 19.443 | 2.282 | 38.312 | 1.00 | 17.57 | 6 |
| ATOM | 1443 | O | MET | 185 | 19.856 | 2.124 | 37.150 | 1.00 | 18.11 | 8 |
| ATOM | 1444 | N | VAL | 186 | 20.082 | 1.815 | 39.371 | 1.00 | 16.26 | 7 |
| ATOM | 1445 | CA | VAL | 186 | 21.331 | 1.081 | 39.245 | 1.00 | 17.86 | 6 |
| ATOM | 1446 | CB | VAL | 186 | 22.435 | 1.743 | 40.082 | 1.00 | 17.41 | 6 |
| ATOM | 1447 | CG1 | VAL | 186 | 23.687 | 0.843 | 40.125 | 1.00 | 17.30 | 6 |
| ATOM | 1448 | CG2 | VAL | 186 | 22.743 | 3.126 | 39.517 | 1.00 | 16.87 | 6 |
| ATOM | 1449 | C | VAL | 186 | 21.202 | −0.354 | 39.696 | 1.00 | 19.41 | 6 |
| ATOM | 1450 | O | VAL | 186 | 20.772 | −0.601 | 40.807 | 1.00 | 20.23 | 8 |
| ATOM | 1451 | N | ASP | 187 | 21.563 | −1.298 | 38.827 | 1.00 | 19.70 | 7 |
| ATOM | 1452 | CA | ASP | 187 | 21.547 | −2.702 | 39.196 | 1.00 | 20.61 | 6 |
| ATOM | 1453 | CB | ASP | 187 | 21.138 | −3.572 | 38.002 | 1.00 | 21.92 | 6 |
| ATOM | 1454 | CG | ASP | 187 | 21.400 | −5.055 | 38.233 | 1.00 | 24.28 | 6 |
| ATOM | 1455 | OD1 | ASP | 187 | 21.152 | −5.559 | 39.352 | 1.00 | 27.34 | 8 |
| ATOM | 1456 | OD2 | ASP | 187 | 21.842 | −5.815 | 37.326 | 1.00 | 28.45 | 8 |
| ATOM | 1457 | C | ASP | 187 | 22.936 | −3.042 | 39.703 | 1.00 | 21.01 | 6 |
| ATOM | 1458 | O | ASP | 187 | 23.866 | −3.187 | 38.907 | 1.00 | 20.34 | 8 |
| ATOM | 1459 | N | ASP | 188 | 23.063 | −3.143 | 41.029 | 1.00 | 20.52 | 7 |
| ATOM | 1460 | CA | ASP | 188 | 24.338 | −3.405 | 41.715 | 1.00 | 23.36 | 6 |
| ATOM | 1461 | CB | ASP | 188 | 24.681 | −2.244 | 42.657 | 1.00 | 22.34 | 6 |
| ATOM | 1462 | CG | ASP | 188 | 26.088 | −2.354 | 43.284 | 1.00 | 22.81 | 6 |
| ATOM | 1463 | OD1 | ASP | 188 | 26.714 | −3.437 | 43.254 | 1.00 | 22.05 | 8 |
| ATOM | 1464 | OD2 | ASP | 188 | 26.641 | −1.387 | 43.835 | 1.00 | 18.74 | 8 |
| ATOM | 1465 | C | ASP | 188 | 24.143 | −4.709 | 42.488 | 1.00 | 25.35 | 6 |
| ATOM | 1466 | O | ASP | 188 | 23.692 | −4.713 | 43.638 | 1.00 | 25.11 | 8 |
| ATOM | 1467 | N | PRO | 189 | 24.448 | −5.816 | 41.816 | 1.00 | 27.44 | 7 |
| ATOM | 1468 | CA | PRO | 189 | 24.207 | −7.166 | 42.355 | 1.00 | 28.76 | 6 |
| ATOM | 1469 | CB | PRO | 189 | 24.585 | −8.074 | 41.183 | 1.00 | 29.39 | 6 |
| ATOM | 1470 | CG | PRO | 189 | 25.589 | −7.268 | 40.431 | 1.00 | 29.28 | 6 |
| ATOM | 1471 | CD | PRO | 189 | 25.010 | −5.852 | 40.452 | 1.00 | 27.89 | 6 |
| ATOM | 1472 | C | PRO | 189 | 25.052 | −7.531 | 43.572 | 1.00 | 29.51 | 6 |
| ATOM | 1473 | O | PRO | 189 | 24.782 | −8.546 | 44.222 | 1.00 | 30.88 | 8 |
| ATOM | 1474 | N | ASN | 190 | 26.056 | −6.729 | 43.883 | 1.00 | 28.01 | 7 |
| ATOM | 1475 | CA | ASN | 190 | 26.867 | −7.057 | 45.037 | 1.00 | 28.91 | 6 |
| ATOM | 1476 | CB | ASN | 190 | 28.334 | −6.836 | 44.696 | 1.00 | 29.57 | 6 |
| ATOM | 1477 | CG | ASN | 190 | 28.844 | −7.876 | 43.739 | 1.00 | 32.60 | 6 |
| ATOM | 1478 | OD1 | ASN | 190 | 28.572 | −9.045 | 43.921 | 1.00 | 35.71 | 8 |
| ATOM | 1479 | ND2 | ASN | 190 | 29.574 | −7.458 | 42.700 | 1.00 | 34.00 | 7 |
| ATOM | 1480 | C | ASN | 190 | 26.477 | −6.375 | 46.351 | 1.00 | 27.95 | 6 |
| ATOM | 1481 | O | ASN | 190 | 27.211 | −6.446 | 47.320 | 1.00 | 28.11 | 8 |
| ATOM | 1482 | N | ILE | 191 | 25.326 | −5.716 | 46.394 | 1.00 | 25.79 | 7 |
| ATOM | 1483 | CA | ILE | 191 | 24.893 | −5.074 | 47.636 | 1.00 | 25.26 | 6 |
| ATOM | 1484 | CB | ILE | 191 | 25.314 | −3.587 | 47.658 | 1.00 | 25.60 | 6 |
| ATOM | 1485 | CG1 | ILE | 191 | 25.049 | −2.966 | 49.035 | 1.00 | 25.88 | 6 |
| ATOM | 1486 | CD1 | ILE | 191 | 25.646 | −1.606 | 49.166 | 1.00 | 30.59 | 6 |
| ATOM | 1487 | CG2 | ILE | 191 | 24.600 | −2.792 | 46.599 | 1.00 | 24.20 | 6 |
| ATOM | 1488 | C | ILE | 191 | 23.389 | −5.181 | 47.701 | 1.00 | 24.63 | 6 |
| ATOM | 1489 | O | ILE | 191 | 22.760 | −5.107 | 46.670 | 1.00 | 24.77 | 8 |
| ATOM | 1490 | N | ASP | 192 | 22.794 | −5.340 | 48.886 | 1.00 | 23.49 | 7 |
| ATOM | 1491 | CA | ASP | 192 | 21.337 | −5.457 | 48.949 | 1.00 | 22.82 | 6 |
| ATOM | 1492 | CB | ASP | 192 | 20.855 | −6.138 | 50.237 | 1.00 | 25.09 | 6 |
| ATOM | 1493 | CG | ASP | 192 | 21.025 | −5.263 | 51.451 | 1.00 | 26.27 | 6 |
| ATOM | 1494 | OD1 | ASP | 192 | 22.130 | −5.266 | 52.031 | 1.00 | 34.29 | 8 |
| ATOM | 1495 | OD2 | ASP | 192 | 20.134 | −4.538 | 51.905 | 1.00 | 28.78 | 8 |
| ATOM | 1496 | C | ASP | 192 | 20.719 | −4.066 | 48.822 | 1.00 | 21.41 | 6 |
| ATOM | 1497 | O | ASP | 192 | 21.353 | −3.061 | 49.112 | 1.00 | 19.63 | 8 |
| ATOM | 1498 | N | LYS | 193 | 19.463 | −4.033 | 48.407 | 1.00 | 18.55 | 7 |
| ATOM | 1499 | CA | LYS | 193 | 18.832 | −2.778 | 48.074 | 1.00 | 18.32 | 6 |
| ATOM | 1500 | CB | LYS | 193 | 17.473 | −3.039 | 47.410 | 1.00 | 18.45 | 6 |
| ATOM | 1501 | CG | LYS | 193 | 17.598 | −3.238 | 45.863 | 1.00 | 21.28 | 6 |
| ATOM | 1502 | CD | LYS | 193 | 16.332 | −3.710 | 45.228 | 1.00 | 26.46 | 6 |
| ATOM | 1503 | CE | LYS | 193 | 16.528 | −3.854 | 43.691 | 1.00 | 25.13 | 6 |
| ATOM | 1504 | NZ | LYS | 193 | 16.607 | −2.522 | 43.100 | 1.00 | 23.54 | 7 |
| ATOM | 1505 | C | LYS | 193 | 18.700 | −1.890 | 49.309 | 1.00 | 17.76 | 6 |
| ATOM | 1506 | O | LYS | 193 | 18.876 | −0.689 | 49.228 | 1.00 | 16.66 | 8 |
| ATOM | 1507 | N | ASN | 194 | 18.366 | −2.473 | 50.449 | 1.00 | 17.55 | 7 |
| ATOM | 1508 | CA | ASN | 194 | 18.160 | −1.649 | 51.639 | 1.00 | 18.40 | 6 |
| ATOM | 1509 | CB | ASN | 194 | 17.442 | −2.424 | 52.771 | 1.00 | 18.15 | 6 |

APPENDIX A-continued

| ATOM | 1510 | CG | ASN | 194 | 16.002 | −2.792 | 52.398 | 1.00 | 21.26 | 6 |
| --- | --- | --- | --- | --- | --- | --- | --- | --- | --- | --- |
| ATOM | 1511 | OD1 | ASN | 194 | 15.423 | −2.188 | 51.498 | 1.00 | 21.02 | 8 |
| ATOM | 1512 | ND2 | ASN | 194 | 15.437 | −3.829 | 53.048 | 1.00 | 24.00 | 7 |
| ATOM | 1513 | C | ASN | 194 | 19.457 | −1.027 | 52.096 | 1.00 | 18.97 | 6 |
| ATOM | 1514 | O | ASN | 194 | 19.487 | 0.140 | 52.454 | 1.00 | 18.67 | 8 |
| ATOM | 1515 | N | THR | 195 | 20.545 | −1.788 | 52.026 | 1.00 | 19.57 | 7 |
| ATOM | 1516 | CA | THR | 195 | 21.827 | −1.263 | 52.421 | 1.00 | 20.21 | 6 |
| ATOM | 1517 | CB | THR | 195 | 22.859 | −2.377 | 52.518 | 1.00 | 21.59 | 6 |
| ATOM | 1518 | OG1 | THR | 195 | 22.397 | −3.353 | 53.461 | 1.00 | 23.22 | 8 |
| ATOM | 1519 | CG2 | THR | 195 | 24.133 | −1.843 | 53.159 | 1.00 | 23.32 | 6 |
| ATOM | 1520 | C | THR | 195 | 22.305 | −0.222 | 51.409 | 1.00 | 19.75 | 6 |
| ATOM | 1521 | O | THR | 195 | 22.922 | 0.781 | 51.774 | 1.00 | 18.92 | 8 |
| ATOM | 1522 | N | GLN | 196 | 22.008 | −0.489 | 50.141 | 1.00 | 18.42 | 7 |
| ATOM | 1523 | CA | GLN | 196 | 22.291 | 0.431 | 49.059 | 1.00 | 18.03 | 6 |
| ATOM | 1524 | CB | GLN | 196 | 21.732 | −0.155 | 47.750 | 1.00 | 17.49 | 6 |
| ATOM | 1525 | CG | GLN | 196 | 22.130 | 0.645 | 46.527 | 1.00 | 19.41 | 6 |
| ATOM | 1526 | CD | GLN | 196 | 21.429 | 0.195 | 45.274 | 1.00 | 20.21 | 6 |
| ATOM | 1527 | OE1 | GLN | 196 | 20.205 | 0.076 | 45.268 | 1.00 | 18.46 | 8 |
| ATOM | 1528 | NE2 | GLN | 196 | 22.197 | −0.054 | 44.197 | 1.00 | 18.64 | 7 |
| ATOM | 1529 | C | GLN | 196 | 21.720 | 1.849 | 49.280 | 1.00 | 17.67 | 6 |
| ATOM | 1530 | O | GLN | 196 | 22.432 | 2.862 | 49.208 | 1.00 | 16.14 | 8 |
| ATOM | 1531 | N | ILE | 197 | 20.425 | 1.929 | 49.525 | 1.00 | 15.54 | 7 |
| ATOM | 1532 | CA | ILE | 197 | 19.831 | 3.236 | 49.698 | 1.00 | 15.80 | 6 |
| ATOM | 1533 | CB | ILE | 197 | 18.285 | 3.162 | 49.634 | 1.00 | 14.73 | 6 |
| ATOM | 1534 | CG1 | ILE | 197 | 17.726 | 4.543 | 49.251 | 1.00 | 13.18 | 6 |
| ATOM | 1535 | CD1 | ILE | 197 | 16.302 | 4.493 | 48.723 | 1.00 | 14.05 | 6 |
| ATOM | 1536 | CG2 | ILE | 197 | 17.714 | 2.680 | 50.980 | 1.00 | 14.17 | 6 |
| ATOM | 1537 | C | ILE | 197 | 20.320 | 3.956 | 50.983 | 1.00 | 16.54 | 6 |
| ATOM | 1538 | O | ILE | 197 | 20.298 | 5.171 | 51.046 | 1.00 | 15.77 | 8 |
| ATOM | 1539 | N | LYS | 198 | 20.715 | 3.198 | 52.007 | 1.00 | 17.03 | 7 |
| ATOM | 1540 | CA | LYS | 198 | 21.174 | 3.793 | 53.250 | 1.00 | 20.19 | 6 |
| ATOM | 1541 | CB | LYS | 198 | 21.062 | 2.770 | 54.402 | 1.00 | 19.57 | 6 |
| ATOM | 1542 | CG | LYS | 198 | 19.656 | 2.669 | 54.878 | 1.00 | 21.77 | 6 |
| ATOM | 1543 | CD | LYS | 198 | 19.421 | 1.480 | 55.805 | 1.00 | 29.06 | 6 |
| ATOM | 1544 | CE | LYS | 198 | 20.010 | 1.671 | 57.155 | 1.00 | 32.65 | 6 |
| ATOM | 1545 | NZ | LYS | 198 | 20.282 | 0.327 | 57.775 | 1.00 | 34.79 | 7 |
| ATOM | 1546 | C | LYS | 198 | 22.592 | 4.318 | 53.179 | 1.00 | 20.71 | 6 |
| ATOM | 1547 | O | LYS | 198 | 22.933 | 5.272 | 53.895 | 1.00 | 23.08 | 8 |
| ATOM | 1548 | N | THR | 199 | 23.395 | 3.736 | 52.299 | 1.00 | 19.58 | 7 |
| ATOM | 1549 | CA | THR | 199 | 24.796 | 4.081 | 52.236 | 1.00 | 21.17 | 6 |
| ATOM | 1550 | CB | THR | 199 | 25.715 | 2.853 | 52.454 | 1.00 | 21.10 | 6 |
| ATOM | 1551 | OG1 | THR | 199 | 25.480 | 1.875 | 51.432 | 1.00 | 21.22 | 8 |
| ATOM | 1552 | CG2 | THR | 199 | 25.371 | 2.157 | 53.774 | 1.00 | 23.02 | 6 |
| ATOM | 1553 | C | THR | 199 | 25.203 | 4.765 | 50.950 | 1.00 | 19.94 | 6 |
| ATOM | 1554 | O | THR | 199 | 26.144 | 5.538 | 50.967 | 1.00 | 20.02 | 8 |
| ATOM | 1555 | N | THR | 200 | 24.529 | 4.498 | 49.834 | 1.00 | 18.23 | 7 |
| ATOM | 1556 | CA | THR | 200 | 24.946 | 5.137 | 48.588 | 1.00 | 17.33 | 6 |
| ATOM | 1557 | CB | THR | 200 | 26.011 | 4.238 | 47.840 | 1.00 | 18.32 | 6 |
| ATOM | 1558 | OG1 | THR | 200 | 26.238 | 4.738 | 46.527 | 1.00 | 16.61 | 8 |
| ATOM | 1559 | CG2 | THR | 200 | 25.467 | 2.792 | 47.569 | 1.00 | 18.26 | 6 |
| ATOM | 1560 | C | THR | 200 | 23.699 | 5.464 | 47.737 | 1.00 | 15.92 | 6 |
| ATOM | 1561 | O | THR | 200 | 23.521 | 4.965 | 46.646 | 1.00 | 15.46 | 8 |
| ATOM | 1562 | N | PRO | 201 | 22.791 | 6.267 | 48.267 | 1.00 | 15.34 | 7 |
| ATOM | 1563 | CA | PRO | 201 | 21.524 | 6.509 | 47.551 | 1.00 | 14.84 | 6 |
| ATOM | 1564 | CB | PRO | 201 | 20.759 | 7.476 | 48.472 | 1.00 | 15.38 | 6 |
| ATOM | 1565 | CG | PRO | 201 | 21.868 | 8.096 | 49.355 | 1.00 | 14.04 | 6 |
| ATOM | 1566 | CD | PRO | 201 | 22.834 | 6.969 | 49.573 | 1.00 | 16.57 | 6 |
| ATOM | 1567 | C | PRO | 201 | 21.754 | 7.136 | 46.187 | 1.00 | 14.48 | 6 |
| ATOM | 1568 | O | PRO | 201 | 20.925 | 6.979 | 45.313 | 1.00 | 12.64 | 8 |
| ATOM | 1569 | N | TYR | 202 | 22.847 | 7.878 | 46.039 | 1.00 | 12.86 | 7 |
| ATOM | 1570 | CA | TYR | 202 | 23.244 | 8.352 | 44.713 | 1.00 | 12.75 | 6 |
| ATOM | 1571 | CB | TYR | 202 | 23.329 | 9.874 | 44.648 | 1.00 | 11.68 | 6 |
| ATOM | 1572 | CG | TYR | 202 | 21.968 | 10.515 | 44.732 | 1.00 | 12.75 | 6 |
| ATOM | 1573 | CD1 | TYR | 202 | 21.402 | 10.850 | 45.980 | 1.00 | 13.47 | 6 |
| ATOM | 1574 | CE1 | TYR | 202 | 20.115 | 11.452 | 46.071 | 1.00 | 12.76 | 6 |
| ATOM | 1575 | CZ | TYR | 202 | 19.408 | 11.669 | 44.892 | 1.00 | 12.83 | 6 |
| ATOM | 1576 | OH | TYR | 202 | 18.147 | 12.203 | 44.914 | 1.00 | 12.82 | 8 |
| ATOM | 1577 | CE2 | TYR | 202 | 19.947 | 11.318 | 43.658 | 1.00 | 13.44 | 6 |
| ATOM | 1578 | CD2 | TYR | 202 | 21.213 | 10.726 | 43.581 | 1.00 | 13.31 | 6 |
| ATOM | 1579 | C | TYR | 202 | 24.564 | 7.774 | 44.300 | 1.00 | 13.47 | 6 |
| ATOM | 1580 | O | TYR | 202 | 25.543 | 7.843 | 45.053 | 1.00 | 14.13 | 8 |
| ATOM | 1581 | N | TYR | 203 | 24.600 | 7.197 | 43.100 | 1.00 | 13.41 | 7 |
| ATOM | 1582 | CA | TYR | 203 | 25.880 | 6.719 | 42.534 | 1.00 | 14.01 | 6 |
| ATOM | 1583 | CB | TYR | 203 | 25.634 | 5.508 | 41.608 | 1.00 | 14.85 | 6 |
| ATOM | 1584 | CG | TYR | 203 | 25.449 | 4.189 | 42.366 | 1.00 | 17.12 | 6 |
| ATOM | 1585 | CD1 | TYR | 203 | 24.420 | 4.029 | 43.283 | 1.00 | 16.86 | 6 |
| ATOM | 1586 | CE1 | TYR | 203 | 24.266 | 2.829 | 44.003 | 1.00 | 16.88 | 6 |
| ATOM | 1587 | CZ | TYR | 203 | 25.140 | 1.784 | 43.736 | 1.00 | 17.25 | 6 |
| ATOM | 1588 | OH | TYR | 203 | 25.006 | 0.593 | 44.395 | 1.00 | 18.37 | 8 |

APPENDIX A-continued

| | | | | | | | | |
|---|---|---|---|---|---|---|---|---|
| ATOM | 1589 CE2 | TYR | 203 | 26.182 | 1.931 | 42.797 | 1.00 17.85 | 6 |
| ATOM | 1590 CD2 | TYR | 203 | 26.324 | 3.098 | 42.136 | 1.00 16.90 | 6 |
| ATOM | 1591 C | TYR | 203 | 26.474 | 7.835 | 41.703 | 1.00 14.48 | 6 |
| ATOM | 1592 O | TYR | 203 | 25.742 | 8.704 | 41.210 | 1.00 15.97 | 8 |
| ATOM | 1593 N | ILE | 204 | 27.792 | 7.800 | 41.491 | 1.00 14.35 | 7 |
| ATOM | 1594 CA | ILE | 204 | 28.474 | 8.765 | 40.648 | 1.00 15.03 | 6 |
| ATOM | 1595 CB | ILE | 204 | 29.793 | 9.202 | 41.313 | 1.00 15.33 | 6 |
| ATOM | 1596 CG1 | ILE | 204 | 29.503 | 9.892 | 42.631 | 1.00 15.85 | 6 |
| ATOM | 1597 CD1 | ILE | 204 | 30.781 | 10.048 | 43.521 | 1.00 20.79 | 6 |
| ATOM | 1598 CG2 | ILE | 204 | 30.578 | 10.212 | 40.428 | 1.00 16.51 | 6 |
| ATOM | 1599 C | ILE | 204 | 28.783 | 8.134 | 39.295 | 1.00 15.34 | 6 |
| ATOM | 1600 O | ILE | 204 | 29.416 | 7.074 | 39.200 | 1.00 15.30 | 8 |
| ATOM | 1601 N | LEU | 205 | 28.296 | 8.769 | 38.247 | 1.00 15.60 | 7 |
| ATOM | 1602 CA | LEU | 205 | 28.570 | 8.319 | 36.873 | 1.00 16.24 | 6 |
| ATOM | 1603 CB | LEU | 205 | 27.245 | 8.103 | 36.126 | 1.00 16.26 | 6 |
| ATOM | 1604 CG | LEU | 205 | 27.293 | 7.736 | 34.644 | 1.00 17.47 | 6 |
| ATOM | 1605 CD1 | LEU | 205 | 28.196 | 6.520 | 34.385 | 1.00 17.58 | 6 |
| ATOM | 1606 CD2 | LEU | 205 | 25.866 | 7.512 | 34.090 | 1.00 17.63 | 6 |
| ATOM | 1607 C | LEU | 205 | 29.478 | 9.402 | 36.212 | 1.00 16.27 | 6 |
| ATOM | 1608 O | LEU | 205 | 29.128 | 10.591 | 36.117 | 1.00 15.58 | 8 |
| ATOM | 1609 N | LYS | 206 | 30.666 | 8.971 | 35.793 | 1.00 16.06 | 7 |
| ATOM | 1610 CA | LYS | 206 | 31.656 | 9.863 | 35.235 | 1.00 15.79 | 6 |
| ATOM | 1611 CB | LYS | 206 | 33.002 | 9.598 | 35.902 | 1.00 16.54 | 6 |
| ATOM | 1612 CG | LYS | 206 | 33.011 | 9.671 | 37.397 | 1.00 16.83 | 6 |
| ATOM | 1613 CD | LYS | 206 | 34.456 | 9.672 | 37.886 | 1.00 17.57 | 6 |
| ATOM | 1614 CE | LYS | 206 | 34.535 | 9.542 | 39.389 | 1.00 19.31 | 6 |
| ATOM | 1615 NZ | LYS | 206 | 35.908 | 9.651 | 39.898 | 1.00 19.88 | 7 |
| ATOM | 1616 C | LYS | 206 | 31.859 | 9.525 | 33.791 | 1.00 16.67 | 6 |
| ATOM | 1617 O | LYS | 206 | 31.715 | 8.348 | 33.392 | 1.00 16.36 | 8 |
| ATOM | 1618 N | LYS | 207 | 32.210 | 10.552 | 33.026 | 1.00 16.62 | 7 |
| ATOM | 1619 CA | LYS | 207 | 32.628 | 10.386 | 31.625 | 1.00 17.29 | 6 |
| ATOM | 1620 CB | LYS | 207 | 31.655 | 11.023 | 30.625 | 1.00 17.58 | 6 |
| ATOM | 1621 CG | LYS | 207 | 31.928 | 10.518 | 29.203 | 1.00 19.44 | 6 |
| ATOM | 1622 CD | LYS | 207 | 31.120 | 11.237 | 28.084 | 1.00 20.03 | 6 |
| ATOM | 1623 CE | LYS | 207 | 31.710 | 12.609 | 27.739 | 1.00 22.38 | 6 |
| ATOM | 1624 NZ | LYS | 207 | 30.961 | 13.286 | 26.624 | 1.00 23.62 | 7 |
| ATOM | 1625 C | LYS | 207 | 34.009 | 10.997 | 31.412 | 1.00 17.59 | 6 |
| ATOM | 1626 O | LYS | 207 | 34.170 | 12.219 | 31.536 | 1.00 17.66 | 8 |
| ATOM | 1627 N | TYR | 208 | 34.999 | 10.151 | 31.115 | 1.00 16.17 | 7 |
| ATOM | 1628 CA | TYR | 208 | 36.342 | 10.600 | 30.805 | 1.00 16.91 | 6 |
| ATOM | 1629 CB | TYR | 208 | 37.378 | 9.715 | 31.481 | 1.00 17.36 | 6 |
| ATOM | 1630 CG | TYR | 208 | 37.432 | 9.826 | 32.992 | 1.00 17.74 | 6 |
| ATOM | 1631 CD1 | TYR | 208 | 36.812 | 8.880 | 33.818 | 1.00 17.10 | 6 |
| ATOM | 1632 CE1 | TYR | 208 | 36.866 | 9.006 | 35.226 | 1.00 18.57 | 6 |
| ATOM | 1633 CZ | TYR | 208 | 37.541 | 10.035 | 35.790 | 1.00 16.59 | 6 |
| ATOM | 1634 OH | TYR | 208 | 37.619 | 10.157 | 37.187 | 1.00 16.71 | 8 |
| ATOM | 1635 CE2 | TYR | 208 | 38.161 | 10.967 | 34.993 | 1.00 17.50 | 6 |
| ATOM | 1636 CD2 | TYR | 208 | 38.103 | 10.869 | 33.603 | 1.00 17.58 | 6 |
| ATOM | 1637 C | TYR | 208 | 36.577 | 10.464 | 29.329 | 1.00 17.15 | 6 |
| ATOM | 1638 O | TYR | 208 | 36.025 | 9.555 | 28.679 | 1.00 17.78 | 8 |
| ATOM | 1639 N | GLN | 209 | 37.388 | 11.366 | 28.786 | 1.00 17.00 | 7 |
| ATOM | 1640 CA | GLN | 209 | 37.837 | 11.229 | 27.401 | 1.00 17.42 | 6 |
| ATOM | 1641 CB | GLN | 209 | 37.087 | 12.155 | 26.452 | 1.00 17.37 | 6 |
| ATOM | 1642 CG | GLN | 209 | 35.630 | 11.758 | 26.256 | 1.00 18.75 | 6 |
| ATOM | 1643 CD | GLN | 209 | 34.891 | 12.725 | 25.352 | 1.00 19.68 | 6 |
| ATOM | 1644 OE1 | GLN | 209 | 35.072 | 13.937 | 25.455 | 1.00 20.29 | 8 |
| ATOM | 1645 NE2 | GLN | 209 | 34.039 | 12.191 | 24.469 | 1.00 20.98 | 7 |
| ATOM | 1646 C | GLN | 209 | 39.342 | 11.472 | 27.361 | 1.00 18.49 | 6 |
| ATOM | 1647 O | GLN | 209 | 39.898 | 12.106 | 28.265 | 1.00 18.67 | 8 |
| ATOM | 1648 N | TYR | 210 | 39.983 | 10.913 | 26.345 | 1.00 17.69 | 7 |
| ATOM | 1649 CA | TYR | 210 | 41.412 | 11.022 | 26.132 | 1.00 19.64 | 6 |
| ATOM | 1650 CB | TYR | 210 | 42.194 | 10.280 | 27.221 | 1.00 19.01 | 6 |
| ATOM | 1651 CG | TYR | 210 | 41.753 | 8.855 | 27.488 | 1.00 20.14 | 6 |
| ATOM | 1652 CD1 | TYR | 210 | 42.422 | 7.772 | 26.924 | 1.00 21.18 | 6 |
| ATOM | 1653 CE1 | TYR | 210 | 42.013 | 6.440 | 27.210 | 1.00 23.11 | 6 |
| ATOM | 1654 CZ | TYR | 210 | 40.954 | 6.236 | 28.081 | 1.00 23.28 | 6 |
| ATOM | 1655 OH | TYR | 210 | 40.504 | 4.969 | 28.398 | 1.00 26.89 | 8 |
| ATOM | 1656 CE2 | TYR | 210 | 40.306 | 7.293 | 28.636 | 1.00 21.46 | 6 |
| ATOM | 1657 CD2 | TYR | 210 | 40.691 | 8.588 | 28.349 | 1.00 21.44 | 6 |
| ATOM | 1658 C | TYR | 210 | 41.722 | 10.409 | 24.768 | 1.00 19.89 | 6 |
| ATOM | 1659 O | TYR | 210 | 40.871 | 9.740 | 24.178 | 1.00 20.54 | 8 |
| ATOM | 1660 N | TRP | 211 | 42.924 | 10.644 | 24.269 | 1.00 19.87 | 7 |
| ATOM | 1661 CA | TRP | 211 | 43.360 | 10.051 | 23.020 | 1.00 20.07 | 6 |
| ATOM | 1662 CB | TRP | 211 | 44.258 | 11.049 | 22.280 | 1.00 20.27 | 6 |
| ATOM | 1663 CG | TRP | 211 | 43.539 | 12.272 | 21.774 | 1.00 20.99 | 6 |
| ATOM | 1664 CD1 | TRP | 211 | 43.507 | 13.518 | 22.350 | 1.00 22.21 | 6 |
| ATOM | 1665 NE1 | TRP | 211 | 42.766 | 14.381 | 21.572 | 1.00 22.20 | 7 |
| ATOM | 1666 CE2 | TRP | 211 | 42.278 | 13.696 | 20.485 | 1.00 22.58 | 6 |
| ATOM | 1667 CD2 | TRP | 211 | 42.751 | 12.364 | 20.577 | 1.00 22.15 | 6 |

APPENDIX A-continued

| ATOM | 1668 | CE3 | TRP | 211 | 42.443 | 11.467 | 19.538 | 1.00 | 22.37 | 6 |
| --- | --- | --- | --- | --- | --- | --- | --- | --- | --- | --- |
| ATOM | 1669 | CZ3 | TRP | 211 | 41.623 | 11.924 | 18.459 | 1.00 | 20.26 | 6 |
| ATOM | 1670 | CH2 | TRP | 211 | 41.170 | 13.238 | 18.420 | 1.00 | 20.59 | 6 |
| ATOM | 1671 | CZ2 | TRP | 211 | 41.486 | 14.144 | 19.421 | 1.00 | 23.41 | 6 |
| ATOM | 1672 | C | TRP | 211 | 44.166 | 8.776 | 23.316 | 1.00 | 20.89 | 6 |
| ATOM | 1673 | O | TRP | 211 | 44.824 | 8.696 | 24.349 | 1.00 | 19.07 | 8 |
| ATOM | 1674 | N | GLN | 212 | 44.113 | 7.808 | 22.386 | 1.00 | 21.38 | 7 |
| ATOM | 1675 | CA | GLN | 212 | 44.844 | 6.554 | 22.437 | 1.00 | 22.82 | 6 |
| ATOM | 1676 | CB | GLN | 212 | 43.983 | 5.478 | 23.124 | 1.00 | 23.89 | 6 |
| ATOM | 1677 | CG | GLN | 212 | 44.693 | 4.156 | 23.369 | 1.00 | 27.07 | 6 |
| ATOM | 1678 | CD | GLN | 212 | 43.814 | 3.172 | 24.160 | 1.00 | 32.04 | 6 |
| ATOM | 1679 | OE1 | GLN | 212 | 43.444 | 2.100 | 23.651 | 1.00 | 36.71 | 8 |
| ATOM | 1680 | NE2 | GLN | 212 | 43.464 | 3.541 | 25.388 | 1.00 | 31.85 | 7 |
| ATOM | 1681 | C | GLN | 212 | 45.183 | 6.072 | 21.013 | 1.00 | 23.23 | 6 |
| ATOM | 1682 | O | GLN | 212 | 44.365 | 6.180 | 20.116 | 1.00 | 22.16 | 8 |
| ATOM | 1683 | N | ARG | 213 | 46.387 | 5.537 | 20.834 | 1.00 | 23.20 | 7 |
| ATOM | 1684 | CA | ARG | 213 | 46.843 | 4.985 | 19.567 | 1.00 | 25.15 | 6 |
| ATOM | 1685 | CB | ARG | 213 | 48.195 | 4.287 | 19.811 | 1.00 | 25.54 | 6 |
| ATOM | 1686 | CG | ARG | 213 | 48.623 | 3.262 | 18.773 | 1.00 | 32.65 | 6 |
| ATOM | 1687 | CD | ARG | 213 | 49.917 | 2.513 | 19.149 | 1.00 | 37.93 | 6 |
| ATOM | 1688 | NE | ARG | 213 | 49.958 | 1.174 | 18.561 | 1.00 | 45.55 | 7 |
| ATOM | 1689 | CZ | ARG | 213 | 51.071 | 0.466 | 18.377 | 1.00 | 49.11 | 6 |
| ATOM | 1690 | NH1 | ARG | 213 | 52.252 | 0.977 | 18.725 | 1.00 | 52.11 | 7 |
| ATOM | 1691 | NH2 | ARG | 213 | 51.009 | −0.751 | 17.840 | 1.00 | 49.68 | 7 |
| ATOM | 1692 | C | ARG | 213 | 45.828 | 3.987 | 19.028 | 1.00 | 24.43 | 6 |
| ATOM | 1693 | O | ARG | 213 | 45.296 | 3.191 | 19.775 | 1.00 | 22.88 | 8 |
| ATOM | 1694 | N | ALA | 214 | 45.532 | 4.051 | 17.736 | 1.00 | 24.12 | 7 |
| ATOM | 1695 | CA | ALA | 214 | 44.622 | 3.085 | 17.134 | 1.00 | 24.94 | 6 |
| ATOM | 1696 | CB | ALA | 214 | 44.004 | 3.658 | 15.912 | 1.00 | 24.80 | 6 |
| ATOM | 1697 | C | ALA | 214 | 45.404 | 1.831 | 16.771 | 1.00 | 25.87 | 6 |
| ATOM | 1698 | O | ALA | 214 | 46.409 | 1.900 | 16.055 | 1.00 | 26.64 | 8 |
| ATOM | 1699 | N | VAL | 215 | 44.935 | 0.692 | 17.254 | 1.00 | 26.50 | 7 |
| ATOM | 1700 | CA | VAL | 215 | 45.574 | −0.576 | 16.988 | 1.00 | 27.37 | 6 |
| ATOM | 1701 | CB | VAL | 215 | 44.893 | −1.732 | 17.778 | 1.00 | 27.35 | 6 |
| ATOM | 1702 | CG1 | VAL | 215 | 45.651 | −3.047 | 17.566 | 1.00 | 29.27 | 6 |
| ATOM | 1703 | CG2 | VAL | 215 | 44.765 | −1.402 | 19.296 | 1.00 | 28.76 | 6 |
| ATOM | 1704 | C | VAL | 215 | 45.539 | −0.825 | 15.464 | 1.00 | 27.93 | 6 |
| ATOM | 1705 | O | VAL | 215 | 44.474 | −0.733 | 14.815 | 1.00 | 28.82 | 8 |
| ATOM | 1706 | N | GLY | 216 | 46.711 | −1.086 | 14.900 | 1.00 | 28.32 | 7 |
| ATOM | 1707 | CA | GLY | 216 | 46.892 | −1.370 | 13.480 | 1.00 | 28.08 | 6 |
| ATOM | 1708 | C | GLY | 216 | 47.341 | −0.157 | 12.663 | 1.00 | 28.31 | 6 |
| ATOM | 1709 | O | GLY | 216 | 47.745 | −0.286 | 11.487 | 1.00 | 28.90 | 8 |
| ATOM | 1710 | N | SER | 217 | 47.311 | 1.024 | 13.283 | 1.00 | 27.05 | 7 |
| ATOM | 1711 | CA | SER | 217 | 47.568 | 2.265 | 12.561 | 1.00 | 27.33 | 6 |
| ATOM | 1712 | CB | SER | 217 | 46.797 | 3.428 | 13.226 | 1.00 | 27.14 | 6 |
| ATOM | 1713 | OG | SER | 217 | 47.447 | 3.842 | 14.421 | 1.00 | 25.68 | 8 |
| ATOM | 1714 | C | SER | 217 | 49.042 | 2.668 | 12.389 | 1.00 | 27.40 | 6 |
| ATOM | 1715 | O | SER | 217 | 49.325 | 3.652 | 11.716 | 1.00 | 27.19 | 8 |
| ATOM | 1716 | N | ASN | 218 | 49.974 | 1.977 | 13.031 | 1.00 | 27.99 | 7 |
| ATOM | 1717 | CA | ASN | 218 | 51.377 | 2.362 | 12.874 | 1.00 | 30.21 | 6 |
| ATOM | 1718 | CB | ASN | 218 | 52.240 | 1.963 | 14.086 | 1.00 | 31.64 | 6 |
| ATOM | 1719 | CG | ASN | 218 | 53.666 | 2.572 | 14.061 | 1.00 | 36.67 | 6 |
| ATOM | 1720 | OD1 | ASN | 218 | 53.916 | 3.676 | 13.516 | 1.00 | 40.29 | 8 |
| ATOM | 1721 | ND2 | ASN | 218 | 54.614 | 1.842 | 14.665 | 1.00 | 39.01 | 7 |
| ATOM | 1722 | C | ASN | 218 | 51.847 | 1.774 | 11.554 | 1.00 | 29.56 | 6 |
| ATOM | 1723 | O | ASN | 218 | 51.875 | 0.555 | 11.353 | 1.00 | 29.00 | 8 |
| ATOM | 1724 | N | VAL | 219 | 52.186 | 2.658 | 10.633 | 1.00 | 28.68 | 7 |
| ATOM | 1725 | CA | VAL | 219 | 52.527 | 2.237 | 9.283 | 1.00 | 29.03 | 6 |
| ATOM | 1726 | CB | VAL | 219 | 51.479 | 2.736 | 8.309 | 1.00 | 29.36 | 6 |
| ATOM | 1727 | CG1 | VAL | 219 | 51.823 | 2.293 | 6.891 | 1.00 | 32.10 | 6 |
| ATOM | 1728 | CG2 | VAL | 219 | 50.090 | 2.212 | 8.706 | 1.00 | 31.22 | 6 |
| ATOM | 1729 | C | VAL | 219 | 53.846 | 2.840 | 8.867 | 1.00 | 28.66 | 6 |
| ATOM | 1730 | O | VAL | 219 | 54.119 | 3.990 | 9.178 | 1.00 | 28.74 | 8 |
| ATOM | 1731 | N | ALA | 220 | 54.678 | 2.043 | 8.207 | 1.00 | 28.25 | 7 |
| ATOM | 1732 | CA | ALA | 220 | 55.966 | 2.502 | 7.678 | 1.00 | 28.76 | 6 |
| ATOM | 1733 | CB | ALA | 220 | 57.071 | 1.558 | 8.087 | 1.00 | 28.43 | 6 |
| ATOM | 1734 | C | ALA | 220 | 55.871 | 2.558 | 6.170 | 1.00 | 28.65 | 6 |
| ATOM | 1735 | O | ALA | 220 | 55.498 | 1.566 | 5.536 | 1.00 | 28.80 | 8 |
| ATOM | 1736 | N | LEU | 221 | 56.211 | 3.705 | 5.597 | 1.00 | 28.03 | 7 |
| ATOM | 1737 | CA | LEU | 221 | 56.172 | 3.876 | 4.157 | 1.00 | 27.74 | 6 |
| ATOM | 1738 | CB | LEU | 221 | 55.209 | 4.998 | 3.752 | 1.00 | 27.89 | 6 |
| ATOM | 1739 | CG | LEU | 221 | 53.737 | 4.722 | 4.052 | 1.00 | 30.03 | 6 |
| ATOM | 1740 | CD1 | LEU | 221 | 53.393 | 5.216 | 5.427 | 1.00 | 31.93 | 6 |
| ATOM | 1741 | CD2 | LEU | 221 | 52.856 | 5.363 | 3.015 | 1.00 | 33.00 | 6 |
| ATOM | 1742 | C | LEU | 221 | 57.525 | 4.175 | 3.549 | 1.00 | 26.88 | 6 |
| ATOM | 1743 | O | LEU | 221 | 58.306 | 4.975 | 4.077 | 1.00 | 26.12 | 8 |
| ATOM | 1744 | N | ARG | 222 | 57.782 | 3.562 | 2.405 | 1.00 | 26.03 | 7 |
| ATOM | 1745 | CA | ARG | 222 | 58.977 | 3.888 | 1.654 | 1.00 | 26.10 | 6 |
| ATOM | 1746 | CB | ARG | 222 | 59.411 | 2.677 | 0.811 | 1.00 | 26.06 | 6 |

APPENDIX A-continued

| ATOM | 1747 | CG | ARG | 222 | 59.556 | 1.415 | 1.669 | 1.00 | 27.44 | 6 |
|---|---|---|---|---|---|---|---|---|---|---|
| ATOM | 1748 | CD | ARG | 222 | 60.504 | 0.362 | 1.087 | 1.00 | 27.98 | 6 |
| ATOM | 1749 | NE | ARG | 222 | 60.078 | −0.134 | −0.210 | 1.00 | 28.02 | 7 |
| ATOM | 1750 | CZ | ARG | 222 | 60.749 | −1.076 | −0.874 | 1.00 | 27.88 | 6 |
| ATOM | 1751 | NH1 | ARG | 222 | 61.823 | −1.598 | −0.326 | 1.00 | 27.27 | 7 |
| ATOM | 1752 | NH2 | ARG | 222 | 60.368 | −1.498 | −2.066 | 1.00 | 25.57 | 7 |
| ATOM | 1753 | C | ARG | 222 | 58.662 | 5.097 | 0.763 | 1.00 | 25.95 | 6 |
| ATOM | 1754 | O | ARG | 222 | 57.519 | 5.536 | 0.696 | 1.00 | 24.79 | 8 |
| ATOM | 1755 | N | PRO | 223 | 59.667 | 5.653 | 0.097 | 1.00 | 27.28 | 7 |
| ATOM | 1756 | CA | PRO | 223 | 59.423 | 6.764 | −0.827 | 1.00 | 27.86 | 6 |
| ATOM | 1757 | CB | PRO | 223 | 60.810 | 7.019 | −1.456 | 1.00 | 28.54 | 6 |
| ATOM | 1758 | CG | PRO | 223 | 61.776 | 6.531 | −0.440 | 1.00 | 28.30 | 6 |
| ATOM | 1759 | CD | PRO | 223 | 61.101 | 5.314 | 0.201 | 1.00 | 26.38 | 6 |
| ATOM | 1760 | C | PRO | 223 | 58.417 | 6.421 | −1.916 | 1.00 | 28.83 | 6 |
| ATOM | 1761 | O | PRO | 223 | 58.396 | 5.304 | −2.464 | 1.00 | 28.39 | 8 |
| ATOM | 1762 | N | HIS | 224 | 57.553 | 7.392 | −2.198 | 1.00 | 30.30 | 7 |
| ATOM | 1763 | CA | HIS | 224 | 56.664 | 7.351 | −3.359 | 1.00 | 31.30 | 6 |
| ATOM | 1764 | CB | HIS | 224 | 57.481 | 7.427 | −4.670 | 1.00 | 31.76 | 6 |
| ATOM | 1765 | CG | HIS | 224 | 58.239 | 8.715 | −4.844 | 1.00 | 33.09 | 6 |
| ATOM | 1766 | ND1 | HIS | 224 | 57.617 | 9.944 | −4.933 | 1.00 | 35.10 | 7 |
| ATOM | 1767 | CE1 | HIS | 224 | 58.532 | 10.891 | −5.074 | 1.00 | 33.65 | 6 |
| ATOM | 1768 | NE2 | HIS | 224 | 59.724 | 10.321 | −5.074 | 1.00 | 32.34 | 7 |
| ATOM | 1769 | CD2 | HIS | 224 | 59.570 | 8.963 | −4.925 | 1.00 | 32.51 | 6 |
| ATOM | 1770 | C | HIS | 224 | 55.731 | 6.152 | −3.376 | 1.00 | 32.32 | 6 |
| ATOM | 1771 | O | HIS | 224 | 55.645 | 5.434 | −4.358 | 1.00 | 31.53 | 8 |
| ATOM | 1772 | N | GLU | 225 | 55.013 | 5.939 | −2.292 | 1.00 | 33.33 | 7 |
| ATOM | 1773 | CA | GLU | 225 | 54.083 | 4.824 | −2.298 | 1.00 | 34.83 | 6 |
| ATOM | 1774 | CB | GLU | 225 | 54.767 | 3.537 | −1.835 | 1.00 | 34.87 | 6 |
| ATOM | 1775 | CG | GLU | 225 | 55.030 | 3.462 | −0.332 | 1.00 | 36.43 | 6 |
| ATOM | 1776 | CD | GLU | 225 | 55.407 | 2.041 | 0.074 | 1.00 | 39.00 | 6 |
| ATOM | 1777 | OE1 | GLU | 225 | 55.239 | 1.157 | −0.800 | 1.00 | 39.68 | 8 |
| ATOM | 1778 | OE2 | GLU | 225 | 55.878 | 1.798 | 1.215 | 1.00 | 36.77 | 8 |
| ATOM | 1779 | C | GLU | 225 | 52.905 | 5.122 | −1.406 | 1.00 | 34.59 | 6 |
| ATOM | 1780 | O | GLU | 225 | 53.010 | 5.933 | −0.493 | 1.00 | 33.98 | 8 |
| ATOM | 1781 | N | LYS | 226 | 51.786 | 4.466 | −1.711 | 1.00 | 35.26 | 7 |
| ATOM | 1782 | CA | LYS | 226 | 50.584 | 4.518 | −0.900 | 1.00 | 36.61 | 6 |
| ATOM | 1783 | CB | LYS | 226 | 49.333 | 4.649 | −1.775 | 1.00 | 37.95 | 6 |
| ATOM | 1784 | CG | LYS | 226 | 49.396 | 5.708 | −2.898 | 1.00 | 41.54 | 6 |
| ATOM | 1785 | CD | LYS | 226 | 47.973 | 5.908 | −3.492 | 1.00 | 45.54 | 6 |
| ATOM | 1786 | CE | LYS | 226 | 47.809 | 7.220 | −4.292 | 1.00 | 46.19 | 6 |
| ATOM | 1787 | NZ | LYS | 226 | 46.384 | 7.404 | −4.764 | 1.00 | 46.30 | 7 |
| ATOM | 1788 | C | LYS | 226 | 50.542 | 3.157 | −0.232 | 1.00 | 36.32 | 6 |
| ATOM | 1789 | O | LYS | 226 | 50.990 | 2.161 | −0.799 | 1.00 | 35.40 | 8 |
| ATOM | 1790 | N | LYS | 227 | 50.007 | 3.093 | 0.971 | 1.00 | 36.67 | 7 |
| ATOM | 1791 | CA | LYS | 227 | 49.945 | 1.813 | 1.655 | 1.00 | 37.33 | 6 |
| ATOM | 1792 | CB | LYS | 227 | 51.032 | 1.731 | 2.723 | 1.00 | 38.30 | 6 |
| ATOM | 1793 | CG | LYS | 227 | 51.693 | 0.372 | 2.826 | 1.00 | 40.14 | 6 |
| ATOM | 1794 | CD | LYS | 227 | 52.677 | 0.326 | 3.979 | 1.00 | 43.62 | 6 |
| ATOM | 1795 | CE | LYS | 227 | 53.679 | −0.809 | 3.811 | 1.00 | 44.98 | 6 |
| ATOM | 1796 | NZ | LYS | 227 | 54.603 | −0.882 | 4.983 | 1.00 | 46.10 | 7 |
| ATOM | 1797 | C | LYS | 227 | 48.584 | 1.707 | 2.279 | 1.00 | 36.97 | 6 |
| ATOM | 1798 | O | LYS | 227 | 48.123 | 2.639 | 2.917 | 1.00 | 35.01 | 8 |
| ATOM | 1799 | N | SER | 228 | 47.923 | 0.584 | 2.029 | 1.00 | 37.33 | 7 |
| ATOM | 1800 | CA | SER | 228 | 46.607 | 0.340 | 2.566 | 1.00 | 38.11 | 6 |
| ATOM | 1801 | CB | SER | 228 | 45.807 | −0.569 | 1.616 | 1.00 | 38.92 | 6 |
| ATOM | 1802 | OG | SER | 228 | 44.433 | −0.567 | 1.986 | 1.00 | 40.25 | 8 |
| ATOM | 1803 | C | SER | 228 | 46.772 | −0.302 | 3.933 | 1.00 | 37.94 | 6 |
| ATOM | 1804 | O | SER | 228 | 47.727 | −1.043 | 4.174 | 1.00 | 38.11 | 8 |
| ATOM | 1805 | N | TYR | 229 | 45.859 | 0.011 | 4.845 | 1.00 | 36.61 | 7 |
| ATOM | 1806 | CA | TYR | 229 | 45.925 | −0.582 | 6.164 | 1.00 | 36.21 | 6 |
| ATOM | 1807 | CB | TYR | 229 | 46.976 | 0.130 | 7.028 | 1.00 | 36.06 | 6 |
| ATOM | 1808 | CG | TYR | 229 | 46.601 | 1.529 | 7.470 | 1.00 | 34.52 | 6 |
| ATOM | 1809 | CD1 | TYR | 229 | 46.086 | 1.767 | 8.754 | 1.00 | 33.09 | 6 |
| ATOM | 1810 | CE1 | TYR | 229 | 45.747 | 3.041 | 9.162 | 1.00 | 30.78 | 6 |
| ATOM | 1811 | CZ | TYR | 229 | 45.913 | 4.114 | 8.303 | 1.00 | 31.38 | 6 |
| ATOM | 1812 | OH | TYR | 229 | 45.587 | 5.394 | 8.730 | 1.00 | 30.63 | 8 |
| ATOM | 1813 | CE2 | TYR | 229 | 46.423 | 3.913 | 7.036 | 1.00 | 31.92 | 6 |
| ATOM | 1814 | CD2 | TYR | 229 | 46.771 | 2.618 | 6.625 | 1.00 | 33.34 | 6 |
| ATOM | 1815 | C | TYR | 229 | 44.565 | −0.561 | 6.847 | 1.00 | 36.26 | 6 |
| ATOM | 1816 | O | TYR | 229 | 43.594 | 0.020 | 6.344 | 1.00 | 35.42 | 8 |
| ATOM | 1817 | N | THR | 230 | 44.500 | −1.209 | 7.995 | 1.00 | 36.00 | 7 |
| ATOM | 1818 | CA | THR | 230 | 43.268 | −1.235 | 8.745 | 1.00 | 36.23 | 6 |
| ATOM | 1819 | CBA | THR | 230 | 42.589 | −2.605 | 8.552 | 0.50 | 36.51 | 6 |
| ATOM | 1820 | CBB | THR | 230 | 42.503 | −2.572 | 8.576 | 0.50 | 36.52 | 6 |
| ATOM | 1821 | OG1 | THR | 230 | 41.330 | −2.623 | 9.219 | 0.50 | 35.43 | 8 |
| ATOM | 1822 | OG1 | THR | 230 | 43.188 | −3.607 | 9.284 | 0.50 | 37.61 | 8 |
| ATOM | 1823 | CG2 | THR | 230 | 43.375 | −3.699 | 9.249 | 0.50 | 37.40 | 6 |
| ATOM | 1824 | CG2 | THR | 230 | 42.532 | −3.052 | 7.116 | 0.50 | 35.80 | 6 |
| ATOM | 1825 | C | THR | 230 | 43.568 | −0.976 | 10.217 | 1.00 | 36.03 | 6 |

APPENDIX A-continued

| ATOM | 1826 | O   | THR | 230 | 44.574 | −1.438 | 10.758 | 1.00 | 36.07 | 8 |
| --- | --- | --- | --- | --- | --- | --- | --- | --- | --- | --- |
| ATOM | 1827 | N   | TYR | 231 | 42.721 | −0.184 | 10.849 | 1.00 | 35.55 | 7 |
| ATOM | 1828 | CA  | TYR | 231 | 42.864 | 0.039  | 12.280 | 1.00 | 34.99 | 6 |
| ATOM | 1829 | CB  | TYR | 231 | 43.211 | 1.491  | 12.635 | 1.00 | 34.43 | 6 |
| ATOM | 1830 | CG  | TYR | 231 | 42.151 | 2.498  | 12.290 | 1.00 | 34.61 | 6 |
| ATOM | 1831 | CD1 | TYR | 231 | 41.131 | 2.795  | 13.190 | 1.00 | 35.89 | 6 |
| ATOM | 1832 | CE1 | TYR | 231 | 40.171 | 3.708  | 12.887 | 1.00 | 37.86 | 6 |
| ATOM | 1833 | CZ  | TYR | 231 | 40.202 | 4.368  | 11.684 | 1.00 | 38.47 | 6 |
| ATOM | 1834 | OH  | TYR | 231 | 39.212 | 5.280  | 11.425 | 1.00 | 42.00 | 8 |
| ATOM | 1835 | CE2 | TYR | 231 | 41.195 | 4.107  | 10.768 | 1.00 | 38.06 | 6 |
| ATOM | 1836 | CD2 | TYR | 231 | 42.166 | 3.170  | 11.075 | 1.00 | 36.00 | 6 |
| ATOM | 1837 | C   | TYR | 231 | 41.554 | −0.377 | 12.899 | 1.00 | 34.40 | 6 |
| ATOM | 1838 | O   | TYR | 231 | 40.550 | −0.482 | 12.202 | 1.00 | 34.65 | 8 |
| ATOM | 1839 | N   | GLU | 232 | 41.582 | −0.634 | 14.197 | 1.00 | 33.98 | 7 |
| ATOM | 1840 | CA  | GLU | 232 | 40.411 | −1.056 | 14.941 | 1.00 | 34.06 | 6 |
| ATOM | 1841 | CB  | GLU | 232 | 40.835 | −2.131 | 15.926 | 1.00 | 35.33 | 6 |
| ATOM | 1842 | CG  | GLU | 232 | 41.394 | −3.377 | 15.253 | 1.00 | 38.83 | 6 |
| ATOM | 1843 | CD  | GLU | 232 | 41.995 | −4.337 | 16.262 | 1.00 | 45.43 | 6 |
| ATOM | 1844 | OE1 | GLU | 232 | 41.681 | −4.192 | 17.483 | 1.00 | 50.43 | 8 |
| ATOM | 1845 | OE2 | GLU | 232 | 42.771 | −5.226 | 15.839 | 1.00 | 49.21 | 8 |
| ATOM | 1846 | C   | GLU | 232 | 39.780 | 0.082  | 15.733 | 1.00 | 33.58 | 6 |
| ATOM | 1847 | O   | GLU | 232 | 40.465 | 0.981  | 16.193 | 1.00 | 32.52 | 8 |
| ATOM | 1848 | N   | TRP | 233 | 38.472 | 0.031  | 15.902 | 1.00 | 32.38 | 7 |
| ATOM | 1849 | CA  | TRP | 233 | 37.800 | 1.003  | 16.750 | 1.00 | 31.91 | 6 |
| ATOM | 1850 | CB  | TRP | 233 | 37.507 | 2.296  | 16.004 | 1.00 | 31.44 | 6 |
| ATOM | 1851 | CG  | TRP | 233 | 36.609 | 2.129  | 14.801 | 1.00 | 31.38 | 6 |
| ATOM | 1852 | CD1 | TRP | 233 | 36.962 | 1.711  | 13.545 | 1.00 | 30.69 | 6 |
| ATOM | 1853 | NE1 | TRP | 233 | 35.860 | 1.711  | 12.721 | 1.00 | 28.90 | 7 |
| ATOM | 1854 | CE2 | TRP | 233 | 34.772 | 2.140  | 13.443 | 1.00 | 31.72 | 6 |
| ATOM | 1855 | CD2 | TRP | 233 | 35.217 | 2.421  | 14.749 | 1.00 | 31.46 | 6 |
| ATOM | 1856 | CE3 | TRP | 233 | 34.289 | 2.867  | 15.692 | 1.00 | 32.10 | 6 |
| ATOM | 1857 | CZ3 | TRP | 233 | 32.977 | 3.035  | 15.312 | 1.00 | 33.41 | 6 |
| ATOM | 1858 | CH2 | TRP | 233 | 32.560 | 2.751  | 14.006 | 1.00 | 32.64 | 6 |
| ATOM | 1859 | CZ2 | TRP | 233 | 33.447 | 2.306  | 13.054 | 1.00 | 34.16 | 6 |
| ATOM | 1860 | C   | TRP | 233 | 36.539 | 0.346  | 17.258 | 1.00 | 31.84 | 6 |
| ATOM | 1861 | O   | TRP | 233 | 36.274 | −0.820 | 16.938 | 1.00 | 31.79 | 8 |
| ATOM | 1862 | N   | GLY | 234 | 35.757 | 1.084  | 18.032 | 1.00 | 31.69 | 7 |
| ATOM | 1863 | CA  | GLY | 234 | 34.551 | 0.524  | 18.620 | 1.00 | 32.20 | 6 |
| ATOM | 1864 | C   | GLY | 234 | 34.811 | 0.195  | 20.084 | 1.00 | 32.16 | 6 |
| ATOM | 1865 | O   | GLY | 234 | 35.347 | 1.011  | 20.835 | 1.00 | 30.81 | 8 |
| ATOM | 1866 | N   | THR | 235 | 34.464 | −1.016 | 20.482 | 1.00 | 31.87 | 7 |
| ATOM | 1867 | CA  | THR | 235 | 34.689 | −1.429 | 21.852 | 1.00 | 32.19 | 6 |
| ATOM | 1868 | CB  | THR | 235 | 33.510 | −1.024 | 22.746 | 1.00 | 32.02 | 6 |
| ATOM | 1869 | OG1 | THR | 235 | 33.777 | −1.429 | 24.098 | 1.00 | 31.17 | 8 |
| ATOM | 1870 | CG2 | THR | 235 | 32.256 | −1.812 | 22.362 | 1.00 | 30.60 | 6 |
| ATOM | 1871 | C   | THR | 235 | 34.895 | −2.911 | 21.911 | 1.00 | 32.77 | 6 |
| ATOM | 1872 | O   | THR | 235 | 34.333 | −3.643 | 21.099 | 1.00 | 33.69 | 8 |
| ATOM | 1873 | N   | GLU | 236 | 35.710 | −3.349 | 22.859 | 1.00 | 33.55 | 7 |
| ATOM | 1874 | CA  | GLU | 236 | 35.950 | −4.767 | 23.063 | 1.00 | 35.51 | 6 |
| ATOM | 1875 | CB  | GLU | 236 | 37.444 | −5.066 | 23.218 | 1.00 | 36.93 | 6 |
| ATOM | 1876 | CG  | GLU | 236 | 38.249 | −4.947 | 21.932 | 1.00 | 40.57 | 6 |
| ATOM | 1877 | CD  | GLU | 236 | 39.710 | −5.307 | 22.117 | 1.00 | 45.64 | 6 |
| ATOM | 1878 | OE1 | GLU | 236 | 40.121 | −5.561 | 23.274 | 1.00 | 47.22 | 8 |
| ATOM | 1879 | OE2 | GLU | 236 | 40.451 | −5.318 | 21.103 | 1.00 | 48.98 | 8 |
| ATOM | 1880 | C   | GLU | 236 | 35.222 | −5.226 | 24.305 | 1.00 | 35.15 | 6 |
| ATOM | 1881 | O   | GLU | 236 | 35.332 | −6.381 | 24.713 | 1.00 | 36.23 | 8 |
| ATOM | 1882 | N   | ILE | 237 | 34.466 | −4.315 | 24.902 | 1.00 | 34.15 | 7 |
| ATOM | 1883 | CA  | ILE | 237 | 33.718 | −4.616 | 26.100 | 1.00 | 34.18 | 6 |
| ATOM | 1884 | CB  | ILE | 237 | 33.559 | −3.324 | 26.945 | 1.00 | 34.16 | 6 |
| ATOM | 1885 | CG1 | ILE | 237 | 34.933 | −2.768 | 27.303 | 1.00 | 35.18 | 6 |
| ATOM | 1886 | CD1 | ILE | 237 | 35.885 | −3.841 | 27.850 | 1.00 | 37.51 | 6 |
| ATOM | 1887 | CG2 | ILE | 237 | 32.728 | −3.590 | 28.221 | 1.00 | 35.24 | 6 |
| ATOM | 1888 | C   | ILE | 237 | 32.352 | −5.191 | 25.729 | 1.00 | 34.05 | 6 |
| ATOM | 1889 | O   | ILE | 237 | 31.731 | −4.760 | 24.768 | 1.00 | 33.09 | 8 |
| ATOM | 1890 | N   | ASP | 238 | 31.919 | −6.202 | 26.470 | 1.00 | 33.90 | 7 |
| ATOM | 1891 | CA  | ASP | 238 | 30.579 | −6.734 | 26.330 | 1.00 | 34.62 | 6 |
| ATOM | 1892 | CB  | ASP | 238 | 30.503 | −8.040 | 27.085 | 1.00 | 35.03 | 6 |
| ATOM | 1893 | CG  | ASP | 238 | 29.130 | −8.619 | 27.072 | 1.00 | 38.22 | 6 |
| ATOM | 1894 | OD1 | ASP | 238 | 28.187 | −7.967 | 26.564 | 1.00 | 41.51 | 8 |
| ATOM | 1895 | OD2 | ASP | 238 | 28.901 | −9.723 | 27.565 | 1.00 | 41.96 | 8 |
| ATOM | 1896 | C   | ASP | 238 | 29.598 | −5.723 | 26.948 | 1.00 | 33.49 | 6 |
| ATOM | 1897 | O   | ASP | 238 | 29.685 | −5.425 | 28.143 | 1.00 | 32.96 | 8 |
| ATOM | 1898 | N   | GLN | 239 | 28.693 | −5.163 | 26.142 | 1.00 | 32.94 | 7 |
| ATOM | 1899 | CA  | GLN | 239 | 27.803 | −4.113 | 26.671 | 1.00 | 31.54 | 6 |
| ATOM | 1900 | CB  | GLN | 239 | 27.223 | −3.216 | 25.566 | 1.00 | 31.94 | 6 |
| ATOM | 1901 | CG  | GLN | 239 | 28.249 | −2.448 | 24.693 | 1.00 | 29.58 | 6 |
| ATOM | 1902 | CD  | GLN | 239 | 27.695 | −1.137 | 24.107 | 1.00 | 30.48 | 6 |
| ATOM | 1903 | OE1 | GLN | 239 | 26.945 | −0.407 | 24.774 | 1.00 | 28.79 | 8 |
| ATOM | 1904 | NE2 | GLN | 239 | 28.084 | −0.828 | 22.867 | 1.00 | 31.21 | 7 |

APPENDIX A-continued

| ATOM | 1905 | C | GLN | 239 | 26.682 | −4.709 | 27.502 | 1.00 | 32.10 | 6 |
| ATOM | 1906 | O | GLN | 239 | 26.158 | −4.067 | 28.412 | 1.00 | 30.49 | 8 |
| ATOM | 1907 | N | LYS | 240 | 26.298 | −5.936 | 27.160 | 1.00 | 32.35 | 7 |
| ATOM | 1908 | CA | LYS | 240 | 25.242 | −6.644 | 27.877 | 1.00 | 33.68 | 6 |
| ATOM | 1909 | CB | LYS | 240 | 25.071 | −8.051 | 27.297 | 1.00 | 35.01 | 6 |
| ATOM | 1910 | CG | LYS | 240 | 23.933 | −8.217 | 26.304 | 1.00 | 39.31 | 6 |
| ATOM | 1911 | CD | LYS | 240 | 24.141 | −9.498 | 25.516 | 1.00 | 44.91 | 6 |
| ATOM | 1912 | CE | LYS | 240 | 22.876 | −10.286 | 25.353 | 1.00 | 48.71 | 6 |
| ATOM | 1913 | NZ | LYS | 240 | 23.237 | −11.695 | 25.004 | 1.00 | 48.70 | 7 |
| ATOM | 1914 | C | LYS | 240 | 25.557 | −6.762 | 29.362 | 1.00 | 33.68 | 6 |
| ATOM | 1915 | O | LYS | 240 | 24.714 | −6.456 | 30.217 | 1.00 | 33.75 | 8 |
| ATOM | 1916 | N | THR | 241 | 26.767 | −7.194 | 29.689 | 1.00 | 33.46 | 7 |
| ATOM | 1917 | CA | THR | 241 | 27.098 | −7.407 | 31.096 | 1.00 | 33.86 | 6 |
| ATOM | 1918 | CB | THR | 241 | 28.041 | −8.612 | 31.254 | 1.00 | 34.13 | 6 |
| ATOM | 1919 | OG1 | THR | 241 | 29.289 | −8.341 | 30.589 | 1.00 | 36.87 | 8 |
| ATOM | 1920 | CG2 | THR | 241 | 27.484 | −9.823 | 30.526 | 1.00 | 35.50 | 6 |
| ATOM | 1921 | C | THR | 241 | 27.662 | −6.197 | 31.838 | 1.00 | 32.93 | 6 |
| ATOM | 1922 | O | THR | 241 | 27.948 | −6.268 | 33.036 | 1.00 | 32.73 | 8 |
| ATOM | 1923 | N | THR | 242 | 27.827 | −5.083 | 31.138 | 1.00 | 31.40 | 7 |
| ATOM | 1924 | CA | THR | 242 | 28.320 | −3.879 | 31.803 | 1.00 | 30.30 | 6 |
| ATOM | 1925 | CB | THR | 242 | 29.571 | −3.341 | 31.119 | 1.00 | 30.54 | 6 |
| ATOM | 1926 | OG1 | THR | 242 | 29.335 | −3.209 | 29.707 | 1.00 | 29.14 | 8 |
| ATOM | 1927 | CG2 | THR | 242 | 30.663 | −4.350 | 31.219 | 1.00 | 32.11 | 6 |
| ATOM | 1928 | C | THR | 242 | 27.255 | −2.816 | 31.856 | 1.00 | 29.12 | 6 |
| ATOM | 1929 | O | THR | 242 | 26.425 | −2.824 | 32.756 | 1.00 | 29.57 | 8 |
| ATOM | 1930 | N | ILE | 243 | 27.242 | −1.946 | 30.861 | 1.00 | 28.03 | 7 |
| ATOM | 1931 | CA | ILE | 243 | 26.334 | −0.800 | 30.827 | 1.00 | 27.34 | 6 |
| ATOM | 1932 | CB | ILE | 243 | 26.817 | 0.234 | 29.794 | 1.00 | 27.41 | 6 |
| ATOM | 1933 | CG1 | ILE | 243 | 26.106 | 1.566 | 29.993 | 1.00 | 28.75 | 6 |
| ATOM | 1934 | CD1 | ILE | 243 | 27.006 | 2.755 | 29.772 | 1.00 | 26.84 | 6 |
| ATOM | 1935 | CG2 | ILE | 243 | 26.710 | −0.276 | 28.358 | 1.00 | 27.86 | 6 |
| ATOM | 1936 | C | ILE | 243 | 24.838 | −1.105 | 30.683 | 1.00 | 27.49 | 6 |
| ATOM | 1937 | O | ILE | 243 | 23.994 | −0.472 | 31.354 | 1.00 | 27.08 | 8 |
| ATOM | 1938 | N | ILE | 244 | 24.481 | −2.051 | 29.823 | 1.00 | 27.26 | 7 |
| ATOM | 1939 | CA | ILE | 244 | 23.074 | −2.363 | 29.691 | 1.00 | 27.12 | 6 |
| ATOM | 1940 | CB | ILE | 244 | 22.799 | −3.340 | 28.534 | 1.00 | 27.58 | 6 |
| ATOM | 1941 | CG1 | ILE | 244 | 23.289 | −2.767 | 27.215 | 1.00 | 28.16 | 6 |
| ATOM | 1942 | CD1 | ILE | 244 | 23.391 | −3.833 | 26.086 | 1.00 | 30.85 | 6 |
| ATOM | 1943 | CG2 | ILE | 244 | 21.275 | −3.660 | 28.483 | 1.00 | 27.13 | 6 |
| ATOM | 1944 | C | ILE | 244 | 22.541 | −2.965 | 30.983 | 1.00 | 27.72 | 6 |
| ATOM | 1945 | O | ILE | 244 | 21.572 | −2.486 | 31.548 | 1.00 | 27.73 | 8 |
| ATOM | 1946 | N | ASN | 245 | 23.147 | −4.029 | 31.475 | 1.00 | 28.46 | 7 |
| ATOM | 1947 | CA | ASN | 245 | 22.528 | −4.633 | 32.656 | 1.00 | 29.08 | 6 |
| ATOM | 1948 | CB | ASN | 245 | 23.029 | −6.068 | 32.885 | 1.00 | 30.30 | 6 |
| ATOM | 1949 | CG | ASN | 245 | 22.213 | −7.148 | 32.059 | 1.00 | 34.15 | 6 |
| ATOM | 1950 | OD1 | ASN | 245 | 21.211 | −6.848 | 31.367 | 1.00 | 36.81 | 8 |
| ATOM | 1951 | ND2 | ASN | 245 | 22.660 | −8.393 | 32.145 | 1.00 | 36.56 | 7 |
| ATOM | 1952 | C | ASN | 245 | 22.660 | −3.768 | 33.914 | 1.00 | 27.57 | 6 |
| ATOM | 1953 | O | ASN | 245 | 21.910 | −3.952 | 34.861 | 1.00 | 28.00 | 8 |
| ATOM | 1954 | N | THR | 246 | 23.592 | −2.818 | 33.927 | 1.00 | 25.64 | 7 |
| ATOM | 1955 | CA | THR | 246 | 23.771 | −1.967 | 35.109 | 1.00 | 24.67 | 6 |
| ATOM | 1956 | CB | THR | 246 | 25.265 | −1.583 | 35.332 | 1.00 | 25.32 | 6 |
| ATOM | 1957 | OG1 | THR | 246 | 26.091 | −2.759 | 35.324 | 1.00 | 27.22 | 8 |
| ATOM | 1958 | CG2 | THR | 246 | 25.465 | −1.070 | 36.727 | 1.00 | 24.58 | 6 |
| ATOM | 1959 | C | THR | 246 | 22.934 | −0.696 | 35.083 | 1.00 | 23.37 | 6 |
| ATOM | 1960 | O | THR | 246 | 22.371 | −0.319 | 36.099 | 1.00 | 23.21 | 8 |
| ATOM | 1961 | N | LEU | 247 | 22.856 | −0.035 | 33.931 | 1.00 | 22.19 | 7 |
| ATOM | 1962 | CA | LEU | 247 | 22.145 | 1.242 | 33.808 | 1.00 | 21.50 | 6 |
| ATOM | 1963 | CB | LEU | 247 | 23.124 | 2.333 | 33.402 | 1.00 | 20.42 | 6 |
| ATOM | 1964 | CG | LEU | 247 | 24.200 | 2.675 | 34.451 | 1.00 | 19.37 | 6 |
| ATOM | 1965 | CD1 | LEU | 247 | 25.235 | 3.597 | 33.849 | 1.00 | 18.61 | 6 |
| ATOM | 1966 | CD2 | LEU | 247 | 23.526 | 3.287 | 35.711 | 1.00 | 19.22 | 6 |
| ATOM | 1967 | C | LEU | 247 | 20.994 | 1.259 | 32.809 | 1.00 | 22.50 | 6 |
| ATOM | 1968 | O | LEU | 247 | 20.256 | 2.235 | 32.746 | 1.00 | 22.45 | 8 |
| ATOM | 1969 | N | GLY | 248 | 20.850 | 0.213 | 32.002 | 1.00 | 22.03 | 7 |
| ATOM | 1970 | CA | GLY | 248 | 19.743 | 0.198 | 31.049 | 1.00 | 23.81 | 6 |
| ATOM | 1971 | C | GLY | 248 | 19.945 | 1.033 | 29.785 | 1.00 | 24.17 | 6 |
| ATOM | 1972 | O | GLY | 248 | 18.984 | 1.488 | 29.156 | 1.00 | 24.72 | 8 |
| ATOM | 1973 | N | PHE | 249 | 21.197 | 1.270 | 29.413 | 1.00 | 23.29 | 7 |
| ATOM | 1974 | CA | PHE | 249 | 21.459 | 1.916 | 28.120 | 1.00 | 24.97 | 6 |
| ATOM | 1975 | CB | PHE | 249 | 21.437 | 3.463 | 28.151 | 1.00 | 23.89 | 6 |
| ATOM | 1976 | CG | PHE | 249 | 22.615 | 4.109 | 28.808 | 1.00 | 25.19 | 6 |
| ATOM | 1977 | CD1 | PHE | 249 | 23.721 | 4.497 | 28.061 | 1.00 | 23.71 | 6 |
| ATOM | 1978 | CE1 | PHE | 249 | 24.777 | 5.136 | 28.649 | 1.00 | 24.73 | 6 |
| ATOM | 1979 | CZ | PHE | 249 | 24.723 | 5.444 | 30.022 | 1.00 | 25.94 | 6 |
| ATOM | 1980 | CE2 | PHE | 249 | 23.621 | 5.086 | 30.752 | 1.00 | 24.83 | 6 |
| ATOM | 1981 | CD2 | PHE | 249 | 22.565 | 4.463 | 30.149 | 1.00 | 24.43 | 6 |
| ATOM | 1982 | C | PHE | 249 | 22.699 | 1.326 | 27.470 | 1.00 | 24.89 | 6 |
| ATOM | 1983 | O | PHE | 249 | 23.504 | 0.673 | 28.140 | 1.00 | 23.66 | 8 |

APPENDIX A-continued

| | | | | | | | | | |
|---|---|---|---|---|---|---|---|---|---|
| ATOM | 1984 | N | GLN | 250 | 22.805 | 1.535 | 26.160 | 1.00 | 25.06 | 7 |
| ATOM | 1985 | CA | GLN | 250 | 23.959 | 1.063 | 25.379 | 1.00 | 26.16 | 6 |
| ATOM | 1986 | CB | GLN | 250 | 23.557 | −0.078 | 24.435 | 1.00 | 26.60 | 6 |
| ATOM | 1987 | CG | GLN | 250 | 22.547 | 0.318 | 23.364 | 1.00 | 26.94 | 6 |
| ATOM | 1988 | CD | GLN | 250 | 21.950 | −0.886 | 22.635 | 1.00 | 29.58 | 6 |
| ATOM | 1989 | OE1 | GLN | 250 | 21.576 | −1.869 | 23.268 | 1.00 | 28.95 | 8 |
| ATOM | 1990 | NE2 | GLN | 250 | 21.853 | −0.801 | 21.306 | 1.00 | 27.73 | 7 |
| ATOM | 1991 | C | GLN | 250 | 24.547 | 2.190 | 24.553 | 1.00 | 26.39 | 6 |
| ATOM | 1992 | O | GLN | 250 | 23.892 | 3.219 | 24.331 | 1.00 | 26.25 | 8 |
| ATOM | 1993 | N | ILE | 251 | 25.779 | 1.987 | 24.082 | 1.00 | 26.88 | 7 |
| ATOM | 1994 | CA | ILE | 251 | 26.406 | 2.949 | 23.207 | 1.00 | 27.78 | 6 |
| ATOM | 1995 | CB | ILE | 251 | 27.855 | 3.199 | 23.556 | 1.00 | 27.57 | 6 |
| ATOM | 1996 | CG1 | ILE | 251 | 28.010 | 3.656 | 25.020 | 1.00 | 27.46 | 6 |
| ATOM | 1997 | CD1 | ILE | 251 | 27.177 | 4.839 | 25.365 | 1.00 | 27.59 | 6 |
| ATOM | 1998 | CG2 | ILE | 251 | 28.363 | 4.285 | 22.656 | 1.00 | 27.65 | 6 |
| ATOM | 1999 | C | ILE | 251 | 26.318 | 2.363 | 21.822 | 1.00 | 27.82 | 6 |
| ATOM | 2000 | O | ILE | 251 | 26.730 | 1.228 | 21.602 | 1.00 | 28.35 | 8 |
| ATOM | 2001 | N | ASN | 252 | 25.747 | 3.124 | 20.901 | 1.00 | 28.19 | 7 |
| ATOM | 2002 | CA | ASN | 252 | 25.614 | 2.657 | 19.513 | 1.00 | 28.95 | 6 |
| ATOM | 2003 | CB | ASN | 252 | 24.313 | 3.162 | 18.905 | 1.00 | 29.06 | 6 |
| ATOM | 2004 | CG | ASN | 252 | 23.141 | 2.332 | 19.316 | 1.00 | 29.57 | 6 |
| ATOM | 2005 | OD1 | ASN | 252 | 23.290 | 1.365 | 20.069 | 1.00 | 30.23 | 8 |
| ATOM | 2006 | ND2 | ASN | 252 | 21.952 | 2.693 | 18.824 | 1.00 | 29.27 | 7 |
| ATOM | 2007 | C | ASN | 252 | 26.802 | 3.050 | 18.646 | 1.00 | 29.28 | 6 |
| ATOM | 2008 | O | ASN | 252 | 27.719 | 3.751 | 19.096 | 1.00 | 28.72 | 8 |
| ATOM | 2009 | N | ILE | 253 | 26.781 | 2.618 | 17.384 | 1.00 | 29.27 | 7 |
| ATOM | 2010 | CA | ILE | 253 | 27.946 | 2.795 | 16.507 | 1.00 | 31.05 | 6 |
| ATOM | 2011 | CB | ILE | 253 | 27.658 | 2.030 | 15.169 | 1.00 | 30.27 | 6 |
| ATOM | 2012 | CG1 | ILE | 253 | 28.900 | 1.933 | 14.289 | 1.00 | 30.97 | 6 |
| ATOM | 2013 | CD1 | ILE | 253 | 28.775 | 0.896 | 13.190 | 1.00 | 36.74 | 6 |
| ATOM | 2014 | CG2 | ILE | 253 | 26.491 | 2.666 | 14.416 | 1.00 | 30.93 | 6 |
| ATOM | 2015 | C | ILE | 253 | 28.355 | 4.273 | 16.299 | 1.00 | 30.95 | 6 |
| ATOM | 2016 | O | ILE | 253 | 29.497 | 4.617 | 15.934 | 1.00 | 30.99 | 8 |
| ATOM | 2017 | N | ASP | 254 | 27.350 | 5.089 | 16.509 | 1.00 | 30.72 | 7 |
| ATOM | 2018 | CA | ASP | 254 | 27.246 | 6.530 | 16.528 | 1.00 | 31.58 | 6 |
| ATOM | 2019 | CB | ASP | 254 | 25.706 | 6.693 | 16.828 | 1.00 | 33.30 | 6 |
| ATOM | 2020 | CG | ASP | 254 | 25.202 | 8.129 | 16.771 | 1.00 | 36.78 | 6 |
| ATOM | 2021 | OD1 | ASP | 254 | 25.691 | 9.001 | 17.545 | 1.00 | 46.14 | 8 |
| ATOM | 2022 | OD2 | ASP | 254 | 24.278 | 8.479 | 16.020 | 1.00 | 37.79 | 8 |
| ATOM | 2023 | C | ASP | 254 | 28.031 | 7.125 | 17.734 | 1.00 | 30.69 | 6 |
| ATOM | 2024 | O | ASP | 254 | 28.313 | 8.334 | 17.814 | 1.00 | 29.02 | 8 |
| ATOM | 2025 | N | SER | 255 | 28.381 | 6.264 | 18.682 | 1.00 | 29.83 | 7 |
| ATOM | 2026 | CA | SER | 255 | 28.867 | 6.721 | 20.003 | 1.00 | 28.41 | 6 |
| ATOM | 2027 | CB | SER | 255 | 30.123 | 7.589 | 19.927 | 1.00 | 28.94 | 6 |
| ATOM | 2028 | OG | SER | 255 | 31.273 | 6.790 | 19.696 | 1.00 | 28.48 | 8 |
| ATOM | 2029 | C | SER | 255 | 27.759 | 7.457 | 20.765 | 1.00 | 28.22 | 6 |
| ATOM | 2030 | O | SER | 255 | 27.996 | 8.059 | 21.825 | 1.00 | 26.41 | 8 |
| ATOM | 2031 | N | GLY | 256 | 26.540 | 7.412 | 20.244 | 1.00 | 27.36 | 7 |
| ATOM | 2032 | CA | GLY | 256 | 25.442 | 8.022 | 20.977 | 1.00 | 27.94 | 6 |
| ATOM | 2033 | C | GLY | 256 | 24.786 | 6.967 | 21.851 | 1.00 | 27.58 | 6 |
| ATOM | 2034 | O | GLY | 256 | 24.980 | 5.778 | 21.646 | 1.00 | 26.73 | 8 |
| ATOM | 2035 | N | MET | 257 | 23.994 | 7.394 | 22.817 | 1.00 | 27.53 | 7 |
| ATOM | 2036 | CA | MET | 257 | 23.389 | 6.420 | 23.704 | 1.00 | 28.62 | 6 |
| ATOM | 2037 | CB | MET | 257 | 23.330 | 6.933 | 25.150 | 1.00 | 28.81 | 6 |
| ATOM | 2038 | CG | MET | 257 | 22.762 | 8.329 | 25.289 | 1.00 | 30.04 | 6 |
| ATOM | 2039 | SD | MET | 257 | 22.848 | 8.923 | 27.011 | 1.00 | 31.24 | 16 |
| ATOM | 2040 | CE | MET | 257 | 21.825 | 10.348 | 26.849 | 1.00 | 29.67 | 6 |
| ATOM | 2041 | C | MET | 257 | 21.990 | 6.023 | 23.222 | 1.00 | 28.74 | 6 |
| ATOM | 2042 | O | MET | 257 | 21.291 | 6.814 | 22.596 | 1.00 | 29.08 | 8 |
| ATOM | 2043 | N | LYS | 258 | 21.607 | 4.795 | 23.552 | 1.00 | 28.87 | 7 |
| ATOM | 2044 | CA | LYS | 258 | 20.326 | 4.216 | 23.179 | 1.00 | 29.59 | 6 |
| ATOM | 2045 | CB | LYS | 258 | 20.528 | 3.287 | 21.960 | 1.00 | 30.48 | 6 |
| ATOM | 2046 | CG | LYS | 258 | 19.528 | 2.138 | 21.771 | 1.00 | 32.50 | 6 |
| ATOM | 2047 | CD | LYS | 258 | 18.144 | 2.573 | 21.487 | 1.00 | 36.63 | 6 |
| ATOM | 2048 | CE | LYS | 258 | 17.310 | 1.371 | 20.958 | 1.00 | 39.66 | 6 |
| ATOM | 2049 | NZ | LYS | 258 | 16.741 | 0.509 | 22.068 | 1.00 | 41.43 | 7 |
| ATOM | 2050 | C | LYS | 258 | 19.802 | 3.486 | 24.408 | 1.00 | 29.10 | 6 |
| ATOM | 2051 | O | LYS | 258 | 20.510 | 2.713 | 25.017 | 1.00 | 27.97 | 8 |
| ATOM | 2052 | N | PHE | 259 | 18.565 | 3.753 | 24.801 | 1.00 | 30.01 | 7 |
| ATOM | 2053 | CA | PHE | 259 | 18.043 | 3.169 | 26.038 | 1.00 | 31.22 | 6 |
| ATOM | 2054 | CB | PHE | 259 | 17.167 | 4.196 | 26.791 | 1.00 | 30.03 | 6 |
| ATOM | 2055 | CG | PHE | 259 | 17.962 | 5.357 | 27.332 | 1.00 | 29.70 | 6 |
| ATOM | 2056 | CD1 | PHE | 259 | 18.280 | 6.432 | 26.523 | 1.00 | 26.99 | 6 |
| ATOM | 2057 | CE1 | PHE | 259 | 19.072 | 7.476 | 27.015 | 1.00 | 29.14 | 6 |
| ATOM | 2058 | CZ | PHE | 259 | 19.526 | 7.444 | 28.330 | 1.00 | 29.70 | 6 |
| ATOM | 2059 | CE2 | PHE | 259 | 19.200 | 6.364 | 29.151 | 1.00 | 27.99 | 6 |
| ATOM | 2060 | CD2 | PHE | 259 | 18.439 | 5.341 | 28.649 | 1.00 | 26.20 | 6 |
| ATOM | 2061 | C | PHE | 259 | 17.363 | 1.816 | 25.858 | 1.00 | 32.51 | 6 |
| ATOM | 2062 | O | PHE | 259 | 16.573 | 1.627 | 24.937 | 1.00 | 33.43 | 8 |

APPENDIX A-continued

| ATOM | 2063 | N   | ASP | 260 | 17.687 | 0.864   | 26.725 | 1.00 | 33.26 | 7 |
|------|------|-----|-----|-----|--------|---------|--------|------|-------|---|
| ATOM | 2064 | CA  | ASP | 260 | 17.107 | −0.471  | 26.658 | 1.00 | 35.06 | 6 |
| ATOM | 2065 | CB  | ASP | 260 | 18.201 | −1.519  | 26.627 | 1.00 | 34.05 | 6 |
| ATOM | 2066 | CG  | ASP | 260 | 19.075 | −1.421  | 25.426 | 1.00 | 35.07 | 6 |
| ATOM | 2067 | OD1 | ASP | 260 | 18.584 | −1.021  | 24.349 | 1.00 | 34.06 | 8 |
| ATOM | 2068 | OD2 | ASP | 260 | 20.263 | −1.779  | 25.468 | 1.00 | 33.76 | 8 |
| ATOM | 2069 | C   | ASP | 260 | 16.263 | −0.813  | 27.880 | 1.00 | 36.87 | 6 |
| ATOM | 2070 | O   | ASP | 260 | 16.314 | −0.116  | 28.885 | 1.00 | 37.45 | 8 |
| ATOM | 2071 | N   | ILE | 261 | 15.523 | −1.918  | 27.797 | 1.00 | 38.94 | 7 |
| ATOM | 2072 | CA  | ILE | 261 | 14.844 | −2.469  | 28.975 | 1.00 | 40.80 | 6 |
| ATOM | 2073 | CB  | ILE | 261 | 13.508 | −3.135  | 28.617 | 1.00 | 41.08 | 6 |
| ATOM | 2074 | CG1 | ILE | 261 | 12.650 | −2.219  | 27.751 | 1.00 | 42.66 | 6 |
| ATOM | 2075 | CD1 | ILE | 261 | 11.216 | −2.670  | 27.674 | 1.00 | 43.89 | 6 |
| ATOM | 2076 | CG2 | ILE | 261 | 12.759 | −3.544  | 29.893 | 1.00 | 42.11 | 6 |
| ATOM | 2077 | C   | ILE | 261 | 15.770 | −3.559  | 29.437 | 1.00 | 41.24 | 6 |
| ATOM | 2078 | O   | ILE | 261 | 15.877 | −4.586  | 28.760 | 1.00 | 42.41 | 8 |
| ATOM | 2079 | N   | PRO | 262 | 16.425 | −3.352  | 30.575 | 1.00 | 41.67 | 7 |
| ATOM | 2080 | CA  | PRO | 262 | 17.445 | −4.283  | 31.072 | 1.00 | 42.02 | 6 |
| ATOM | 2081 | CB  | PRO | 262 | 18.060 | −3.557  | 32.279 | 1.00 | 42.10 | 6 |
| ATOM | 2082 | CG  | PRO | 262 | 17.423 | −2.185  | 32.339 | 1.00 | 42.37 | 6 |
| ATOM | 2083 | CD  | PRO | 262 | 16.191 | −2.221  | 31.492 | 1.00 | 41.81 | 6 |
| ATOM | 2084 | C   | PRO | 262 | 16.882 | −5.598  | 31.552 | 1.00 | 42.25 | 6 |
| ATOM | 2085 | O   | PRO | 262 | 15.737 | −5.622  | 31.988 | 1.00 | 40.99 | 8 |
| ATOM | 2086 | N   | GLU | 263 | 17.715 | −6.645  | 31.521 | 1.00 | 43.25 | 7 |
| ATOM | 2087 | CA  | GLU | 263 | 17.359 | −7.998  | 31.966 | 1.00 | 43.81 | 6 |
| ATOM | 2088 | CB  | GLU | 263 | 18.530 | −8.981  | 31.701 | 1.00 | 44.96 | 6 |
| ATOM | 2089 | CG  | GLU | 263 | 19.047 | −8.998  | 30.256 | 1.00 | 47.58 | 6 |
| ATOM | 2090 | CD  | GLU | 263 | 20.188 | −9.996  | 30.012 | 1.00 | 51.87 | 6 |
| ATOM | 2091 | OE1 | GLU | 263 | 20.176 | −11.095 | 30.621 | 1.00 | 52.52 | 8 |
| ATOM | 2092 | OE2 | GLU | 263 | 21.110 | −9.692  | 29.200 | 1.00 | 52.83 | 8 |
| ATOM | 2093 | C   | GLU | 263 | 16.968 | −7.999  | 33.444 | 1.00 | 43.63 | 6 |
| ATOM | 2094 | O   | GLU | 263 | 16.091 | −8.763  | 33.879 | 1.00 | 43.40 | 8 |
| ATOM | 2095 | N   | VAL | 264 | 17.630 | −7.136  | 34.209 | 1.00 | 42.75 | 7 |
| ATOM | 2096 | CA  | VAL | 264 | 17.368 | −6.947  | 35.627 | 1.00 | 42.27 | 6 |
| ATOM | 2097 | CB  | VAL | 264 | 18.342 | −7.775  | 36.500 | 1.00 | 42.25 | 6 |
| ATOM | 2098 | CG1 | VAL | 264 | 18.453 | −7.184  | 37.882 | 1.00 | 42.69 | 6 |
| ATOM | 2099 | CG2 | VAL | 264 | 17.902 | −9.238  | 36.590 | 1.00 | 43.45 | 6 |
| ATOM | 2100 | C   | VAL | 264 | 17.595 | −5.449  | 35.896 | 1.00 | 41.05 | 6 |
| ATOM | 2101 | O   | VAL | 264 | 18.525 | −4.858  | 35.346 | 1.00 | 41.86 | 8 |
| ATOM | 2102 | N   | GLY | 265 | 16.754 | −4.826  | 36.711 | 1.00 | 39.37 | 7 |
| ATOM | 2103 | CA  | GLY | 265 | 16.919 | −3.397  | 36.965 | 1.00 | 36.79 | 6 |
| ATOM | 2104 | C   | GLY | 265 | 15.910 | −2.550  | 36.216 | 1.00 | 34.73 | 6 |
| ATOM | 2105 | O   | GLY | 265 | 15.368 | −2.978  | 35.195 | 1.00 | 34.79 | 8 |
| ATOM | 2106 | N   | GLY | 266 | 15.625 | −1.363  | 36.752 | 1.00 | 32.58 | 7 |
| ATOM | 2107 | CA  | GLY | 266 | 14.687 | −0.433  | 36.143 | 1.00 | 29.56 | 6 |
| ATOM | 2108 | C   | GLY | 266 | 15.251 | 0.456   | 35.043 | 1.00 | 27.22 | 6 |
| ATOM | 2109 | O   | GLY | 266 | 14.504 | 0.940   | 34.215 | 1.00 | 27.04 | 8 |
| ATOM | 2110 | N   | GLY | 267 | 16.562 | 0.674   | 35.023 | 1.00 | 25.23 | 7 |
| ATOM | 2111 | CA  | GLY | 267 | 17.161 | 1.529   | 33.993 | 1.00 | 22.65 | 6 |
| ATOM | 2112 | C   | GLY | 267 | 17.117 | 3.043   | 34.244 | 1.00 | 22.06 | 6 |
| ATOM | 2113 | O   | GLY | 267 | 16.667 | 3.497   | 35.286 | 1.00 | 20.65 | 8 |
| ATOM | 2114 | N   | THR | 268 | 17.608 | 3.818   | 33.277 | 1.00 | 21.25 | 7 |
| ATOM | 2115 | CA  | THR | 268 | 17.744 | 5.260   | 33.441 | 1.00 | 20.68 | 6 |
| ATOM | 2116 | CB  | THR | 268 | 19.238 | 5.634   | 33.337 | 1.00 | 20.70 | 6 |
| ATOM | 2117 | OG1 | THR | 268 | 19.820 | 4.891   | 32.252 | 1.00 | 22.25 | 8 |
| ATOM | 2118 | CG2 | THR | 268 | 20.010 | 5.160   | 34.569 | 1.00 | 20.51 | 6 |
| ATOM | 2119 | C   | THR | 268 | 16.962 | 6.057   | 32.406 | 1.00 | 20.75 | 6 |
| ATOM | 2120 | O   | THR | 268 | 17.257 | 7.242   | 32.173 | 1.00 | 19.21 | 8 |
| ATOM | 2121 | N   | ASP | 269 | 15.954 | 5.433   | 31.789 | 1.00 | 20.33 | 7 |
| ATOM | 2122 | CA  | ASP | 269 | 15.242 | 6.120   | 30.731 | 1.00 | 22.28 | 6 |
| ATOM | 2123 | CB  | ASP | 269 | 14.126 | 5.266   | 30.125 | 1.00 | 23.20 | 6 |
| ATOM | 2124 | CG  | ASP | 269 | 13.606 | 5.851   | 28.831 | 1.00 | 27.85 | 6 |
| ATOM | 2125 | OD1 | ASP | 269 | 14.392 | 5.881   | 27.860 | 1.00 | 29.68 | 8 |
| ATOM | 2126 | OD2 | ASP | 269 | 12.460 | 6.354   | 28.694 | 1.00 | 30.38 | 8 |
| ATOM | 2127 | C   | ASP | 269 | 14.664 | 7.451   | 31.192 | 1.00 | 21.61 | 6 |
| ATOM | 2128 | O   | ASP | 269 | 14.554 | 8.381   | 30.397 | 1.00 | 21.52 | 8 |
| ATOM | 2129 | N   | GLU | 270 | 14.294 | 7.530   | 32.470 | 1.00 | 19.63 | 7 |
| ATOM | 2130 | CA  | GLU | 270 | 13.660 | 8.724   | 32.972 | 1.00 | 19.15 | 6 |
| ATOM | 2131 | CB  | GLU | 270 | 12.700 | 8.414   | 34.136 | 1.00 | 19.45 | 6 |
| ATOM | 2132 | CG  | GLU | 270 | 11.415 | 7.743   | 33.684 | 1.00 | 20.21 | 6 |
| ATOM | 2133 | CD  | GLU | 270 | 10.689 | 7.017   | 34.807 | 1.00 | 22.07 | 6 |
| ATOM | 2134 | OE1 | GLU | 270 | 11.274 | 6.799   | 35.884 | 1.00 | 25.09 | 8 |
| ATOM | 2135 | OE2 | GLU | 270 | 9.542  | 6.620   | 34.610 | 1.00 | 24.66 | 8 |
| ATOM | 2136 | C   | GLU | 270 | 14.623 | 9.837   | 33.341 | 1.00 | 19.09 | 6 |
| ATOM | 2137 | O   | GLU | 270 | 14.175 | 10.893  | 33.801 | 1.00 | 18.41 | 8 |
| ATOM | 2138 | N   | ILE | 271 | 15.928 | 9.605   | 33.176 | 1.00 | 17.34 | 7 |
| ATOM | 2139 | CA  | ILE | 271 | 16.883 | 10.675  | 33.406 | 1.00 | 17.80 | 6 |
| ATOM | 2140 | CB  | ILE | 271 | 17.795 | 10.421  | 34.661 | 1.00 | 16.77 | 6 |
| ATOM | 2141 | CG1 | ILE | 271 | 18.600 | 9.126   | 34.502 | 1.00 | 17.40 | 6 |

APPENDIX A-continued

| | | | | | | | | | |
|---|---|---|---|---|---|---|---|---|---|
| ATOM | 2142 | CD1 | ILE | 271 | 19.840 | 9.058 | 35.402 | 1.00 | 15.95 | 6 |
| ATOM | 2143 | CG2 | ILE | 271 | 16.925 | 10.376 | 35.962 | 1.00 | 15.03 | 6 |
| ATOM | 2144 | C | ILE | 271 | 17.719 | 10.923 | 32.151 | 1.00 | 17.52 | 6 |
| ATOM | 2145 | O | ILE | 271 | 18.806 | 11.519 | 32.207 | 1.00 | 17.45 | 8 |
| ATOM | 2146 | N | LYS | 272 | 17.238 | 10.450 | 31.023 | 1.00 | 18.14 | 7 |
| ATOM | 2147 | CA | LYS | 272 | 18.003 | 10.636 | 29.783 | 1.00 | 19.94 | 6 |
| ATOM | 2148 | CB | LYS | 272 | 17.308 | 9.987 | 28.565 | 1.00 | 21.74 | 6 |
| ATOM | 2149 | CG | LYS | 272 | 16.011 | 10.636 | 28.185 | 1.00 | 23.59 | 6 |
| ATOM | 2150 | CD | LYS | 272 | 15.279 | 9.808 | 27.112 | 1.00 | 27.19 | 6 |
| ATOM | 2151 | CE | LYS | 272 | 13.768 | 9.780 | 27.371 | 1.00 | 31.96 | 6 |
| ATOM | 2152 | NZ | LYS | 272 | 13.076 | 9.605 | 26.055 | 1.00 | 34.76 | 7 |
| ATOM | 2153 | C | LYS | 272 | 18.384 | 12.076 | 29.438 | 1.00 | 20.14 | 6 |
| ATOM | 2154 | O | LYS | 272 | 19.455 | 12.313 | 28.854 | 1.00 | 20.40 | 8 |
| ATOM | 2155 | N | THR | 273 | 17.542 | 13.033 | 29.784 | 1.00 | 19.83 | 7 |
| ATOM | 2156 | CA | THR | 273 | 17.866 | 14.438 | 29.524 | 1.00 | 20.23 | 6 |
| ATOM | 2157 | CB | THR | 273 | 16.649 | 15.324 | 29.816 | 1.00 | 20.70 | 6 |
| ATOM | 2158 | OG1 | THR | 273 | 15.653 | 15.089 | 28.816 | 1.00 | 21.84 | 8 |
| ATOM | 2159 | CG2 | THR | 273 | 16.981 | 16.800 | 29.664 | 1.00 | 20.51 | 6 |
| ATOM | 2160 | C | THR | 273 | 19.030 | 14.859 | 30.409 | 1.00 | 19.95 | 6 |
| ATOM | 2161 | O | THR | 273 | 19.935 | 15.575 | 29.976 | 1.00 | 19.28 | 8 |
| ATOM | 2162 | N | GLN | 274 | 19.000 | 14.411 | 31.652 | 1.00 | 18.86 | 7 |
| ATOM | 2163 | CA | GLN | 274 | 20.064 | 14.699 | 32.611 | 1.00 | 18.83 | 6 |
| ATOM | 2164 | CB | GLN | 274 | 19.710 | 14.076 | 33.953 | 1.00 | 17.71 | 6 |
| ATOM | 2165 | CG | GLN | 274 | 20.863 | 14.142 | 34.989 | 1.00 | 18.26 | 6 |
| ATOM | 2166 | CD | GLN | 274 | 20.519 | 13.393 | 36.252 | 1.00 | 17.39 | 6 |
| ATOM | 2167 | OE1 | GLN | 274 | 19.337 | 13.198 | 36.556 | 1.00 | 17.70 | 8 |
| ATOM | 2168 | NE2 | GLN | 274 | 21.539 | 13.010 | 37.020 | 1.00 | 14.07 | 7 |
| ATOM | 2169 | C | GLN | 274 | 21.377 | 14.101 | 32.127 | 1.00 | 19.36 | 6 |
| ATOM | 2170 | O | GLN | 274 | 22.435 | 14.726 | 32.192 | 1.00 | 18.64 | 8 |
| ATOM | 2171 | N | LEU | 275 | 21.307 | 12.860 | 31.664 | 1.00 | 19.46 | 7 |
| ATOM | 2172 | CA | LEU | 275 | 22.504 | 12.230 | 31.137 | 1.00 | 19.50 | 6 |
| ATOM | 2173 | CB | LEU | 275 | 22.239 | 10.767 | 30.798 | 1.00 | 17.97 | 6 |
| ATOM | 2174 | CG | LEU | 275 | 21.865 | 9.863 | 31.971 | 1.00 | 18.96 | 6 |
| ATOM | 2175 | CD1 | LEU | 275 | 21.716 | 8.421 | 31.462 | 1.00 | 20.33 | 6 |
| ATOM | 2176 | CD2 | LEU | 275 | 22.911 | 9.937 | 33.089 | 1.00 | 22.09 | 6 |
| ATOM | 2177 | C | LEU | 275 | 23.046 | 12.980 | 29.925 | 1.00 | 19.79 | 6 |
| ATOM | 2178 | O | LEU | 275 | 24.238 | 13.181 | 29.792 | 1.00 | 19.21 | 8 |
| ATOM | 2179 | N | ASN | 276 | 22.169 | 13.347 | 29.009 | 1.00 | 19.72 | 7 |
| ATOM | 2180 | CA | ASN | 276 | 22.606 | 14.018 | 27.796 | 1.00 | 21.12 | 6 |
| ATOM | 2181 | CB | ASN | 276 | 21.366 | 14.307 | 26.930 | 1.00 | 20.45 | 6 |
| ATOM | 2182 | CG | ASN | 276 | 21.629 | 15.283 | 25.802 | 1.00 | 23.58 | 6 |
| ATOM | 2183 | OD1 | ASN | 276 | 21.037 | 16.363 | 25.750 | 1.00 | 27.52 | 8 |
| ATOM | 2184 | ND2 | ASN | 276 | 22.449 | 14.884 | 24.855 | 1.00 | 22.64 | 7 |
| ATOM | 2185 | C | ASN | 276 | 23.316 | 15.318 | 28.182 | 1.00 | 20.99 | 6 |
| ATOM | 2186 | O | ASN | 276 | 24.423 | 15.621 | 27.723 | 1.00 | 22.17 | 8 |
| ATOM | 2187 | N | GLU | 277 | 22.682 | 16.078 | 29.056 | 1.00 | 20.14 | 7 |
| ATOM | 2188 | CA | GLU | 277 | 23.211 | 17.366 | 29.418 | 1.00 | 20.94 | 6 |
| ATOM | 2189 | CB | GLU | 277 | 22.090 | 18.220 | 30.040 | 1.00 | 20.97 | 6 |
| ATOM | 2190 | CG | GLU | 277 | 20.966 | 18.505 | 29.057 | 1.00 | 27.76 | 6 |
| ATOM | 2191 | CD | GLU | 277 | 20.020 | 19.587 | 29.550 | 1.00 | 34.16 | 6 |
| ATOM | 2192 | OE1 | GLU | 277 | 20.316 | 20.207 | 30.619 | 1.00 | 35.36 | 8 |
| ATOM | 2193 | OE2 | GLU | 277 | 19.007 | 19.819 | 28.845 | 1.00 | 34.69 | 8 |
| ATOM | 2194 | C | GLU | 277 | 24.462 | 17.329 | 30.318 | 1.00 | 19.87 | 6 |
| ATOM | 2195 | O | GLU | 277 | 25.423 | 18.043 | 30.053 | 1.00 | 20.09 | 8 |
| ATOM | 2196 | N | GLU | 278 | 24.447 | 16.504 | 31.363 | 1.00 | 18.56 | 7 |
| ATOM | 2197 | CA | GLU | 278 | 25.517 | 16.485 | 32.353 | 1.00 | 18.37 | 6 |
| ATOM | 2198 | CB | GLU | 278 | 24.962 | 16.118 | 33.753 | 1.00 | 18.01 | 6 |
| ATOM | 2199 | CG | GLU | 278 | 23.955 | 17.165 | 34.261 | 1.00 | 20.11 | 6 |
| ATOM | 2200 | CD | GLU | 278 | 23.358 | 16.843 | 35.631 | 1.00 | 26.02 | 6 |
| ATOM | 2201 | OE1 | GLU | 278 | 23.880 | 15.950 | 36.323 | 1.00 | 27.58 | 8 |
| ATOM | 2202 | OE2 | GLU | 278 | 22.342 | 17.493 | 36.034 | 1.00 | 28.20 | 8 |
| ATOM | 2203 | C | GLU | 278 | 26.702 | 15.617 | 31.938 | 1.00 | 18.97 | 6 |
| ATOM | 2204 | O | GLU | 278 | 27.845 | 15.856 | 32.351 | 1.00 | 19.18 | 8 |
| ATOM | 2205 | N | LEU | 279 | 26.467 | 14.626 | 31.095 | 1.00 | 19.29 | 7 |
| ATOM | 2206 | CA | LEU | 279 | 27.594 | 13.848 | 30.592 | 1.00 | 19.99 | 6 |
| ATOM | 2207 | CB | LEU | 279 | 27.284 | 12.369 | 30.652 | 1.00 | 19.92 | 6 |
| ATOM | 2208 | CG | LEU | 279 | 27.014 | 11.845 | 32.062 | 1.00 | 19.70 | 6 |
| ATOM | 2209 | CD1 | LEU | 279 | 26.770 | 10.360 | 32.017 | 1.00 | 21.96 | 6 |
| ATOM | 2210 | CD2 | LEU | 279 | 28.203 | 12.174 | 32.988 | 1.00 | 21.59 | 6 |
| ATOM | 2211 | C | LEU | 279 | 28.012 | 14.247 | 29.191 | 1.00 | 21.97 | 6 |
| ATOM | 2212 | O | LEU | 279 | 29.066 | 13.817 | 28.717 | 1.00 | 21.74 | 8 |
| ATOM | 2213 | N | LYS | 280 | 27.202 | 15.091 | 28.556 | 1.00 | 22.04 | 7 |
| ATOM | 2214 | CA | LYS | 280 | 27.462 | 15.543 | 27.180 | 1.00 | 24.73 | 6 |
| ATOM | 2215 | CB | LYS | 280 | 28.695 | 16.463 | 27.088 | 1.00 | 24.67 | 6 |
| ATOM | 2216 | CG | LYS | 280 | 28.759 | 17.482 | 28.207 | 1.00 | 28.11 | 6 |
| ATOM | 2217 | CD | LYS | 280 | 30.146 | 18.094 | 28.309 | 1.00 | 33.66 | 6 |
| ATOM | 2218 | CE | LYS | 280 | 30.096 | 19.495 | 28.922 | 1.00 | 38.26 | 6 |
| ATOM | 2219 | NZ | LYS | 280 | 30.952 | 20.459 | 28.122 | 1.00 | 41.55 | 7 |
| ATOM | 2220 | C | LYS | 280 | 27.599 | 14.390 | 26.227 | 1.00 | 24.96 | 6 |

APPENDIX A-continued

| ATOM | 2221 | O   | LYS | 280 | 28.577 | 14.301 | 25.451 | 1.00 | 24.99 | 8 |
|------|------|-----|-----|-----|--------|--------|--------|------|-------|---|
| ATOM | 2222 | N   | ILE | 281 | 26.606 | 13.514 | 26.265 | 1.00 | 26.20 | 7 |
| ATOM | 2223 | CA  | ILE | 281 | 26.558 | 12.376 | 25.369 | 1.00 | 28.12 | 6 |
| ATOM | 2224 | CB  | ILE | 281 | 26.419 | 11.101 | 26.188 | 1.00 | 28.80 | 6 |
| ATOM | 2225 | CG1 | ILE | 281 | 27.711 | 10.809 | 26.955 | 1.00 | 29.35 | 6 |
| ATOM | 2226 | CD1 | ILE | 281 | 27.512 | 9.757  | 27.993 | 1.00 | 28.87 | 6 |
| ATOM | 2227 | CG2 | ILE | 281 | 26.094 | 9.929  | 25.293 | 1.00 | 30.46 | 6 |
| ATOM | 2228 | C   | ILE | 281 | 25.319 | 12.554 | 24.507 | 1.00 | 28.14 | 6 |
| ATOM | 2229 | O   | ILE | 281 | 24.238 | 12.804 | 25.019 | 1.00 | 26.88 | 8 |
| ATOM | 2230 | N   | GLU | 282 | 25.491 | 12.458 | 23.198 | 1.00 | 28.01 | 7 |
| ATOM | 2231 | CA  | GLU | 282 | 24.385 | 12.624 | 22.277 | 1.00 | 30.14 | 6 |
| ATOM | 2232 | CB  | GLU | 282 | 24.946 | 12.862 | 20.863 | 1.00 | 31.17 | 6 |
| ATOM | 2233 | CG  | GLU | 282 | 25.596 | 14.231 | 20.716 | 1.00 | 36.07 | 6 |
| ATOM | 2234 | CD  | GLU | 282 | 26.110 | 14.526 | 19.319 | 1.00 | 45.46 | 6 |
| ATOM | 2235 | OE1 | GLU | 282 | 26.154 | 13.598 | 18.461 | 1.00 | 48.18 | 8 |
| ATOM | 2236 | OE2 | GLU | 282 | 26.476 | 15.709 | 19.081 | 1.00 | 49.66 | 8 |
| ATOM | 2237 | C   | GLU | 282 | 23.487 | 11.394 | 22.267 | 1.00 | 30.23 | 6 |
| ATOM | 2238 | O   | GLU | 282 | 23.925 | 10.287 | 22.570 | 1.00 | 30.26 | 8 |
| ATOM | 2239 | N   | TYR | 283 | 22.218 | 11.608 | 21.952 | 1.00 | 30.08 | 7 |
| ATOM | 2240 | CA  | TYR | 283 | 21.322 | 10.512 | 21.662 | 1.00 | 30.84 | 6 |
| ATOM | 2241 | CB  | TYR | 283 | 19.890 | 11.014 | 21.514 | 1.00 | 29.92 | 6 |
| ATOM | 2242 | CG  | TYR | 283 | 19.308 | 11.611 | 22.785 | 1.00 | 31.24 | 6 |
| ATOM | 2243 | CD1 | TYR | 283 | 18.988 | 12.954 | 22.868 | 1.00 | 31.42 | 6 |
| ATOM | 2244 | CE1 | TYR | 283 | 18.435 | 13.495 | 24.031 | 1.00 | 32.42 | 6 |
| ATOM | 2245 | CZ  | TYR | 283 | 18.229 | 12.696 | 25.107 | 1.00 | 31.46 | 6 |
| ATOM | 2246 | OH  | TYR | 283 | 17.706 | 13.232 | 26.245 | 1.00 | 31.66 | 8 |
| ATOM | 2247 | CE2 | TYR | 283 | 18.524 | 11.371 | 25.052 | 1.00 | 31.02 | 6 |
| ATOM | 2248 | CD2 | TYR | 283 | 19.066 | 10.829 | 23.889 | 1.00 | 31.85 | 6 |
| ATOM | 2249 | C   | TYR | 283 | 21.784 | 9.931  | 20.334 | 1.00 | 31.54 | 6 |
| ATOM | 2250 | O   | TYR | 283 | 22.176 | 10.672 | 19.408 | 1.00 | 32.27 | 8 |
| ATOM | 2251 | N   | SER | 284 | 21.755 | 8.609  | 20.236 | 1.00 | 31.86 | 7 |
| ATOM | 2252 | CA  | SER | 284 | 22.164 | 7.938  | 19.013 | 1.00 | 32.60 | 6 |
| ATOM | 2253 | CB  | SER | 284 | 22.284 | 6.437  | 19.237 | 1.00 | 31.76 | 6 |
| ATOM | 2254 | OG  | SER | 284 | 22.555 | 5.766  | 18.018 | 1.00 | 32.72 | 8 |
| ATOM | 2255 | C   | SER | 284 | 21.193 | 8.204  | 17.882 | 1.00 | 34.14 | 6 |
| ATOM | 2256 | O   | SER | 284 | 20.007 | 8.431  | 18.117 | 1.00 | 33.92 | 8 |
| ATOM | 2257 | N   | HIS | 285 | 21.712 | 8.170  | 16.655 | 1.00 | 35.88 | 7 |
| ATOM | 2258 | CA  | HIS | 285 | 20.885 | 8.334  | 15.455 | 1.00 | 38.62 | 6 |
| ATOM | 2259 | CB  | HIS | 285 | 21.426 | 9.485  | 14.604 | 1.00 | 40.22 | 6 |
| ATOM | 2260 | CG  | HIS | 285 | 21.121 | 10.844 | 15.153 | 1.00 | 43.63 | 6 |
| ATOM | 2261 | ND1 | HIS | 285 | 21.409 | 11.209 | 16.451 | 1.00 | 48.29 | 7 |
| ATOM | 2262 | CE1 | HIS | 285 | 21.034 | 12.461 | 16.651 | 1.00 | 49.07 | 6 |
| ATOM | 2263 | NE2 | HIS | 285 | 20.519 | 12.925 | 15.526 | 1.00 | 49.45 | 7 |
| ATOM | 2264 | CD2 | HIS | 285 | 20.567 | 11.935 | 14.571 | 1.00 | 47.70 | 6 |
| ATOM | 2265 | C   | HIS | 285 | 20.916 | 7.036  | 14.651 | 1.00 | 38.78 | 6 |
| ATOM | 2266 | O   | HIS | 285 | 20.421 | 6.960  | 13.520 | 1.00 | 39.79 | 8 |
| ATOM | 2267 | N   | GLU | 286 | 21.516 | 6.013  | 15.240 | 1.00 | 38.72 | 7 |
| ATOM | 2268 | CA  | GLU | 286 | 21.674 | 4.723  | 14.615 | 1.00 | 38.74 | 6 |
| ATOM | 2269 | CB  | GLU | 286 | 23.155 | 4.337  | 14.542 | 1.00 | 39.32 | 6 |
| ATOM | 2270 | CG  | GLU | 286 | 24.062 | 5.338  | 13.841 | 1.00 | 39.88 | 6 |
| ATOM | 2271 | CD  | GLU | 286 | 23.966 | 5.326  | 12.313 | 1.00 | 40.68 | 6 |
| ATOM | 2272 | OE1 | GLU | 286 | 23.326 | 4.423  | 11.700 | 1.00 | 36.00 | 8 |
| ATOM | 2273 | OE2 | GLU | 286 | 24.562 | 6.244  | 11.713 | 1.00 | 41.26 | 8 |
| ATOM | 2274 | C   | GLU | 286 | 20.943 | 3.662  | 15.393 | 1.00 | 38.55 | 6 |
| ATOM | 2275 | O   | GLU | 286 | 20.494 | 3.880  | 16.520 | 1.00 | 37.84 | 8 |
| ATOM | 2276 | N   | THR | 287 | 20.839 | 2.489  | 14.788 | 1.00 | 38.29 | 7 |
| ATOM | 2277 | CA  | THR | 287 | 20.176 | 1.390  | 15.437 | 1.00 | 38.74 | 6 |
| ATOM | 2278 | CB  | THR | 287 | 19.057 | 0.855  | 14.531 | 1.00 | 39.52 | 6 |
| ATOM | 2279 | OG1 | THR | 287 | 18.283 | −0.112 | 15.244 | 1.00 | 42.46 | 8 |
| ATOM | 2280 | CG2 | THR | 287 | 19.623 | 0.071  | 13.378 | 1.00 | 39.89 | 6 |
| ATOM | 2281 | C   | THR | 287 | 21.165 | 0.292  | 15.820 | 1.00 | 38.47 | 6 |
| ATOM | 2282 | O   | THR | 287 | 20.848 | −0.593 | 16.621 | 1.00 | 38.83 | 8 |
| ATOM | 2283 | N   | LYS | 288 | 22.378 | 0.354  | 15.281 | 1.00 | 37.58 | 7 |
| ATOM | 2284 | CA  | LYS | 288 | 23.366 | −0.685 | 15.572 | 1.00 | 37.11 | 6 |
| ATOM | 2285 | CB  | LYS | 288 | 24.330 | −0.860 | 14.392 | 1.00 | 37.29 | 6 |
| ATOM | 2286 | CG  | LYS | 288 | 25.285 | −2.028 | 14.547 | 1.00 | 38.36 | 6 |
| ATOM | 2287 | CD  | LYS | 288 | 26.125 | −2.227 | 13.287 | 1.00 | 42.82 | 6 |
| ATOM | 2288 | CE  | LYS | 288 | 26.879 | −3.577 | 13.291 | 1.00 | 43.75 | 6 |
| ATOM | 2289 | NZ  | LYS | 288 | 27.999 | −3.673 | 14.294 | 1.00 | 39.26 | 7 |
| ATOM | 2290 | C   | LYS | 288 | 24.175 | −0.401 | 16.844 | 1.00 | 36.52 | 6 |
| ATOM | 2291 | O   | LYS | 288 | 24.735 | 0.662  | 16.968 | 1.00 | 36.20 | 8 |
| ATOM | 2292 | N   | ILE | 289 | 24.224 | −1.368 | 17.761 | 1.00 | 35.39 | 7 |
| ATOM | 2293 | CA  | ILE | 289 | 25.019 | −1.282 | 18.974 | 1.00 | 34.71 | 6 |
| ATOM | 2294 | CB  | ILE | 289 | 24.728 | −2.495 | 19.882 | 1.00 | 35.23 | 6 |
| ATOM | 2295 | CG1 | ILE | 289 | 25.372 | −2.310 | 21.257 | 1.00 | 36.17 | 6 |
| ATOM | 2296 | CD1 | ILE | 289 | 24.818 | −3.237 | 22.343 | 1.00 | 38.91 | 6 |
| ATOM | 2297 | CG2 | ILE | 289 | 25.242 | −3.770 | 19.259 | 1.00 | 34.32 | 6 |
| ATOM | 2298 | C   | ILE | 289 | 26.491 | −1.265 | 18.628 | 1.00 | 34.70 | 6 |
| ATOM | 2299 | O   | ILE | 289 | 26.893 | −1.922 | 17.689 | 1.00 | 34.48 | 8 |

APPENDIX A-continued

| ATOM | 2300 | N | MET | 290 | 27.310 | −0.528 | 19.378 | 1.00 | 34.01 | 7 |
|---|---|---|---|---|---|---|---|---|---|---|
| ATOM | 2301 | CA | MET | 290 | 28.737 | −0.532 | 19.050 | 1.00 | 34.87 | 6 |
| ATOM | 2302 | CB | MET | 290 | 29.516 | 0.528 | 19.818 | 1.00 | 33.88 | 6 |
| ATOM | 2303 | CG | MET | 290 | 30.977 | 0.571 | 19.359 | 1.00 | 35.22 | 6 |
| ATOM | 2304 | SD | MET | 290 | 31.904 | 1.636 | 20.407 | 1.00 | 35.28 | 16 |
| ATOM | 2305 | CE | MET | 290 | 31.190 | 3.231 | 19.966 | 1.00 | 35.84 | 6 |
| ATOM | 2306 | C | MET | 290 | 29.397 | −1.873 | 19.330 | 1.00 | 35.09 | 6 |
| ATOM | 2307 | O | MET | 290 | 29.286 | −2.426 | 20.434 | 1.00 | 34.26 | 8 |
| ATOM | 2308 | N | GLU | 291 | 30.123 | −2.375 | 18.345 | 1.00 | 36.10 | 7 |
| ATOM | 2309 | CA | GLU | 291 | 30.884 | −3.593 | 18.529 | 1.00 | 37.19 | 6 |
| ATOM | 2310 | CB | GLU | 291 | 30.399 | −4.654 | 17.550 | 1.00 | 38.37 | 6 |
| ATOM | 2311 | CG | GLU | 291 | 28.886 | −4.731 | 17.432 | 1.00 | 42.56 | 6 |
| ATOM | 2312 | CD | GLU | 291 | 28.433 | −5.961 | 16.682 | 1.00 | 47.99 | 6 |
| ATOM | 2313 | OE1 | GLU | 291 | 29.306 | −6.700 | 16.158 | 1.00 | 50.26 | 8 |
| ATOM | 2314 | OE2 | GLU | 291 | 27.202 | −6.192 | 16.631 | 1.00 | 52.09 | 8 |
| ATOM | 2315 | C | GLU | 291 | 32.361 | −3.275 | 18.291 | 1.00 | 37.24 | 6 |
| ATOM | 2316 | O | GLU | 291 | 32.818 | −2.177 | 18.593 | 1.00 | 36.12 | 8 |
| ATOM | 2317 | N | LYS | 292 | 33.089 | −4.252 | 17.767 | 1.00 | 37.51 | 7 |
| ATOM | 2318 | CA | LYS | 292 | 34.489 | −4.108 | 17.391 | 1.00 | 39.10 | 6 |
| ATOM | 2319 | CB | LYS | 292 | 35.278 | −5.321 | 17.907 | 1.00 | 39.44 | 6 |
| ATOM | 2320 | CG | LYS | 292 | 36.754 | −5.334 | 17.579 | 1.00 | 42.36 | 6 |
| ATOM | 2321 | CD | LYS | 292 | 37.478 | −6.442 | 18.355 | 1.00 | 47.20 | 6 |
| ATOM | 2322 | CE | LYS | 292 | 38.985 | −6.450 | 18.076 | 1.00 | 50.85 | 6 |
| ATOM | 2323 | NZ | LYS | 292 | 39.825 | −6.822 | 19.280 | 1.00 | 52.45 | 7 |
| ATOM | 2324 | C | LYS | 292 | 34.568 | −4.009 | 15.852 | 1.00 | 39.22 | 6 |
| ATOM | 2325 | O | LYS | 292 | 34.054 | −4.882 | 15.151 | 1.00 | 37.32 | 8 |
| ATOM | 2326 | N | TYR | 293 | 35.208 | −2.957 | 15.333 | 1.00 | 40.12 | 7 |
| ATOM | 2327 | CA | TYR | 293 | 35.310 | −2.750 | 13.876 | 1.00 | 41.40 | 6 |
| ATOM | 2328 | CB | TYR | 293 | 34.467 | −1.548 | 13.448 | 1.00 | 41.70 | 6 |
| ATOM | 2329 | CG | TYR | 293 | 33.072 | −1.595 | 13.988 | 1.00 | 39.82 | 6 |
| ATOM | 2330 | CD1 | TYR | 293 | 32.699 | −0.787 | 15.060 | 1.00 | 38.74 | 6 |
| ATOM | 2331 | CE1 | TYR | 293 | 31.425 | −0.837 | 15.571 | 1.00 | 38.77 | 6 |
| ATOM | 2332 | CZ | TYR | 293 | 30.507 | −1.710 | 15.016 | 1.00 | 38.05 | 6 |
| ATOM | 2333 | OH | TYR | 293 | 29.246 | −1.754 | 15.528 | 1.00 | 38.38 | 8 |
| ATOM | 2334 | CE2 | TYR | 293 | 30.855 | −2.533 | 13.953 | 1.00 | 40.12 | 6 |
| ATOM | 2335 | CD2 | TYR | 293 | 32.124 | −2.469 | 13.445 | 1.00 | 39.01 | 6 |
| ATOM | 2336 | C | TYR | 293 | 36.718 | −2.541 | 13.338 | 1.00 | 42.46 | 6 |
| ATOM | 2337 | O | TYR | 293 | 37.663 | −2.361 | 14.100 | 1.00 | 42.09 | 8 |
| ATOM | 2338 | N | GLN | 294 | 36.837 | −2.573 | 12.006 | 1.00 | 43.58 | 7 |
| ATOM | 2339 | CA | GLN | 294 | 38.098 | −2.262 | 11.314 | 1.00 | 45.02 | 6 |
| ATOM | 2340 | CB | GLN | 294 | 38.780 | −3.517 | 10.806 | 1.00 | 45.24 | 6 |
| ATOM | 2341 | CG | GLN | 294 | 38.854 | −4.607 | 11.836 | 1.00 | 48.98 | 6 |
| ATOM | 2342 | CD | GLN | 294 | 40.175 | −5.351 | 11.796 | 1.00 | 52.81 | 6 |
| ATOM | 2343 | OE1 | GLN | 294 | 40.735 | −5.571 | 10.721 | 1.00 | 54.24 | 8 |
| ATOM | 2344 | NE2 | GLN | 294 | 40.677 | −5.742 | 12.974 | 1.00 | 54.69 | 7 |
| ATOM | 2345 | C | GLN | 294 | 37.818 | −1.338 | 10.143 | 1.00 | 45.22 | 6 |
| ATOM | 2346 | O | GLN | 294 | 37.040 | −1.671 | 9.261 | 1.00 | 44.76 | 8 |
| ATOM | 2347 | N | GLU | 295 | 38.426 | −0.161 | 10.148 | 1.00 | 44.99 | 7 |
| ATOM | 2348 | CA | GLU | 295 | 38.161 | 0.785 | 9.095 | 1.00 | 45.31 | 6 |
| ATOM | 2349 | CB | GLU | 295 | 38.021 | 2.202 | 9.648 | 1.00 | 46.18 | 6 |
| ATOM | 2350 | CG | GLU | 295 | 37.578 | 3.220 | 8.603 | 1.00 | 50.34 | 6 |
| ATOM | 2351 | CD | GLU | 295 | 36.233 | 2.886 | 7.977 | 1.00 | 56.01 | 6 |
| ATOM | 2352 | OE1 | GLU | 295 | 35.481 | 2.093 | 8.584 | 1.00 | 59.39 | 8 |
| ATOM | 2353 | OE2 | GLU | 295 | 35.923 | 3.409 | 6.872 | 1.00 | 59.28 | 8 |
| ATOM | 2354 | C | GLU | 295 | 39.298 | 0.721 | 8.112 | 1.00 | 44.71 | 6 |
| ATOM | 2355 | O | GLU | 295 | 40.470 | 0.836 | 8.487 | 1.00 | 43.54 | 8 |
| ATOM | 2356 | N | GLN | 296 | 38.955 | 0.522 | 6.850 | 1.00 | 44.25 | 7 |
| ATOM | 2357 | CA | GLN | 296 | 39.983 | 0.478 | 5.812 | 1.00 | 45.12 | 6 |
| ATOM | 2358 | CB | GLN | 296 | 39.400 | −0.104 | 4.524 | 1.00 | 45.30 | 6 |
| ATOM | 2359 | CG | GLN | 296 | 40.402 | −0.268 | 3.385 | 1.00 | 49.64 | 6 |
| ATOM | 2360 | CD | GLN | 296 | 39.763 | −0.921 | 2.165 | 1.00 | 54.67 | 6 |
| ATOM | 2361 | OE1 | GLN | 296 | 38.595 | −1.336 | 2.214 | 1.00 | 56.66 | 8 |
| ATOM | 2362 | NE2 | GLN | 296 | 40.521 | −1.022 | 1.076 | 1.00 | 55.43 | 7 |
| ATOM | 2363 | C | GLN | 296 | 40.461 | 1.898 | 5.586 | 1.00 | 44.64 | 6 |
| ATOM | 2364 | O | GLN | 296 | 39.653 | 2.828 | 5.543 | 1.00 | 45.54 | 8 |
| ATOM | 2365 | N | SER | 297 | 41.767 | 2.097 | 5.483 | 1.00 | 43.68 | 7 |
| ATOM | 2366 | CA | SER | 297 | 42.251 | 3.431 | 5.221 | 1.00 | 43.00 | 6 |
| ATOM | 2367 | CB | SER | 297 | 42.498 | 4.215 | 6.508 | 1.00 | 44.19 | 6 |
| ATOM | 2368 | OG | SER | 297 | 42.410 | 5.603 | 6.243 | 1.00 | 46.27 | 8 |
| ATOM | 2369 | C | SER | 297 | 43.500 | 3.380 | 4.383 | 1.00 | 41.94 | 6 |
| ATOM | 2370 | O | SER | 297 | 43.995 | 2.302 | 4.041 | 1.00 | 41.17 | 8 |
| ATOM | 2371 | N | GLU | 298 | 44.005 | 4.549 | 4.035 | 1.00 | 40.42 | 7 |
| ATOM | 2372 | CA | GLU | 298 | 45.159 | 4.591 | 3.163 | 1.00 | 40.07 | 6 |
| ATOM | 2373 | CB | GLU | 298 | 44.693 | 4.823 | 1.720 | 1.00 | 39.98 | 6 |
| ATOM | 2374 | CG | GLU | 298 | 45.366 | 3.919 | 0.712 | 1.00 | 44.50 | 6 |
| ATOM | 2375 | CD | GLU | 298 | 45.165 | 4.364 | −0.732 | 1.00 | 48.17 | 6 |
| ATOM | 2376 | OE1 | GLU | 298 | 44.801 | 5.542 | −0.969 | 1.00 | 50.96 | 8 |
| ATOM | 2377 | OE2 | GLU | 298 | 45.392 | 3.529 | −1.631 | 1.00 | 48.74 | 8 |
| ATOM | 2378 | C | GLU | 298 | 46.056 | 5.731 | 3.597 | 1.00 | 38.61 | 6 |

APPENDIX A-continued

| ATOM | 2379 | O | GLU | 298 | 45.555 | 6.743 | 4.089 | 1.00 | 37.35 | 8 |
|---|---|---|---|---|---|---|---|---|---|---|
| ATOM | 2380 | N | ILE | 299 | 47.370 | 5.537 | 3.456 | 1.00 | 37.32 | 7 |
| ATOM | 2381 | CA | ILE | 299 | 48.348 | 6.598 | 3.674 | 1.00 | 37.12 | 6 |
| ATOM | 2382 | CB | ILE | 299 | 49.407 | 6.271 | 4.745 | 1.00 | 37.27 | 6 |
| ATOM | 2383 | CG1 | ILE | 299 | 48.794 | 5.880 | 6.073 | 1.00 | 37.54 | 6 |
| ATOM | 2384 | CD1 | ILE | 299 | 47.809 | 6.891 | 6.647 | 1.00 | 37.63 | 6 |
| ATOM | 2385 | CG2 | ILE | 299 | 50.352 | 7.468 | 4.909 | 1.00 | 38.20 | 6 |
| ATOM | 2386 | C | ILE | 299 | 49.111 | 6.773 | 2.387 | 1.00 | 36.13 | 6 |
| ATOM | 2387 | O | ILE | 299 | 49.583 | 5.797 | 1.794 | 1.00 | 35.78 | 8 |
| ATOM | 2388 | N | ASP | 300 | 49.257 | 8.014 | 1.967 | 1.00 | 34.91 | 7 |
| ATOM | 2389 | CA | ASP | 300 | 49.991 | 8.322 | 0.752 | 1.00 | 34.60 | 6 |
| ATOM | 2390 | CB | ASP | 300 | 49.132 | 9.259 | −0.100 | 1.00 | 35.34 | 6 |
| ATOM | 2391 | CG | ASP | 300 | 49.459 | 9.194 | −1.575 | 1.00 | 39.89 | 6 |
| ATOM | 2392 | OD1 | ASP | 300 | 50.650 | 9.040 | −1.942 | 1.00 | 43.03 | 8 |
| ATOM | 2393 | OD2 | ASP | 300 | 48.570 | 9.303 | −2.451 | 1.00 | 45.15 | 8 |
| ATOM | 2394 | C | ASP | 300 | 51.280 | 9.034 | 1.154 | 1.00 | 32.84 | 6 |
| ATOM | 2395 | O | ASP | 300 | 51.244 | 9.890 | 2.023 | 1.00 | 31.64 | 8 |
| ATOM | 2396 | N | ASN | 301 | 52.413 | 8.615 | 0.580 | 1.00 | 31.48 | 7 |
| ATOM | 2397 | CA | ASN | 301 | 53.704 | 9.288 | 0.754 | 1.00 | 30.62 | 6 |
| ATOM | 2398 | CB | ASN | 301 | 54.703 | 8.456 | 1.540 | 1.00 | 30.30 | 6 |
| ATOM | 2399 | CG | ASN | 301 | 56.081 | 9.083 | 1.527 | 1.00 | 28.62 | 6 |
| ATOM | 2400 | OD1 | ASN | 301 | 56.202 | 10.299 | 1.487 | 1.00 | 26.65 | 8 |
| ATOM | 2401 | ND2 | ASN | 301 | 57.119 | 8.268 | 1.543 | 1.00 | 25.07 | 7 |
| ATOM | 2402 | C | ASN | 301 | 54.325 | 9.625 | −0.602 | 1.00 | 30.92 | 6 |
| ATOM | 2403 | O | ASN | 301 | 55.125 | 8.850 | −1.159 | 1.00 | 30.58 | 8 |
| ATOM | 2404 | N | PRO | 302 | 53.992 | 10.805 | −1.104 | 1.00 | 30.80 | 7 |
| ATOM | 2405 | CA | PRO | 302 | 54.424 | 11.234 | −2.432 | 1.00 | 31.42 | 6 |
| ATOM | 2406 | CB | PRO | 302 | 53.394 | 12.310 | −2.806 | 1.00 | 31.93 | 6 |
| ATOM | 2407 | CG | PRO | 302 | 52.669 | 12.663 | −1.558 | 1.00 | 31.61 | 6 |
| ATOM | 2408 | CD | PRO | 302 | 53.201 | 11.836 | −0.415 | 1.00 | 31.61 | 6 |
| ATOM | 2409 | C | PRO | 302 | 55.784 | 11.877 | −2.427 | 1.00 | 31.56 | 6 |
| ATOM | 2410 | O | PRO | 302 | 56.062 | 12.666 | −3.322 | 1.00 | 32.42 | 8 |
| ATOM | 2411 | N | THR | 303 | 56.623 | 11.579 | −1.448 | 1.00 | 31.02 | 7 |
| ATOM | 2412 | CA | THR | 303 | 57.910 | 12.249 | −1.388 | 1.00 | 29.81 | 6 |
| ATOM | 2413 | CB | THR | 303 | 58.116 | 12.856 | −0.010 | 1.00 | 30.12 | 6 |
| ATOM | 2414 | OG1 | THR | 303 | 58.410 | 11.801 | 0.913 | 1.00 | 29.24 | 8 |
| ATOM | 2415 | CG2 | THR | 303 | 56.805 | 13.453 | 0.530 | 1.00 | 28.90 | 6 |
| ATOM | 2416 | C | THR | 303 | 59.029 | 11.249 | −1.633 | 1.00 | 29.87 | 6 |
| ATOM | 2417 | O | THR | 303 | 58.806 | 10.050 | −1.627 | 1.00 | 29.22 | 8 |
| ATOM | 2418 | N | ASP | 304 | 60.242 | 11.756 | −1.814 | 1.00 | 29.17 | 7 |
| ATOM | 2419 | CA | ASP | 304 | 61.393 | 10.903 | −2.050 | 1.00 | 30.09 | 6 |
| ATOM | 2420 | CB | ASP | 304 | 62.385 | 11.637 | −2.976 | 1.00 | 31.39 | 6 |
| ATOM | 2421 | CG | ASP | 304 | 63.602 | 10.795 | −3.314 | 1.00 | 34.58 | 6 |
| ATOM | 2422 | OD1 | ASP | 304 | 64.000 | 10.003 | −2.451 | 1.00 | 42.73 | 8 |
| ATOM | 2423 | OD2 | ASP | 304 | 64.222 | 10.823 | −4.396 | 1.00 | 39.86 | 8 |
| ATOM | 2424 | C | ASP | 304 | 62.086 | 10.400 | −0.770 | 1.00 | 29.52 | 6 |
| ATOM | 2425 | O | ASP | 304 | 63.177 | 9.831 | −0.846 | 1.00 | 29.39 | 8 |
| ATOM | 2426 | N | GLN | 305 | 61.477 | 10.626 | 0.399 | 1.00 | 29.10 | 7 |
| ATOM | 2427 | CA | GLN | 305 | 62.017 | 10.137 | 1.672 | 1.00 | 28.55 | 6 |
| ATOM | 2428 | CB | GLN | 305 | 62.234 | 11.279 | 2.682 | 1.00 | 29.39 | 6 |
| ATOM | 2429 | CG | GLN | 305 | 63.347 | 12.278 | 2.357 | 1.00 | 30.07 | 6 |
| ATOM | 2430 | CD | GLN | 305 | 62.945 | 13.323 | 1.313 | 1.00 | 33.12 | 6 |
| ATOM | 2431 | OE1 | GLN | 305 | 61.905 | 13.992 | 1.449 | 1.00 | 33.76 | 8 |
| ATOM | 2432 | NE2 | GLN | 305 | 63.769 | 13.471 | 0.282 | 1.00 | 31.21 | 7 |
| ATOM | 2433 | C | GLN | 305 | 61.039 | 9.147 | 2.315 | 1.00 | 28.07 | 6 |
| ATOM | 2434 | O | GLN | 305 | 59.851 | 9.124 | 2.001 | 1.00 | 26.36 | 8 |
| ATOM | 2435 | N | SER | 306 | 61.526 | 8.366 | 3.261 | 1.00 | 27.77 | 7 |
| ATOM | 2436 | CA | SER | 306 | 60.646 | 7.419 | 3.934 | 1.00 | 27.19 | 6 |
| ATOM | 2437 | CBA | SER | 306 | 61.461 | 6.335 | 4.635 | 0.50 | 28.35 | 6 |
| ATOM | 2438 | CBB | SER | 306 | 61.457 | 6.299 | 4.581 | 0.50 | 28.01 | 6 |
| ATOM | 2439 | OGA | SER | 306 | 61.821 | 6.740 | 5.946 | 0.50 | 28.89 | 8 |
| ATOM | 2440 | OGB | SER | 306 | 62.056 | 5.478 | 3.590 | 0.50 | 25.43 | 8 |
| ATOM | 2441 | C | SER | 306 | 59.791 | 8.158 | 4.945 | 1.00 | 27.53 | 6 |
| ATOM | 2442 | O | SER | 306 | 60.107 | 9.284 | 5.295 | 1.00 | 25.95 | 8 |
| ATOM | 2443 | N | MET | 307 | 58.730 | 7.522 | 5.436 | 1.00 | 26.72 | 7 |
| ATOM | 2444 | CA | MET | 307 | 57.863 | 8.181 | 6.386 | 1.00 | 27.38 | 6 |
| ATOM | 2445 | CB | MET | 307 | 56.843 | 8.974 | 5.606 | 1.00 | 28.26 | 6 |
| ATOM | 2446 | CG | MET | 307 | 55.633 | 9.433 | 6.355 | 1.00 | 33.32 | 6 |
| ATOM | 2447 | SD | MET | 307 | 54.450 | 9.999 | 5.114 | 1.00 | 42.72 | 16 |
| ATOM | 2448 | CE | MET | 307 | 53.788 | 8.591 | 4.637 | 1.00 | 42.05 | 6 |
| ATOM | 2449 | C | MET | 307 | 57.185 | 7.163 | 7.281 | 1.00 | 27.05 | 6 |
| ATOM | 2450 | O | MET | 307 | 57.000 | 6.012 | 6.882 | 1.00 | 26.84 | 8 |
| ATOM | 2451 | N | ASN | 308 | 56.837 | 7.593 | 8.496 | 1.00 | 25.96 | 7 |
| ATOM | 2452 | CA | ASN | 308 | 56.122 | 6.765 | 9.457 | 1.00 | 26.17 | 6 |
| ATOM | 2453 | CB | ASN | 308 | 56.979 | 6.517 | 10.715 | 1.00 | 27.27 | 6 |
| ATOM | 2454 | CG | ASN | 308 | 58.400 | 5.946 | 10.381 | 1.00 | 33.22 | 6 |
| ATOM | 2455 | OD1 | ASN | 308 | 59.425 | 6.418 | 10.910 | 1.00 | 41.31 | 8 |
| ATOM | 2456 | ND2 | ASN | 308 | 58.455 | 4.949 | 9.498 | 1.00 | 36.38 | 7 |
| ATOM | 2457 | C | ASN | 308 | 54.825 | 7.484 | 9.811 | 1.00 | 24.83 | 6 |

APPENDIX A-continued

| ATOM | 2458 | O | ASN | 308 | 54.792 | 8.715 | 9.870 | 1.00 | 21.98 | 8 |
|---|---|---|---|---|---|---|---|---|---|---|
| ATOM | 2459 | N | SER | 309 | 53.757 | 6.721 | 10.054 | 1.00 | 23.42 | 7 |
| ATOM | 2460 | CA | SER | 309 | 52.469 | 7.318 | 10.408 | 1.00 | 23.65 | 6 |
| ATOM | 2461 | CB | SER | 309 | 51.525 | 7.249 | 9.209 | 1.00 | 23.90 | 6 |
| ATOM | 2462 | OG | SER | 309 | 50.272 | 7.881 | 9.467 | 1.00 | 23.53 | 8 |
| ATOM | 2463 | C | SER | 309 | 51.870 | 6.529 | 11.545 | 1.00 | 23.83 | 6 |
| ATOM | 2464 | O | SER | 309 | 52.198 | 5.359 | 11.732 | 1.00 | 23.87 | 8 |
| ATOM | 2465 | N | ILE | 310 | 51.027 | 7.182 | 12.323 | 1.00 | 23.41 | 7 |
| ATOM | 2466 | CA | ILE | 310 | 50.284 | 6.509 | 13.355 | 1.00 | 23.02 | 6 |
| ATOM | 2467 | CB | ILE | 310 | 51.080 | 6.450 | 14.676 | 1.00 | 23.79 | 6 |
| ATOM | 2468 | CG1 | ILE | 310 | 50.380 | 5.517 | 15.683 | 1.00 | 24.63 | 6 |
| ATOM | 2469 | CD1 | ILE | 310 | 51.230 | 5.084 | 16.850 | 1.00 | 29.17 | 6 |
| ATOM | 2470 | CG2 | ILE | 310 | 51.243 | 7.826 | 15.245 | 1.00 | 25.05 | 6 |
| ATOM | 2471 | C | ILE | 310 | 48.997 | 7.291 | 13.524 | 1.00 | 22.76 | 6 |
| ATOM | 2472 | O | ILE | 310 | 48.946 | 8.488 | 13.254 | 1.00 | 21.65 | 8 |
| ATOM | 2473 | N | GLY | 311 | 47.957 | 6.624 | 14.002 | 1.00 | 22.69 | 7 |
| ATOM | 2474 | CA | GLY | 311 | 46.687 | 7.278 | 14.194 | 1.00 | 22.34 | 6 |
| ATOM | 2475 | C | GLY | 311 | 46.194 | 7.223 | 15.626 | 1.00 | 22.53 | 6 |
| ATOM | 2476 | O | GLY | 311 | 46.567 | 6.326 | 16.393 | 1.00 | 22.50 | 8 |
| ATOM | 2477 | N | PHE | 312 | 45.384 | 8.212 | 15.984 | 1.00 | 21.28 | 7 |
| ATOM | 2478 | CA | PHE | 312 | 44.761 | 8.240 | 17.302 | 1.00 | 21.67 | 6 |
| ATOM | 2479 | CB | PHE | 312 | 45.295 | 9.417 | 18.097 | 1.00 | 20.26 | 6 |
| ATOM | 2480 | CG | PHE | 312 | 46.769 | 9.319 | 18.392 | 1.00 | 21.84 | 6 |
| ATOM | 2481 | CD1 | PHE | 312 | 47.705 | 9.902 | 17.549 | 1.00 | 20.29 | 6 |
| ATOM | 2482 | CE1 | PHE | 312 | 49.048 | 9.804 | 17.801 | 1.00 | 21.74 | 6 |
| ATOM | 2483 | CZ | PHE | 312 | 49.480 | 9.147 | 18.928 | 1.00 | 21.21 | 6 |
| ATOM | 2484 | CE2 | PHE | 312 | 48.560 | 8.560 | 19.783 | 1.00 | 21.27 | 6 |
| ATOM | 2485 | CD2 | PHE | 312 | 47.214 | 8.642 | 19.509 | 1.00 | 20.72 | 6 |
| ATOM | 2486 | C | PHE | 312 | 43.254 | 8.346 | 17.219 | 1.00 | 21.57 | 6 |
| ATOM | 2487 | O | PHE | 312 | 42.710 | 8.886 | 16.254 | 1.00 | 21.74 | 8 |
| ATOM | 2488 | N | LEU | 313 | 42.606 | 7.832 | 18.256 | 1.00 | 21.12 | 7 |
| ATOM | 2489 | CA | LEU | 313 | 41.155 | 7.900 | 18.441 | 1.00 | 21.27 | 6 |
| ATOM | 2490 | CB | LEU | 313 | 40.575 | 6.490 | 18.431 | 1.00 | 20.92 | 6 |
| ATOM | 2491 | CG | LEU | 313 | 40.633 | 5.814 | 17.060 | 1.00 | 22.77 | 6 |
| ATOM | 2492 | CD1 | LEU | 313 | 40.501 | 4.320 | 17.197 | 1.00 | 22.09 | 6 |
| ATOM | 2493 | CD2 | LEU | 313 | 39.485 | 6.409 | 16.207 | 1.00 | 22.33 | 6 |
| ATOM | 2494 | C | LEU | 313 | 40.863 | 8.508 | 19.793 | 1.00 | 21.04 | 6 |
| ATOM | 2495 | O | LEU | 313 | 41.634 | 8.320 | 20.740 | 1.00 | 20.30 | 8 |
| ATOM | 2496 | N | THR | 314 | 39.730 | 9.212 | 19.886 | 1.00 | 20.61 | 7 |
| ATOM | 2497 | CA | THR | 314 | 39.262 | 9.715 | 21.162 | 1.00 | 20.74 | 6 |
| ATOM | 2498 | CB | THR | 314 | 38.277 | 10.876 | 20.986 | 1.00 | 20.92 | 6 |
| ATOM | 2499 | OG1 | THR | 314 | 38.995 | 12.025 | 20.547 | 1.00 | 21.70 | 8 |
| ATOM | 2500 | CG2 | THR | 314 | 37.702 | 11.311 | 22.356 | 1.00 | 19.63 | 6 |
| ATOM | 2501 | C | THR | 314 | 38.555 | 8.561 | 21.808 | 1.00 | 20.78 | 6 |
| ATOM | 2502 | O | THR | 314 | 37.655 | 7.966 | 21.203 | 1.00 | 20.21 | 8 |
| ATOM | 2503 | N | ILE | 315 | 39.002 | 8.220 | 23.010 | 1.00 | 19.73 | 7 |
| ATOM | 2504 | CA | ILE | 315 | 38.375 | 7.185 | 23.802 | 1.00 | 20.16 | 6 |
| ATOM | 2505 | CB | ILE | 315 | 39.408 | 6.424 | 24.636 | 1.00 | 20.41 | 6 |
| ATOM | 2506 | CG1 | ILE | 315 | 40.542 | 5.868 | 23.765 | 1.00 | 21.20 | 6 |
| ATOM | 2507 | CD1 | ILE | 315 | 40.067 | 4.794 | 22.752 | 1.00 | 24.32 | 6 |
| ATOM | 2508 | CG2 | ILE | 315 | 38.699 | 5.252 | 25.369 | 1.00 | 21.62 | 6 |
| ATOM | 2509 | C | ILE | 315 | 37.400 | 7.836 | 24.753 | 1.00 | 19.80 | 6 |
| ATOM | 2510 | O | ILE | 315 | 37.688 | 8.897 | 25.291 | 1.00 | 19.11 | 8 |
| ATOM | 2511 | N | THR | 316 | 36.236 | 7.213 | 24.949 | 1.00 | 19.97 | 7 |
| ATOM | 2512 | CA | THR | 316 | 35.307 | 7.687 | 25.989 | 1.00 | 20.51 | 6 |
| ATOM | 2513 | CB | THR | 316 | 33.959 | 8.025 | 25.379 | 1.00 | 20.66 | 6 |
| ATOM | 2514 | OG1 | THR | 316 | 34.126 | 9.139 | 24.507 | 1.00 | 22.95 | 8 |
| ATOM | 2515 | CG2 | THR | 316 | 32.968 | 8.553 | 26.448 | 1.00 | 20.91 | 6 |
| ATOM | 2516 | C | THR | 316 | 35.157 | 6.582 | 27.013 | 1.00 | 21.15 | 6 |
| ATOM | 2517 | O | THR | 316 | 34.858 | 5.429 | 26.661 | 1.00 | 22.13 | 8 |
| ATOM | 2518 | N | SER | 317 | 35.341 | 6.908 | 28.289 | 1.00 | 20.54 | 7 |
| ATOM | 2519 | CA | SER | 317 | 35.205 | 5.915 | 29.341 | 1.00 | 21.14 | 6 |
| ATOM | 2520 | CB | SER | 317 | 36.506 | 5.821 | 30.156 | 1.00 | 20.54 | 6 |
| ATOM | 2521 | OG | SER | 317 | 36.413 | 4.788 | 31.128 | 1.00 | 23.88 | 8 |
| ATOM | 2522 | C | SER | 317 | 34.055 | 6.325 | 30.283 | 1.00 | 20.36 | 6 |
| ATOM | 2523 | O | SER | 317 | 34.121 | 7.348 | 30.931 | 1.00 | 20.59 | 8 |
| ATOM | 2524 | N | LEU | 318 | 33.012 | 5.512 | 30.325 | 1.00 | 19.68 | 7 |
| ATOM | 2525 | CA | LEU | 318 | 31.876 | 5.746 | 31.217 | 1.00 | 18.93 | 6 |
| ATOM | 2526 | CB | LEU | 318 | 30.609 | 5.347 | 30.486 | 1.00 | 19.48 | 6 |
| ATOM | 2527 | CG | LEU | 318 | 30.111 | 6.473 | 29.578 | 1.00 | 22.02 | 6 |
| ATOM | 2528 | CD1 | LEU | 318 | 28.838 | 6.084 | 28.794 | 1.00 | 22.84 | 6 |
| ATOM | 2529 | CD2 | LEU | 318 | 29.840 | 7.673 | 30.426 | 1.00 | 24.03 | 6 |
| ATOM | 2530 | C | LEU | 318 | 32.122 | 4.857 | 32.431 | 1.00 | 17.72 | 6 |
| ATOM | 2531 | O | LEU | 318 | 32.344 | 3.654 | 32.281 | 1.00 | 18.19 | 8 |
| ATOM | 2532 | N | GLU | 319 | 32.122 | 5.427 | 33.632 | 1.00 | 15.71 | 7 |
| ATOM | 2533 | CA | GLU | 319 | 32.480 | 4.647 | 34.822 | 1.00 | 16.28 | 6 |
| ATOM | 2534 | CB | GLU | 319 | 33.923 | 4.969 | 35.254 | 1.00 | 17.04 | 6 |
| ATOM | 2535 | CG | GLU | 319 | 34.973 | 4.687 | 34.168 | 1.00 | 18.74 | 6 |
| ATOM | 2536 | CD | GLU | 319 | 36.370 | 5.249 | 34.485 | 1.00 | 22.97 | 6 |

APPENDIX A-continued

| ATOM | 2537 | OE1 | GLU | 319 | 36.661 | 5.593 | 35.636 | 1.00 | 23.41 | 8 |
| ATOM | 2538 | OE2 | GLU | 319 | 37.213 | 5.354 | 33.570 | 1.00 | 27.15 | 8 |
| ATOM | 2539 | C | GLU | 319 | 31.511 | 4.994 | 35.947 | 1.00 | 15.36 | 6 |
| ATOM | 2540 | O | GLU | 319 | 31.270 | 6.146 | 36.221 | 1.00 | 14.57 | 8 |
| ATOM | 2541 | N | LEU | 320 | 30.994 | 3.973 | 36.602 | 1.00 | 15.72 | 7 |
| ATOM | 2542 | CA | LEU | 320 | 29.978 | 4.138 | 37.621 | 1.00 | 16.33 | 6 |
| ATOM | 2543 | CB | LEU | 320 | 28.767 | 3.291 | 37.243 | 1.00 | 17.81 | 6 |
| ATOM | 2544 | CG | LEU | 320 | 27.581 | 3.346 | 38.197 | 1.00 | 17.66 | 6 |
| ATOM | 2545 | CD1 | LEU | 320 | 26.931 | 4.706 | 38.126 | 1.00 | 20.85 | 6 |
| ATOM | 2546 | CD2 | LEU | 320 | 26.541 | 2.262 | 37.847 | 1.00 | 16.62 | 6 |
| ATOM | 2547 | C | LEU | 320 | 30.501 | 3.677 | 38.966 | 1.00 | 16.79 | 6 |
| ATOM | 2548 | O | LEU | 320 | 31.073 | 2.576 | 39.071 | 1.00 | 16.95 | 8 |
| ATOM | 2549 | N | TYR | 321 | 30.258 | 4.503 | 39.988 | 1.00 | 15.93 | 7 |
| ATOM | 2550 | CA | TYR | 321 | 30.780 | 4.284 | 41.340 | 1.00 | 16.57 | 6 |
| ATOM | 2551 | CB | TYR | 321 | 31.810 | 5.373 | 41.660 | 1.00 | 15.66 | 6 |
| ATOM | 2552 | CG | TYR | 321 | 32.977 | 5.440 | 40.675 | 1.00 | 16.98 | 6 |
| ATOM | 2553 | CD1 | TYR | 321 | 32.832 | 6.075 | 39.446 | 1.00 | 17.64 | 6 |
| ATOM | 2554 | CE1 | TYR | 321 | 33.860 | 6.135 | 38.558 | 1.00 | 17.82 | 6 |
| ATOM | 2555 | CZ | TYR | 321 | 35.076 | 5.549 | 38.863 | 1.00 | 19.46 | 6 |
| ATOM | 2556 | OH | TYR | 321 | 36.113 | 5.622 | 37.941 | 1.00 | 20.08 | 8 |
| ATOM | 2557 | CE2 | TYR | 321 | 35.266 | 4.922 | 40.065 | 1.00 | 18.74 | 6 |
| ATOM | 2558 | CD2 | TYR | 321 | 34.199 | 4.844 | 40.968 | 1.00 | 17.35 | 6 |
| ATOM | 2559 | C | TYR | 321 | 29.727 | 4.376 | 42.440 | 1.00 | 16.97 | 6 |
| ATOM | 2560 | O | TYR | 321 | 28.854 | 5.279 | 42.409 | 1.00 | 15.24 | 8 |
| ATOM | 2561 | N | ARG | 322 | 29.800 | 3.433 | 43.388 | 1.00 | 16.87 | 7 |
| ATOM | 2562 | CA | ARG | 322 | 29.053 | 3.550 | 44.629 | 1.00 | 19.25 | 6 |
| ATOM | 2563 | CB | ARG | 322 | 29.263 | 2.355 | 45.520 | 1.00 | 20.47 | 6 |
| ATOM | 2564 | CG | ARG | 322 | 28.574 | 1.123 | 45.181 | 1.00 | 22.11 | 6 |
| ATOM | 2565 | CD | ARG | 322 | 28.581 | 0.114 | 46.343 | 1.00 | 24.83 | 6 |
| ATOM | 2566 | NE | ARG | 322 | 28.383 | −1.211 | 45.786 | 1.00 | 25.24 | 7 |
| ATOM | 2567 | CZ | ARG | 322 | 28.946 | −2.308 | 46.225 | 1.00 | 27.50 | 6 |
| ATOM | 2568 | NH1 | ARG | 322 | 29.765 | −2.275 | 47.279 | 1.00 | 25.39 | 7 |
| ATOM | 2569 | NH2 | ARG | 322 | 28.671 | −3.449 | 45.598 | 1.00 | 27.87 | 7 |
| ATOM | 2570 | C | ARG | 322 | 29.756 | 4.664 | 45.382 | 1.00 | 20.71 | 6 |
| ATOM | 2571 | O | ARG | 322 | 30.954 | 4.882 | 45.187 | 1.00 | 19.27 | 8 |
| ATOM | 2572 | N | TYR | 323 | 29.054 | 5.370 | 46.256 | 1.00 | 22.22 | 7 |
| ATOM | 2573 | CA | TYR | 323 | 29.755 | 6.380 | 47.045 | 1.00 | 24.39 | 6 |
| ATOM | 2574 | CB | TYR | 323 | 29.495 | 7.816 | 46.620 | 1.00 | 24.97 | 6 |
| ATOM | 2575 | CG | TYR | 323 | 30.459 | 8.732 | 47.365 | 1.00 | 28.53 | 6 |
| ATOM | 2576 | CD1 | TYR | 323 | 31.737 | 8.942 | 46.880 | 1.00 | 30.15 | 6 |
| ATOM | 2577 | CE1 | TYR | 323 | 32.634 | 9.742 | 47.527 | 1.00 | 31.62 | 6 |
| ATOM | 2578 | CZ | TYR | 323 | 32.309 | 10.327 | 48.726 | 1.00 | 30.41 | 6 |
| ATOM | 2579 | OH | TYR | 323 | 33.265 | 11.123 | 49.325 | 1.00 | 32.48 | 8 |
| ATOM | 2580 | CE2 | TYR | 323 | 31.061 | 10.120 | 49.282 | 1.00 | 30.74 | 6 |
| ATOM | 2581 | CD2 | TYR | 323 | 30.133 | 9.292 | 48.596 | 1.00 | 31.01 | 6 |
| ATOM | 2582 | C | TYR | 323 | 29.386 | 6.294 | 48.471 | 1.00 | 26.23 | 6 |
| ATOM | 2583 | O | TYR | 323 | 28.250 | 6.759 | 48.814 | 1.00 | 25.96 | 8 |
| ATOM | 2584 | N | ASN | 324 | 30.367 | 5.751 | 49.240 | 1.00 | 26.21 | 7 |
| ATOM | 2585 | CA | ASN | 324 | 30.370 | 5.419 | 50.685 | 1.00 | 28.47 | 6 |
| ATOM | 2586 | CB | ASN | 324 | 30.755 | 3.925 | 50.882 | 1.00 | 29.49 | 6 |
| ATOM | 2587 | CG | ASN | 324 | 32.325 | 3.656 | 50.780 | 1.00 | 33.04 | 6 |
| ATOM | 2588 | OD1 | ASN | 324 | 33.079 | 4.465 | 50.252 | 1.00 | 37.52 | 8 |
| ATOM | 2589 | ND2 | ASN | 324 | 32.780 | 2.494 | 51.289 | 1.00 | 35.78 | 7 |
| ATOM | 2590 | C | ASN | 324 | 31.414 | 6.156 | 51.516 | 1.00 | 25.97 | 6 |
| ATOM | 2591 | O | ASN | 324 | 31.955 | 5.549 | 52.436 | 1.00 | 27.48 | 8 |
| ATOM | 2592 | N | GLY | 325 | 31.690 | 7.425 | 51.229 | 1.00 | 23.93 | 7 |
| ATOM | 2593 | CA | GLY | 325 | 32.811 | 8.095 | 51.866 | 1.00 | 20.57 | 6 |
| ATOM | 2594 | C | GLY | 325 | 34.040 | 7.979 | 50.963 | 1.00 | 19.94 | 6 |
| ATOM | 2595 | O | GLY | 325 | 35.055 | 8.620 | 51.219 | 1.00 | 18.49 | 8 |
| ATOM | 2596 | N | SER | 326 | 33.949 | 7.093 | 49.972 | 1.00 | 19.94 | 7 |
| ATOM | 2597 | CA | SER | 326 | 34.949 | 6.894 | 48.929 | 1.00 | 18.85 | 6 |
| ATOM | 2598 | CB | SER | 326 | 36.101 | 5.977 | 49.377 | 1.00 | 20.39 | 6 |
| ATOM | 2599 | OG | SER | 326 | 35.768 | 4.595 | 49.288 | 1.00 | 21.74 | 8 |
| ATOM | 2600 | C | SER | 326 | 34.215 | 6.294 | 47.742 | 1.00 | 18.84 | 6 |
| ATOM | 2601 | O | SER | 326 | 33.091 | 5.833 | 47.893 | 1.00 | 18.76 | 8 |
| ATOM | 2602 | N | GLU | 327 | 34.831 | 6.334 | 46.559 | 1.00 | 18.30 | 7 |
| ATOM | 2603 | CA | GLU | 327 | 34.200 | 5.836 | 45.348 | 1.00 | 17.57 | 6 |
| ATOM | 2604 | CB | GLU | 327 | 34.683 | 6.664 | 44.145 | 1.00 | 16.77 | 6 |
| ATOM | 2605 | CG | GLU | 327 | 34.343 | 8.151 | 44.291 | 1.00 | 19.93 | 6 |
| ATOM | 2606 | CD | GLU | 327 | 34.963 | 9.015 | 43.222 | 1.00 | 23.34 | 6 |
| ATOM | 2607 | OE1 | GLU | 327 | 35.744 | 8.512 | 42.406 | 1.00 | 26.62 | 8 |
| ATOM | 2608 | OE2 | GLU | 327 | 34.653 | 10.195 | 43.184 | 1.00 | 27.01 | 8 |
| ATOM | 2609 | C | GLU | 327 | 34.585 | 4.371 | 45.116 | 1.00 | 18.46 | 6 |
| ATOM | 2610 | O | GLU | 327 | 35.784 | 4.031 | 45.111 | 1.00 | 17.86 | 8 |
| ATOM | 2611 | N | ILE | 328 | 33.591 | 3.518 | 44.886 | 1.00 | 17.43 | 7 |
| ATOM | 2612 | CA | ILE | 328 | 33.839 | 2.107 | 44.571 | 1.00 | 17.81 | 6 |
| ATOM | 2613 | CB | ILE | 328 | 33.135 | 1.184 | 45.616 | 1.00 | 18.36 | 6 |
| ATOM | 2614 | CG1 | ILE | 328 | 33.766 | 1.415 | 46.993 | 1.00 | 19.02 | 6 |
| ATOM | 2615 | CD1 | ILE | 328 | 33.013 | 0.725 | 48.168 | 1.00 | 20.92 | 6 |

APPENDIX A-continued

| ATOM | 2616 | CG2 | ILE | 328 | 33.288 | −0.303 | 45.221 | 1.00 | 16.78 | 6 |
|------|------|-----|-----|-----|--------|--------|--------|------|-------|---|
| ATOM | 2617 | C | ILE | 328 | 33.295 | 1.832 | 43.173 | 1.00 | 17.83 | 6 |
| ATOM | 2618 | O | ILE | 328 | 32.110 | 1.923 | 42.949 | 1.00 | 17.61 | 8 |
| ATOM | 2619 | N | ARG | 329 | 34.166 | 1.528 | 42.222 | 1.00 | 18.40 | 7 |
| ATOM | 2620 | CA | ARG | 329 | 33.720 | 1.351 | 40.853 | 1.00 | 18.45 | 6 |
| ATOM | 2621 | CB | ARG | 329 | 34.927 | 1.412 | 39.885 | 1.00 | 18.42 | 6 |
| ATOM | 2622 | CG | ARG | 329 | 34.537 | 1.636 | 38.443 | 1.00 | 20.80 | 6 |
| ATOM | 2623 | CD | ARG | 329 | 35.741 | 1.716 | 37.467 | 1.00 | 23.08 | 6 |
| ATOM | 2624 | NE | ARG | 329 | 36.462 | 0.450 | 37.448 | 1.00 | 27.62 | 7 |
| ATOM | 2625 | CZ | ARG | 329 | 37.759 | 0.305 | 37.261 | 1.00 | 30.31 | 6 |
| ATOM | 2626 | NH1 | ARG | 329 | 38.533 | 1.349 | 37.034 | 1.00 | 31.35 | 7 |
| ATOM | 2627 | NH2 | ARG | 329 | 38.291 | −0.917 | 37.278 | 1.00 | 35.53 | 7 |
| ATOM | 2628 | C | ARG | 329 | 32.990 | 0.029 | 40.699 | 1.00 | 19.84 | 6 |
| ATOM | 2629 | O | ARG | 329 | 33.503 | −1.012 | 41.134 | 1.00 | 20.25 | 8 |
| ATOM | 2630 | N | ILE | 330 | 31.808 | 0.048 | 40.068 | 1.00 | 19.47 | 7 |
| ATOM | 2631 | CA | ILE | 330 | 31.078 | −1.193 | 39.854 | 1.00 | 19.41 | 6 |
| ATOM | 2632 | CB | ILE | 330 | 29.712 | −1.221 | 40.588 | 1.00 | 19.81 | 6 |
| ATOM | 2633 | CG1 | ILE | 330 | 28.725 | −0.220 | 39.987 | 1.00 | 20.44 | 6 |
| ATOM | 2634 | CD1 | ILE | 330 | 27.249 | −0.591 | 40.232 | 1.00 | 22.01 | 6 |
| ATOM | 2635 | CG2 | ILE | 330 | 29.894 | −0.929 | 42.041 | 1.00 | 19.97 | 6 |
| ATOM | 2636 | C | ILE | 330 | 30.908 | −1.489 | 38.357 | 1.00 | 20.88 | 6 |
| ATOM | 2637 | O | ILE | 330 | 30.456 | −2.565 | 37.990 | 1.00 | 19.62 | 8 |
| ATOM | 2638 | N | MET | 331 | 31.295 | −0.540 | 37.511 | 1.00 | 20.35 | 7 |
| ATOM | 2639 | CA | MET | 331 | 31.143 | −0.719 | 36.086 | 1.00 | 22.25 | 6 |
| ATOM | 2640 | CB | MET | 331 | 29.678 | −0.550 | 35.681 | 1.00 | 22.98 | 6 |
| ATOM | 2641 | CG | MET | 331 | 29.449 | −1.010 | 34.240 | 1.00 | 25.82 | 6 |
| ATOM | 2642 | SD | MET | 331 | 29.638 | 0.366 | 33.088 | 1.00 | 34.47 | 16 |
| ATOM | 2643 | CE | MET | 331 | 28.029 | 1.022 | 33.574 | 1.00 | 24.46 | 6 |
| ATOM | 2644 | C | MET | 331 | 31.994 | 0.270 | 35.295 | 1.00 | 21.98 | 6 |
| ATOM | 2645 | O | MET | 331 | 32.107 | 1.427 | 35.670 | 1.00 | 21.76 | 8 |
| ATOM | 2646 | N | GLN | 332 | 32.573 | −0.187 | 34.190 | 1.00 | 22.62 | 7 |
| ATOM | 2647 | CA | GLN | 332 | 33.257 | 0.716 | 33.266 | 1.00 | 22.51 | 6 |
| ATOM | 2648 | CB | GLN | 332 | 34.738 | 0.812 | 33.580 | 1.00 | 24.37 | 6 |
| ATOM | 2649 | CG | GLN | 332 | 35.434 | −0.545 | 33.620 | 1.00 | 27.57 | 6 |
| ATOM | 2650 | CD | GLN | 332 | 36.967 | −0.461 | 33.607 | 1.00 | 30.74 | 6 |
| ATOM | 2651 | OE1 | GLN | 332 | 37.551 | 0.580 | 33.287 | 1.00 | 31.85 | 8 |
| ATOM | 2652 | NE2 | GLN | 332 | 37.610 | −1.562 | 33.958 | 1.00 | 34.43 | 7 |
| ATOM | 2653 | C | GLN | 332 | 33.135 | 0.172 | 31.872 | 1.00 | 22.76 | 6 |
| ATOM | 2654 | O | GLN | 332 | 33.078 | −1.038 | 31.690 | 1.00 | 22.96 | 8 |
| ATOM | 2655 | N | ILE | 333 | 33.130 | 1.063 | 30.891 | 1.00 | 21.44 | 7 |
| ATOM | 2656 | CA | ILE | 333 | 33.161 | 0.651 | 29.493 | 1.00 | 22.51 | 6 |
| ATOM | 2657 | CB | ILE | 333 | 31.740 | 0.426 | 28.901 | 1.00 | 21.43 | 6 |
| ATOM | 2658 | CG1 | ILE | 333 | 31.816 | 0.252 | 27.378 | 1.00 | 23.08 | 6 |
| ATOM | 2659 | CD1 | ILE | 333 | 30.497 | −0.266 | 26.723 | 1.00 | 24.98 | 6 |
| ATOM | 2660 | CG2 | ILE | 333 | 30.860 | 1.589 | 29.216 | 1.00 | 22.93 | 6 |
| ATOM | 2661 | C | ILE | 333 | 33.899 | 1.729 | 28.757 | 1.00 | 22.48 | 6 |
| ATOM | 2662 | O | ILE | 333 | 33.694 | 2.919 | 29.038 | 1.00 | 20.41 | 8 |
| ATOM | 2663 | N | GLN | 334 | 34.817 | 1.311 | 27.884 | 1.00 | 22.69 | 7 |
| ATOM | 2664 | CA | GLN | 334 | 35.523 | 2.242 | 27.030 | 1.00 | 24.21 | 6 |
| ATOM | 2665 | CB | GLN | 334 | 37.035 | 2.093 | 27.158 | 1.00 | 24.61 | 6 |
| ATOM | 2666 | CG | GLN | 334 | 37.576 | 2.615 | 28.461 | 1.00 | 26.64 | 6 |
| ATOM | 2667 | CD | GLN | 334 | 37.426 | 1.596 | 29.550 | 1.00 | 28.86 | 6 |
| ATOM | 2668 | OE1 | GLN | 334 | 37.716 | 0.407 | 29.331 | 1.00 | 29.24 | 8 |
| ATOM | 2669 | NE2 | GLN | 334 | 36.981 | 2.038 | 30.729 | 1.00 | 28.14 | 7 |
| ATOM | 2670 | C | GLN | 334 | 35.121 | 2.005 | 25.576 | 1.00 | 24.44 | 6 |
| ATOM | 2671 | O | GLN | 334 | 34.937 | 0.863 | 25.152 | 1.00 | 24.74 | 8 |
| ATOM | 2672 | N | THR | 335 | 34.931 | 3.089 | 24.840 | 1.00 | 24.49 | 7 |
| ATOM | 2673 | CA | THR | 335 | 34.587 | 3.000 | 23.418 | 1.00 | 24.19 | 6 |
| ATOM | 2674 | CB | THR | 335 | 33.091 | 3.313 | 23.180 | 1.00 | 24.61 | 6 |
| ATOM | 2675 | OG1 | THR | 335 | 32.785 | 4.648 | 23.584 | 1.00 | 24.40 | 8 |
| ATOM | 2676 | CG2 | THR | 335 | 32.172 | 2.432 | 24.067 | 1.00 | 24.08 | 6 |
| ATOM | 2677 | C | THR | 335 | 35.439 | 4.004 | 22.660 | 1.00 | 24.33 | 6 |
| ATOM | 2678 | O | THR | 335 | 35.929 | 4.963 | 23.260 | 1.00 | 23.57 | 8 |
| ATOM | 2679 | N | SER | 336 | 35.626 | 3.786 | 21.355 | 1.00 | 24.05 | 7 |
| ATOM | 2680 | CA | SER | 336 | 36.336 | 4.757 | 20.535 | 1.00 | 24.28 | 6 |
| ATOM | 2681 | CB | SER | 336 | 37.698 | 4.226 | 20.085 | 1.00 | 25.52 | 6 |
| ATOM | 2682 | OG | SER | 336 | 37.537 | 3.045 | 19.323 | 1.00 | 25.50 | 8 |
| ATOM | 2683 | C | SER | 336 | 35.455 | 5.095 | 19.340 | 1.00 | 25.02 | 6 |
| ATOM | 2684 | O | SER | 336 | 34.717 | 4.255 | 18.854 | 1.00 | 25.14 | 8 |
| ATOM | 2685 | N | ASP | 337 | 35.565 | 6.326 | 18.878 | 1.00 | 26.15 | 7 |
| ATOM | 2686 | CA | ASP | 337 | 34.697 | 6.945 | 17.879 | 1.00 | 26.49 | 6 |
| ATOM | 2687 | CB | ASP | 337 | 34.233 | 8.270 | 18.478 | 1.00 | 27.20 | 6 |
| ATOM | 2688 | CG | ASP | 337 | 33.317 | 9.056 | 17.571 | 1.00 | 30.15 | 6 |
| ATOM | 2689 | OD1 | ASP | 337 | 33.169 | 8.678 | 16.378 | 1.00 | 31.90 | 8 |
| ATOM | 2690 | OD2 | ASP | 337 | 32.728 | 10.093 | 17.983 | 1.00 | 31.19 | 8 |
| ATOM | 2691 | C | ASP | 337 | 35.494 | 7.191 | 16.600 | 1.00 | 27.44 | 6 |
| ATOM | 2692 | O | ASP | 337 | 36.372 | 8.063 | 16.543 | 1.00 | 25.70 | 8 |
| ATOM | 2693 | N | ASN | 338 | 35.184 | 6.408 | 15.572 | 1.00 | 28.67 | 7 |
| ATOM | 2694 | CA | ASN | 338 | 35.950 | 6.475 | 14.336 | 1.00 | 29.72 | 6 |

APPENDIX A-continued

| | | | | | | | | | |
|---|---|---|---|---|---|---|---|---|---|
| ATOM | 2695 | CB | ASN | 338 | 35.573 | 5.359 | 13.373 | 1.00 | 30.90 | 6 |
| ATOM | 2696 | CG | ASN | 338 | 34.235 | 5.569 | 12.751 | 1.00 | 33.42 | 6 |
| ATOM | 2697 | OD1 | ASN | 338 | 33.246 | 5.834 | 13.447 | 1.00 | 37.48 | 8 |
| ATOM | 2698 | ND2 | ASN | 338 | 34.180 | 5.451 | 11.421 | 1.00 | 36.43 | 7 |
| ATOM | 2699 | C | ASN | 338 | 35.881 | 7.846 | 13.697 | 1.00 | 29.54 | 6 |
| ATOM | 2700 | O | ASN | 338 | 36.752 | 8.199 | 12.900 | 1.00 | 29.80 | 8 |
| ATOM | 2701 | N | ASP | 339 | 34.887 | 8.652 | 14.075 | 1.00 | 29.39 | 7 |
| ATOM | 2702 | CA | ASP | 339 | 34.822 | 10.000 | 13.519 | 1.00 | 29.69 | 6 |
| ATOM | 2703 | CB | ASP | 339 | 33.418 | 10.594 | 13.676 | 1.00 | 30.79 | 6 |
| ATOM | 2704 | CG | ASP | 339 | 32.472 | 10.116 | 12.582 | 1.00 | 34.05 | 6 |
| ATOM | 2705 | OD1 | ASP | 339 | 32.962 | 9.699 | 11.503 | 1.00 | 36.08 | 8 |
| ATOM | 2706 | OD2 | ASP | 339 | 31.236 | 10.119 | 12.694 | 1.00 | 39.26 | 8 |
| ATOM | 2707 | C | ASP | 339 | 35.889 | 10.914 | 14.137 | 1.00 | 28.46 | 6 |
| ATOM | 2708 | O | ASP | 339 | 36.095 | 12.058 | 13.700 | 1.00 | 28.03 | 8 |
| ATOM | 2709 | N | THR | 340 | 36.585 | 10.413 | 15.147 | 1.00 | 26.59 | 7 |
| ATOM | 2710 | CA | THR | 340 | 37.630 | 11.234 | 15.752 | 1.00 | 26.02 | 6 |
| ATOM | 2711 | CB | THR | 340 | 37.601 | 11.172 | 17.284 | 1.00 | 25.49 | 6 |
| ATOM | 2712 | OG1 | THR | 340 | 37.868 | 9.830 | 17.722 | 1.00 | 25.73 | 8 |
| ATOM | 2713 | CG2 | THR | 340 | 36.209 | 11.501 | 17.806 | 1.00 | 25.32 | 6 |
| ATOM | 2714 | C | THR | 340 | 39.016 | 10.820 | 15.311 | 1.00 | 26.06 | 6 |
| ATOM | 2715 | O | THR | 340 | 40.009 | 11.335 | 15.822 | 1.00 | 25.69 | 8 |
| ATOM | 2716 | N | TYR | 341 | 39.092 | 9.900 | 14.363 | 1.00 | 25.65 | 7 |
| ATOM | 2717 | CA | TYR | 341 | 40.376 | 9.349 | 13.950 | 1.00 | 25.00 | 6 |
| ATOM | 2718 | CB | TYR | 341 | 40.142 | 8.201 | 12.941 | 1.00 | 24.96 | 6 |
| ATOM | 2719 | CG | TYR | 341 | 41.390 | 7.464 | 12.527 | 1.00 | 25.13 | 6 |
| ATOM | 2720 | CD1 | TYR | 341 | 42.126 | 6.722 | 13.449 | 1.00 | 24.82 | 6 |
| ATOM | 2721 | CE1 | TYR | 341 | 43.274 | 6.029 | 13.068 | 1.00 | 23.02 | 6 |
| ATOM | 2722 | CZ | TYR | 341 | 43.690 | 6.078 | 11.746 | 1.00 | 23.13 | 6 |
| ATOM | 2723 | OH | TYR | 341 | 44.830 | 5.414 | 11.337 | 1.00 | 23.03 | 8 |
| ATOM | 2724 | CE2 | TYR | 341 | 42.973 | 6.793 | 10.824 | 1.00 | 23.70 | 6 |
| ATOM | 2725 | CD2 | TYR | 341 | 41.818 | 7.488 | 11.216 | 1.00 | 24.01 | 6 |
| ATOM | 2726 | C | TYR | 341 | 41.250 | 10.439 | 13.354 | 1.00 | 25.40 | 6 |
| ATOM | 2727 | O | TYR | 341 | 40.819 | 11.185 | 12.458 | 1.00 | 24.19 | 8 |
| ATOM | 2728 | N | ASN | 342 | 42.485 | 10.535 | 13.834 | 1.00 | 24.18 | 7 |
| ATOM | 2729 | CA | ASN | 342 | 43.408 | 11.490 | 13.248 | 1.00 | 25.03 | 6 |
| ATOM | 2730 | CB | ASN | 342 | 43.624 | 12.669 | 14.189 | 1.00 | 25.27 | 6 |
| ATOM | 2731 | CG | ASN | 342 | 42.541 | 13.686 | 14.071 | 1.00 | 28.12 | 6 |
| ATOM | 2732 | OD1 | ASN | 342 | 42.648 | 14.618 | 13.249 | 1.00 | 27.52 | 8 |
| ATOM | 2733 | ND2 | ASN | 342 | 41.469 | 13.526 | 14.872 | 1.00 | 28.01 | 7 |
| ATOM | 2734 | C | ASN | 342 | 44.718 | 10.814 | 13.067 | 1.00 | 24.50 | 6 |
| ATOM | 2735 | O | ASN | 342 | 45.121 | 10.042 | 13.928 | 1.00 | 23.57 | 8 |
| ATOM | 2736 | N | VAL | 343 | 45.399 | 11.080 | 11.958 | 1.00 | 23.84 | 7 |
| ATOM | 2737 | CA | VAL | 343 | 46.731 | 10.504 | 11.801 | 1.00 | 25.03 | 6 |
| ATOM | 2738 | CB | VAL | 343 | 46.886 | 9.783 | 10.448 | 1.00 | 25.59 | 6 |
| ATOM | 2739 | CG1 | VAL | 343 | 46.020 | 8.541 | 10.415 | 1.00 | 25.77 | 6 |
| ATOM | 2740 | CG2 | VAL | 343 | 46.512 | 10.727 | 9.302 | 1.00 | 27.23 | 6 |
| ATOM | 2741 | C | VAL | 343 | 47.824 | 11.568 | 11.920 | 1.00 | 25.28 | 6 |
| ATOM | 2742 | O | VAL | 343 | 47.594 | 12.776 | 11.681 | 1.00 | 25.83 | 8 |
| ATOM | 2743 | N | THR | 344 | 49.024 | 11.143 | 12.285 | 1.00 | 24.65 | 7 |
| ATOM | 2744 | CA | THR | 344 | 50.119 | 12.094 | 12.319 | 1.00 | 24.07 | 6 |
| ATOM | 2745 | CB | THR | 344 | 50.282 | 12.756 | 13.723 | 1.00 | 24.49 | 6 |
| ATOM | 2746 | OG1 | THR | 344 | 51.266 | 13.799 | 13.667 | 1.00 | 22.96 | 8 |
| ATOM | 2747 | CG2 | THR | 344 | 50.833 | 11.769 | 14.772 | 1.00 | 23.04 | 6 |
| ATOM | 2748 | C | THR | 344 | 51.341 | 11.373 | 11.814 | 1.00 | 24.80 | 6 |
| ATOM | 2749 | O | THR | 344 | 51.436 | 10.150 | 11.874 | 1.00 | 24.06 | 8 |
| ATOM | 2750 | N | SER | 345 | 52.279 | 12.123 | 11.275 | 1.00 | 25.21 | 7 |
| ATOM | 2751 | CA | SER | 345 | 53.398 | 11.480 | 10.616 | 1.00 | 25.86 | 6 |
| ATOM | 2752 | CB | SER | 345 | 53.244 | 11.704 | 9.118 | 1.00 | 26.41 | 6 |
| ATOM | 2753 | OG | SER | 345 | 53.335 | 13.098 | 8.850 | 1.00 | 27.85 | 8 |
| ATOM | 2754 | C | SER | 345 | 54.764 | 11.966 | 11.027 | 1.00 | 26.06 | 6 |
| ATOM | 2755 | O | SER | 345 | 54.912 | 12.980 | 11.730 | 1.00 | 25.50 | 8 |
| ATOM | 2756 | N | TYR | 346 | 55.773 | 11.217 | 10.579 | 1.00 | 26.09 | 7 |
| ATOM | 2757 | CA | TYR | 346 | 57.155 | 11.579 | 10.797 | 1.00 | 27.19 | 6 |
| ATOM | 2758 | CB | TYR | 346 | 57.696 | 10.904 | 12.028 | 1.00 | 28.10 | 6 |
| ATOM | 2759 | CG | TYR | 346 | 59.053 | 11.404 | 12.323 | 1.00 | 31.74 | 6 |
| ATOM | 2760 | CD1 | TYR | 346 | 59.264 | 12.749 | 12.540 | 1.00 | 33.97 | 6 |
| ATOM | 2761 | CE1 | TYR | 346 | 60.535 | 13.239 | 12.805 | 1.00 | 38.78 | 6 |
| ATOM | 2762 | CZ | TYR | 346 | 61.607 | 12.379 | 12.842 | 1.00 | 38.75 | 6 |
| ATOM | 2763 | OH | TYR | 346 | 62.870 | 12.885 | 13.104 | 1.00 | 42.21 | 8 |
| ATOM | 2764 | CE2 | TYR | 346 | 61.426 | 11.032 | 12.619 | 1.00 | 38.59 | 6 |
| ATOM | 2765 | CD2 | TYR | 346 | 60.143 | 10.545 | 12.352 | 1.00 | 35.13 | 6 |
| ATOM | 2766 | C | TYR | 346 | 57.972 | 11.117 | 9.602 | 1.00 | 26.44 | 6 |
| ATOM | 2767 | O | TYR | 346 | 57.999 | 9.939 | 9.313 | 1.00 | 25.99 | 8 |
| ATOM | 2768 | N | PRO | 347 | 58.600 | 12.031 | 8.880 | 1.00 | 26.17 | 7 |
| ATOM | 2769 | CA | PRO | 347 | 58.556 | 13.472 | 9.156 | 1.00 | 26.58 | 6 |
| ATOM | 2770 | CB | PRO | 347 | 59.415 | 14.076 | 8.029 | 1.00 | 26.19 | 6 |
| ATOM | 2771 | CG | PRO | 347 | 60.252 | 12.969 | 7.550 | 1.00 | 26.76 | 6 |
| ATOM | 2772 | CD | PRO | 347 | 59.403 | 11.708 | 7.699 | 1.00 | 26.44 | 6 |
| ATOM | 2773 | C | PRO | 347 | 57.142 | 14.011 | 9.069 | 1.00 | 26.70 | 6 |

APPENDIX A-continued

| | | | | | | | | | |
|---|---|---|---|---|---|---|---|---|---|
| ATOM | 2774 | O | PRO | 347 | 56.326 | 13.446 | 8.336 | 1.00 | 27.18 | 8 |
| ATOM | 2775 | N | ASN | 348 | 56.855 | 15.093 | 9.781 | 1.00 | 27.35 | 7 |
| ATOM | 2776 | CA | ASN | 348 | 55.465 | 15.608 | 9.858 | 1.00 | 26.28 | 6 |
| ATOM | 2777 | CB | ASN | 348 | 55.215 | 16.329 | 11.194 | 1.00 | 26.82 | 6 |
| ATOM | 2778 | CG | ASN | 348 | 53.731 | 16.640 | 11.431 | 1.00 | 27.18 | 6 |
| ATOM | 2779 | OD1 | ASN | 348 | 52.928 | 16.663 | 10.497 | 1.00 | 27.73 | 8 |
| ATOM | 2780 | ND2 | ASN | 348 | 53.363 | 16.868 | 12.698 | 1.00 | 29.13 | 7 |
| ATOM | 2781 | C | ASN | 348 | 55.080 | 16.486 | 8.658 | 1.00 | 26.55 | 6 |
| ATOM | 2782 | O | ASN | 348 | 55.263 | 17.714 | 8.667 | 1.00 | 25.87 | 8 |
| ATOM | 2783 | N | HIS | 349 | 54.542 | 15.843 | 7.625 | 1.00 | 27.30 | 7 |
| ATOM | 2784 | CA | HIS | 349 | 54.159 | 16.524 | 6.402 | 1.00 | 28.17 | 6 |
| ATOM | 2785 | CB | HIS | 349 | 53.731 | 15.544 | 5.307 | 1.00 | 29.18 | 6 |
| ATOM | 2786 | CG | HIS | 349 | 54.810 | 14.618 | 4.842 | 1.00 | 31.65 | 6 |
| ATOM | 2787 | ND1 | HIS | 349 | 54.586 | 13.654 | 3.881 | 1.00 | 36.29 | 7 |
| ATOM | 2788 | CE1 | HIS | 349 | 55.713 | 13.000 | 3.643 | 1.00 | 35.61 | 6 |
| ATOM | 2789 | NE2 | HIS | 349 | 56.656 | 13.493 | 4.426 | 1.00 | 33.08 | 7 |
| ATOM | 2790 | CD2 | HIS | 349 | 56.118 | 14.513 | 5.181 | 1.00 | 33.56 | 6 |
| ATOM | 2791 | C | HIS | 349 | 53.013 | 17.483 | 6.651 | 1.00 | 28.27 | 6 |
| ATOM | 2792 | O | HIS | 349 | 52.938 | 18.523 | 6.010 | 1.00 | 27.10 | 8 |
| ATOM | 2793 | N | GLN | 350 | 52.099 | 17.117 | 7.551 | 1.00 | 28.40 | 7 |
| ATOM | 2794 | CA | GLN | 350 | 50.980 | 17.999 | 7.855 | 1.00 | 29.63 | 6 |
| ATOM | 2795 | CB | GLN | 350 | 49.892 | 17.291 | 8.680 | 1.00 | 30.24 | 6 |
| ATOM | 2796 | CG | GLN | 350 | 48.560 | 18.066 | 8.716 | 1.00 | 37.06 | 6 |
| ATOM | 2797 | CD | GLN | 350 | 47.334 | 17.150 | 8.807 | 1.00 | 42.75 | 6 |
| ATOM | 2798 | OE1 | GLN | 350 | 47.329 | 16.052 | 8.232 | 1.00 | 46.97 | 8 |
| ATOM | 2799 | NE2 | GLN | 350 | 46.300 | 17.600 | 9.519 | 1.00 | 45.33 | 7 |
| ATOM | 2800 | C | GLN | 350 | 51.455 | 19.281 | 8.548 | 1.00 | 28.60 | 6 |
| ATOM | 2801 | O | GLN | 350 | 50.985 | 20.376 | 8.235 | 1.00 | 28.27 | 8 |
| ATOM | 2802 | N | GLN | 351 | 52.365 | 19.152 | 9.502 | 1.00 | 27.78 | 7 |
| ATOM | 2803 | CA | GLN | 351 | 52.884 | 20.342 | 10.150 | 1.00 | 27.40 | 6 |
| ATOM | 2804 | CB | GLN | 351 | 53.797 | 20.007 | 11.319 | 1.00 | 28.11 | 6 |
| ATOM | 2805 | CG | GLN | 351 | 54.343 | 21.260 | 11.984 | 1.00 | 31.14 | 6 |
| ATOM | 2806 | CD | GLN | 351 | 55.507 | 20.983 | 12.890 | 1.00 | 35.94 | 6 |
| ATOM | 2807 | OE1 | GLN | 351 | 56.348 | 20.133 | 12.583 | 1.00 | 39.32 | 8 |
| ATOM | 2808 | NE2 | GLN | 351 | 55.575 | 21.701 | 14.011 | 1.00 | 36.83 | 7 |
| ATOM | 2809 | C | GLN | 351 | 53.660 | 21.169 | 9.125 | 1.00 | 26.25 | 6 |
| ATOM | 2810 | O | GLN | 351 | 53.572 | 22.397 | 9.112 | 1.00 | 24.72 | 8 |
| ATOM | 2811 | N | ALA | 352 | 54.410 | 20.506 | 8.250 | 1.00 | 24.50 | 7 |
| ATOM | 2812 | CA | ALA | 352 | 55.142 | 21.262 | 7.241 | 1.00 | 23.52 | 6 |
| ATOM | 2813 | CB | ALA | 352 | 56.031 | 20.338 | 6.386 | 1.00 | 24.36 | 6 |
| ATOM | 2814 | C | ALA | 352 | 54.230 | 22.142 | 6.344 | 1.00 | 23.52 | 6 |
| ATOM | 2815 | O | ALA | 352 | 54.508 | 23.336 | 6.111 | 1.00 | 20.72 | 8 |
| ATOM | 2816 | N | LEU | 353 | 53.160 | 21.558 | 5.808 | 1.00 | 23.48 | 7 |
| ATOM | 2817 | CA | LEU | 353 | 52.254 | 22.362 | 4.967 | 1.00 | 24.68 | 6 |
| ATOM | 2818 | CB | LEU | 353 | 51.146 | 21.485 | 4.373 | 1.00 | 26.25 | 6 |
| ATOM | 2819 | CG | LEU | 353 | 51.665 | 20.316 | 3.518 | 1.00 | 28.14 | 6 |
| ATOM | 2820 | CD1 | LEU | 353 | 50.688 | 19.097 | 3.572 | 1.00 | 34.75 | 6 |
| ATOM | 2821 | CD2 | LEU | 353 | 51.921 | 20.740 | 2.087 | 1.00 | 31.15 | 6 |
| ATOM | 2822 | C | LEU | 353 | 51.621 | 23.509 | 5.769 | 1.00 | 24.81 | 6 |
| ATOM | 2823 | O | LEU | 353 | 51.403 | 24.632 | 5.262 | 1.00 | 24.45 | 8 |
| ATOM | 2824 | N | LEU | 354 | 51.294 | 23.245 | 7.015 | 1.00 | 24.22 | 7 |
| ATOM | 2825 | CA | LEU | 354 | 50.682 | 24.307 | 7.814 | 1.00 | 24.42 | 6 |
| ATOM | 2826 | CB | LEU | 354 | 50.185 | 23.761 | 9.158 | 1.00 | 25.84 | 6 |
| ATOM | 2827 | CG | LEU | 354 | 49.429 | 24.715 | 10.082 | 1.00 | 28.08 | 6 |
| ATOM | 2828 | CD1 | LEU | 354 | 48.249 | 25.345 | 9.361 | 1.00 | 28.14 | 6 |
| ATOM | 2829 | CD2 | LEU | 354 | 48.957 | 23.985 | 11.373 | 1.00 | 28.29 | 6 |
| ATOM | 2830 | C | LEU | 354 | 51.699 | 25.427 | 8.027 | 1.00 | 23.83 | 6 |
| ATOM | 2831 | O | LEU | 354 | 51.368 | 26.616 | 7.929 | 1.00 | 23.72 | 8 |
| ATOM | 2832 | N | LEU | 355 | 52.937 | 25.047 | 8.317 | 1.00 | 21.77 | 7 |
| ATOM | 2833 | CA | LEU | 355 | 53.964 | 26.033 | 8.554 | 1.00 | 21.84 | 6 |
| ATOM | 2834 | CB | LEU | 355 | 55.283 | 25.359 | 8.890 | 1.00 | 22.17 | 6 |
| ATOM | 2835 | CG | LEU | 355 | 55.441 | 24.804 | 10.311 | 1.00 | 24.15 | 6 |
| ATOM | 2836 | CD1 | LEU | 355 | 56.741 | 24.052 | 10.453 | 1.00 | 25.55 | 6 |
| ATOM | 2837 | CD2 | LEU | 355 | 55.351 | 25.931 | 11.341 | 1.00 | 25.28 | 6 |
| ATOM | 2838 | C | LEU | 355 | 54.166 | 26.923 | 7.329 | 1.00 | 23.00 | 6 |
| ATOM | 2839 | O | LEU | 355 | 54.512 | 28.109 | 7.455 | 1.00 | 21.91 | 8 |
| ATOM | 2840 | N | LEU | 356 | 54.009 | 26.333 | 6.152 | 1.00 | 22.25 | 7 |
| ATOM | 2841 | CA | LEU | 356 | 54.226 | 27.083 | 4.919 | 1.00 | 23.68 | 6 |
| ATOM | 2842 | CB | LEU | 356 | 54.223 | 26.163 | 3.715 | 1.00 | 23.56 | 6 |
| ATOM | 2843 | CG | LEU | 356 | 55.452 | 25.282 | 3.436 | 1.00 | 26.94 | 6 |
| ATOM | 2844 | CD1 | LEU | 356 | 55.116 | 24.361 | 2.232 | 1.00 | 27.68 | 6 |
| ATOM | 2845 | CD2 | LEU | 356 | 56.692 | 26.074 | 3.127 | 1.00 | 26.68 | 6 |
| ATOM | 2846 | C | LEU | 356 | 53.219 | 28.235 | 4.708 | 1.00 | 22.64 | 6 |
| ATOM | 2847 | O | LEU | 356 | 53.453 | 29.095 | 3.856 | 1.00 | 22.97 | 8 |
| ATOM | 2848 | N | THR | 357 | 52.125 | 28.263 | 5.469 | 1.00 | 21.78 | 7 |
| ATOM | 2849 | CA | THR | 357 | 51.159 | 29.362 | 5.322 | 1.00 | 21.30 | 6 |
| ATOM | 2850 | CB | THR | 357 | 49.800 | 29.022 | 5.907 | 1.00 | 21.68 | 6 |
| ATOM | 2851 | OG1 | THR | 357 | 49.950 | 28.692 | 7.289 | 1.00 | 19.41 | 8 |
| ATOM | 2852 | CG2 | THR | 357 | 49.266 | 27.765 | 5.263 | 1.00 | 22.06 | 6 |

APPENDIX A-continued

| ATOM | 2853 | C | THR | 357 | 51.633 | 30.663 | 5.950 | 1.00 | 20.95 | 6 |
|---|---|---|---|---|---|---|---|---|---|---|
| ATOM | 2854 | O | THR | 357 | 51.019 | 31.720 | 5.763 | 1.00 | 20.99 | 8 |
| ATOM | 2855 | N | ASN | 358 | 52.677 | 30.591 | 6.757 | 1.00 | 20.43 | 7 |
| ATOM | 2856 | CA | ASN | 358 | 53.254 | 31.839 | 7.293 | 1.00 | 20.33 | 6 |
| ATOM | 2857 | CB | ASN | 358 | 52.490 | 32.343 | 8.525 | 1.00 | 20.60 | 6 |
| ATOM | 2858 | CG | ASN | 358 | 52.574 | 31.396 | 9.711 | 1.00 | 20.83 | 6 |
| ATOM | 2859 | OD1 | ASN | 358 | 53.126 | 30.294 | 9.625 | 1.00 | 21.43 | 8 |
| ATOM | 2860 | ND2 | ASN | 358 | 52.010 | 31.822 | 10.828 | 1.00 | 20.56 | 7 |
| ATOM | 2861 | C | ASN | 358 | 54.774 | 31.773 | 7.512 | 1.00 | 20.25 | 6 |
| ATOM | 2862 | O | ASN | 358 | 55.321 | 32.486 | 8.334 | 1.00 | 18.92 | 8 |
| ATOM | 2863 | N | HIS | 359 | 55.444 | 30.913 | 6.745 | 1.00 | 20.73 | 7 |
| ATOM | 2864 | CA | HIS | 359 | 56.898 | 30.799 | 6.782 | 1.00 | 22.16 | 6 |
| ATOM | 2865 | CB | HIS | 359 | 57.342 | 29.552 | 7.582 | 1.00 | 22.11 | 6 |
| ATOM | 2866 | CG | HIS | 359 | 57.106 | 29.651 | 9.059 | 1.00 | 23.86 | 6 |
| ATOM | 2867 | ND1 | HIS | 359 | 55.869 | 29.460 | 9.636 | 1.00 | 22.27 | 7 |
| ATOM | 2868 | CE1 | HIS | 359 | 55.968 | 29.601 | 10.946 | 1.00 | 25.32 | 6 |
| ATOM | 2869 | NE2 | HIS | 359 | 57.234 | 29.863 | 11.240 | 1.00 | 23.99 | 7 |
| ATOM | 2870 | CD2 | HIS | 359 | 57.964 | 29.899 | 10.080 | 1.00 | 23.41 | 6 |
| ATOM | 2871 | C | HIS | 359 | 57.410 | 30.614 | 5.366 | 1.00 | 23.55 | 6 |
| ATOM | 2872 | O | HIS | 359 | 56.650 | 30.169 | 4.499 | 1.00 | 23.57 | 8 |
| ATOM | 2873 | N | ALA | 360 | 58.678 | 30.955 | 5.138 | 1.00 | 23.41 | 7 |
| ATOM | 2874 | CA | ALA | 360 | 59.361 | 30.670 | 3.869 | 1.00 | 26.33 | 6 |
| ATOM | 2875 | CB | ALA | 360 | 60.705 | 31.437 | 3.812 | 1.00 | 25.03 | 6 |
| ATOM | 2876 | C | ALA | 360 | 59.667 | 29.176 | 3.735 | 1.00 | 27.43 | 6 |
| ATOM | 2877 | O | ALA | 360 | 59.687 | 28.467 | 4.724 | 1.00 | 27.98 | 8 |
| ATOM | 2878 | N | TYR | 361 | 59.985 | 28.725 | 2.516 | 1.00 | 29.38 | 7 |
| ATOM | 2879 | CA | TYR | 361 | 60.412 | 27.345 | 2.284 | 1.00 | 30.77 | 6 |
| ATOM | 2880 | CB | TYR | 361 | 60.690 | 27.091 | 0.795 | 1.00 | 31.63 | 6 |
| ATOM | 2881 | CG | TYR | 361 | 59.453 | 26.725 | 0.011 | 1.00 | 35.20 | 6 |
| ATOM | 2882 | CD1 | TYR | 361 | 58.924 | 27.574 | −0.958 | 1.00 | 38.21 | 6 |
| ATOM | 2883 | CE1 | TYR | 361 | 57.768 | 27.225 | −1.654 | 1.00 | 39.63 | 6 |
| ATOM | 2884 | CZ | TYR | 361 | 57.149 | 26.019 | −1.382 | 1.00 | 39.50 | 6 |
| ATOM | 2885 | OH | TYR | 361 | 56.003 | 25.638 | −2.030 | 1.00 | 40.54 | 8 |
| ATOM | 2886 | CE2 | TYR | 361 | 57.654 | 25.189 | −0.428 | 1.00 | 40.16 | 6 |
| ATOM | 2887 | CD2 | TYR | 361 | 58.796 | 25.542 | 0.262 | 1.00 | 37.99 | 6 |
| ATOM | 2888 | C | TYR | 361 | 61.675 | 27.105 | 3.087 | 1.00 | 31.36 | 6 |
| ATOM | 2889 | O | TYR | 361 | 61.794 | 26.124 | 3.785 | 1.00 | 31.45 | 8 |
| ATOM | 2890 | N | GLU | 362 | 62.611 | 28.040 | 3.025 | 1.00 | 32.11 | 7 |
| ATOM | 2891 | CA | GLU | 362 | 63.863 | 27.843 | 3.751 | 1.00 | 32.94 | 6 |
| ATOM | 2892 | CB | GLU | 362 | 64.885 | 28.948 | 3.417 | 1.00 | 33.37 | 6 |
| ATOM | 2893 | CG | GLU | 362 | 65.608 | 28.691 | 2.092 | 1.00 | 40.24 | 6 |
| ATOM | 2894 | CD | GLU | 362 | 66.108 | 29.961 | 1.406 | 1.00 | 46.53 | 6 |
| ATOM | 2895 | OE1 | GLU | 362 | 67.313 | 30.036 | 1.068 | 1.00 | 50.70 | 8 |
| ATOM | 2896 | OE2 | GLU | 362 | 65.290 | 30.885 | 1.180 | 1.00 | 50.30 | 8 |
| ATOM | 2897 | C | GLU | 362 | 63.595 | 27.716 | 5.248 | 1.00 | 31.55 | 6 |
| ATOM | 2898 | O | GLU | 362 | 64.243 | 26.928 | 5.922 | 1.00 | 31.11 | 8 |
| ATOM | 2899 | N | GLU | 363 | 62.646 | 28.497 | 5.773 | 1.00 | 30.36 | 7 |
| ATOM | 2900 | CA | GLU | 363 | 62.318 | 28.401 | 7.197 | 1.00 | 30.18 | 6 |
| ATOM | 2901 | CB | GLU | 363 | 61.340 | 29.512 | 7.634 | 1.00 | 29.67 | 6 |
| ATOM | 2902 | CG | GLU | 363 | 61.994 | 30.898 | 7.667 | 1.00 | 30.29 | 6 |
| ATOM | 2903 | CD | GLU | 363 | 61.039 | 32.024 | 8.052 | 1.00 | 29.88 | 6 |
| ATOM | 2904 | OE1 | GLU | 363 | 59.788 | 31.830 | 7.989 | 1.00 | 25.77 | 8 |
| ATOM | 2905 | OE2 | GLU | 363 | 61.541 | 33.123 | 8.403 | 1.00 | 30.51 | 8 |
| ATOM | 2906 | C | GLU | 363 | 61.718 | 27.040 | 7.541 | 1.00 | 29.66 | 6 |
| ATOM | 2907 | O | GLU | 363 | 62.120 | 26.387 | 8.489 | 1.00 | 30.14 | 8 |
| ATOM | 2908 | N | VAL | 364 | 60.730 | 26.620 | 6.772 | 1.00 | 28.63 | 7 |
| ATOM | 2909 | CA | VAL | 364 | 60.124 | 25.326 | 7.034 | 1.00 | 28.54 | 6 |
| ATOM | 2910 | CB | VAL | 364 | 58.928 | 25.099 | 6.132 | 1.00 | 28.06 | 6 |
| ATOM | 2911 | CG1 | VAL | 364 | 58.307 | 23.732 | 6.407 | 1.00 | 27.11 | 6 |
| ATOM | 2912 | CG2 | VAL | 364 | 57.914 | 26.227 | 6.398 | 1.00 | 27.01 | 6 |
| ATOM | 2913 | C | VAL | 364 | 61.158 | 24.203 | 6.903 | 1.00 | 29.12 | 6 |
| ATOM | 2914 | O | VAL | 364 | 61.207 | 23.289 | 7.723 | 1.00 | 28.49 | 8 |
| ATOM | 2915 | N | GLU | 365 | 62.006 | 24.304 | 5.893 | 1.00 | 29.89 | 7 |
| ATOM | 2916 | CA | GLU | 365 | 63.033 | 23.302 | 5.682 | 1.00 | 31.71 | 6 |
| ATOM | 2917 | CB | GLU | 365 | 63.939 | 23.710 | 4.523 | 1.00 | 31.83 | 6 |
| ATOM | 2918 | CG | GLU | 365 | 65.108 | 22.780 | 4.262 | 1.00 | 37.75 | 6 |
| ATOM | 2919 | CD | GLU | 365 | 66.045 | 23.348 | 3.210 | 1.00 | 44.45 | 6 |
| ATOM | 2920 | OE1 | GLU | 365 | 65.574 | 23.632 | 2.080 | 1.00 | 46.60 | 8 |
| ATOM | 2921 | OE2 | GLU | 365 | 67.248 | 23.533 | 3.521 | 1.00 | 47.21 | 8 |
| ATOM | 2922 | C | GLU | 365 | 63.843 | 23.136 | 6.957 | 1.00 | 31.50 | 6 |
| ATOM | 2923 | O | GLU | 365 | 64.126 | 22.012 | 7.383 | 1.00 | 31.23 | 8 |
| ATOM | 2924 | N | GLU | 366 | 64.208 | 24.273 | 7.556 | 1.00 | 32.01 | 7 |
| ATOM | 2925 | CA | GLU | 366 | 64.969 | 24.293 | 8.800 | 1.00 | 31.56 | 6 |
| ATOM | 2926 | CB | GLU | 366 | 65.429 | 25.726 | 9.148 | 1.00 | 32.31 | 6 |
| ATOM | 2927 | CG | GLU | 366 | 65.953 | 25.792 | 10.569 | 1.00 | 33.36 | 6 |
| ATOM | 2928 | CD | GLU | 366 | 66.627 | 27.106 | 10.962 | 1.00 | 32.72 | 6 |
| ATOM | 2929 | OE1 | GLU | 366 | 67.078 | 27.919 | 10.092 | 1.00 | 30.13 | 8 |
| ATOM | 2930 | OE2 | GLU | 366 | 66.713 | 27.302 | 12.189 | 1.00 | 31.13 | 8 |
| ATOM | 2931 | C | GLU | 366 | 64.183 | 23.735 | 9.976 | 1.00 | 31.42 | 6 |

APPENDIX A-continued

| ATOM | 2932 | O   | GLU | 366 | 64.715 | 22.964 | 10.781 | 1.00 | 31.20 | 8 |
|------|------|-----|-----|-----|--------|--------|--------|------|-------|---|
| ATOM | 2933 | N   | ILE | 367 | 62.910 | 24.104 | 10.077 | 1.00 | 30.50 | 7 |
| ATOM | 2934 | CA  | ILE | 367 | 62.102 | 23.683 | 11.219 | 1.00 | 31.03 | 6 |
| ATOM | 2935 | CB  | ILE | 367 | 60.791 | 24.477 | 11.248 | 1.00 | 31.38 | 6 |
| ATOM | 2936 | CG1 | ILE | 367 | 61.081 | 25.960 | 11.517 | 1.00 | 32.06 | 6 |
| ATOM | 2937 | CD1 | ILE | 367 | 59.887 | 26.857 | 11.298 | 1.00 | 31.33 | 6 |
| ATOM | 2938 | CG2 | ILE | 367 | 59.807 | 23.868 | 12.289 | 1.00 | 32.79 | 6 |
| ATOM | 2939 | C   | ILE | 367 | 61.764 | 22.196 | 11.207 | 1.00 | 31.23 | 6 |
| ATOM | 2940 | O   | ILE | 367 | 61.742 | 21.538 | 12.261 | 1.00 | 31.97 | 8 |
| ATOM | 2941 | N   | THR | 368 | 61.503 | 21.656 | 10.024 | 1.00 | 29.94 | 7 |
| ATOM | 2942 | CA  | THR | 368 | 60.971 | 20.285 | 9.956  | 1.00 | 30.36 | 6 |
| ATOM | 2943 | CB  | THR | 368 | 59.832 | 20.236 | 8.969  | 1.00 | 29.67 | 6 |
| ATOM | 2944 | OG1 | THR | 368 | 60.335 | 20.597 | 7.675  | 1.00 | 25.65 | 8 |
| ATOM | 2945 | CG2 | THR | 368 | 58.789 | 21.305 | 9.303  | 1.00 | 29.43 | 6 |
| ATOM | 2946 | C   | THR | 368 | 61.949 | 19.253 | 9.496  | 1.00 | 31.18 | 6 |
| ATOM | 2947 | O   | THR | 368 | 61.656 | 18.058 | 9.565  | 1.00 | 30.69 | 8 |
| ATOM | 2948 | N   | ASN | 369 | 63.089 | 19.708 | 8.991  | 1.00 | 32.33 | 7 |
| ATOM | 2949 | CA  | ASN | 369 | 64.090 | 18.820 | 8.410  | 1.00 | 33.86 | 6 |
| ATOM | 2950 | CB  | ASN | 369 | 64.395 | 17.661 | 9.337  | 1.00 | 34.67 | 6 |
| ATOM | 2951 | CG  | ASN | 369 | 65.547 | 17.950 | 10.245 | 1.00 | 38.67 | 6 |
| ATOM | 2952 | OD1 | ASN | 369 | 65.403 | 18.663 | 11.244 | 1.00 | 41.85 | 8 |
| ATOM | 2953 | ND2 | ASN | 369 | 66.717 | 17.389 | 9.914  | 1.00 | 43.00 | 7 |
| ATOM | 2954 | C   | ASN | 369 | 63.668 | 18.269 | 7.072  | 1.00 | 33.65 | 6 |
| ATOM | 2955 | O   | ASN | 369 | 64.329 | 17.385 | 6.525  | 1.00 | 33.74 | 8 |
| ATOM | 2956 | N   | ILE | 370 | 62.569 | 18.784 | 6.535  | 1.00 | 32.60 | 7 |
| ATOM | 2957 | CA  | ILE | 370 | 62.108 | 18.335 | 5.219  | 1.00 | 31.66 | 6 |
| ATOM | 2958 | CB  | ILE | 370 | 60.585 | 18.352 | 5.203  | 1.00 | 30.27 | 6 |
| ATOM | 2959 | CG1 | ILE | 370 | 60.035 | 17.402 | 6.278  | 1.00 | 31.28 | 6 |
| ATOM | 2960 | CD1 | ILE | 370 | 58.513 | 17.566 | 6.480  | 1.00 | 29.28 | 6 |
| ATOM | 2961 | CG2 | ILE | 370 | 60.053 | 17.962 | 3.867  | 1.00 | 30.67 | 6 |
| ATOM | 2962 | C   | ILE | 370 | 62.692 | 19.201 | 4.083  | 1.00 | 31.92 | 6 |
| ATOM | 2963 | O   | ILE | 370 | 62.564 | 20.417 | 4.119  | 1.00 | 32.03 | 8 |
| ATOM | 2964 | N   | PRO | 371 | 63.322 | 18.582 | 3.081  | 1.00 | 31.96 | 7 |
| ATOM | 2965 | CA  | PRO | 371 | 63.966 | 19.323 | 1.979  | 1.00 | 32.27 | 6 |
| ATOM | 2966 | CB  | PRO | 371 | 64.525 | 18.203 | 1.074  | 1.00 | 32.20 | 6 |
| ATOM | 2967 | CG  | PRO | 371 | 64.559 | 16.971 | 1.925  | 1.00 | 32.47 | 6 |
| ATOM | 2968 | CD  | PRO | 371 | 63.468 | 17.118 | 2.944  | 1.00 | 32.31 | 6 |
| ATOM | 2969 | C   | PRO | 371 | 62.995 | 20.190 | 1.165  | 1.00 | 32.78 | 6 |
| ATOM | 2970 | O   | PRO | 371 | 61.833 | 19.825 | 1.005  | 1.00 | 32.03 | 8 |
| ATOM | 2971 | N   | LYS | 372 | 63.480 | 21.301 | 0.609  | 1.00 | 33.20 | 7 |
| ATOM | 2972 | CA  | LYS | 372 | 62.602 | 22.185 | −0.145 | 1.00 | 34.19 | 6 |
| ATOM | 2973 | CB  | LYS | 372 | 63.358 | 23.419 | −0.614 | 1.00 | 34.79 | 6 |
| ATOM | 2974 | CG  | LYS | 372 | 62.546 | 24.356 | −1.500 | 1.00 | 37.40 | 6 |
| ATOM | 2975 | CD  | LYS | 372 | 63.358 | 25.585 | −1.890 | 1.00 | 40.48 | 6 |
| ATOM | 2976 | CE  | LYS | 372 | 62.477 | 26.664 | −2.541 | 1.00 | 42.87 | 6 |
| ATOM | 2977 | NZ  | LYS | 372 | 63.221 | 27.949 | −2.921 | 1.00 | 42.97 | 7 |
| ATOM | 2978 | C   | LYS | 372 | 61.910 | 21.486 | −1.313 | 1.00 | 34.18 | 6 |
| ATOM | 2979 | O   | LYS | 372 | 60.714 | 21.676 | −1.533 | 1.00 | 34.13 | 8 |
| ATOM | 2980 | N   | SER | 373 | 62.633 | 20.637 | −2.040 | 1.00 | 33.91 | 7 |
| ATOM | 2981 | CA  | SER | 373 | 61.985 | 19.981 | −3.167 | 1.00 | 34.44 | 6 |
| ATOM | 2982 | CB  | SER | 373 | 62.962 | 19.094 | −3.947 | 1.00 | 34.43 | 6 |
| ATOM | 2983 | OG  | SER | 373 | 63.449 | 18.056 | −3.113 | 1.00 | 35.06 | 8 |
| ATOM | 2984 | C   | SER | 373 | 60.801 | 19.167 | −2.641 | 1.00 | 33.82 | 6 |
| ATOM | 2985 | O   | SER | 373 | 59.741 | 19.146 | −3.246 | 1.00 | 34.52 | 8 |
| ATOM | 2986 | N   | THR | 374 | 60.966 | 18.522 | −1.494 | 1.00 | 33.11 | 7 |
| ATOM | 2987 | CA  | THR | 374 | 59.878 | 17.723 | −0.946 | 1.00 | 32.49 | 6 |
| ATOM | 2988 | CB  | THR | 374 | 60.354 | 16.913 | 0.250  | 1.00 | 31.67 | 6 |
| ATOM | 2989 | OG1 | THR | 374 | 61.284 | 15.919 | −0.201 | 1.00 | 29.97 | 8 |
| ATOM | 2990 | CG2 | THR | 374 | 59.199 | 16.119 | 0.831  | 1.00 | 32.68 | 6 |
| ATOM | 2991 | C   | THR | 374 | 58.727 | 18.604 | −0.520 | 1.00 | 32.93 | 6 |
| ATOM | 2992 | O   | THR | 374 | 57.557 | 18.238 | −0.692 | 1.00 | 32.94 | 8 |
| ATOM | 2993 | N   | LEU | 375 | 59.061 | 19.746 | 0.077  | 1.00 | 33.37 | 7 |
| ATOM | 2994 | CA  | LEU | 375 | 58.044 | 20.706 | 0.507  | 1.00 | 34.34 | 6 |
| ATOM | 2995 | CB  | LEU | 375 | 58.704 | 21.928 | 1.128  | 1.00 | 33.19 | 6 |
| ATOM | 2996 | CG  | LEU | 375 | 59.304 | 21.691 | 2.503  | 1.00 | 32.05 | 6 |
| ATOM | 2997 | CD1 | LEU | 375 | 59.938 | 22.969 | 3.007  | 1.00 | 32.39 | 6 |
| ATOM | 2998 | CD2 | LEU | 375 | 58.271 | 21.140 | 3.501  | 1.00 | 27.25 | 6 |
| ATOM | 2999 | C   | LEU | 375 | 57.182 | 21.106 | −0.690 | 1.00 | 35.96 | 6 |
| ATOM | 3000 | O   | LEU | 375 | 55.960 | 21.233 | −0.597 | 1.00 | 35.77 | 8 |
| ATOM | 3001 | N   | ILE | 376 | 57.827 | 21.302 | −1.828 | 1.00 | 38.13 | 7 |
| ATOM | 3002 | CA  | ILE | 376 | 57.085 | 21.646 | −3.021 | 1.00 | 40.35 | 6 |
| ATOM | 3003 | CB  | ILE | 376 | 58.034 | 22.131 | −4.081 | 1.00 | 41.10 | 6 |
| ATOM | 3004 | CG1 | ILE | 376 | 58.695 | 23.432 | −3.600 | 1.00 | 41.14 | 6 |
| ATOM | 3005 | CD1 | ILE | 376 | 59.731 | 23.993 | −4.570 | 1.00 | 40.40 | 6 |
| ATOM | 3006 | CG2 | ILE | 376 | 57.283 | 22.299 | −5.408 | 1.00 | 40.19 | 6 |
| ATOM | 3007 | C   | ILE | 376 | 56.227 | 20.470 | −3.518 | 1.00 | 41.89 | 6 |
| ATOM | 3008 | O   | ILE | 376 | 55.050 | 20.654 | −3.861 | 1.00 | 42.20 | 8 |
| ATOM | 3009 | N   | LYS | 377 | 56.803 | 19.268 | −3.540 | 1.00 | 43.39 | 7 |
| ATOM | 3010 | CA  | LYS | 377 | 56.046 | 18.079 | −3.927 | 1.00 | 45.21 | 6 |

APPENDIX A-continued

| ATOM | 3011 | CB | LYS | 377 | 56.883 | 16.802 | −3.807 | 1.00 | 45.49 | 6 |
|------|------|------|------|-----|--------|--------|--------|------|-------|---|
| ATOM | 3012 | CG | LYS | 377 | 57.897 | 16.574 | −4.920 | 1.00 | 47.21 | 6 |
| ATOM | 3013 | CD | LYS | 377 | 58.246 | 15.089 | −5.046 | 1.00 | 49.22 | 6 |
| ATOM | 3014 | CE | LYS | 377 | 59.375 | 14.862 | −6.072 | 1.00 | 52.20 | 6 |
| ATOM | 3015 | NZ | LYS | 377 | 59.102 | 13.758 | −7.049 | 1.00 | 51.97 | 7 |
| ATOM | 3016 | C | LYS | 377 | 54.834 | 17.936 | −3.023 | 1.00 | 46.08 | 6 |
| ATOM | 3017 | O | LYS | 377 | 53.741 | 17.629 | −3.492 | 1.00 | 46.19 | 8 |
| ATOM | 3018 | N | LEU | 378 | 55.033 | 18.165 | −1.728 | 1.00 | 47.08 | 7 |
| ATOM | 3019 | CA | LEU | 378 | 53.959 | 18.025 | −0.751 | 1.00 | 48.35 | 6 |
| ATOM | 3020 | CB | LEU | 378 | 54.466 | 18.323 | 0.663 | 1.00 | 47.65 | 6 |
| ATOM | 3021 | CG | LEU | 378 | 55.213 | 17.143 | 1.277 | 1.00 | 45.25 | 6 |
| ATOM | 3022 | CD1 | LEU | 378 | 55.972 | 17.562 | 2.515 | 1.00 | 42.59 | 6 |
| ATOM | 3023 | CD2 | LEU | 378 | 54.219 | 16.034 | 1.593 | 1.00 | 45.24 | 6 |
| ATOM | 3024 | C | LEU | 378 | 52.804 | 18.943 | −1.105 | 1.00 | 50.15 | 6 |
| ATOM | 3025 | O | LEU | 378 | 51.644 | 18.507 | −1.182 | 1.00 | 50.40 | 8 |
| ATOM | 3026 | N | LYS | 379 | 53.135 | 20.213 | −1.315 | 1.00 | 52.15 | 7 |
| ATOM | 3027 | CA | LYS | 379 | 52.157 | 21.212 | −1.698 | 1.00 | 54.76 | 6 |
| ATOM | 3028 | CB | LYS | 379 | 52.835 | 22.566 | −1.957 | 1.00 | 54.59 | 6 |
| ATOM | 3029 | CG | LYS | 379 | 51.831 | 23.706 | −2.104 | 1.00 | 55.76 | 6 |
| ATOM | 3030 | CD | LYS | 379 | 52.136 | 24.573 | −3.299 | 1.00 | 58.11 | 6 |
| ATOM | 3031 | CE | LYS | 379 | 51.095 | 25.665 | −3.488 | 1.00 | 59.87 | 6 |
| ATOM | 3032 | NZ | LYS | 379 | 51.175 | 26.247 | −4.865 | 1.00 | 61.75 | 7 |
| ATOM | 3033 | C | LYS | 379 | 51.431 | 20.789 | −2.971 | 1.00 | 56.28 | 6 |
| ATOM | 3034 | O | LYS | 379 | 50.244 | 21.082 | −3.146 | 1.00 | 56.86 | 8 |
| ATOM | 3035 | N | LYS | 380 | 52.143 | 20.103 | −3.858 | 1.00 | 57.91 | 7 |
| ATOM | 3036 | CA | LYS | 380 | 51.546 | 19.688 | −5.123 | 1.00 | 59.59 | 6 |
| ATOM | 3037 | CB | LYS | 380 | 52.597 | 19.151 | −6.096 | 1.00 | 59.54 | 6 |
| ATOM | 3038 | CG | LYS | 380 | 53.411 | 20.299 | −6.696 | 1.00 | 60.77 | 6 |
| ATOM | 3039 | CD | LYS | 380 | 54.578 | 19.845 | −7.574 | 1.00 | 63.22 | 6 |
| ATOM | 3040 | CE | LYS | 380 | 55.322 | 21.067 | −8.148 | 1.00 | 63.77 | 6 |
| ATOM | 3041 | NZ | LYS | 380 | 56.489 | 20.748 | −9.045 | 1.00 | 65.45 | 7 |
| ATOM | 3042 | C | LYS | 380 | 50.302 | 18.808 | −4.962 | 1.00 | 60.38 | 6 |
| ATOM | 3043 | O | LYS | 380 | 49.421 | 18.837 | −5.816 | 1.00 | 60.91 | 8 |
| ATOM | 3044 | N | HIS | 381 | 50.226 | 18.037 | −3.877 | 1.00 | 61.48 | 7 |
| ATOM | 3045 | CA | HIS | 381 | 48.970 | 17.355 | −3.512 | 1.00 | 62.33 | 6 |
| ATOM | 3046 | CB | HIS | 381 | 48.750 | 16.049 | −4.288 | 1.00 | 62.90 | 6 |
| ATOM | 3047 | CG | HIS | 381 | 47.417 | 15.413 | −4.027 | 1.00 | 64.70 | 6 |
| ATOM | 3048 | ND1 | HIS | 381 | 46.222 | 16.043 | −4.306 | 1.00 | 67.47 | 7 |
| ATOM | 3049 | CE1 | HIS | 381 | 45.217 | 15.255 | −3.959 | 1.00 | 67.81 | 6 |
| ATOM | 3050 | NE2 | HIS | 381 | 45.717 | 14.134 | −3.468 | 1.00 | 67.20 | 7 |
| ATOM | 3051 | CD2 | HIS | 381 | 47.090 | 14.206 | −3.502 | 1.00 | 66.78 | 6 |
| ATOM | 3052 | C | HIS | 381 | 48.873 | 17.109 | −2.015 | 1.00 | 62.30 | 6 |
| ATOM | 3053 | O | HIS | 381 | 47.923 | 17.553 | −1.355 | 1.00 | 62.52 | 8 |
| ATOM | 3054 | O | HOH | 1 | −4.940 | 2.739 | 51.300 | 1.00 | 13.59 | 8 |
| ATOM | 3055 | O | HOH | 2 | 25.742 | 8.671 | 47.673 | 1.00 | 27.05 | 8 |
| ATOM | 3056 | O | HOH | 3 | −3.517 | 2.893 | 48.336 | 1.00 | 15.60 | 8 |
| ATOM | 3057 | O | HOH | 4 | −8.316 | 13.907 | 36.957 | 1.00 | 16.84 | 8 |
| ATOM | 3058 | O | HOH | 5 | 40.079 | 15.598 | 34.844 | 1.00 | 20.33 | 8 |
| ATOM | 3059 | O | HOH | 6 | −9.583 | 11.806 | 55.959 | 1.00 | 17.59 | 8 |
| ATOM | 3060 | O | HOH | 7 | 38.572 | 17.255 | 38.495 | 1.00 | 16.16 | 8 |
| ATOM | 3061 | O | HOH | 8 | 5.055 | 8.745 | 56.047 | 1.00 | 12.36 | 8 |
| ATOM | 3062 | O | HOH | 9 | 7.215 | 6.351 | 42.532 | 1.00 | 13.68 | 8 |
| ATOM | 3063 | O | HOH | 10 | 18.294 | 11.999 | 38.859 | 1.00 | 14.28 | 8 |
| ATOM | 3064 | O | HOH | 11 | 9.030 | 4.049 | 59.671 | 1.00 | 15.17 | 8 |
| ATOM | 3065 | O | HOH | 12 | 10.796 | −4.224 | 54.584 | 1.00 | 18.10 | 8 |
| ATOM | 3066 | O | HOH | 13 | 35.040 | 8.481 | 21.834 | 1.00 | 25.13 | 8 |
| ATOM | 3067 | O | HOH | 14 | −0.177 | −0.219 | 54.429 | 1.00 | 14.78 | 8 |
| ATOM | 3068 | O | HOH | 15 | −2.705 | 15.521 | 46.533 | 1.00 | 15.09 | 8 |
| ATOM | 3069 | O | HOH | 16 | 15.039 | −0.246 | 41.690 | 1.00 | 19.51 | 8 |
| ATOM | 3070 | O | HOH | 17 | 6.783 | 18.287 | 40.572 | 1.00 | 16.97 | 8 |
| ATOM | 3071 | O | HOH | 18 | −7.578 | 11.251 | 61.781 | 1.00 | 17.70 | 8 |
| ATOM | 3072 | O | HOH | 19 | 33.866 | 22.460 | 36.848 | 1.00 | 26.97 | 8 |
| ATOM | 3073 | O | HOH | 20 | −0.642 | 10.361 | 63.163 | 1.00 | 18.51 | 8 |
| ATOM | 3074 | O | HOH | 21 | −7.828 | 8.278 | 55.056 | 1.00 | 15.96 | 8 |
| ATOM | 3075 | O | HOH | 22 | −3.872 | 4.140 | 62.606 | 1.00 | 24.90 | 8 |
| ATOM | 3076 | O | HOH | 23 | 14.791 | 12.625 | 49.020 | 1.00 | 16.37 | 8 |
| ATOM | 3077 | O | HOH | 24 | 20.762 | 19.335 | 52.108 | 1.00 | 24.18 | 8 |
| ATOM | 3078 | O | HOH | 25 | −7.037 | 15.670 | 38.729 | 1.00 | 21.15 | 8 |
| ATOM | 3079 | O | HOH | 26 | 7.091 | −5.594 | 42.475 | 1.00 | 24.73 | 8 |
| ATOM | 3080 | O | HOH | 27 | 15.370 | 6.619 | 35.140 | 1.00 | 23.33 | 8 |
| ATOM | 3081 | O | HOH | 28 | −13.344 | 10.978 | 58.454 | 1.00 | 28.15 | 8 |
| ATOM | 3082 | O | HOH | 29 | 8.698 | 4.977 | 36.298 | 1.00 | 21.26 | 8 |
| ATOM | 3083 | O | HOH | 30 | 19.471 | 0.752 | 18.708 | 1.00 | 35.44 | 8 |
| ATOM | 3084 | O | HOH | 31 | −4.693 | 16.959 | 36.316 | 1.00 | 28.41 | 8 |
| ATOM | 3085 | O | HOH | 32 | 29.068 | 17.447 | 34.129 | 1.00 | 21.58 | 8 |
| ATOM | 3086 | O | HOH | 33 | 24.441 | 17.281 | 50.115 | 1.00 | 25.98 | 8 |
| ATOM | 3087 | O | HOH | 34 | 20.175 | 12.802 | 40.552 | 1.00 | 20.72 | 8 |
| ATOM | 3088 | O | HOH | 35 | −6.740 | 12.321 | 35.310 | 1.00 | 19.82 | 8 |
| ATOM | 3089 | O | HOH | 36 | 54.273 | 12.591 | 21.744 | 1.00 | 30.70 | 8 |

APPENDIX A-continued

| ATOM | 3090 | O | HOH | 37 | 34.547 | 12.334 | 41.733 | 1.00 | 33.29 | 8 |
|---|---|---|---|---|---|---|---|---|---|---|
| ATOM | 3091 | O | HOH | 38 | 38.892 | 18.070 | 35.305 | 1.00 | 24.79 | 8 |
| ATOM | 3092 | O | HOH | 39 | 37.401 | 23.538 | 33.996 | 1.00 | 31.34 | 8 |
| ATOM | 3093 | O | HOH | 40 | 19.146 | −0.732 | 43.097 | 1.00 | 23.69 | 8 |
| ATOM | 3094 | O | HOH | 41 | 47.473 | 22.161 | −2.721 | 1.00 | 41.37 | 8 |
| ATOM | 3095 | O | HOH | 42 | 54.246 | −0.773 | 8.041 | 1.00 | 33.84 | 8 |
| ATOM | 3096 | O | HOH | 43 | 42.784 | 18.534 | 32.687 | 1.00 | 33.94 | 8 |
| ATOM | 3097 | O | HOH | 44 | 16.702 | 5.572 | 23.213 | 1.00 | 31.73 | 8 |
| ATOM | 3098 | O | HOH | 45 | 62.683 | 30.268 | 0.949 | 1.00 | 31.19 | 8 |
| ATOM | 3099 | O | HOH | 46 | 43.374 | 13.698 | 27.423 | 1.00 | 19.99 | 8 |
| ATOM | 3100 | O | HOH | 47 | 2.102 | 8.069 | 39.349 | 1.00 | 19.03 | 8 |
| ATOM | 3101 | O | HOH | 48 | 34.811 | 21.393 | 42.575 | 1.00 | 26.07 | 8 |
| ATOM | 3102 | O | HOH | 49 | 42.215 | 0.861 | 18.416 | 1.00 | 28.65 | 8 |
| ATOM | 3103 | O | HOH | 50 | 30.354 | 11.286 | 24.526 | 1.00 | 28.71 | 8 |
| ATOM | 3104 | O | HOH | 51 | 50.812 | 18.282 | 13.391 | 1.00 | 38.39 | 8 |
| ATOM | 3105 | O | HOH | 52 | 37.335 | 7.747 | 46.430 | 1.00 | 21.58 | 8 |
| ATOM | 3106 | O | HOH | 53 | 16.668 | 13.895 | 35.830 | 1.00 | 20.36 | 8 |
| ATOM | 3107 | O | HOH | 54 | 17.914 | 0.627 | 46.605 | 1.00 | 15.68 | 8 |
| ATOM | 3108 | O | HOH | 55 | 23.887 | 15.109 | 39.154 | 1.00 | 23.72 | 8 |
| ATOM | 3109 | O | HOH | 56 | −5.400 | 1.688 | 53.789 | 1.00 | 21.67 | 8 |
| ATOM | 3110 | O | HOH | 57 | 37.838 | 14.330 | 19.708 | 1.00 | 26.14 | 8 |
| ATOM | 3111 | O | HOH | 58 | 19.429 | 5.844 | 57.408 | 1.00 | 26.01 | 8 |
| ATOM | 3112 | O | HOH | 59 | −2.975 | 22.193 | 42.812 | 1.00 | 36.93 | 8 |
| ATOM | 3113 | O | HOH | 60 | 48.564 | 5.903 | 10.255 | 1.00 | 24.13 | 8 |
| ATOM | 3114 | O | HOH | 61 | −5.227 | 4.275 | 60.349 | 1.00 | 31.75 | 8 |
| ATOM | 3115 | O | HOH | 62 | −1.113 | 21.011 | 57.590 | 1.00 | 20.75 | 8 |
| ATOM | 3116 | O | HOH | 63 | 5.130 | 20.181 | 54.234 | 1.00 | 23.47 | 8 |
| ATOM | 3117 | O | HOH | 64 | 13.078 | 11.943 | 29.936 | 1.00 | 29.38 | 8 |
| ATOM | 3118 | O | HOH | 65 | 15.748 | 9.708 | 61.215 | 1.00 | 28.88 | 8 |
| ATOM | 3119 | O | HOH | 66 | 4.842 | 14.822 | 57.449 | 1.00 | 16.67 | 8 |
| ATOM | 3120 | O | HOH | 67 | 39.187 | 6.138 | 35.294 | 1.00 | 33.65 | 8 |
| ATOM | 3121 | O | HOH | 68 | 18.367 | 18.203 | 46.735 | 1.00 | 25.68 | 8 |
| ATOM | 3122 | O | HOH | 69 | −4.805 | 6.005 | 34.531 | 1.00 | 30.60 | 8 |
| ATOM | 3123 | O | HOH | 70 | 12.308 | −5.274 | 43.933 | 1.00 | 35.52 | 8 |
| ATOM | 3124 | O | HOH | 71 | 5.049 | −5.740 | 58.934 | 1.00 | 34.26 | 8 |
| ATOM | 3125 | O | HOH | 72 | 60.150 | 14.503 | −2.400 | 1.00 | 31.94 | 8 |
| ATOM | 3126 | O | HOH | 73 | −10.909 | −1.285 | 45.071 | 1.00 | 26.72 | 8 |
| ATOM | 3127 | O | HOH | 74 | 1.212 | 28.031 | 46.837 | 1.00 | 29.91 | 8 |
| ATOM | 3128 | O | HOH | 75 | 5.765 | 23.016 | 43.188 | 1.00 | 46.58 | 8 |
| ATOM | 3129 | O | HOH | 76 | 32.111 | 15.197 | 48.158 | 1.00 | 37.86 | 8 |
| ATOM | 3130 | O | HOH | 77 | −1.549 | 23.660 | 54.514 | 1.00 | 33.92 | 8 |
| ATOM | 3131 | O | HOH | 78 | 51.613 | 30.181 | 13.520 | 1.00 | 33.68 | 8 |
| ATOM | 3132 | O | HOH | 79 | 19.663 | 15.294 | 44.900 | 1.00 | 35.99 | 8 |
| ATOM | 3133 | O | HOH | 80 | 16.154 | −7.083 | 44.092 | 1.00 | 36.85 | 8 |
| ATOM | 3134 | O | HOH | 81 | 14.225 | −1.619 | 39.383 | 1.00 | 22.61 | 8 |
| ATOM | 3135 | O | HOH | 82 | 22.602 | 15.338 | 57.796 | 1.00 | 21.69 | 8 |
| ATOM | 3136 | O | HOH | 83 | 21.576 | 14.514 | 20.940 | 1.00 | 43.18 | 8 |
| ATOM | 3137 | O | HOH | 84 | 17.917 | −6.633 | 47.524 | 1.00 | 30.41 | 8 |
| ATOM | 3138 | O | HOH | 85 | 41.582 | 2.806 | 26.901 | 1.00 | 38.06 | 8 |
| ATOM | 3139 | O | HOH | 86 | 44.228 | 14.529 | 32.800 | 1.00 | 22.02 | 8 |
| ATOM | 3140 | O | HOH | 87 | 33.947 | 10.865 | 20.904 | 1.00 | 32.70 | 8 |
| ATOM | 3141 | O | HOH | 88 | 6.906 | −10.292 | 51.144 | 1.00 | 38.12 | 8 |
| ATOM | 3142 | O | HOH | 89 | −3.144 | 0.182 | 57.258 | 1.00 | 29.02 | 8 |
| ATOM | 3143 | O | HOH | 90 | 7.163 | 2.984 | 62.017 | 1.00 | 25.51 | 8 |
| ATOM | 3144 | O | HOH | 91 | 60.009 | 3.218 | −2.672 | 1.00 | 24.10 | 8 |
| ATOM | 3145 | O | HOH | 92 | 37.043 | 1.625 | 42.641 | 1.00 | 27.65 | 8 |
| ATOM | 3146 | O | HOH | 93 | 31.096 | 21.574 | 43.285 | 1.00 | 33.93 | 8 |
| ATOM | 3147 | O | HOH | 94 | 63.197 | −1.352 | 1.992 | 1.00 | 27.75 | 8 |
| ATOM | 3148 | O | HOH | 95 | 32.659 | 15.462 | 26.098 | 1.00 | 22.94 | 8 |
| ATOM | 3149 | O | HOH | 96 | −4.383 | 1.063 | 36.346 | 1.00 | 32.85 | 8 |
| ATOM | 3150 | O | HOH | 97 | 22.660 | 2.187 | 12.482 | 1.00 | 43.35 | 8 |
| ATOM | 3151 | O | HOH | 98 | 0.844 | 16.723 | 59.295 | 1.00 | 32.30 | 8 |
| ATOM | 3152 | O | HOH | 99 | 15.887 | 7.991 | 58.848 | 1.00 | 27.05 | 8 |
| ATOM | 3153 | O | HOH | 100 | 46.466 | 20.172 | 23.883 | 1.00 | 33.95 | 8 |
| ATOM | 3154 | O | HOH | 101 | 23.009 | 17.046 | 22.678 | 1.00 | 43.65 | 8 |
| ATOM | 3155 | O | HOH | 102 | −12.618 | 14.357 | 43.588 | 1.00 | 22.31 | 8 |
| ATOM | 3156 | O | HOH | 103 | 12.694 | −0.553 | 43.106 | 1.00 | 16.86 | 8 |
| ATOM | 3157 | O | HOH | 104 | −7.459 | 18.293 | 37.544 | 1.00 | 19.23 | 8 |
| ATOM | 3158 | O | HOH | 105 | 13.394 | −2.895 | 44.299 | 1.00 | 22.53 | 8 |
| ATOM | 3159 | O | HOH | 106 | 42.614 | 16.378 | 33.994 | 1.00 | 29.09 | 8 |
| ATOM | 3160 | O | HOH | 107 | 12.932 | −5.138 | 52.527 | 1.00 | 29.05 | 8 |
| ATOM | 3161 | O | HOH | 108 | −7.573 | 8.860 | 63.070 | 1.00 | 26.12 | 8 |
| ATOM | 3162 | O | HOH | 109 | 53.993 | 31.843 | 3.440 | 1.00 | 30.60 | 8 |
| ATOM | 3163 | O | HOH | 110 | 32.333 | 21.702 | 39.076 | 1.00 | 30.50 | 8 |
| ATOM | 3164 | O | HOH | 111 | 36.733 | 10.387 | 49.490 | 1.00 | 32.16 | 8 |
| ATOM | 3165 | O | HOH | 112 | 60.051 | 31.487 | 12.168 | 1.00 | 31.36 | 8 |
| ATOM | 3166 | O | HOH | 113 | 48.368 | 13.727 | 28.631 | 1.00 | 33.37 | 8 |
| ATOM | 3167 | O | HOH | 114 | 22.744 | 11.386 | 57.228 | 1.00 | 23.45 | 8 |
| ATOM | 3168 | O | HOH | 115 | 28.709 | −4.644 | 41.762 | 1.00 | 29.06 | 8 |

APPENDIX A-continued

| ATOM | 3169 | O | HOH | 116 | 31.378 | 6.211 | 16.882 | 1.00 | 32.92 | 8 |
|---|---|---|---|---|---|---|---|---|---|---|
| ATOM | 3170 | O | HOH | 117 | 14.419 | 20.180 | 56.727 | 1.00 | 24.97 | 8 |
| ATOM | 3171 | O | HOH | 118 | 39.301 | 22.094 | 29.916 | 1.00 | 37.15 | 8 |
| ATOM | 3172 | O | HOH | 119 | 65.553 | 20.449 | −1.895 | 1.00 | 33.46 | 8 |
| ATOM | 3173 | O | HOH | 120 | 33.606 | −7.330 | 28.551 | 1.00 | 39.64 | 8 |
| ATOM | 3174 | O | HOH | 121 | 19.327 | −5.047 | 41.165 | 1.00 | 32.41 | 8 |
| ATOM | 3175 | O | HOH | 122 | 20.692 | 7.403 | 52.673 | 1.00 | 27.37 | 8 |
| ATOM | 3176 | O | HOH | 123 | 32.922 | 18.707 | 29.589 | 1.00 | 38.41 | 8 |
| ATOM | 3177 | O | HOH | 124 | −7.270 | 1.208 | 56.826 | 1.00 | 37.89 | 8 |
| ATOM | 3178 | O | HOH | 125 | −18.108 | 7.009 | 55.119 | 1.00 | 27.78 | 8 |
| ATOM | 3179 | O | HOH | 126 | −11.149 | 12.460 | 58.102 | 1.00 | 25.97 | 8 |
| ATOM | 3180 | O | HOH | 127 | −10.324 | 9.398 | 63.951 | 1.00 | 41.07 | 8 |
| ATOM | 3181 | O | HOH | 128 | 5.497 | 15.051 | 60.983 | 1.00 | 32.02 | 8 |
| ATOM | 3182 | O | HOH | 129 | 13.769 | 18.056 | 36.153 | 1.00 | 35.66 | 8 |
| ATOM | 3183 | O | HOH | 130 | 18.875 | −0.379 | 36.465 | 1.00 | 29.52 | 8 |
| ATOM | 3184 | O | HOH | 131 | 20.807 | −3.072 | 42.716 | 1.00 | 25.41 | 8 |
| ATOM | 3185 | O | HOH | 132 | −5.185 | 4.146 | 38.077 | 1.00 | 33.57 | 8 |
| ATOM | 3186 | O | HOH | 133 | −0.905 | 8.949 | 32.105 | 1.00 | 37.16 | 8 |
| ATOM | 3187 | O | HOH | 134 | 18.886 | 18.892 | 51.903 | 1.00 | 23.76 | 8 |
| ATOM | 3188 | O | HOH | 135 | 34.473 | 16.315 | 44.357 | 1.00 | 35.09 | 8 |
| ATOM | 3189 | O | HOH | 136 | 15.742 | 0.022 | 44.617 | 1.00 | 33.90 | 8 |
| ATOM | 3190 | O | HOH | 137 | −3.212 | 1.250 | 68.673 | 1.00 | 44.15 | 8 |
| ATOM | 3191 | O | HOH | 138 | 6.967 | −2.964 | 38.603 | 1.00 | 37.58 | 8 |
| ATOM | 3192 | O | HOH | 139 | −5.390 | 6.367 | 39.347 | 1.00 | 34.73 | 8 |
| ATOM | 3193 | O | HOH | 140 | 37.651 | 1.491 | 23.342 | 1.00 | 36.95 | 8 |
| ATOM | 3194 | O | HOH | 141 | −17.651 | 9.458 | 54.222 | 1.00 | 37.30 | 8 |
| ATOM | 3195 | O | HOH | 142 | 1.065 | −2.410 | 38.740 | 1.00 | 39.65 | 8 |
| ATOM | 3196 | O | HOH | 143 | 52.732 | 7.876 | −4.141 | 1.00 | 41.10 | 8 |
| ATOM | 3197 | O | HOH | 144 | 43.320 | 21.174 | 22.682 | 1.00 | 36.13 | 8 |
| ATOM | 3198 | O | HOH | 145 | 27.988 | −6.004 | 23.521 | 1.00 | 34.51 | 8 |
| ATOM | 3199 | O | HOH | 146 | 58.958 | 12.204 | 4.109 | 1.00 | 43.90 | 8 |
| ATOM | 3200 | O | HOH | 147 | −10.163 | −0.402 | 40.662 | 1.00 | 42.32 | 8 |
| ATOM | 3201 | O | HOH | 148 | −10.845 | 7.364 | 39.342 | 1.00 | 33.06 | 8 |
| ATOM | 3202 | O | HOH | 149 | 57.685 | −0.040 | −1.227 | 1.00 | 34.88 | 8 |
| ATOM | 3203 | O | HOH | 150 | 39.026 | 15.169 | 14.760 | 1.00 | 42.96 | 8 |
| ATOM | 3204 | O | HOH | 151 | 1.875 | −7.230 | 60.376 | 1.00 | 33.71 | 8 |
| ATOM | 3205 | O | HOH | 152 | 8.463 | 20.105 | 42.690 | 1.00 | 37.36 | 8 |
| ATOM | 3206 | O | HOH | 153 | −10.657 | 7.120 | 42.903 | 1.00 | 42.19 | 8 |
| ATOM | 3207 | O | HOH | 154 | 16.347 | 15.141 | 26.109 | 1.00 | 36.06 | 8 |
| ATOM | 3208 | O | HOH | 155 | 38.171 | 5.327 | 44.251 | 1.00 | 38.46 | 8 |
| ATOM | 3209 | O | HOH | 156 | −11.655 | 12.457 | 50.558 | 1.00 | 26.05 | 8 |
| ATOM | 3210 | O | HOH | 157 | 38.516 | 12.042 | 11.728 | 1.00 | 46.12 | 8 |
| ATOM | 3211 | O | HOH | 158 | 33.128 | 22.889 | 33.447 | 1.00 | 36.90 | 8 |
| ATOM | 3212 | O | HOH | 159 | 4.944 | 12.306 | 32.651 | 1.00 | 35.42 | 8 |
| ATOM | 3213 | O | HOH | 160 | 60.442 | 34.860 | 10.358 | 1.00 | 30.70 | 8 |
| ATOM | 3214 | O | HOH | 161 | 34.904 | −3.092 | 46.722 | 1.00 | 34.75 | 8 |
| ATOM | 3215 | O | HOH | 162 | −7.517 | 6.098 | 61.889 | 1.00 | 30.85 | 8 |
| ATOM | 3216 | O | HOH | 163 | 20.452 | 16.729 | 37.555 | 1.00 | 37.84 | 8 |
| ATOM | 3217 | O | HOH | 164 | −4.935 | 2.238 | 57.836 | 1.00 | 28.25 | 8 |
| ATOM | 3218 | O | HOH | 165 | −6.922 | 23.720 | 53.496 | 1.00 | 42.04 | 8 |
| ATOM | 3219 | O | HOH | 166 | 25.504 | 12.522 | 55.282 | 1.00 | 30.57 | 8 |
| ATOM | 3220 | O | HOH | 167 | 40.105 | 1.765 | 24.822 | 1.00 | 30.46 | 8 |
| ATOM | 3221 | O | HOH | 168 | 31.292 | 21.107 | 31.631 | 1.00 | 40.03 | 8 |
| ATOM | 3222 | O | HOH | 169 | 31.620 | 10.074 | 22.499 | 1.00 | 36.06 | 8 |
| ATOM | 3223 | O | HOH | 170 | 46.166 | 21.236 | −4.622 | 1.00 | 40.48 | 8 |
| ATOM | 3224 | O | HOH | 171 | 5.419 | 20.134 | 57.128 | 1.00 | 39.34 | 8 |
| ATOM | 3225 | O | HOH | 172 | 33.686 | 12.301 | 51.516 | 1.00 | 35.16 | 8 |
| ATOM | 3226 | O | HOH | 173 | 37.788 | 14.928 | 17.128 | 1.00 | 31.52 | 8 |
| ATOM | 3227 | O | HOH | 174 | 14.089 | 17.658 | 32.141 | 1.00 | 31.18 | 8 |
| ATOM | 3228 | O | HOH | 175 | 34.156 | 11.678 | 45.087 | 1.00 | 35.13 | 8 |
| ATOM | 3229 | O | HOH | 176 | 13.354 | 21.580 | 49.828 | 1.00 | 41.93 | 8 |
| ATOM | 3230 | O | HOH | 177 | 47.059 | 14.389 | 33.466 | 1.00 | 32.45 | 8 |
| ATOM | 3231 | O | HOH | 178 | 38.114 | −1.762 | 20.115 | 1.00 | 41.88 | 8 |
| ATOM | 3232 | O | HOH | 179 | −8.792 | −3.040 | 41.616 | 1.00 | 32.98 | 8 |
| ATOM | 3233 | O | HOH | 180 | 26.528 | −10.099 | 24.359 | 1.00 | 50.58 | 8 |
| ATOM | 3234 | O | HOH | 181 | −14.683 | 23.284 | 41.107 | 1.00 | 40.49 | 8 |
| ATOM | 3235 | O | HOH | 182 | 10.690 | 6.914 | 26.742 | 1.00 | 43.07 | 8 |
| ATOM | 3236 | O | HOH | 183 | 50.149 | −0.926 | 14.601 | 1.00 | 40.59 | 8 |
| ATOM | 3237 | O | HOH | 184 | 4.524 | −7.900 | 61.031 | 1.00 | 33.26 | 8 |
| ATOM | 3238 | O | HOH | 185 | 26.334 | 17.218 | 44.763 | 1.00 | 29.84 | 8 |
| ATOM | 3239 | O | HOH | 186 | 63.367 | 33.015 | 4.501 | 1.00 | 40.38 | 8 |
| ATOM | 3240 | O | HOH | 187 | 38.723 | 1.215 | 20.890 | 1.00 | 34.37 | 8 |
| ATOM | 3241 | O | HOH | 188 | 29.546 | −4.658 | 36.094 | 1.00 | 37.06 | 8 |
| ATOM | 3242 | O | HOH | 189 | 4.569 | −9.309 | 49.365 | 1.00 | 33.86 | 8 |
| ATOM | 3243 | O | HOH | 190 | −2.137 | 24.704 | 57.223 | 1.00 | 41.71 | 8 |
| ATOM | 3244 | O | HOH | 191 | 28.419 | 14.529 | 17.178 | 1.00 | 44.58 | 8 |
| ATOM | 3245 | O | HOH | 192 | 9.822 | −7.538 | 40.577 | 1.00 | 37.47 | 8 |
| ATOM | 3246 | O | HOH | 193 | 17.500 | −5.272 | 51.057 | 1.00 | 36.32 | 8 |
| ATOM | 3247 | O | HOH | 194 | 59.434 | 19.367 | −6.305 | 1.00 | 43.76 | 8 |

APPENDIX A-continued

| | | | | | | | | | | |
|---|---|---|---|---|---|---|---|---|---|---|
| ATOM | 3248 | O | HOH | 195 | 44.292 | 15.866 | 11.866 | 1.00 | 43.52 | 8 |
| ATOM | 3249 | O | HOH | 196 | 51.633 | 28.109 | 10.640 | 1.00 | 32.65 | 8 |
| ATOM | 3250 | O | HOH | 197 | 4.559 | −2.040 | 38.267 | 1.00 | 34.76 | 8 |
| ATOM | 3251 | O | HOH | 198 | 10.339 | −0.620 | 62.920 | 1.00 | 34.81 | 8 |
| ATOM | 3252 | O | HOH | 199 | 42.387 | 3.135 | 20.193 | 1.00 | 38.64 | 8 |
| ATOM | 3253 | O | HOH | 200 | 16.755 | 17.496 | 43.261 | 1.00 | 28.02 | 8 |
| ATOM | 3254 | O | HOH | 201 | 16.877 | 2.427 | 30.734 | 1.00 | 32.13 | 8 |
| ATOM | 3255 | O | HOH | 202 | 4.112 | 3.492 | 30.918 | 1.00 | 26.20 | 8 |
| ATOM | 3256 | O | HOH | 203 | 12.515 | 16.795 | 39.774 | 1.00 | 30.65 | 8 |
| ATOM | 3257 | O | HOH | 204 | 16.619 | 16.737 | 33.267 | 1.00 | 31.18 | 8 |
| ATOM | 3258 | O | HOH | 205 | 30.907 | 7.660 | 23.678 | 1.00 | 36.60 | 8 |
| ATOM | 3259 | O | HOH | 206 | 63.654 | 29.148 | 11.065 | 1.00 | 39.95 | 8 |
| ATOM | 3260 | O | HOH | 207 | 62.485 | 10.024 | 6.309 | 1.00 | 36.66 | 8 |
| ATOM | 3261 | O | HOH | 208 | 60.256 | 8.286 | 9.288 | 1.00 | 38.53 | 8 |
| ATOM | 3262 | O | HOH | 209 | −7.785 | 20.041 | 46.350 | 1.00 | 40.46 | 8 |
| ATOM | 3263 | O | HOH | 210 | 7.397 | −0.672 | 32.112 | 1.00 | 43.69 | 8 |
| ATOM | 3264 | O | HOH | 211 | 58.761 | 30.582 | 0.081 | 1.00 | 41.30 | 8 |
| ATOM | 3265 | O | HOH | 212 | 33.310 | 6.218 | 21.488 | 1.00 | 32.22 | 8 |
| ATOM | 3266 | O | HOH | 213 | 58.805 | 16.583 | 11.081 | 1.00 | 33.65 | 8 |
| ATOM | 3267 | O | HOH | 214 | 52.763 | 15.353 | 21.885 | 1.00 | 45.13 | 8 |
| ATOM | 3268 | O | HOH | 215 | 60.763 | 14.246 | 4.066 | 1.00 | 28.42 | 8 |
| ATOM | 3269 | O | HOH | 216 | −7.013 | 22.731 | 43.412 | 1.00 | 36.10 | 8 |
| ATOM | 3270 | O | HOH | 217 | 47.613 | −2.360 | 10.022 | 1.00 | 38.25 | 8 |
| ATOM | 3271 | O | HOH | 218 | 48.775 | 15.791 | 12.359 | 1.00 | 39.21 | 8 |
| ATOM | 3272 | O | HOH | 219 | 28.698 | 5.228 | 53.885 | 1.00 | 42.64 | 8 |
| ATOM | 3273 | O | HOH | 220 | 35.827 | −1.807 | 42.298 | 1.00 | 32.73 | 8 |
| ATOM | 3274 | O | HOH | 221 | 30.851 | 5.941 | 24.767 | 1.00 | 25.97 | 8 |
| ATOM | 3275 | O | HOH | 222 | 31.586 | −0.093 | 53.204 | 1.00 | 45.14 | 8 |
| ATOM | 3276 | O | HOH | 223 | 22.078 | 6.124 | 56.388 | 1.00 | 36.95 | 8 |
| ATOM | 3277 | O | HOH | 224 | 35.392 | 15.479 | 23.418 | 1.00 | 38.92 | 8 |
| ATOM | 3278 | O | HOH | 225 | 9.294 | 6.626 | 61.225 | 1.00 | 32.83 | 8 |
| ATOM | 3279 | O | HOH | 226 | −0.133 | 14.734 | 35.886 | 1.00 | 41.95 | 8 |
| ATOM | 3280 | O | HOH | 227 | 24.682 | −5.722 | 51.063 | 1.00 | 38.24 | 8 |
| ATOM | 3281 | O | HOH | 228 | 17.670 | −0.968 | 38.818 | 1.00 | 34.32 | 8 |
| ATOM | 3282 | O | HOH | 229 | 30.405 | 13.028 | 51.826 | 1.00 | 32.82 | 8 |
| ATOM | 3283 | O | HOH | 230 | 27.990 | 11.360 | 22.599 | 1.00 | 43.21 | 8 |
| ATOM | 3284 | O | HOH | 231 | 40.172 | −9.571 | 13.226 | 1.00 | 42.49 | 8 |
| ATOM | 3285 | O | HOH | 232 | 44.176 | 17.857 | 18.523 | 1.00 | 44.83 | 8 |
| ATOM | 3286 | O | HOH | 233 | 64.537 | 8.490 | 3.724 | 1.00 | 42.83 | 8 |
| ATOM | 3287 | O | HOH | 234 | 35.248 | 13.773 | 20.749 | 1.00 | 36.22 | 8 |
| ATOM | 3288 | O | HOH | 235 | 52.212 | 12.776 | 3.292 | 1.00 | 38.21 | 8 |
| ATOM | 3289 | O | HOH | 236 | −14.090 | 9.605 | 60.933 | 1.00 | 37.41 | 8 |
| ATOM | 3290 | O | HOH | 237 | 35.477 | 24.895 | 37.622 | 1.00 | 42.01 | 8 |
| ATOM | 3291 | O | HOH | 238 | −7.486 | 4.567 | 36.735 | 1.00 | 42.76 | 8 |
| ATOM | 3292 | O | HOH | 239 | 6.113 | −10.403 | 60.449 | 1.00 | 43.93 | 8 |
| ATOM | 3293 | O | HOH | 240 | 11.107 | 23.682 | 48.858 | 1.00 | 42.47 | 8 |
| ATOM | 3294 | O | HOH | 241 | −2.038 | 17.305 | 34.449 | 1.00 | 33.03 | 8 |
| ATOM | 3295 | O | HOH | 242 | 0.920 | 22.713 | 56.806 | 1.00 | 30.05 | 8 |
| ATOM | 3296 | O | HOH | 243 | 18.939 | 18.057 | 32.762 | 1.00 | 39.05 | 8 |
| ATOM | 3297 | O | HOH | 244 | 26.975 | 11.248 | 53.225 | 1.00 | 34.05 | 8 |
| ATOM | 3298 | O | HOH | 245 | 10.673 | 19.033 | 57.040 | 1.00 | 39.09 | 8 |
| ATOM | 3299 | O | HOH | 246 | 27.504 | 19.374 | 31.127 | 1.00 | 35.56 | 8 |
| ATOM | 3300 | O | HOH | 247 | 41.720 | 17.750 | 20.970 | 1.00 | 33.09 | 8 |
| ATOM | 3301 | O | HOH | 248 | −14.075 | 6.476 | 60.512 | 1.00 | 36.34 | 8 |
| ATOM | 3302 | O | HOH | 249 | 11.576 | −3.323 | 36.570 | 1.00 | 39.72 | 8 |
| ATOM | 3303 | O | HOH | 250 | 4.802 | 20.363 | 39.605 | 1.00 | 50.13 | 8 |
| ATOM | 3304 | O | HOH | 251 | 35.204 | 18.895 | 50.305 | 1.00 | 43.85 | 8 |
| ATOM | 3305 | O | HOH | 252 | 12.399 | 19.443 | 54.360 | 1.00 | 36.25 | 8 |
| ATOM | 3306 | O | HOH | 253 | 16.384 | 16.012 | 37.495 | 1.00 | 33.42 | 8 |
| ATOM | 3307 | O | HOH | 254 | 10.129 | 12.031 | 33.654 | 1.00 | 35.78 | 8 |
| ATOM | 3308 | O | HOH | 255 | −18.794 | 6.131 | 59.746 | 1.00 | 39.78 | 8 |
| ATOM | 3309 | O | HOH | 256 | 55.328 | −0.281 | 10.755 | 1.00 | 45.39 | 8 |
| ATOM | 3310 | O | HOH | 257 | 46.460 | 11.731 | −0.619 | 1.00 | 39.38 | 8 |
| ATOM | 3311 | O | HOH | 258 | −11.089 | 2.150 | 46.148 | 1.00 | 32.96 | 8 |
| ATOM | 3312 | O | HOH | 259 | 48.316 | 20.790 | 7.436 | 1.00 | 39.17 | 8 |
| ATOM | 3313 | O | HOH | 260 | 42.543 | 21.700 | 27.547 | 1.00 | 41.64 | 8 |
| ATOM | 3314 | O | HOH | 261 | 14.168 | −6.042 | 41.870 | 1.00 | 40.09 | 8 |
| ATOM | 3315 | O | HOH | 262 | 26.856 | 13.708 | 57.368 | 1.00 | 37.96 | 8 |
| ATOM | 3316 | O | HOH | 263 | 17.563 | −3.286 | 40.443 | 1.00 | 42.56 | 8 |
| ATOM | 3317 | O | HOH | 264 | 53.136 | 6.936 | 26.067 | 1.00 | 43.26 | 8 |
| ATOM | 3318 | O | HOH | 265 | 56.575 | −2.030 | 6.422 | 1.00 | 48.76 | 8 |
| ATOM | 3319 | O | HOH | 266 | 49.735 | 10.855 | 29.152 | 1.00 | 46.07 | 8 |
| ATOM | 3320 | O | HOH | 267 | 39.963 | 23.362 | 21.368 | 1.00 | 39.48 | 8 |
| ATOM | 3321 | O | HOH | 268 | 3.695 | 22.743 | 40.209 | 1.00 | 40.66 | 8 |
| ATOM | 3322 | O | HOH | 269 | −4.794 | 17.786 | 38.996 | 1.00 | 30.73 | 8 |
| ATOM | 3323 | O | HOH | 270 | −11.650 | 5.394 | 61.995 | 1.00 | 45.79 | 8 |
| ATOM | 3324 | O | HOH | 271 | 57.446 | 5.752 | 19.747 | 1.00 | 41.23 | 8 |
| ATOM | 3325 | O | HOH | 272 | 45.199 | 5.102 | 26.107 | 1.00 | 45.82 | 8 |
| ATOM | 3326 | O | HOH | 273 | 8.021 | −6.271 | 61.126 | 1.00 | 42.70 | 8 |

APPENDIX A-continued

```
ATOM   3327  O    HOH  274   -2.750  23.018  50.699  1.00  38.18  8
ATOM   3328  O    HOH  275   49.226   8.848  28.465  1.00  41.12  8
ATOM   3329  O    HOH  276   45.382  18.765  16.382  1.00  46.33  8
ATOM   3330  O    HOH  277   36.980  19.043  23.342  1.00  40.75  8
ATOM   3331  O    HOH  278   14.043  -4.554  33.163  1.00  44.85  8
ATOM   3332  O    HOH  279   28.871   9.143  52.278  1.00  37.86  8
ATOM   3333  O    HOH  280   12.533  21.581  43.074  1.00  45.31  8
ATOM   3334  O    HOH  281   44.591   6.981   7.087  1.00  35.60  8
ATOM   3335  O    HOH  282   15.406  18.517  25.995  1.00  44.43  8
ATOM   3336  O    HOH  283   40.115   4.361  30.746  1.00  40.66  8
ATOM   3337  O    HOH  284   23.620  19.746  52.323  1.00  44.95  8
ATOM   3338  O    HOH  285   29.155   2.644  53.203  1.00  37.44  8
ATOM   3339  O    HOH  286   -5.182  18.972  37.153  1.00  34.21  8
ATOM   3340  O    HOH  287   32.647  19.479  26.889  1.00  42.13  8
ATOM   3341  O    HOH  288   12.696  19.733  51.583  1.00  37.56  8
ATOM   3342  O    HOH  289   30.040  12.623  15.157  1.00  42.37  8
ATOM   3343  O    HOH  290    7.604 -10.459  46.221  1.00  43.74  8
ATOM   3344  O    HOH  291   14.364  19.505  28.168  1.00  35.20  8
ATOM   3345  O    HOH  292    4.398  -0.273  67.730  1.00  41.40  8
ATOM   3346  O    HOH  293   19.589  20.553  53.184  1.00  36.39  8
ATOM   3347  O    HOH  294   14.115  16.921  38.047  1.00  42.25  8
ATOM   3348  O    HOH  295   -5.817  22.444  39.532  1.00  45.45  8
END
```

APPENDIX 1

Polypeptide sequence from strain PS149B1, 44 kDa toxin gene:

| Num | AA | Structure | Domain | Homology | Similarity | Accessibility |
|---|---|---|---|---|---|---|
| 1 | M | — | | | | — |
| | L | C | D1 | |

APPENDIX 1-continued

Polypeptide sequence from strain PS149B1, 44 kDa toxin gene:

| Num | AA | Structure | Domain | Homology | Similarity | Accessibility |
|---|---|---|---|---|---|---|
|  | Q | C |  |  | G | R1/2q |  |
| 90 | K | S |  |  |  | R1k/2r |  |
|  | W | S |  |  | G | R1/2w |  |
|  | Q | S |  |  | G |  |  |
|  | I | S |  |  | G |  |  |
|  | K | S |  |  |  |  |  |
|  | A | S |  |  |  |  | 30* |
|  | N | S |  |  |  |  |  |
|  | G | C |  |  |  | R1/2g | 30 |
|  | S | C |  |  | G |  | 30* |
|  | S | S |  |  |  |  |  |
| 100 | Y | S |  |  | G |  |  |
|  | V | S |  |  |  |  |  |
|  | I | S |  |  | G | R1i |  |
|  | Q | S |  |  |  |  |  |
|  | S | S |  |  |  | R1s |  |
|  | D | S |  |  |  |  |  |
|  | N | C |  |  | G | R1n | 30 |
|  | G | C |  |  | G | R2g |  |
|  | K | S |  |  | G | R2k |  |
|  | V | S |  |  |  |  |  |
| 110 | L | S |  |  | G | R1/21 |  |
|  | T | S |  |  | G |  |  |
|  | A | S |  |  | G |  |  |
|  | G | S |  |  | G | R1g |  |
|  | T | S |  |  |  |  | 30* |
|  | G | S |  |  | G | R2g | 30 |
|  | Q | C |  |  |  |  | 30* |
|  | A | C |  |  |  |  |  |
|  | L | S |  |  | G |  | 30* |
|  | G | S |  |  | G | R2g |  |
| 120 | L | S |  |  |  |  |  |
|  | I | S |  |  |  |  |  |
|  | R | S |  |  |  | R1r |  |
|  | L | S |  |  | G | R1l |  |
|  | T | S |  |  | G |  |  |
|  | D | C |  |  | G |  | 30* |
|  | E | C |  |  | G |  | 30* |
|  | S | C |  |  |  | R1s |  |
|  | S | C |  |  |  |  | 30* |
|  | N | C |  |  |  |  | 30* |
| 130 | N | C |  |  |  |  |  |
|  | P | C |  |  |  | R2p |  |
|  | N | C |  |  | G | R1/2n |  |
|  | Q | C |  |  | G | R1/2q |  |
|  | Q | S |  |  | G | R1r2k |  |
|  | W | S |  |  | G | R1/2w |  |
|  | N | S |  |  | G |  |  |
|  | L | S |  |  | G | /R2 |  |
|  | T | S |  |  | G |  |  |
|  | S | S |  |  |  |  |  |
| 140 | V | S |  |  |  |  |  |
|  | Q | S |  |  |  |  |  |
|  | T | S |  |  | G | R1t |  |
|  | I | S | /D1 |  | G | R1I |  |
|  | Q | c |  |  |  |  | 30* |
|  | L | C |  |  | G |  |  |
|  | P | C |  |  | G |  |  |
|  | Q | C |  |  |  | /R1 | 30* |
|  | K | C |  |  |  |  | 30* |
|  | P | C |  |  | G |  |  |
| 150 | I | C |  |  |  |  | 30* |
|  | I | C |  |  | G |  |  |
|  | D | C | D2? |  | G |  |  |
|  | T | C |  |  |  |  | 30* |
|  | K | C |  |  |  |  | 30* |
|  | L | C |  |  | G |  |  |
|  | K | C |  |  |  |  | 30* |
|  | D | C |  |  | G |  |  |
|  | Y | C |  |  |  |  |  |
|  | P | C |  |  | G |  |  |
| 160 | K | C |  |  |  |  |  |
|  | Y | C |  |  | G |  |  |
|  | S | C |  |  | G |  | 30 |
|  | P | — |  |  |  |  |  |
|  | T | — |  |  | G |  |  |
|  | G | C |  |  | G |  | 30 |
|  | N | C |  |  |  |  | 30* |
|  | I | C |  |  | G |  |  |
|  | D | C |  |  |  |  | 30* |
|  | N | S |  | D2 |  |  | 30* |
| 170 | G | S |  |  |  |  |  |
|  | T | S |  |  | G |  |  |
|  | S | C |  |  |  |  | 30* |
|  | P | C |  |  |  |  | 30* |
|  | Q | S |  |  | G |  |  |
|  | L | S |  |  | G |  |  |
|  | M | S |  |  | G |  |  |
|  | G | S |  |  | R |  |  |
|  | W | S |  |  | R |  |  |
|  | T | S |  |  | R |  |  |
| 180 | L | S |  |  | R |  |  |
|  | V | S |  |  | R |  |  |
|  | P | S |  |  | R |  |  |
|  | C | S |  |  | R |  |  |
|  | I | C |  |  | R |  |  |
|  | M | C |  |  | R |  |  |
|  | V | C |  |  | R |  |  |
|  | N(D?) | C |  |  | R |  |  |
|  | D | C |  |  | R |  |  |
|  | P | C |  |  |  |  | 30* |
| 190 | N | C |  |  |  |  | 30* |
|  | I | C |  |  | G |  |  |
|  | D | C |  |  |  |  | 30* |
|  | K | H |  |  |  |  |  |
|  | N | H |  |  |  |  |  |
|  | T | H |  |  | G |  |  |
|  | Q | H |  |  | G |  |  |
|  | I | H |  |  | G |  |  |
|  | K | H |  |  | O |  | 30 |
|  | T | C |  |  | O |  |  |
| 200 | T | C |  |  | O |  |  |
|  | P | S |  |  | O |  |  |
|  | Y | S |  |  | O |  |  |
|  | Y | S |  |  | O |  |  |
|  | I | S |  |  | O |  |  |
|  | L | S |  |  | O |  |  |
|  | K | S |  |  | O |  |  |
|  | K | S |  |  | O |  |  |
|  | Y | S |  |  | O |  |  |
|  | Q | S |  |  | O |  |  |
| 210 | Y | S |  |  | O |  |  |
|  | W | S |  |  | O |  |  |
|  | Q | S |  |  |  |  | 30* |
|  | R | S |  |  |  |  | 30* |
|  | A | S |  |  | G |  |  |
|  | V | C |  |  |  |  | 30* |
|  | G | C |  |  | G |  |  |
|  | S | C |  |  | G |  |  |
|  | N | C |  |  |  |  | 30* |
|  | V | S |  |  |  |  |  |
| 220 | A | S |  |  |  |  |  |
|  | L | S |  |  |  |  |  |
|  | R | C |  |  |  |  | 30* |
|  | P | C |  |  |  |  |  |
|  | H | C |  |  | G |  | 30 |
|  | E | S |  |  |  |  |  |
|  | K | S |  |  | G |  | 30 |
|  | K | S |  |  |  |  |  |
|  | S | S |  |  |  |  | 30* |
|  | Y | S |  |  |  |  |  |
| 230 | T | S |  |  |  |  |  |
|  | Y | S |  |  | G |  |  |
|  | E | S |  |  | G |  |  |
|  | W | S |  |  | G |  |  |
|  | G | S |  |  | G |  |  |
|  | T | S |  |  | G |  |  |
|  | E | C |  |  |  |  | 30* |

APPENDIX 1-continued

Polypeptide sequence from strain PS149B1, 44 kDa toxin gene:

| Num | AA | Structure | Domain | Homology | Similarity | Accessibility |
|---|---|---|---|---|---|---|
|  | I | C |  |  |  |  |
|  | D | C |  |  |  | 30* |
|  | Q | C |  | G | hyd |  |
| 240 | K | C |  | G |  | 30 |
|  | T | C |  | G |  | 30 |
|  | T | C |  |  |  |  |
|  | I | H |  |  |  |  |
|  | I | H |  | G |  |  |
|  | N | H |  | G |  |  |
|  | T | H |  | G |  |  |
|  | L | C |  |  |  |  |
|  | G | S |  | G |  |  |
|  | F | S |  |  |  |  |
| 250 | Q | S |  | G |  |  |
|  | I | S |  | R |  |  |
|  | N | S |  | R |  |  |
|  | I | S |  | R |  |  |
|  | D | C |  | R |  |  |
|  | S | C |  | R |  |  |
|  | G | S |  | R |  |  |
|  | M | S |  | O |  |  |
|  | K | S |  | O |  |  |
|  | F | S |  | O |  |  |
| 260 | D | S |  |  |  |  |
|  | I | C |  |  |  | 30* |
|  | P | C |  | G | /hyd |  |
|  | E | C |  | G |  | 30 |
|  | V | C |  | G |  | 30 |
|  | G | C |  | G |  |  |
|  | G | C |  | G |  |  |
|  | G | C |  | G |  |  |
|  | T | C |  |  |  |  |
|  | D | C |  |  |  |  |
| 270 | E | C |  |  |  |  |
|  | I | C |  | G |  |  |
|  | K | H |  |  |  |  |
|  | T | H |  | G |  |  |
|  | Q | H |  | G |  |  |
|  | L | H |  |  |  |  |
|  | N | H |  |  |  |  |
|  | E | H |  | G |  | 30 |
|  | E | H |  | G |  |  |
|  | L | H |  | G |  |  |
| 280 | K | C |  | G |  | 30 |
|  | I | C |  |  |  |  |
|  | E | C |  | G |  | 30 |
|  | Y | C |  | G |  |  |
|  | S | C |  | G |  |  |
|  | H | C |  |  |  | 30* |
|  | E | C |  | G |  | 30 |
|  | T | C |  |  |  | 30* |
|  | K | S |  | G |  |  |
|  | I | S |  |  |  |  |
| 290 | M | S |  | G |  |  |
|  | E | S |  |  |  | 30 |
|  | K | S |  | G |  | 30 |
|  | Y | S |  | G |  |  |
|  | Q | S |  |  |  | 30* |
|  | E | S |  |  |  |  |
|  | Q | S |  |  |  | 30* |
|  | S | S |  |  |  |  |
|  | E | S |  |  |  | 30* |
|  | I | S |  |  |  |  |
| 300 | D | S |  | G |  |  |
|  | N | S |  | G |  |  |
|  | P | C |  |  |  |  |
|  | T | C |  |  |  |  |
|  | D | C |  |  |  | 30* |
|  | Q | C |  |  |  |  |
|  | S | C |  |  |  | 30* |
|  | M | S |  | R |  |  |
|  | N | S |  | R |  |  |
|  | S | S |  | R |  |  |
| 310 | I | S |  | R |  |  |
|  | G | S |  | R |  |  |
|  | F | S |  | R |  |  |
|  | L | S |  | R |  |  |
|  | T | S |  | R |  |  |
|  | I | S |  | R |  |  |
|  | T | S |  | R |  |  |
|  | S | S |  | R |  |  |
|  | L | S |  | R |  |  |
|  | E | S |  | R |  |  |
| 320 | L | S |  | R |  |  |
|  | Y | S |  | R |  |  |
|  | R | S |  | R |  |  |
|  | Y | S |  | O |  |  |
|  | N | S |  | O |  | 30 |
|  | G | C |  | O |  | 30 |
|  | S | S |  |  |  |  |
|  | E | S |  |  |  | 30* |
|  | I | S |  |  |  |  |
|  | R | S |  |  |  | 30* |
| 330 | I | S |  |  |  |  |
|  | M | S |  |  |  |  |
|  | Q | S |  |  |  |  |
|  | I | S |  | G |  |  |
|  | Q | S |  |  |  |  |
|  | T | S |  | G |  |  |
|  | S | C |  |  |  |  |
|  | D | C |  |  |  |  |
|  | N | C |  |  |  |  |
|  | D | C |  | G |  | 30 |
| 340 | T | C |  | G |  |  |
|  | Y | C |  | G |  |  |
|  | N | S |  |  |  |  |
|  | V | S |  |  |  |  |
|  | T | S |  |  |  |  |
|  | S | S |  |  |  |  |
|  | Y | S |  | G |  | 30 |
|  | P | C | /D2 | G |  |  |
|  | N | C |  |  |  |  |
|  | H | H | D3 | G |  |  |
| 350 | Q | H |  |  |  | 30* |
|  | Q | H |  |  |  | 30* |
|  | A | H |  |  |  |  |
|  | L | H |  | G |  |  |
|  | L | H |  | G |  | 30 |
|  | L | H |  | G |  |  |
|  | L | H |  | G |  |  |
|  | T | C |  | G |  | 30 |
|  | N | C |  | G |  | 30 |
|  | H | C |  | G |  |  |
| 360 | S | C |  | G |  |  |
|  | Y | H |  | G |  |  |
|  | E | H |  | G |  | 30 |
|  | E | H |  | G |  | 30 |
|  | V | H |  | G |  |  |
|  | E | H |  |  |  |  |
|  | E | H |  |  |  | 30* |
|  | I | H |  |  |  | 30* |
|  | T | H |  | G |  |  |
|  | N | C |  |  |  | 30* |
| 370 | I | C |  | G |  |  |
|  | P | C |  |  |  |  |
|  | K | H |  | G |  | 30 |
|  | S | H |  |  |  | 30* |
|  | T | H |  |  |  |  |
|  | L | H |  | G |  |  |
|  | K(I?) | H |  |  |  |  |
|  | K | H |  |  |  | 30* |
|  | L | H |  | G |  |  |
|  | K | H |  | G |  | 30 |
| 380 | K | C |  |  |  | 30* |
|  | Y(H?) | C | /D3 |  |  | 30* |
|  | Y | — |  |  |  |  |
|  | F | — |  |  |  |  |

Appendix 2

```
              *        20         *        40         *        60         *        80
149B1 : MLDTNKVYEISN HANGLY AA TYLS DDDSGVSLVN KN DIDDYNLKWFLFPIDDDQYIITSYA N  KVW N DKINVSTYS N  :  86
167H2 : MLDTNKIYEISN YANGLHAA  TYLS DDDSGVSLVN NN DIDDYNLKWFLFPIDDNQYIITSYA N  KVW N DKINVSTYS N  :  86
80JJ1 : MLDTNKVYEISN LANGLY TS YLS DDDSGVSLV KE EDIDDYNLKWFLFPIDNNQYIITSYG N  KVW K DKINVSTYS N  :  86
69Q   : MLDTNKVYEISN LANGLY TS YLS DDDSGVSLN KKE EDIDDYNLKWFLFPIDNNQYIITSYG N  KVW N DKINVSTYS N  :  86
201L3 : MLETNKIYEISN KANGLY AT TYLS FDNSGVSLHN KNES DIDDYNLKWFLFPIDNNQYIITSY GV KNKVY TANG NKINVTT SAEN :  86
        M6dTNK6YEISN ANGLy    TYLS1D1SGVSL6  K  d DI1DYNL4WFLFPID11QYIITSY aNncKVWnv n1KINV3TYSstN

*       100         *       120         *       140         *       160         *
149B1 : S QWQIK NGS VIQ DNGKVLTAGTGA LGLI  LTDESSN PNQQWNLT VQTI LPQ E IIDTK IDYEK YS PTC IDN-G I : 171
167H2 : S QWQIK NAS VIQ NNGKVLTAGTGC LGLI  LTDES DN PNQQWNLT PVQTI LPP TIDT Y YEK QR IID K-G I : 171
80JJ1 : S QWQIK KDS IIQ DNGKVLTAGVGE LGIV  LTDEF EN SNQQWNLT PVQTI LPQ K KIDE IDHP EYSETG INP-K I : 171
69Q   : S QWQIK KDS IIQ DNGKVLTAC VGE LGIV  LTDEF EN SNQQWNLT PVQTI LPQ K KIDE IDHP EYSETC INP-K I : 171
201L3 : SA QWQIR NSS GY INN NNGKILTAGTGC LGLI YLTDEI E SNQQWNLT QTI SLP SQE IDDTT V YEK QS TK SINYNG I : 172
        S  QkWQI4a   SsY6I2s1NGK6LTAG G2sLG66rLTDE p 1 NQQWNLT 6QTIqLP kP ID kLkD P YS TGnI1    T

180         *       200         *       220         *       240         *
149B1 : S QLMGWTLVPCIMV DPNI- TQI TTPYYI LKKY Q QR VGS VALR  SS YEWGTI IDQKTTI INTLG QIN DS : 256
167H2 : P QLMGWTLIPCIMV DPNI- TQI TTPYYI LKKY  W QQC VGS VALR  K SIAYEWGTI IDQKTTI INTLG QIN DS : 256
80JJ1 : T QLMGWTLVPCIMV ANLM- TQI TTPYYI FKK Y N LAKGS VSL    SD YEWGTL KNQKTTI INTVGL QIN DS : 256
69Q   : T QLMGWTLVPCIMV DSGI- TQI TTPYYI PKK Y N LAKGS VSL    SD YEWGTL KNQKTTI INTVGL QIN DS : 256
201L3 : AL QLMGWTLIPCIMV YEKTI ASTH TQI TTPYYI LKKY QR VLATGSGL SVPA VK STE YEWGTD DQKTSVI NTL GQIN TD K : 258
        pQLMGWTL6PCIMVnD Id  knTQIkTTPYYI  KKY  yW  A  GSn6 6  pH K  35   YEWGTe 1QKT36INT6G QIN iD3g

60         *       280         *       300         *       320         *       340
149B1 : MK DIPEVGGGT DE IKTQ NEELKIEYS H KY EQS IDN -DGSM N IGF TITSELYR NG IRT QI DSN D Y : 341
167H2 : MK DIPEVGGGT DE IKTQL NEELKIEYS R KN KYQS IDN -DGSM N IGF TITSELYR NG SV K DSND D Y : 341
80JJ1 : MK EVPEVGGGT ED IKTQL EELKVEYS ID N LT KY H IDN -SNQP N ICL IYTSELYRK NG IKID TSD H D Y : 341
69Q   : MK EVPEVGGGT ED IKTQL EELKVEYS I E N LT KY H IDN -SNQP N ICL IYTSELYRK NG IKID TSD H D Y : 341
201L3 : LK ATPEVGGGT TD IRTQI TEELKVEYS SENK RL KQS FDVDNLNY DEALIA VGF VETSFELYR MGN -VLITSI KTNK DTY : 343
        6Kf 6PEVGGGT   I4TQ6 EELK6EYS EtKiM  KYq2 se6DNp t12 6Ns6G 6    TSlELYRyNG e6 6m I T31 DTY

*       360         *       380
149B1 : N SYPNH QC LLLLTNHSYEEV IN KS IK LK Y-- : 383
167H2 : N SYPDH QC LLLLTNHSYEEV IN IS IK LK Y-- : 383
80JJ1 : T SYPNH KE LLLLTNHSYEEV IL KH LK H EKK : 385
69Q   : T SYPNH KE LLLLTNHSYEEV IL KH LK H EKK : 385
201L3 : NTV YPNH KEV LLLLTNHSYEEV TAL TG SL ER QNL KNN KKR : 387
        t3YP1H 2aLLLLTNHSYEEVee6T  IpK   L kLKk 5f
```

Appendix 3

```
              *        20         *        40         *        60         *        80
149B1 :                                                                              :  86
167H2 :                                                                              :  86
80JJ1 :                                                                              :  86
69Q   :                                                                              :  86
201L3 :                                                                              :  86
        M6dTNK6YEISN ANGLy    TYLS1D1SGVSL6  K  d DI1DYNL4WFLFPID11QYIITSY aNncKVWnv n1KINV3TYSstN

*       100         *       120         *       140         *       160         *
149B1 :                                                                              : 171
167H2 :                                                                              : 171
80JJ1 :                                                                              : 171
69Q   :                                                                              : 171
201L3 :                                                                              : 172
        S  QkWQI4a   SsY6I2s1NGK6LTAG G2sLG66rLTDE p 1 NQQWNLT 6QTIqLP kP ID kLkD P YS TGnI1    T

180         *       200         *       220         *       240         *
149B1 :                                                                              : 256
167H2 :                                                                              : 256
80JJ1 :                                                                              : 256
69Q   :                                                                              : 256
201L3 :                                                                              : 258
        pQLMGWTL6PCIMVnD Id  knTQIkTTPYYI  KKY  yW  A  GSn6 6  pH K  35   YEWGTe 1QKT36INT6G QIN iD3g

60         *       280         *       300         *       320         *       340
149B1 :                                                                              : 341
167H2 :                                                                              : 341
80JJ1 :                                                                              : 341
69Q   :                                                                              : 341
201L3 :                                                                              : 343
        6Kf 6PEVGGGT   I4TQ6 EELK6EYS EtKiM  KYq2 se6DNp t12 6Ns6G 6    TSlELYRyNG e6 6m I T31 DTY
```

-continued

Appendix 3

```
                *         360         *         380
149B1 :  NV  P  C  LLLL            I  P      K K    -- : 383
167H2 :  NV  P  C  LLLL            I  P      K K    -- : 383
80JJ1 :  L   P  K  LLLL            I  P      K K       : 385
69Q   :  L   P  K  LLLL            I  P      K K       : 385
201L3 :  NV  P  K V LLL         L  L  SR     K KKK     : 387
         t3YP1H 2aLLLLTNHSYEEVee6T IpK  L kLKk 5f
```

APPENDIX 4

| From | Residue changed | To | Resulting Change | substitution present only in 201L3 |
|---|---|---|---|---|
| L | 2 | I | conservative | yes |
| D | 3 | E | conservative | yes |
| V | 7 | I | similar | no |
| H | 13 | Y | nonconservative nonpolar | no |
| H | 13 | L | nonconservative change to a hydrophobic group predominating in other homologs | no |
| H | 13 | K | conservative polar charged | yes |
| Y | 18 | H | nonconservative polar charged | no |
| A | 19 | T | nonconservative polar | no |
| A | 20 | S | nonconservative polar | no |
| A | 20 | T | nonconservative polar | yes |
| L | 25 | F | nonconservative hydrophobic aromatic | yes |
| D | 27 | N | similar | yes |
| M | 33 | L | similar | yes |
| N | 34 | S | conservative polar uncharged | no |
| N | 36 | K | conservative polar charged | no |
| D | 38 | E | conservative | no |
| D | 38 | S | conservative polar uncharged | yes |
| D | 41 | N | similar | yes |
| K | 46 | R | conservative polar charged | no |
| D | 54 | N | similar | no |
| D | 55 | N | similar | no |
| A | 63 | G | conservative small | no |
| A | 64 | V | conservative nonpolar | yes |
| N | 66 | K | conservative polar charged | yes |
| C | 67 | N | nonconservative | yes |
| N | 71 | T | conservative polar uncharged | yes |
| V | 72 | A | conservative small | yes |
| N | 73 | K | conservative polar charged | no |
| N | 74 | G | nonconservative small | yes |
| D | 75 | N | similar | yes |
| S | 80 | T | similar | yes |
| S | 84 | A | nonconservative small | yes |
| T | 85 | E | nonconservative charged | yes |
| I | 88 | A | conservative small | yes |
| I | 88 | V | similar | no |
| K | 90 | Q | conservative polar uncharged | yes |
| K | 94 | R | similar | yes |
| A | 95 | N | nonconservative polar uncharged | yes |
| N | 96 | S | conservative polar uncharged | yes |
| N | 96 | K | conservative polar charged | no |
| G | 97 | A | conservative small | no |
| G | 97 | D | nonconservative charged | no |
| G | 97 | S | nonconservative polar | yes |
| S | 99 | G | nonconservative small | yes |
| V | 101 | I | similar | no |
| Q | 103 | E | similar | yes |
| S | 104 | N | conservative polar uncharged | yes |
| D | 105 | N | similar | no |
| V | 109 | I | similar | yes |
| T | 114 | V | nonconservative nonpolar | no |
| Q | 116 | E | similar | no |
| A | 117 | S | nonconservative change to polar group predominating in other homologs | no |
| L | 120 | I | similar | no |
| I | 121 | L | similar | yes |

APPENDIX 4-continued

| From | Residue changed | To | Resulting Change | substitution present only in 201L3 |
|---|---|---|---|---|
| I | 121 | V | similar | no |
| R | 122 | Y | nonconservative nonpolar | yes |
| S | 127 | I | nonconservative nonpolar | yes |
| S | 127 | F | nonconservative nonpolar aromatic | no |
| S | 128 | P | noncoservative change predominates in all other homologs | no |
| N | 129 | E | conservative polar charged | no |
| N | 129 | D | similar | no |
| N | 130 | D | similar | yes |
| P | 131 | S | nonconservative | no |
| S | 139 | P | nonconservative | no |
| V | 140 | I | similar | yes |
| Q | 144 | S | conservative polar uncharged | yes |
| Q | 147 | P | nonconservative | no |
| Q | 147 | S | conservative polar uncharged | yes |
| K | 148 | Q | conservative polar uncharged | yes |
| I | 150 | K | nonconservative polar charged | no |
| I | 150 | T | nonconservative polar uncharged | no |
| T | 153 | E | nonconservative polar charged | no |
| K | 154 | T | nonconservative polar uncharged | yes |
| K | 156 | V | nonconservative nonpolar | yes |
| Y | 158 | H | nonconservative polar charged | no |
| K | 160 | E | conservative positive charge | no |
| P | 163 | Q | nonconservative polar uncharged | no |
| P | 163 | E | nonconservative polar charged | no |
| P | 163 | T | nonconservative polar uncharged | yes |
| N | 166 | S | conservative polar uncharged | yes |
| D | 168 | N | similar | no |
| N | 169 | P | nonconservative | no |
| N | 169 | K | conservative charged | no |
| N | 169 | Y | nonconservative nonpolar | yes |
| G | 170 | K | nonconservative charged | no |
| S | 172 | P | nonconservative | no |
| S | 172 | A | nonconservative small | yes |
| S | 172 | T | similar | no |
| P | 173 | L | nonconservative nonpolar | yes |
| V | 181 | I | similar | no |
| N | 187 | Y | nonconservative nonpolar | yes |
| P | 189 | S | nonconservative | no |
| P | 189 | K | nonconservative | yes |
| N | 190 | G | nonconservative small | no |
| N | 190 | K | conervative polar charged | no |
| N | 190 | T | conservative polar uncharged | yes |
| D | 192 | A | nonconservative small | yes |
| K | 193 | T | conservative polar uncharged | yes |
| N | 194 | H | conservative polar charged | yes |
| K | 198 | T | conservative polar uncharged | yes |
| L | 205 | F | conservative aromatic | no |
| Q | 209 | K | conservative polar charged | no |
| Y | 210 | R | nonconservative polar charged | yes |
| Q | 212 | N | conservative polar uncharged | no |
| Q | 212 | V | nonconservative nonpolar | yes |
| R | 213 | L | nonconservative nonpolar | no |
| R | 213 | Q | conservative polar uncharged | no |
| V | 215 | T | nonconservative polar uncharged | yes |
| V | 215 | K | nonconservative polar charged | no |
| N | 218 | G | nonconservative small | yes |
| V | 219 | L | similar | yes |
| A | 220 | S | nonconservative polar uncharged | no |

APPENDIX 4-continued

| From | Residue changed | To | Resulting Change | substitution present only in 201L3 |
|---|---|---|---|---|
| L | 221 | V | similar | yes |
| R | 222 | P | nonconservative | yes |
| R | 222 | L | nonconservative nonpolar | no |
| P | 223 | A | nonconservative | yes |
| E | 225 | Q | conservative polar uncharged | no |
| E | 225 | V | nonconservative nonpolar | yes |
| K | 227 | R | similar | no |
| K | 227 | S | conservative polar uncharged | yes |
| S | 228 | T | similar | yes |
| Y | 229 | F | similar | yes |
| T | 230 | A | nonconservative small | no |
| T | 230 | D | conservative polar charged | no |
| T | 230 | E | conservative polar charged | yes |
| E | 236 | D | conservative | yes |
| I | 237 | K | nonconservative polar charged | no |
| I | 237 | T | nonconservative polar uncharged | yes |
| D | 238 | N | similar | no |
| T | 242 | S | similar | no |
| I | 243 | V | similar | yes |
| L | 247 | V | similar | no |
| F | 249 | L | conservative nonpolar | no |
| I | 253 | T | nonconservative polar uncharged | yes |
| S | 255 | T | similar | yes |
| G | 256 | K | nonconservative polar charged | yes |
| M | 257 | L | similar | yes |
| F | 259 | A | conservative small | yes |
| D | 260 | E | conservative | no |
| D | 260 | T | conservative polar uncharged | yes |
| I | 261 | V | similar | no |
| D | 269 | E | conservative | no |
| D | 269 | T | conservative polar uncharged | yes |
| E | 270 | D | conservative | no |
| K | 272 | R | similar | yes |
| L | 275 | I | similar | yes |
| N | 276 | T | conservative polar uncharged | no |
| I | 281 | V | similar | no |
| H | 285 | R | conservative positive charge | no |
| H | 285 | T | conservative polar uncharged | no |
| H | 285 | S | conservative polar uncharged | yes |
| T | 287 | N | conservative polar uncharged | yes |
| I | 289 | E | nonconservative polar charged | yes |
| E | 291 | T | conservative polar uncharged | no |
| E | 291 | R | conservative polar charged | yes |
| Q | 294 | K | conservative polar charged | yes |
| E | 295 | Q | similar | yes |
| Q | 296 | H | conservative polar charged | no |
| Q | 296 | S | conservative polar uncharged | yes |
| S | 297 | F | nonconservative nonpolar | yes |
| E | 298 | D | conservative polar charged | yes |
| I | 299 | V | similar | yes |
| P | 302 | L | nonconservative | yes |
| T | 303 | Y | nonconservative nonpolar | yes |
| D | 304 | N | similar | no |
| Q | 305 | E | similar | yes |
| S | 306 | P | nonconservative | no |
| S | 306 | A | nonconservative small | yes |
| M | 307 | L | similar | yes |
| S | 309 | A | nonconservative small | yes |
| I | 310 | V | similar | yes |
| F | 312 | L | conservative nonpolar | no |
| L | 313 | I | similar | yes |
| T | 314 | I | nonconservative nonpolar | no |
| T | 314 | V | nonconservative nonpolar | yes |
| I | 315 | Y | conservative nonpolar | no |
| I | 315 | E | nonconservative polar charged | yes |
| L | 318 | F | conservative nonpolar | yes |
| Y | 323 | M | conservative nonpolar | yes |
| S | 326 | T | similar | no |
| S | 326 | N | conservative polar charged | yes |
| I | 328 | V | similar | yes |
| R | 329 | S | conservative polar uncharged | no |
| R | 329 | K | similar | no |
| R | 329 | L | nonconservative nonpolar | yes |
| I | 330 | V | similar | no |
| M | 331 | T | nonconservative polar uncharged | yes |
| Q | 332 | K | conservative polar charged | no |
| Q | 332 | D | conservative polar charged | no |
| Q | 332 | S | conservative polar uncharged | yes |
| Q | 334 | E | conservative polar charged | no |
| Q | 334 | K | conservative polar charged | yes |
| S | 336 | T | similar | yes |
| D | 337 | N | similar | yes |
| N | 338 | H | conservative polar charged | no |
| N | 338 | K | conservative polar charged | yes |
| N | 342 | T | conservative polar uncharged | no |
| V | 343 | L | similar | no |
| V | 343 | T | nonconservative polar charged | yes |
| T | 344 | V | nonconservative polar uncharged | yes |
| S | 345 | T | similar | yes |
| N | 348 | D | similar | no |
| Q | 350 | K | conservative polar charged | no |
| Q | 351 | E | similar | no |
| A | 352 | V | conservative nonpolar | no |
| E | 365 | T | conservative polar uncharged | yes |
| E | 366 | A | nonconservative nonpolar small | yes |
| I | 367 | L | similar | yes |
| N | 369 | K | conservative polar charged | no |
| N | 369 | G | nonconservative polar small | yes |
| P | 371 | S | nonconservative | yes |
| S | 373 | I | nonconservative nonpolar | no |
| S | 373 | H | conservative polar charged | no |
| S | 373 | E | conservative polar charged | yes |
| T | 374 | S | similar | no |
| T | 374 | R | conservative polar charged | yes |
| K | 376 | I | nonconservative nonpolar | no |
| K | 376 | Q | conservative polar uncharged | yes |
| K | 377 | N | conservative polar uncharged | yes |
| K | 380 | N | conservative polar uncharged | yes |
| Y | 381 | H | conservative polar charged | no |
| Y | 381 | N | nonconservative polar uncharged | yes |
| Y | 382 | W | similar | yes |
| F | 383 | K | nonconservative polar charged | yes |

The invention claimed is:

1. A modified Cry35 protein (Cry35-M) comprising a modified protease cleavage site that decreases the processing of Domain 3 of said protein in a plant cell and/or increases protease processing of Domain 3 in an insect cell wherein said modifications occur at one or more of the following in Domain 3:

(a) modification of one or more of the four leucines occurring at positions corresponding to 353-356, (b) modification of one or more lysines at amino acids corresponding to positions 372, 376, 377, 379 or 380, (c) modification of the loop amino acids corresponding to positions 370-372 which creates a protease cleavage site, and/or (d) modification of the loop amino acids corresponding to positions 357-360 which creates a protease cleavage site;

wherein said corresponding amino acid positions of said Cry35-M protein are those that correspond to the stated amino acid positions when said Cry35 protein sequence is aligned with SEQ ID NO: 1.

2. A modified Cry35-M of claim 1 wherein the modification at positions 370-372 comprises replacing the amino acids at these positions to Ala-Pro-Phe.

3. A modified Cry35-M of claim 1 wherein the modification at positions 357-360 comprises replacing the amino acids at these positions to Ala-Pro-Phe-Ala.

4. A modified Cry35-M of claim 1 wherein Leu 354 is changed to Phe which increases the Cry35-M processing by an insect protease.

5. The modified Cry35-M of claim 4 wherein said protein comprises SEQ ID NO: 2.

6. The modified Cry35-M of claim 3 wherein said protein comprises SEQ ID NO: 21.

7. A method of inhibiting a rootworm pest wherein said method comprises contacting said pest with a protein according to claim 1.

8. A method of modifying a Cry35 protein wherein said method comprises substituting at least one amino acid residue to obtain a Cry35-M protein according to claim 1.

* * * * *